(12) United States Patent
Stacey et al.

(10) Patent No.: US 8,580,501 B2
(45) Date of Patent: Nov. 12, 2013

(54) GENETIC VARIANTS ON CHR 5P12 AND 10Q26 AS MARKERS FOR USE IN BREAST CANCER RISK ASSESSMENT, DIAGNOSIS, PROGNOSIS AND TREATMENT

(75) Inventors: Simon Stacey, Kopavogur (IS); Patrick Sulem, Reykjavik (IS); Andrei Manolescu, Reykjavik (IS)

(73) Assignee: deCODE Genetics ehf., Reykjavik (IS)

( * ) Notice: Subject to any disclaimer, the term of this patent is extended or adjusted under 35 U.S.C. 154(b) by 112 days.

(21) Appl. No.: 12/303,238

(22) PCT Filed: May 21, 2008

(86) PCT No.: PCT/IS2008/000012
§ 371 (c)(1),
(2), (4) Date: Dec. 4, 2008

(87) PCT Pub. No.: WO2008/146309
PCT Pub. Date: Dec. 4, 2008

(65) Prior Publication Data
US 2011/0015081 A1    Jan. 20, 2011

(30) Foreign Application Priority Data

May 25, 2007   (IS) ............................................. 8647
Dec. 21, 2007   (IS) ............................................. 8700

(51) Int. Cl.
*C12Q 1/68* (2006.01)
*C07H 21/02* (2006.01)
*C07H 21/04* (2006.01)

(52) U.S. Cl.
USPC ......... 435/6.11; 435/6.1; 435/6.14; 536/23.5; 536/24.31; 536/24.33

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. | |
| 5,223,409 A | 6/1993 | Ladner et al. | |
| 5,288,644 A | 2/1994 | Beavis et al. | |
| 5,445,934 A | 8/1995 | Fodor et al. | |
| 5,700,637 A | 12/1997 | Southern | |
| 5,744,305 A | 4/1998 | Fodor et al. | |
| 5,945,334 A | 8/1999 | Besemer et al. | |
| 6,054,270 A | 4/2000 | Southern | |
| 6,300,063 B1 | 10/2001 | Lipshutz et al. | |
| 6,429,027 B1 | 8/2002 | Chee et al. | |
| 6,733,977 B2 | 5/2004 | Besemer et al. | |
| 6,858,394 B1 | 2/2005 | Chee et al. | |
| 7,364,858 B2 | 4/2008 | Barany et al. | |
| 2005/0053958 A1 | 3/2005 | Roth et al. | |
| 2006/0234223 A1 | 10/2006 | Darvasi et al. | |
| 2006/0240454 A1* | 10/2006 | Gould et al. | ...................... 435/6 |
| 2007/0092900 A1 | 4/2007 | Stacey et al. | |
| 2011/0015081 A1* | 1/2011 | Stacey et al. | ...................... 506/7 |

FOREIGN PATENT DOCUMENTS

| | | |
|---|---|---|
| EP | 0619321 | 10/1994 |
| WO | WO-89/10977 | 11/1989 |
| WO | WO-90/02809 | 3/1990 |
| WO | WO-90/15070 | 12/1990 |
| WO | WO-91/17271 | 11/1991 |
| WO | WO-92/01047 | 1/1992 |
| WO | WO-92/09690 | 6/1992 |
| WO | WO-92/10092 | 6/1992 |
| WO | WO-92/15679 | 9/1992 |
| WO | WO-92/18619 | 10/1992 |
| WO | WO-92/20791 | 11/1992 |
| WO | WO-93/01288 | 1/1993 |
| WO | WO-2004/028346 | 4/2004 |

OTHER PUBLICATIONS

NCBI Database, National Center for Biotechnology Information, National Library of Medicine (Bethesda, MD, USA), rs10941679, ss20232203, Feb. 21, 2004.*
NCBI Database, National Center for Biotechnology Information, National Library of Medicine (Bethesda, MD, USA), rs4415084, ss5907142, Jan. 2, 2003.*
NCBI Database, National Center for Biotechnology Information, National Library of Medicine (Bethesda, MD, USA), rs1219648, ss2528991, Nov. 3, 2000.*
NCBI SNP Database for rs4415084, National Center for Biotechnology Information, National Library of Medicine (Bethesda, MD, USA), (ss24222259, including "Submitter Method ID AFD_CHIP_HYB," May 18, 2004.*
Hirschhorn et al. Genetics in Medicine. vol. 4, No. 2, pp. 45-61, Mar. 2002.*
Lucentini et al. The Scientist (2004) vol. 18, p. 20.*
Wacholder et al. J. Natl. Cancer Institute (2004) 96(6):434-442).*
Langdahl et al. Journal of Bone and Mineral Research (2000) 15: 402-414.*
Wall et al. Nature Reviews Genetics (2003) 4:587-597.*
Halushka et al. Nature. Jul. 1999. 22: 239-247.*
Natrajan et al. Cellular Oncology. Abstracts of the 1st MC-GARD Meeting. May 3, 2007. p. 104-105, abstract 03.*
Agami, RNAi and related mechanisms and their potential use for therapy. Curr. Opin. Chem. Biol. 6(6):829-34 (2002).
Altschul et al., A rapid classification protocol for the CATH Domain Database to support structural genomics. Nucl. Acids Res., 25(1):3389-402 (1997).
Altschul et al., Applications and statistics for multiple high-scoring sequements in molecular sequences. Proc. Natl. Acad. Sci. USA, 90:5873-7 (1993).
Amarzguioui et al. Approaches for chemically synthesized siRNA and vector-mediated RNAi. FEBS Lett. 579(26):5974-81 (2005).
Amundadottir et al., A common variant associated with prostate cancer in European and African populations. Nat. Genet. 38: 652-8 (2006).

(Continued)

Primary Examiner — Carla Myers
(74) Attorney, Agent, or Firm — Marshall, Gerstein & Borun LLP

(57) ABSTRACT

The invention pertains to certain genetic variants on Chr5p12 and Chr10q26 as susceptibility variants of breast cancer. Methods of disease management, including diagnosing increased and/or decreased susceptibility to breast cancer, methods of predicting response to therapy and methods of predicting prognosis using such variants are described. The invention further relates to kits useful in the methods of the invention.

22 Claims, 1 Drawing Sheet

(56) References Cited

OTHER PUBLICATIONS

Amundadottir et al., Cancer as a complex phenotype: Pattern of cancer distribution within and beyond the nuclear family. *PLoS Med*, 1:e65 (2004).
Anglian Breast Cancer Study Group, Prevalence and penetrance of BRCA1 and BRCA2 mutations in a population-based series of breast cancer cases. Anglian Breast Cancer Study Group. *Br. J. Cancer*, 83:1301-8 (2000).
Anon, American Society of Clinical Oncology Policy Statement Update: Genetic Testing for Cancer Susceptibility. *J. Clin. Oncol*, 21:2397-406 (2003).
Antoniou, et al., A comprehensive model for familial breast cancer incorporating BRCA1, BRCA2 and other genes. *Br. J Cancer*, 86:76-83 (2002).
Arason, et al., A population study of mutations and LOH at breast cancer gene loci in tumours from sister pairs: Two recurrent mutations seem to account for all BRCA1/BRCA2 linked breast cancer in Iceland. *J. Med. Genet.* 35:446-9 (1998).
Aston et al., Oligogenic combinations associate with breast cancer risk in women under 53 years of age. *Hum. Genet.* 116(3): 208-21 (2005).
Balmain et al., The genetics and genomics of cancer. *Nat. Genet.* 33(suppl.): 238-44 (2003).
Barrett et al., Evaluating coverage of genome-wide association studies. *Nat. Genet.* 38:659-62 (2006).
Bennett, Efficiency of antisense oligonucleotide drug delivery. *Antisense Nucl. Acid Drug Dev.* 12(3):215-24 (2002).
Bergthorsson et al., Identification of a novel splice-site mutation of the BRCA1 gene in two breast cancer families: screening reveals low frequency in Icelandic breast cancer patients. *Hum. Mutat.* Suppl 1 :S195-7 (1998).
Bernstein et al., Study design: evaluating gene-environment interactions in the etiology of breast cancer—the WECARE study. *Breast Cancer Res.* 6(3):R199-214 (2004).
Bier et al., DNA microarrays. *Adv. Biochem. Eng. Biotechnol.* 109:433-53 (2008).
Bosher et al., RNA interference: genetic wand and genetic watchdog. *Nat. Cell Biol.* 2(2):E31-6 (2000).
Breast Cancer Association Consortium, Commonly studied single-nucleotide polymorphisms and breast cancer: results from the Breast Cancer Association Consortium. *J. Natl. Cancer Inst.* 98:1382-96 (2006).
Broeks et al., Excess risk for contralateral breast cancer in CHEK2*1100delC germline mutation carriers. *Breast Cancer Res. Treat.* 83(1): 91-3 (2004).
Brummelkamp et al., A system for stable expression of short interfering RNAs in mammalian cells. *Science*, 296(5567): 550-3 (2002).
Burnet et al., Normal tissue radiosensitivity—how important is it? *Clin. Oncol. (R Coll. Radiol.)* 8(1): 25-34 (1996).
Carim et al., Cloning, expression, and mapping of PDCD9, the human homolog of Gallus gallus pro-apoptotic protein p52. *Cytogenet. Cell Genet.* 87(1-2): 85-8 (1999).
Carter, Methods and strategies for analyzing copy numner variation using DNA microarrays. *Nat. Genet.* 39:S16-21 (2007).
Cass et al., Improved survival in women with BRCA-Associated ovarian carcinoma. *Cancer*, 97:2187-95 (2003).
Cavdar Koc et al., A new face on apoptosis: death-associated protein 3 and PDCD9 are mitochondrial ribosomal proteins. *FEBS Lett*, 492:166-70 (2001).
Chappuis, et al., A significant response to neoadjuvant chemotherapy in BRCA1/2 related breast cancer. *J. Med. Genet.* 39:608-10 (2002).
CHEK2 Breast Cancer Case-Control Consortium, CHEK2*1100delC and susceptibility to breast cancer: a collaborative analysis involving 10,860 breast cancer cases and 9,065 controls from 10 studies. *Am. J. Hum. Genet.* 74:1175-82 (2004).
Chen et al., Fluorescence polarization in homogeneous nucleic acid analysis. *Genome Res.* 9(5):492-8 (1999).
Chen et al., The evolution of gene regulation by transcription factors and microRNAs. *Nat. Rev. Genet.* 8(2): 93-103 (2007).
Chen, Clinical development of antisense oligonucleotides as anti-cancer therapeutics. *Methods Mol. Med.* 75:621-636 (2003).
Chi et al., Genomewide view of gene silencing by small interfering RNAs. *Proc. Natl. Acad. Sci. USA*, 100(11):6343-6 (2003).
Church et al., Genome sequencing. *Proc. Natl. Acad. Sci. USA*, 81(7):1991-5 (1988).
Collaborative Group on Hormonal Factors in Breast Cancer, Familial breast cancer: collaborative reanalysis of individual data from 52 epidemiological studies including 58,209 women with breast cancer and 101,986 women without the disease. *Lancet*, 358:1389-99 (2001).
Cotton et al., Reactivity of cytosine and thymine in single-base-pair mismatches with hydroxylamine and osmium tetroxide and its application to the study of mutations. *Proc. Natl. Acad. Sci. USA*, 85(12):4397-401 (1985).
Cox et al., A common coding variant in CASP8 is associated with breast cancer risk. *Nat. Genet.* 39:352-8 (2007).
Cuzick et al., Overview of the main outcomes in breast-cancer prevention trials. Lancet, 361: 296-300 (2003).
Daly et al., High-resolution haplotype structure in the human genome. *Nature Genet.* 29(2):229-32 (2001).
Dawson et al., A first-generation linkage disequilibrium map of human chromosome 22. *Nature*, 418(6897):544-8 (2002).
de Bock, et al., Tumour characteristics and prognosis of breast cancer patients carrying the germline CHEK2*1100delC variant. *J. Med. Genet.* 41:731-5 (2004).
Devlin et al., A comparison of linkage disequilibrium measures for fine-scale mapping. *Genomics*, 29:311-22 (1995).
Devlin et al., Genomic control for association studies. *Biometrics*, 55:997-1004 (1999).
Dias et al., Antisense oligonucleotides: Basic concepts and mechanisms. *Mol. Cancer Ther.* 1(5):347-55 (2002).
Dumitrescu et al., Understanding breast cancer risk—where do we stand in 2005? *J. Cell Mol. Med.* 9(1):208-21 (2005).
Easton, How many more breast cancer predisposition genes are there? *Breast Cancer Res.* 1:14-7 (1999).
Eerola, et al., Survival of breast cancer patients in BRCA1, BRCA2, and non-BRCA1/2 breast cancer families: a relative survival analysis from Finland. *Int. J. Cancer*, 93: 368-72 (2001).
Eifel et al., National Institutes of Health Consensus Development Conference Statement: adjuvant therapy for breast cancer, Nov. 1-3, 2000. *J. Natl. Cancer Inst.* 93:979-89 (2001).
Estivill et al., Copy number variants and common disorders: filling the gaps and exploring complexity in genome-wide association studies. *PLoS Genet.* 3:1787-99 (2007).
Falk et al., Haplotype relative risks: an easy reliable way to construct a proper control sample for risk calculations. *Ann. Hum. Genet.* 51(Pt 3):227-33 (1987).
Fan et al., Illumina universal bead arrays. *Methods Enzymol.* 410:57-73 (2006).
Farmer et al., Targeting the DNA repair defect in BRCA mutant caells as a therapeutic strategy. *Nature*, 434:917-21 (2005).
Fire et al., Potent specific genetic interference by double-stranded RNA in *Caenorhabditis elegans*. *Nature*, 391(6669):806-11 (1998).
Flavell et al., Analysis of the beta-delta-globin gene loci in normal and Hb Lepore DNA: direct determination of gene linkage and intergene distance. *Cell*, 15(1):25-41 (1978).
Frayling, Genome-wide association studies provide new insights into type 2 diabetes aetiology. *Nat. Rev. Genet.* 8:657-62 (2007).
Fuchs et al., Targeting recombinant antibodies to the surgace of *Escherichia coli*: Fusion to a peptidoglycan associated lipoprotein. *Bio/Technology*, 9: 1370-2 (1991).
Gabriel et al., The structure of haplotype blocks in the human genome. *Science*, 296(5576):2225-9 (2002).
Galfre et al., Antibodies to major histocompatibility antigens produced by hybrid cell lines. *Nature*, 266(5602):550-2 (1977).
Geever et al., Direct identification of sickle cell anemia by blot hybridization. *Proc. Natl. Acad. Sci. USA*, 78(8):5081-5 (1981).
Gibbs et al., Detection of single DNA base differences by competitive oligonucleotide priming. *Nucl. Acids Res.* 17:2437-48 (1989).
Goffin et al., Impact of germline BRCA1 mutations and overexpression of p53 on prognocic and response to treatment following breast carcinoma. *Cancer*, 97:527-36 (2003).

(56) References Cited

OTHER PUBLICATIONS

Goldhirsch et al., Meeting highlights: International Consensus Panel on the Treatment of Primary Breast Cancer. *J. Natl. Cancer Inst.* 90(21):1601-8 (1998).
Gorski et al., Breast cancer predisposing alleles in Poland. *Breast Cancer Res. Treat.* 92:19-24 (2005).
Grant et al. Variant of transcription factor 7-like 2 (TCF7L2) gene confers risk of type 2 diabetes. *Nat. Genet.* 38:320-3 (2006).
Gretarsdottir et al., The gene encoding phosphodiesterase 4D confers risk of ischemic stroke. *Nat. Genet.* 35:131-8 (2003).
Griffiths et al., Human anti-self antibodies with high specificity from phage display libraries. *EMBO J.* 12(2):725-34 (1993).
Gudmundsson et al., Common sequence variants on 2p15 and Xp11.22 confer susceptibility to prostate cancer. *Nat. Genet.* 40:281-3 (2008).
Gudmundsson et al., Frequent occurrence of BRCA2 linkage in Icelandic breast cancer families and segregation of a common BRCA2 haplotype. *Am. J. Hum. Genet.* 58:749-56 (1996).
Gudmundsson et al., Genome-wide association study identifies a second prostate cancer susceptibility variant at 8q24. *Nat. Genet.* 39:631-7 (2007).
Gudmundsson et al., Two variants on chromosome 17 confer prostate cancer risk, and the one in TCF2 protects against type 2 diabetes. *Nat. Genet.* 39:977-83 (2007).
Haiman et al., Multiple regions within 8q24 independently affect risk for prostate cancer. *Nat. Genet.* 39(5):638-44 (2007).
Hay et al., Bacteriophage cloning and *Escherichia coli* expression of a human IgM Fab. *Hum. Antibodies Hybridomas* 3(2):81-5 (1992).
Helgadottir et al., A common variant on chromosome 9p21 affects the risk of myocardial infarction. *Science*, 316:1491-93 (2007).
Hill et al., Linkage disequilibrium in finite populations. *Theor. Appl. Genet.* 38:226-231 (1968).
Hoeller et al., Increasing the rate of late toxicity by changing the score? A comparison of RTOG/EORTC and LENT/SOMA scores. *Int. J. Radiat. Oncol. Biol. Phys.* 55:1013-8 (2003).
Hoheisel, Microarray technology: Beyonf transcript profiling and genotype analysis. *Nat. Rev. Genet.* 7:200-10 (2006).
Howard et al., Signalling pathways implicated in early mammary gland morphogenesis and breast cancer. *PLoS Genet.* 2(8):e112 (2006).
Huijts, et al., Clinical correlates of low-risk variants in FGFR2, TNRC9, MAP3K1, LSP1 and 8q24 in a Dutch cohort of incident breast cancer cases. *Breast Cancer Res.* 9(6):R78 (2007).
Hunter, Genetics: A touch of elegance with RNAi. *Curr. Biol.* 9:R440-2 (1999).
Huse et al., Generation of a large combinatorial library of the immunoglobulin repertoire in phase lambda. *Science* 246(4935):1275-81 (1989).
Jeffreys et al., Intensely punctate meiotic recombination in the class II region of the major histocompatibility complex. *Nat. Genet.* 29(2):217-22 (2001).
Jemal et al., Cancer statistics, 2006. *CA Cancer J. Clin.* 56: 106-30 (2006).
Kim et al., Strategies for silencing human disease using RNA interference. *Nature Rev. Genet.* 8(3):173-204 (2007).
Kim et al., Synthetic dsRNA Dicer substrates enhance RNAi potency and efficacy. *Nat. Biotechnol.* 23(2):222-6 (2005).
Kohler et al., Continuous cultures of fused cells secreting antibody of predefined specificity. *Nature*, 256:495-7 (1975).
Kozbor et al., The production of monoclonal antibodies from human lymphocytes. *Immunol. Today* 4(3): 72-9 (1983).
Kurreck, Antisense technologies. *Eur. J. Biochem.* 270:1628-44 (2003).
Kutyavin et al., A novel endonuclease IV post-PCR genotyping system. *Nucl. Acids Res.* 34: e128 (2006).
Lavery et al., Antisense and RNAi: powerful tools in drug target discovery and validation. *Curr. Opin. Drug Discov. Devel.* 6(4):561-9 (2003).

Leach et al., Screening with magnetic resonance imaging and mammography of a UK population at high familial risk of breast cancer: a prospective multicentre cohort study (MARIBS). *Lancet*, 365(9473):1769-78 (2005).
Lerner, How to make a hybridoma. *Yale J. Biol. Med.* 54(5):387-402 (1981).
Lewontin, The Interaction of Selection and Linkage. I. General Considerations; Heterotic Models. *Genetics*, 49:49-67 (1964).
Lichtenstein et al., Environmental and heritable factors in the causation of cancer. *N. Engl. J. Med.* 343:78-85 (2000).
Maniatis et al., The first linkage disequilibrium (LD) maps: Delineation of hot and cold blocks by diplotype analysis. *Proc. Natl. Acad. Sci. USA*, 99:2228-33 (2002).
Mantel et al., Statistical aspects of the analysis of data from retrospective studies of disease. *J. Natl. Cancer Inst.* 22:719-48 (1959).
Marques et al., A structural basis for discriminating between self and nonself double-stranded RNAs in mammalian cells. *Nat. Biotechnol.* 24(5):559-65 (2006).
Martino et al., The role of selective estrogen receptor modulators in the prevention of breast cancer: comparison of the clinical trials. *Oncologist*, 9:116-25 (2004).
Mathieu et al., The poor responsiveness of infiltrating lobular breast carcinomas to neoadjuvant chemotherapy can be explained by their biological profile. *Eur. J. Cancer*, 40:342-51 (2004).
May et al., Crossover clustering and rapid decay of linkage disequilibrium in the Xp/Yp pseudoautosomal gene SHOX. *Nat. Genet.* 31(3):272-5 (2002).
McManus et al., Gene silencing in mammals by small interfering RNAs. *Nat. Rev. Genet.* 3:737-47 (2002).
McVean et al., The fine-scale structure of recombination rate variation in the human genome. *Science*, 304:581-4 (2004).
Metcalfe et al., Contralateral breast cancer un BRCA1 and BRCA2 mutation carrier. *J. Clin. Oncol.* 22:2328-35 (2004).
Mockler et al., Applications of DNA tiling arrays for whole-genome analysis. *Genomics*, 85:1-15 (2005).
Moller, et al., Survival in prospectively ascertained familial breast cancer: analysis of a series stratified by tumour characteristics, BRCA mutations and oophorectomy. *Int. J. Cancer*, 101 :555-9 (2002).
Myers et al., A fine-scale map of recombination rates and hotspots across the human genome. *Science*, 310(5746):321-4 (2005).
Myers et al., Detection of single base substitutions by ribonuclease cleavage at mismatches in RNA:DNA duplexes. *Science*, 230(4731):1242-6 (1985).
Myers et al., The distribution and causes of meiotic recombination in the human genome. *Biochem. Soc. Trans.* 34(Pt 4):526-30 (2006).
Narod et al., BRCA1 and BRCA2: 1994 and beyond. *Nat. Rev. Cancer*, 4(9):665-76 (2004).
Nicolae et al., Measuring the relative information in allele-sharing linkage studies. *Biometrics*, 60(2):368-75 (2004).
Nielsen et al., Peptide nucleic acid (PNA). A DNA mimic with a peptide backbone. *Bioconjug. Chem.* 5:3-7 (1994).
Nielsen et al., Sequence-selective recognition of DNA by strand displacement with a thymine-substituted polyamide. *Science*, 254:1497-1500 (1991).
Orita et al., Detection of polymorphisms of human DNA by gel electrophoresis as single-strand conformation polymorphisms. *Proc. Natl. Acad. Sci. USA*, 86(8):2766-70 (1989).
Parkin et al., Global cancer statistics, 2002. *CA Cancer.J. Clin.* 55(2):74-108 (2005).
Patil et al., Blocks of limited haplotype diversity revealed by high-resolution scanning of human chromosome 21. *Science*, 294(5547):1719-23 (2001).
Pearson et al., Improved tools for biological sequence comparison. *Proc. Natl. Acad. Sci. USA*, 85:2444-8 (1988).
Peto et al., High constant incidence in twins and other relatives of women with breast cancer. *Nat. Genet.* 26:411-4 (2000).
Pharoah et al., Polygenic susceptibility to breast cancer and implications for prevention. *Nat Genet*, 31:33-6 (2002).
Pharoah, Genetic susceptibility, predicting risk and preventing cancer. *Recent Results Cancer Res.* 163: 7-18; discussion 264-6 (2003).

(56) References Cited

OTHER PUBLICATIONS

Phillips et al., Chromosome-wide distribution of haplotype blocks and the role of recombination hot spots. *Nat. Genet.* 33(3):382-7 (2003).
Plasterk et al., The silence of the genes. *Curr. Opin. Genet. Dev.* 10(5):562-7 (2000).
Ragoussis et al., Affymetrix GeneChip system: moving from research to the clinic. *Expert Rev. Mal. Diagn.* 6(2):145-52 (2006).
Redon et al., Global variation in copy number in the human genome. *Nature*, 444(7118):444-54 (2006).
Reich et al., Linkage disequilibrium in the human genome. *Lett. Nature*, 411:199-204 (2001).
Renwick et al., ATM mutations that cause ataxia-telangiectasia are breast cancer susceptibility alleles. *Nat. Genet.* 38:873-5 (2006).
Reynolds, et al., Rational siRNA design for RNA interference. *Nat. Biotechnol.* 22:326-30 (2004).
Risch et al., The future of genetic studies of complex human diseases. *Science*, 273:1516-7 (1996).
Risch et al., The relative power of family-based and case-control designs for linkage disequilibrium studies of complex human diseases I. DNA pooling. *Genome Res.*, 8(12):1273-88 (1998).
Saiki et al., Analysis of enzymatically amplified beta-globin and HLA-DQ alpha DNA with allele-specific oligonucleotide probes. *Nature*, 324:163-6 (1986).
Sanger et al., DNA sequencing with chain-terminating inhibitors. *Proc. Natl. Acad. Sci. USA*, 74(12):5463-7 (1977).
Sheffield et al., Attachment of a 40-base-pair G + C-rich sequence (GC-clamp) to genomic DNA fragments by the polymerase chain reaction results in improved detection of single-base changes. *Proc. Natl. Acad. Sci. USA*, 86(1):232-6 (1989).
Shi, Mammalian RNAi for the masses. *Trends Genet.* 19:9-12 (2003).
Shuey et al., RNAi: gene-silencing in therapeutic intervention. *Drug Discov. Today*, 7(20):1040-6 (2002).
Sinilnikova et al., Acetyl-CoA carboxylase alpha gene and breast cancer susceptibility. *Carcinogenesis*, 25(12): 2417-24 (2004).
Sinilnikova et al., Haplotype-based analysis of common variation in the acetyl-CoA carboxyiase alpha gene and breast cancer risk: A case-control study nested within the European prospective investigation into cancer and nutrition. *Cancer Epidemiol. Biomark. Prev.* 16(3): 409-15 (2007).
Siolas et al., Synthetic shRNAs as potent RNAi triggers. *Nat. Biotechnol.* 23(2):227-31 (2005).
Skol et al., Joint analysis is more efficient than replication-based analysis for two-stage genome-wide association studies. *Nat. Genet.* 38(2): 209-13 (2006).
Smith et al., A genome wide linkage search for breast cancer susceptibility genes. *Genes Chromosomes Cancer*, 45:646-55 (2006).
Smith et al., A high-density admixture map for disease gene discovery in African Americans. *Am. J. Hum. Genet.* 74:1001-13 (2004).
Stacey et al., Common variants on chromosomes 2q35 and 16q12 confer susceptibility to estrogen receptor-positive breast cancer. *Nat. Genet.* 39(7): 865-9 (2007).
Stacey et al., The BARD1 Cys557Ser variant and breast cancer risk in Iceland. *PLoS Med.* 3(7): e217 (2006).
Steinthorsdottir et al., A variant in CDKAL1 influences insulin response and risk of type 2 diabetes. *Nat. Genet.* 39:770-5 (2007).
Stephens et al., Antisense oligonucleotide therapy and cancer. *Curr. Opin. Mol. Ther.* 5(2):118-22 (2003).
Stumpf et al., A Y chromosome census of the British Isles *Curr. Biol.* 13:1-8 (2003).
Styrkarsdottir et al., Multiple genetic loci for bone mineral density and fracture. *N. Engl. J. Med.* 358(22): 2355-65 (2008).
Sun et al., A novel 52 kDa protein induces apoptosis and concurrently activates c-Jun N-terminal kinase 1 (JNK1) in mouse C3H10T1/2 fibroblasts. *Gene*, 208(2):157-66 (1998).
Terwilliger et al., A haplotype-based 'haplotype relative risk' approach to detecting allelic associates. *Hum. Hered.* 42:337-46 (1992).
Theodorou et al., Fgf10 is an oncogene activated by MMTV insertional mutagenesis in mouse mammary tumors and overexpressed in a subset of human breast carcinomas. *Oncogene*, 23(36):6047-55 (2004).
Thompson, Applications of antisense and siRNAs during preclinical drug development. *Drug Discovery Today*, 7(17):912-7 (2002).
Thorgeirsson et al., A variant associated with nicotine dependence, lung cancer and peripheral arterial disease. *Nature*, 452:638-42 (2008).
Thorlacius et al., Study of a single BRCA2 mutation with high carrier frequency in a small population. *Am. J. Hum. Genet.* 60:1079-84 (1997).
Torellis et al., ADVANCE and ADAM: two algorithms for the analysis of global similarity between homologous informational sequences. *Comput. Appl. Biosci.* 10(1):3-5 (1994).
Tulinius et al., The effect of a single BRCA2 mutation on cancer in Iceland. *J. Med. Genet.* 39:457-62 (2002).
Vickers et al., Efficient reduction of target RNAs by small interfering RNA and RNase H-dependent antisense agents. *J. Biol. Chem.* 278:7108-18 (2003).
Wall et al., Haplotype blocks and linkage disequilibrium in the human genome. *Nat. Rev. Genet.* 4(8):587-97 (2003).
Wang et al., Antisense anticancer oligonucleotide therapeutics. *Curr. Cancer Drug Targets* 1(3):177-96 (2001).
Wang et al., Distribution of recombination crossovers and the origin of haplotype blocks: the interplay of population history, recombination, and mutation. *Am. J. Hum. Genet.* 71(5):1227-34 (2002).
Warner et al., Surveillance of BRCA1 and BRCA2 mutation carriers with magnetic resonance imaging, ultrasound, mammography, and clinical breast examination. *JAMA*, 292(11):1317-25 (2004).
Xia et al., siRNA-mediated gene silencing in vitro and in vivo. *Nat. Biotechnol.* 20(10):1006-10 (2002).
Yeager et al, Genome-wide association study of prostate cancer identifies a second risk locus at 8q24. *Nat. Genet.* 39:645-9 (2007).
Zhang et al., A dynamic programming algorithm for haplotype block partitioning. *Proc. Natl. Acad. Sci. USA*, 99:7335-9 (2002).
Stacey et al., Common variants on chromosome 5p12 confer susceptibility to estrogen receptor-positive breast cancer. *Nat. Genet.* 40(6): 703-6 (2008).
International Search Report and Written Opinion of the International Searching Authority, PCT/IS2008/000012, dated Aug. 2008.
International Preliminary Report on Patent Ability, PCT/IS2008/000012, dated Dec. 1, 2009.

\* cited by examiner

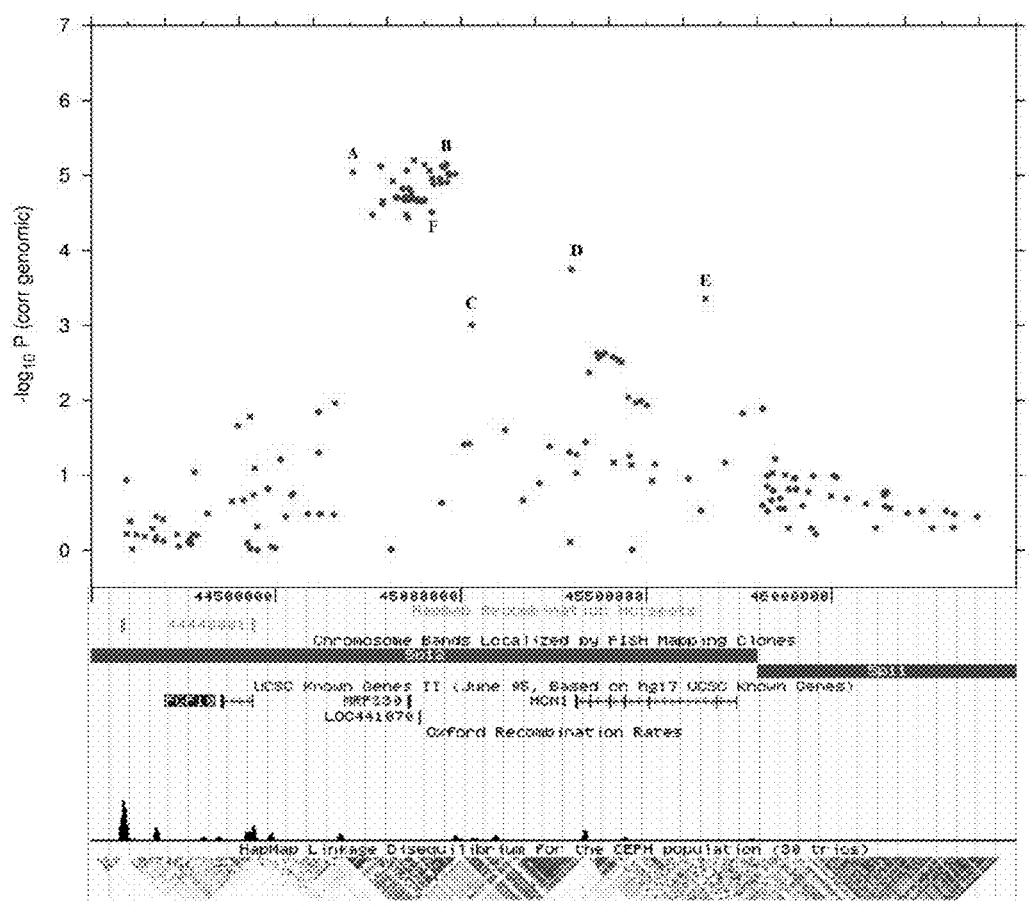

SEQUENCE LISTING

```
<160> NUMBER OF SEQ ID NOS: 237

<210> SEQ ID NO 1
<211> LENGTH: 599
<212> TYPE: DNA
<213> ORGANISM: Homo sapiens

<400> SEQUENCE: 1
tttgtagcct aggaggaata ggctaaacca tatagcctag gtatatagca ggtgattcca      60
tctaggtttt tgtaaatatt ctctgtgatg tttacataat gacaaaaatc acctagtgat     120
gtatttctca gaacaaagtc ttatcaagca gcatgactat atagttgatc cttgaacaac     180
actggagtta ggggtgtata catctcacat aggcaaaaat ccaagcataa cttttttaaa     240
tccccaaaac ttaactacta atagcctact attgaaggga ggccttacta atagcataar     300
tagttgacta aaacatatt tttattttat atgcattata ttacaataaa gtaagataga      360
gaaaagcaaa tgtttttaag acaattataa ggaagagaaa atatatttat tattcattaa     420
gtgaaagtag atcatcataa aggtcttcat cctcatcaac ttcatgttgt ttaggctgat     480
gaggaagagg aggagttagt cttgtttttct caggggtagt agaggcagaa taaaatctgt    540
gtataagtgg acccacatgg ttcaaacttg tgttgttcaa gggtcaattg tatatgtag     599

<210> SEQ ID NO 2
<211> LENGTH: 599
<212> TYPE: DNA
<213> ORGANISM: Homo sapiens

<400> SEQUENCE: 2
agctgggcca gagaggatgg ggttagaatg ggcttgactc tggcttgaag ctgatggccc      60
aggcaccatg tttccaggcc tcataatggc tacctgtcca gacaccagaa tccagaggca     120
caaatcaaag atgtaagcta acagacaaat caatcaagta tcaaaatat cagagaagca      180 acaattttat gactttaaca tatctaacag agaaagcata atcctgtttc aacaaaccca     240
ggcaaaaatg tctaaattaa cttttgaaga aatttttatt ttattttacc aacagttttm     300
aaaccagctt tatttaccaa agaccactaa agttacatga acttgaaagc attttagcta     360
gccatttagt ttatgggcac tcatttattt ataagtcagt ttagtacctg tagacaatgt     420
agacatacat gcatagacac atacatactt agacataaca tacagcacac acatacacac     480
acacacacac acacacacac ttgtccaaag attattattt aatgttagac ctgagagaaa     540
```

```
cctgcccatg actcttgggg tctctgtgag aaagacagga agtcccaaaa gatggggtc      599
```

<210> SEQ ID NO 3
<211> LENGTH: 599
<212> TYPE: DNA
<213> ORGANISM: Homo sapiens

<400> SEQUENCE: 3

```
ttttattgta aacatattta cactagatca cctagtatct tattttttaaa tgtgctgaat     60
tttgcatatt catcttttta tgtgcttcat taaatctttta aattgtagac atatatctta   120
taggagttct tgtgaataat tagaaacaat gcagaaatct tgcttccttt gttctaattc   180
tcatatcttc ttttctgaat gactacttta atctcccaga tattctttga gcctgcagtc   240
tcataatact ctgtgttcca tgttcccaac agagttgtat ttctaaaata ataatatgaw   300
caagtcactt tcaggtgtaa attttaaaag aatctttcca ataccatgc aataaagtta    360
aaaatatttg actttgttaa caaaaaaaaa agatattata tattctatct aacgttccag   420
cctcatgttc tacctcttcc ttttcaataa agttttctaa tggcagttga aaatatttca   480
aagtgaaaca gtatagattt gagaacagta ggtgaatatc ttcttaaatc atatcattaa   540
ttaaatgatc tatatcagac tagaggaaaa tttctagtaa tatgctgcaa gacttcact   599
```

<210> SEQ ID NO 4
<211> LENGTH: 599
<212> TYPE: DNA
<213> ORGANISM: Homo sapiens

<400> SEQUENCE: 4

```
catcggcctt gataactttc atactaaaga acttaaattg accacagtct ttgctgagtc     60
acacacaatt atcttcaaga actcacagag gacttaaatg acataaacta gaatatatta   120
tgtctgttct ttcagaagaa gattatgggc catccaggac attactgact taccaaagtg   180
gagaaatagg tgaactcaaa tgttggcttt tcaatgccta gaaaataatg gggttggaat   240
tggctggact tgtatgaatg aaatcataaa atttggggct ggaagtgatc ttagggatcr   300
tgcaatatgt tgccttaatt tatacagaag taaactgagc ctttgaaaag tcaaatctta   360
aatccttagg agttttttc ctaactgaag tacagtgtgg ctagtctgaa cagctgaggt   420
gatgaataaa ggcaattttt aatggctttc tttttgcctc ctctaaatga ttttcttctt   480
ttgggcagat gttccctatt cctggaacat ttgtatccat gaggaaagga ggctatccct   540
actatccatg tcatagctag gaattgtagc atcacactaa tatgagaaag aacctcta     599
```

<210> SEQ ID NO 5
<211> LENGTH: 599
<212> TYPE: DNA
<213> ORGANISM: Homo sapiens

<400> SEQUENCE: 5

```
ataaggaatt tctgccagat ttgaaacagt ccttgttgaa tgacagggat ttcaaatgat     60
taagagaatg gcactgaatt cccacctttg acttctactt gttttagttg aacttctatc   120
aagctttgga acccacttct cccaaatttt tctgaggttc ttgttgaaaa ttattgacag   180
ggccatgcct cagggagaaa aatacccaca aaaaaaacaa caaatcacag ataaggtctg   240
tagtttcaat aatctgttgc taccctgaag atagcactaa agtgattaac caagtctty    300
ctctatgggc agcacttctt caccttttg tctctccaaa ttttcttcct tcatcaaaac    360
tctattgttc tgaattttat ctctttagga ccctactatg gtttgaatat ttgtcacctt   420
```

```
cacaactcat gttgaaattt aatccccaat gtggcagtgt taaaatgtgg ggcctttaag    480
aggtgattgg tcatgtgggt tctgccttca tgagtggatt aaaggtttaa ttagttaatt    540
aataggttat catgggagtg ggactgctgg gtttacaaga agacaaagac atacctcag     599
```

<210> SEQ ID NO 6
<211> LENGTH: 599
<212> TYPE: DNA
<213> ORGANISM: Homo sapiens

<400> SEQUENCE: 6

```
ttaaccaagt cttttctcta tgggcagcac ttcttcacct ttttgtctct ccaaattttc     60
ttccttcatc aaaactctat tgttctgaat tttatctctt taggacccta ctatggtttg    120
aatatttgtc accttcacaa ctcatgttga aatttaatcc ccaatgtggc agtgttaaaa    180 tgtgggcct ttaagaggtg attggtcatg tgggttctgc cttcatgagt ggattaaagg     240
tttaattagt taattaatag gttatcatgg gagtgggact gctgggttta caagaagacr    300
aagacatacc tcagcttaca cactcagctc cttcaccctg tgatgctctg caccatctta    360
ggactttgca gagagtcctc accagcaaga aggccctcac caggtgcagc tccttgacct    420
aagatttttc agcttccata actataagaa gtaacttcct tttctttata aattacctag    480
ttttcaggta ttttattata agcaacagaa aacagactaa gacagacctt tcttagcaat    540
gttatataat aaatgaattc tggctaagta agttaattca tatttatact atattgtat     599
```

<210> SEQ ID NO 7
<211> LENGTH: 599
<212> TYPE: DNA
<213> ORGANISM: Homo sapiens

<400> SEQUENCE: 7

```
gtcttaaaaa ggcatgaata tcttctttta ggaaatacaa aagtaattgt ttaactctat     60
gtcagttgat ttcaacaggt atattcctgg aaattattaa ttttcctaat gctttctgaa    120
taatcctttg tttagtgata tagaatatta aaaagtggct taaataattt cttccctcaa    180
agaacatacc atataattgg ggaaagagag taaactctca ataactaca agcaattcaa      240 cattaggata cctgcatttt gaataataca aaatgcttaa gagtgtatag gattgtttcy    300
atatgagctt cccaaggagg tatttgtgga agaaggaaca tttgaaccag accatggctc    360
aagttagtaa tagaaaattg aagactaagg agggaattca aggcagaaat agcaaatgga    420
cacagacata gagatggcta atgatggcat atgtccaggg agtgtcctgt aatccagttg    480
agctgaagtg tgtgctttag gtagggaaac agtggtgaat cagactagac tacttgtctt    540
ggattaacat tgatcacagt cttaaatatt aaactcttca tacttaaaaa aaacaaaaa     599
```

<210> SEQ ID NO 8
<211> LENGTH: 599
<212> TYPE: DNA
<213> ORGANISM: Homo sapiens

<400> SEQUENCE: 8

```
tggtcagtgt gtgggcagaa ggctaaagat gaccccccaa gattcctgtc ctctggttat     60
ttaatcaaat gctaatctag acactgctgg gaaggttttt tgcagataac ttaagggtac    120
taattagttg acttttaggg gaatgctctt ggattatctg gttaggttca atgtctcatt    180
gagtctttaa aagcaggaga ggaagtcaga gagatttcaa acatgagaaa gattaaatgc    240
actgttgcag gctctgacat ggaggaaccc ccgtgaaata attggagaga agcctctags    300
```

```
agctgagggt tgcccccagc tgaaagccag caaagaaata agacctcagc cttacaattc     360
caagaaactg gattctgcca acaacctgat tgagcttgga agagggtcct tcttggggac     420
tctcaataag agaccagtga gctgataatt tgattatgtc cttgtggttt ctagagcagt     480
aaaactagtg gagtcaatct atatatctga cctacagaac catgggataa tggatgtttg     540
ttgttgttgt tgttgttgtt gttgttttat ttttttaat agttttgggt tcacagcaa      599
```

<210> SEQ ID NO 9
<211> LENGTH: 599
<212> TYPE: DNA
<213> ORGANISM: Homo sapiens

<400> SEQUENCE: 9

```
tcctaacaca ttacttagga aagtcattac ttagctaaaa ttatctgctt aaaggcatgg      60
agttgaggga gattttcaga agctacatta taaagcgatc aacatcaact agtcttttaa     120
tgttaataat agattctgtt ttcctctgtt tttcctcaaa gaaacttaac agctattacg     180
ggaagtatct tattaaaatg tccctataac agtcataaag gaagaggatt atttatttta     240
aagctagaga aactcagata ttaggaagta tatcttatat aaaatatata ttaaataacr     300
ttttttgctc acctgtagga gagaaactct ttgtccaata gtagattta gcctgattct      360 ccatgagatg acctaatgaa acctgatcaa agattctcat ttgaccagtc accctgccct     420
tcctctacaa ctctctgttt atttccaatt taaactggtg tcaagctctc ctcagctgat     480
gacccagata tttctgcact taatcatctt gcctgaaatg agtaaggatg aagtttctat     540
tttgtccttc ttagcctatt tccttgatcc gccatggacc ctggttgtaa tgatcatgc     599
```

<210> SEQ ID NO 10
<211> LENGTH: 599
<212> TYPE: DNA
<213> ORGANISM: Homo sapiens

<400> SEQUENCE: 10

```
cagccatgca tcctcagaga tcatgcacat atttattgtg actgaaactc aggtaagata      60
gaattggcgt ggagcaggaa gaagtaggaa aggtgggaag aaaaaacttt gaagcatttt     120
aaaatagaaa tgaggttgat ttatagtgca gatagaaaac taaggcaaca atgaactata     180
gaacaggaca caggaagggg tcagtttcgg agatgccata gagcatttac tgtggataat     240
gttctctaaa gtagtgacac tgaatgatgt caaggatagt cacacatcag gcaggcgttm     300
acactttgca gggttttatt ttattttttct tttattata ctttaagttt tagggtacat     360
gtgcacaacg tgcaggtttg ttacatatgt atacatgtgc catgttggtg tgctgcaccc     420
attaactcat catttaacgt taggtatatc tcctaatgct atccatcccc ctccccca     480 ccccacaaca ggccccggtg ggtgtgtgat gttacccttc ctgtgtccat gtgttctcat     540
tgttcaattc ccacctatga gtgagaacat gcagtgtttg gttttttgtc cttgcgata     599
```

<210> SEQ ID NO 11
<211> LENGTH: 599
<212> TYPE: DNA
<213> ORGANISM: Homo sapiens

<400> SEQUENCE: 11

```
tggctaagag acaaaaaata atggaagatt taacactaag ccctggttta tctgatctaa      60
tttaaaatgc cccttctca tccacatacc acacttactc agatccaaca gacacaacgg      120
cttacataga ttcccccttc tctcccccctc atccatccct gcacacatat ctgagaaaca     180
```

```
ccttagcatt ggtttcagga tttcctaatg ggctgtggag cagctgtaaa taacacagtg    240
ctattcgagc caattgctct gaaccgggtg atatgatcat attcttttta acgactttcy    300
ctgaggtatg agttgagatt tttctccttc atcctcatgc tgtataatct ggatttatgt    360
tcaacgtgac cgttgagcct tcacaatgaa tttgtcctgt gaaaagatca gttgatacgg    420
agcctggatc ccagattctc accacagagt gggcgctcat tatttgcacg tcagcatcta    480
agtcatcaat ctctagcagc cacactcacc cagatgaagc tccaaaccca ggtcttgtgg    540
atcacatata acccatttct ttttttaatg agtcaataag cctcaattcc tggacatct     599

<210> SEQ ID NO 12
<211> LENGTH: 599
<212> TYPE: DNA
<213> ORGANISM: Homo sapiens

<400> SEQUENCE: 12
ttctctgaga aattcattga aaaggaacct ttcttttcca atatttatga gatttatctc     60
tagtaagaga caacatttaa cataaaatta tattaaggtg ttagattaac tccaaaggct    120
aaatataata tcaagccatt catgcatatc ttacatgaag actttaataa tttcagatca    180
cctttggtat acaaattatc tcctcttact tacaatcact ggcacatcat tccttttcca    240
gaatgtcatg tgaaatttag tcataaaata tgctgatttt tgtctattcc caaattcatr    300
cagaatgtgc cttcactggg ttaaaaagct tcaccaaggc tatctacttg cacactggat    360
acctaagaaa accctcctga tccactctta cttgaagatc tattagttct actatttagg    420
ctctgcttcc agttgggaga catgccacct gatatggttt ggatatttct ccactccaaa    480
tctcatgtta taatgtaatc cccagtgttg catgcaggtg gggcctggta ggaggtgttt    540
tggtcatggg ggcaaatccc tcatgaatga cttagcacca tccccggggt gatgagtga     599

<210> SEQ ID NO 13
<211> LENGTH: 599
<212> TYPE: DNA
<213> ORGANISM: Homo sapiens

<400> SEQUENCE: 13
tttatcaatt gagcaactct caaaatgcat ggcattcaaa aaaatttttat acagtttatg     60 gctaaaatct ttcacatatt ttaattcaat ctcttccatt tttttttcagt gaggaaccac    120 agacatgaag aatgtagatg acacattcca agtcacagag taaattaatg acaggactag    180
aactgcaaaa catttaacg tcctacaaaa ctaaatttt gcgctctaca tacataagta    240
ggggagggtt ttaaagccat agtgctaata aaaaaaagtt gagaaacaga ttgatatgcr    300 taacctatt tacataaact aaatttcagg catcaaagga atgttcacat taaataagtt    360
agggcatttt cttttagagt ggagggaaag gaataaaagt ggaacatagg ggaaaagtat    420
aataattaat taaaagcaca gtagagactt tgcatggatg aaatacaata atgtgccatg    480
aactgaaatg tgattctctt aacgatttct tccttgggtg gccttttatt gccaagacta    540
gaactagcta gctttctgtc acttgtaacc aaaacaatcc taccaaatgc aaattatac     599

<210> SEQ ID NO 14
<211> LENGTH: 599
<212> TYPE: DNA
<213> ORGANISM: Homo sapiens

<400> SEQUENCE: 14 tagttttcc agttctctga agaatctcaa tggcagttta acaggaatag cattcaatat     60
```

```
atagattgct ttacgcagta tggccatttt aatgatactg attttttcta tccatgagta    120
tggaatgttt ttccatttgt ttgtgtcatt tctgatttct ttgaacagtg gtttgtagtc    180
ctccttgtag agctctttca cctccctagt tagttgtatt cttaggcatt ttattctttt    240
tgtggccatg tgaatgggag ttcattcctg atttggcttt cagcttgact gttgttgatk    300
cttaggaatg ctagcgattt ttgcatattg gttttatatc ttgagacttg catgatagtt    360
ttaattttac tttttcaaca aatatttatt aaacacttaa ctacaattaa tccagggatt    420
atgtgacatg gcaacctctt ttattctcac tcctctttgc ttttgttctt agtcaagcag    480 acattttga gtcattttaa ctctgtatta tctcttactc caactgaaga ccaaatcagt    540
tttttctacc tttaaaattt cttaaactga ttttttcttt ttcattcctg gtatcaata    599

<210> SEQ ID NO 15
<211> LENGTH: 599
<212> TYPE: DNA
<213> ORGANISM: Homo sapiens

<400> SEQUENCE: 15
gcagccacag caagccttgc ccaaggagag tctgagctca gacatgccca accctgcccc     60
cacctgatgg tctttctcta cccacccta ccaccctggt agccaaagac aaaggtcata    120
atctaccaca gctgatgtgc tcttgaaagc gccaccttct ggccagaggc caaccaacac    180
aaaaccagtg cacttaacaa aaatacaacc aaggacgctc accgactcta cttctctccc    240
ctgctacctc cactggagca ggtactggta tctacagcta agagacctga agaaggatcr    300
catcacagca ctctttgcag acactcccca gtactagccc agagcccgt acctctgctg    360 gctagctaga tccagaagat aaataacaat tgctgcagtt tgactctcag gaagccccat    420
ccctagggga agggagagag caccacatca agggagcacc ctgtgggaca aaagaatctg    480
aacaacagcc cttgagtccc agatcttccc tctgaaatag tcttcccaaa tgagaaggaa    540
ccagaaaatc aatttgggta atatgaaaaa acgaggttct ttaacacccc caaaagacc    599

<210> SEQ ID NO 16
<211> LENGTH: 599
<212> TYPE: DNA
<213> ORGANISM: Homo sapiens

<400> SEQUENCE: 16
tttggaaggc ttgtcaacaa ttaaaacaac tgggccctac tcccagaagt tcaatatcag     60
aaaactgctc ttgttaacaa attttcctag taatttggct acatgcagtc cttggaacac    120
acatctaaat gatgaatatt ttctatttct ctctgtcagc ttacccagaa gcaggctaaa    180
tatatttctt atagtaactg tacatctgta gtcaggtttt ctaaactagt tgaaagattt    240
gctcatggac tcctttgaga ttatcttctg tgaagaccta gcccatattc cagggctacr    300
ctgttttaca aaatcatgca ctctacactt atttgtgtta tttcatttat atacacatta    360
taatgcctta tgcatagcat ttgtacagtt gtctccaaat gattaaaaaa acactaaatt    420
caagttgatt gaaaatgtat taacacatcc ttaccctttt agacaaaata tactgaacat    480
aattttgaaa tgacttctct cgacatccat tgttacgctg ttagacaaca tacttttgt    540 cttttttta catttttctg tgtcctccct taaagcaaaa ctggaagaag ttactgttt    599

<210> SEQ ID NO 17
<211> LENGTH: 599
<212> TYPE: DNA
<213> ORGANISM: Homo sapiens
```

```
<400> SEQUENCE: 17
ttatgcacct aaaatctgcc tctgcctgtc ctttgctatt accagaggga attaaggatg    60
ggtgaaccca gccatgtttt gggttcgtca acatcttga actactttc cactgttctg    120 ggttaggcaa aacccaaaat atgtttcacc aagcacattt tcccttaatt cttaaaccca    180
ggagtatttt aaggtaaatt taatccatat gcttctgatt catttacact aaactcatca    240
aaatgttctg tcttaagagc tatttgatgt gcaaggacct ttttgaatat tttataagcy    300
ttttaagtcc tatgcattgg gttttcacat tcaaccaaag atcaagtgaa ctcaaatctt    360
aaaatgatga ggtttggttg caaagtctaa aacatcaagg tttgtgaagg ttctaaactt    420
ggttacgtat agttcaatcc ttggtgagaa tatatattaa tttttttgc agaatgtaga    480 ttgcataaca gaatgagtag tgaacaaaat gcaaaatagg gcatggaaat ataaagaagc    540
caagtgacaa ataattcaaa gcagattgaa tgtctgttct ttagcaagaa ccatgcatg    599

<210> SEQ ID NO 18
<211> LENGTH: 599
<212> TYPE: DNA
<213> ORGANISM: Homo sapiens

<400> SEQUENCE: 18
tgggaagtcc aatatcaggg tgctgtcatc tcacgaaggc tttcttatgg cgtgatcaca    60
tggtggtaag caagaggtca agagaagggt aagagggggc tgaacttact cttcataat    120 ggtgctaatt ccacttgtga ggatggagtt ctacaggcct aataacctct aaaaactccc    180
aacactgaat actgttacaa tggcaattac atttcaacat gagttttaga gaggacaaac    240
attcaagcca tagcaggctc caagtgttgt gtactctaca attccggaag cactattak    300 atacactatg ccaccaggtg aaagaagtca ggatctaatt tagaatagaa acagtgagga    360 tggaagaac tatctaggag gtaaattaaa tagaagttgg tgattggata gcggcgtgaa    420
agagaaaaag agatttttgc ttgaacaatt gcatgggtgg atagtgctaa acatagaagg    480
aggagtcagt ttcaggttga cttgaggtag tttgaacttg ttgaggtgtt cttgaaatag    540
tttgaacttg ttgactttga ggtatacatg ggaactctgg tggctggttc taagttata    599

<210> SEQ ID NO 19
<211> LENGTH: 599
<212> TYPE: DNA
<213> ORGANISM: Homo sapiens

<400> SEQUENCE: 19 gagccctga gagtgcaggg atgcccagat ctagagctgc agctgggcag ctgcagctgt    60
gcttgggagt gcaggactcc tgcccctta acttgatagg ggacagggct cctgcctgtt    120
cctggtatct accagctcta ccaccctgg tggagctggt gtcctgcag tggctgctcc    180 agaaaggcta ccactattag taagagatag aacatttca atatggtatg ggagttttca    240
tttatattct tgttctaggt cctgcaaata tcaaggtttt ttctgcatga gataaaatty    300
atattatcct tacaataatc ctataggtgg acacgactgt tttccgtact ttagaagagg    360
gaaccaaggc acaagataac tgcatagcta tctgtggcca cacagcagtg agcaaggttt    420
tgaagaaggc tggtattgcc atcctaaggt atcttaacta ccgtactgtg ctgcttcaca    480
aaacactgca ccaaaacttc tcacagaaaa ttcctggaca caagaaagc tgatgccagt    540 aatttattgg attcaccttt taaggtaata aaaattacct cagtccataa tatatttta    599

<210> SEQ ID NO 20
```

```
<211> LENGTH: 599
<212> TYPE: DNA
<213> ORGANISM: Homo sapiens

<400> SEQUENCE: 20
ctgtgacttc acagaatgtg aagttgaaca ttgaaatagt atcttgataa tattacttta    60
aaatctcact ttgcctgact gtatcaaata accattggtg gctgaagaga aatttgagca   120
agccgaataa ctaatgcttt caatctttac atagtctctg tgagatcaaa tataaattat   180
atgtacttt  attcttataa ataggtttat tgaactcctt gctgagtgta ttttttttctg  240
acctagtaag tgaggtatta tctgaggcaa aacagcatgg agagtgttta tttaccagay   300
ggggaggata aggaaaccag gatctcgtaa cggacttgac atgaatggtg tgtactgtgc   360
cctttccttt ggagcttcag cagctactaa atcctgctgg gcttcctatt gctggctgac   420
aagaaacaga agcctcttcc cacaagtgac tggtggcaga tggatcaagc cactgaaatg   480
ctatgcccca gactttaatc tgtccagctg aactgggtca ttacagagtg tgcttttgca   540
cactgctgct cttaggccgc aatttatgtg tagtgtgggc aatagttagt ttaatttag    599

<210> SEQ ID NO 21
<211> LENGTH: 599
<212> TYPE: DNA
<213> ORGANISM: Homo sapiens

<400> SEQUENCE: 21
agcctcttcc cacaagtgac tggtggcaga tggatcaagc cactgaaatg ctatgcccca    60
gactttaatc tgtccagctg aactgggtca ttacagagtg tgcttttgca cactgctgct   120
cttaggccgc aatttatgtg tagtgtgggc aatagttagt ttaatttagc acatttattt   180
taaacaccta ctatatgcct ggcaaggtgc tgtgtgcttt tcaaaggtta aaaaaaaaa    240
agacatgaac acaatgtatt agcttgttgt gtttcatttt taagggagt  aatgaacgtr   300
aatctaagaa gacatgtaat tgaaataaat caacatacct tggtcctcaa ttttccttta   360
gattagcaaa ttcattcatg agtaattaat gaccagagta gttagggaaa tgaacaggat   420
aaatatgaat aggtatttag ggtaagagaa taatatattt taaaaatctc aaaaattgta   480
attgcacata tggaatttta agtaatggct attattattt acttttttgga tttagattta   540
gaattacaga gaacaatata ataacaattt tatattgttc taatctccta tctacttat    599

<210> SEQ ID NO 22
<211> LENGTH: 599
<212> TYPE: DNA
<213> ORGANISM: Homo sapiens

<400> SEQUENCE: 22
gcttctcttt agttcccaat aatgccaaat tgcttgaatc ctgcaaattc cacattagtg    60
aaaggtctct cagctccctc aagatttatg tctccaactt tcattgaaca gaactattca   120
atcaaaagac ttacactatg tgaaaattgg tgacaacctg ttttggttgg gagggcaaag   180
ctaccagaga tggcaaagat ctattgactg aacaccagaa ctccttccaa attataccaa   240
gccccacttg gagggaatt  ctgtgtctgg aacttaggca gtgaaatgtg agcaccatay   300
ataaatttaa ttgtctccta tttagctcta ttggtatttt tttctcatgt gctaatccta   360
tattttctgg ccattagtaa gtagagaaac caaataaatc tgccatttta aaatgtgtta   420
ccgttataca gtaattacta gcaatagaaa caattccaga acttatatcc tagtacacaa   480
ataagtaggg taagaaaact gtacagaata aactattaaa atagttactg cacataattg   540
```

```
ctcagtaaaa taacgatttt agagtaaaaa tgataattgg ataaaactgt aacagtata      599
```

<210> SEQ ID NO 23
<211> LENGTH: 599
<212> TYPE: DNA
<213> ORGANISM: Homo sapiens

<400> SEQUENCE: 23

```
tataccaagc cccacttgga ggggaattct gtgtctggaa cttaggcagt gaaatgtgag       60
caccatacat aaatttaatt gtctcctatt tagctctatt ggtatttttt tctcatgtgc      120
taatcctata ttttctggcc attagtaagt agagaaacca ataaatctg ccattttaaa      180
atgtgttacc gttatacagt aattactagc aatagaaaca attccagaac ttatatccta     240
gtacacaaat aagtagggta agaaaactgt acagaataaa ctattaaaat agttactgcr     300
cataattgct cagtaaaata acgattttag agtaaaaatg ataattggat aaaactgtaa     360
cagtatattt tgatattcat ggtaggcatt tagataacaa ctgtgtaaaa caaaaggaat     420
ctggagatat attttaagaa attctctaaa tatatcaaaa tctttgttat taagactctt     480
cacctcttat ttatcatgtt cttacaaatg ttttaatttt aggtcagtac ttttatgtaa     540
tccatttgga gtttgaatcc atttgggatt tgaattctca gcacacttgt gttacagag     599
```

<210> SEQ ID NO 24
<211> LENGTH: 599
<212> TYPE: DNA
<213> ORGANISM: Homo sapiens

<400> SEQUENCE: 24

```
tttgacagaa gctgcttctc ctgttatctt gagttttttt ttaaaccaaa cctcttccta       60
aaattatcaa actatctttt actggcatta aattttctag ctttagatca ttcaccttct     120
ttttgcttta aagtgtcaga taatgatctt gttttttcctt gacctatatt agcatctatt    180
ctcatgcctt tcttagacca attctgcatc cacataaaag ttgcattttc aatacaagat     240
taaaagatat tttacaaaaa gtacaagggt tgtttacctg ctggcatagc tgcagcaats    300
gctacatgca tttccttttc ttttttaaca atggacctaa tgatggattt atttatctca     360
aaatggtggg taatcatagc tgcagatctc aacctgtggt acatatcaag caattcaact     420
gtttcttgta atgttatgac ttttctctgc ttcttgggag cacttccagc atcactagtc    480
atataggtcc catggtgtta gtcaaggttt acagtgttac acttaacatt ataaaaata      540
tgtaagaatt gagagtcatc acttttattg caatatgcaa tttactggaa agacaaatt      599
```

<210> SEQ ID NO 25
<211> LENGTH: 599
<212> TYPE: DNA
<213> ORGANISM: Homo sapiens

<400> SEQUENCE: 25

```
tctcagactt gagtagctag gactaaaggc atgagccacc atattcagct aattttttt       60
aaaaaaaatt tcagaggcag catcttacaa tgttccccag gctattctag aacttttggc     120
ctcaaacgaa tctcccacct tggcctccca aagcattggg attacaggca taaaccactg    180
cacctggccc ctgtaatata aaattgatgc acccaaagat cttaggatat atggaactgt    240
aagaagtaat aataaccagg tcctcatagc atcatagact accttttgtt gatttctcts    300
catttcctga gagtctacag gaactaatgc caccataagt cacattttta ttttcccctgt    360
ggcagcacaa gaaattcaag ctttgcagtg tatggtttga tttgagatgt cttaatctaa    420
```

```
tcatcatcca tcatcctcta atctgacaca tcctatatgc cttccctctt cagacccttt      480
ttctttgctc cttgaaacac tcatatgtga tcaacacggt ctcatttatc cttgttatct      540
ttaccttgac taaaaccagg ttatgctact ccctggagg acctctcaaa aggaagctg        599

<210> SEQ ID NO 26
<211> LENGTH: 599
<212> TYPE: DNA
<213> ORGANISM: Homo sapiens

<400> SEQUENCE: 26
tctgacacat cctatatgcc ttccctcttc agacccttt tctttgctcc ttgaaacact        60
catatgtgat caacacggtc tcatttatcc ttgttatctt taccttgact aaaaccaggt     120
tatgctactt ccctggagga cctctcaaaa ggaagctgtt tgttctattt ctttctcatc     180
tgtcccagga ctaggtattg cattaggaga tcccttgctt cccactgctg cttttaaatc     240
atttcatttc cttcttccct tcattcttcc caaatgcaag gtcttccaac tttcatttcr     300
tgctacactc tgccctttat tgctgctctc tggaatttgt ggtcactgtc cctcatacac     360
tgaaaactca catacctcta cctctagccc tgttgtattc ctgatgactt gagcacccaa     420
gggagtgata catacagcac tggtcaatca tttctttacc tgccacacat acagcaatct     480
ttaatttcaa tagccttagc cactcattcc caaataatgc ttggatcatg cacattatca     540
tgagtaaata cacccatgtc tgaaatcctg atttcaagta cttcccaatt tttctgtct      599

<210> SEQ ID NO 27
<211> LENGTH: 599
<212> TYPE: DNA
<213> ORGANISM: Homo sapiens

<400> SEQUENCE: 27
tgaaatcctg atttcaagta cttcccaatt tttctgtctt ttctttactt tcagctcaca      60
gaaacaattc ttccaccata ttaaaaactc taatccaatt cacttgttcc accactttt     120 ttattcatta ttctctcctg tctttacttt cttcctccta tttcttgatg cactatttca     180
atcactcact tctaaacaca ctaggttact ttacctaata cactcaaacc ctcttgggat     240
ccagttttcc accttcttta tgcctatgaa ttttatggaa taaaatgata taaatgggts     300
gactggtttt atttttaaatt accaattgta catttaaaaa catactttct gagaattata     360
gtttccagct tcatccatgt ccctacaaag gacatgaact catcattttt tatggctgca     420
tagtattcca tggtgtatat gtgccacatt ttcttaatcc aatctatcat tgttggacat     480
ttgggttggt tccaagtctt tgctattgtg aatagtgccc caatgaacat acgtgtgcat     540
gtgtctttat agcagcatga tttataatcc tttctcagca aactatcgca aggacaaaa      599

<210> SEQ ID NO 28
<211> LENGTH: 599
<212> TYPE: DNA
<213> ORGANISM: Homo sapiens

<400> SEQUENCE: 28
tgtattatcc tcactagcct ctaaagtgtg tttactatgc catatttta aaaagataaa        60 tctccatttc tcactagata gggctcatta ctctgcttag tgtcatagtg atggcagcag     120
aggcccatct ggagcagctg ctgtggagat gtcacctgca gtggggagg tgtggctggg      180 gctggttgct ctgcggagcc catggggct gggaatagga gagagccctg ctccctgttg      240
aggtggcagt gtgagagccc catgctccca ggtgcaactg cagctgcgca gccaccgcty     300
```

```
gggatccagg catccctgtg ctctagggag cacatgaagc ctcctgcccc tgcatgcttg      360
gaagtgcctg ctcccctttcc ctgggcctct cctgttcccg gcacctgctc cagcacaaag     420
caaagttgta gctgagccca ggtgttgttg tgacctggcc aggtgtgccc gcactcaggg      480
cagtgctgac acaccagccc cctgctgcct cagtcccctc tgaagctttg ggtaccaaca     540
agcccaggga gggagcttgg gtggggcctg agggcggctt ggcgtggacc tgcaggcgc      599
```

<210> SEQ ID NO 29
<211> LENGTH: 599
<212> TYPE: DNA
<213> ORGANISM: Homo sapiens

<400> SEQUENCE: 29

```
tctttctttt cactatacgt gtatcagata gtgtaagacc tgacatatag taggcactta       60
aatctttgta aattaaatag aaaaaaataa aatttcaaaa catatctcat aataatttca     120
cataattata cattataatt aaccagatta atgggttaaa tttattatat gcaggtctag     180
caaggacatt acgatagaga acaaggtgta ttactagtcc catccccacc caatgaacac     240
atcatgcttg taatagaatt gttgaaatac cattaaaaat atccaaactc tatttctaaw     300
atgaattatg gctttcttttc atttgtctct tccattactt cttattcctt ttctaaatct    360
ttagttatgt agacatagtt ttgctgtata atttaaattc tggtttcagt tacttgaatt     420
aatgctccag ttttacttct tggatttggc ttaggcattt ctatagaaca caatacacct     480
gggcatggtt tgccatagaa gttcactttt ggctttataa tcatgcactt gctatcattt      540
ctacatccca taaacataga taacagagtc acacaatctc tctagatctg ggaaattcc     599
```

<210> SEQ ID NO 30
<211> LENGTH: 599
<212> TYPE: DNA
<213> ORGANISM: Homo sapiens

<400> SEQUENCE: 30

```
gccaccatta aagccaaact acaaaattca gaagacagac aactttggaa agcaggcgta       60
agaacaaaca ggctgtctaa ttggatctcc tcatctttta caaataaaat tctagaaaac     120
agcaaaagaa ataagatcta acttcgttta aagttaatgt ttataacaat aatatcatct     180 cttaattttat aatttggggt aataataatt cagtctattt ttttgttggt ggtgatacgt    240
attttattgt gaaaatttgc aaaagtagac tgataggctc acctataaag aagcataaak     300
aatgtaattt tcactcattt taagaatatt atcaaaatca ctatagatat tagttcttaa     360
attatcatat acatatgtgt gtgcatatta tagttctttta gaaatcagct gtgagttata    420
gctgatagta atgtcttaaa atttcctgtt aattttttctc ttctggaggc ataaccaaa     480 ttatattccc ccagggcact gattatataa attataaaac atgaaaatgt taatgcaaat     540
cgggcactac agtaatgcca ataacccaat ataaataaat actgtcagta ctagcaaat     599
```

<210> SEQ ID NO 31
<211> LENGTH: 599
<212> TYPE: DNA
<213> ORGANISM: Homo sapiens

<400> SEQUENCE: 31

```
cacttttcat gtttatggct aaacaaggct caagtcatcg ggccccactt ctgatatgag       60
cttattatca gtggaagaat gaaagcagat gatcccatca tcttttaaag tagtgacatg     120
aggtgatact gacatcatgt aagatctggg tttaaaccac cttaccctcc aacaattatt     180
```

```
tattgaaaaa aattaatgct cttagaaatt tacataagtt tttctgaagg agctaaaaaa    240
acaaatgtta tacccacgtg cttatcgtaa acaagtctc aggtgaaaac agggactaam    300
ttatcttaac ccagagattc tcagcattgt atataaattg caatcagctg ggaggcttta    360
acgatcactg atgcctcttc caagtgtttt gggtgtggtc tgggcctggg gaatttcaaa    420
aactccccag gtgattctaa tgttcaatca cagtgtagac tgctgctttg aaatttaggg    480
gagagagtaa caagttgcac tattactcaa tattttgcat ttggcagaga gtttctgatt    540
tcccattaat ttaattaatt aacactatat ctatatgtac atcccacatg aaattatat    599

<210> SEQ ID NO 32
<211> LENGTH: 599
<212> TYPE: DNA
<213> ORGANISM: Homo sapiens

<400> SEQUENCE: 32
gaagataact cctgaagtct tatgccccta actcctatgt ctctttagat cacaattaaa     60
ttcccaaatc ttaagacagt ggatatactc aaaacatatt gttaaataaa ataaatgaag    120
tgaggtggac tatattttg tttccatata cttaatcctc cttgctgtga aaggttgca    180 catccctttg ttgccacttg acttcagtgc cttctgtgac agaattcatg cctgaccatt    240
gatgtagtgc atgtgccatg tctcagcaga gtttccagag gccttgcctg gttccatcak    300
ctctcttgct ctttctccca gccacatgtc tggcatatcc cagtagaggc tgctcttgtg    360
cttggatcct ggaatgaaaa agacctgcaa cctatcctag ccaggagctg caccagatcc    420
cagactgctg ttataatagt tgtaagattt tatatatatg tgtgtgtgtg tatatatata    480
tatatatata tatacacaca cacacacaca cagcacacct atatacat acacacatat    540 atatgtaaat gtatgtgtat atatacagtg tataatgcag caaaactaac ttatgagtt    599

<210> SEQ ID NO 33
<211> LENGTH: 599
<212> TYPE: DNA
<213> ORGANISM: Homo sapiens

<400> SEQUENCE: 33
tccagtcagt gcatccatgg tgttttgccc ttggaggaag cctgctactg tcatggtaat     60
tgcttctgtg ggttgagggg gactctcact gaagctccca tctttcccag tcccttccca    120
cccacagtga acccctccc taacacctat ttgcatggtt agaaaacatg ccttttcagt    180
aaatgatatg tgacttccat gcacatgtct cataatgaat gtggataaga cctatgactg    240
taatcaattt tttgaaaaat cttatttatc tgttgtcttg cctggattgt atacttacty    300
atttgagtca gactcttgat atttaccgtg aagtcagctg ggaccttact gaaatcaaat    360
gagctcttgc ttctcattgc agtgtctaaa atcatcctgt cttcactcca actctgagct    420
gcatgtatga gactgaaaaa ccattcctag ctcagattct cctgaacaca tttcagagtg    480
aaaaaaagaa ttttgcttga atccggacta caggatatga aagaagtgtt ccggaaagaa    540
agttctcttc cttctttct tggttcaatg aatcctgtgc tttaaatcat gcctctggt    599

<210> SEQ ID NO 34
<211> LENGTH: 599
<212> TYPE: DNA
<213> ORGANISM: Homo sapiens

<400> SEQUENCE: 34
gaaaggtatt aaccacatcc tccaagtaca gaaagtgatg ctcagtgagg ggctattttc     60
```

```
agactaaagt tctagaccag ggctctggag cttcaagagg gtgttccagg ccccagtgag      120
aaaaagtaca gtgggtaaag gaagggacat ggatagaaat gtaagagaaa gaagttgcct      180
ttgttgggga gaaaaatgta tagttttaat atgaggcaaa atattgagag agaattttca      240
atcacaataa cttgagggaa aataaacaac aaatactgtg tggacattaa attagactgk      300
aagagtgtag gctgccttat ctttgtttct aggctcataa tctaaaacct tgcatctctg      360
agccaaggtt tcttcatccg ttgttcaggt gacctcacgg ttggctgaat agtggttcac      420
actggcttct gttttatagc tggcagggta aacttaatgt cttaaataat taggcaagta      480 ctttttattga gcatattctt atagccatac cgaaattcac taagccagac agcttttaaat  540 tagaataagc cacaattgtt ccataatgta gttatacagc tggcattgag aagctttag       599
```

```
<210> SEQ ID NO 35
<211> LENGTH: 599
<212> TYPE: DNA
<213> ORGANISM: Homo sapiens

<400> SEQUENCE: 35
```

```
ccactctatc cccttttcag ctccccatcc atcccactaa aagccacctc caccactcaa      60
taaaacccct gcattcatcc ttcaaatctg tgtgtgacct gattcttctg ggacgctgga      120
caaaagctcg ggacacagaa agctgtcaca ctggcccccg ccccttgccaa aaggcaaagg     180 ttccactggg ctggttaaca atgaagtcat ctgcagatgg caaggctaaa agagcacact      240
gtgacacatg cccatttggg tttgggagtt gcaggatccc accctggat gccactgtar      300 ggttggagcc caggagtgct cactctgcct tctgcacctg tctgtctgca tgctccccct      360
cctgtaaggg atttgagcag cagtggcaac cgaacagaca agccacaccc ctgttgcaca     420
ttttgcaagg gggtcaggga gctctcccat ttcaggacac tgggagacaa gcagtgccaa      480
gatatgttat caaaagtaac agctacttaa aagcaatacc tgtagcactc aagatacaga      540
aaaagagaaa cttctgggga gcttagaaac caaatgatta tcataaaata cagttttttt     599
```

```
<210> SEQ ID NO 36
<211> LENGTH: 599
<212> TYPE: DNA
<213> ORGANISM: Homo sapiens

<400> SEQUENCE: 36
```

```
ggaaatgatt agaataactc ctggaatata cctgcatgat ataaatatgt aattttttta     60
catatgcgcc ttatgtaagt agaatcatat tctaaatact gttttataat ttgctttggt     120
agtgtgatag tatatgtcac agagtttctg tattagttta cataaatgta cattgctctt     180
ttaaagtttt taatataatt tgatattatg gatgtgtaat gtatacttag tttttgcata     240
atttaatttt tttacttgtt tttatttta caaggttgca ggccatatat ttaactgtgy       300
tatgtgctac tgtataacaa aagcagccat agaaaatata gaaacaaatg agagtaactg     360
tgttccaaca aaactttatc tacaaaaatg tgtggctggt ccctaggctg tcgtttgcga     420
acctctgtga tagacataaa agtgtatatg aacataatag cagtaacctg gagaatatct     480
tctgaaagat gataaataag aaaagccagg ataaaagtat gtctactctg tgattatact     540
tatgaacaaa ttgtagatgt aaagaatgaa taaagaactg taaaaaatat aaaacttttt     599
```

```
<210> SEQ ID NO 37
<211> LENGTH: 599
<212> TYPE: DNA
<213> ORGANISM: Homo sapiens
```

<400> SEQUENCE: 37

```
tagtgtgata gtatatgtca cagagtttct gtattagttt acataaatgt acattgctct    60
tttaaagttt ttaatataat ttgatattat ggatgtgtaa tgtatactta gttttttgcat  120
aatttaattt ttttacttgt ttttatttt acaaggttgc aggccatata tttaactgtg   180
ctatgtgcta ctgtataaca aaagcagcca tagaaaatat agaaacaaat gagagtaact   240
gtgttccaac aaaactttat ctacaaaaat gtgtggctgg tccctaggct gtcgtttgcs   300
aacctctgtg atagacataa aagtgtatat gaacataata gcagtaacct ggagaatatc   360
ttctgaaaga tgataaataa gaaaagccag gataaaagta tgtctactct gtgattatac   420
ttatgaacaa attgtagatg taaagaatga ataaagaact gtaaaaaata taaaacttt    480
cagggataag gttgttgatt tatggattgt ttgattttaa ttttaagtat ttacttactc   540
tctgtgccga acaatgttgt tcaataaaag caaatatttg gttctgtaat atcttcctc    599
```

<210> SEQ ID NO 38
<211> LENGTH: 599
<212> TYPE: DNA
<213> ORGANISM: Homo sapiens

<400> SEQUENCE: 38

```
atcttttacc catttctgac ataaacagga cactcattga gaaaaggcac ttccagactt    60
caacctaaga aacataaatg gcagcaagtt acagagaagt cagaaaacat tactttgtta   120
ttgagaactg cttgatctaa aaccaaagca acagagatgt agagtcaaag agaaacaagc   180
aagcatgtgg gatgctcagt ggccacctca ggcacatttt cattgagtct ttcaaataat   240
ggtcatccca attggctaac ctagaacagt ttgcccagac tacaggtgct gcaaaaaatr   300
taattccact ggaaggcacc attgtagtat ttgaaataat ttttaaaagg ctatatggat   360
catgctctat catcttcctt caatctctca tcccacatga tccctcaaa acacaatttt    420
aatgacaaaa atcagaagaa atggacacca tacacacacc taaatcccta atacattttt   480
tgcctctggt tctataaaaa tgtgtgttac caaacataaa taacaagaga aaatacattt   540
tataaatgct aatttatgag gggaatatga aaatgtgcat taacttgaaa aaacatat     599
```

<210> SEQ ID NO 39
<211> LENGTH: 599
<212> TYPE: DNA
<213> ORGANISM: Homo sapiens

<400> SEQUENCE: 39

```
aggtagatat aatgaagagt tattaaaggt gtaataatga ttacagcaat catatcataa    60
ctatgatata aattataatt ataaattata aatatcatt tggggtctag ctgatggaga   120
acttattctt aacccagaca tagtttgtga ttaaggtttt tgatcttgaa taaagcatag   180
tgttatttac aagatatttt agcaaaaata attttttaatt gaagatattt tatgcatcta   240
aaaacattca ttttttatgtt aagctttgaa aaattagtca cccaatcaaa agccttaaak   300
atctttatta cataacaaaa ttatatttaa attgaacatc tttgaaactt ttataacaac   360
atagtctttt ttcaaagtat tctatcacaa tttaaattct tataatttag atttgttttc    420
ttaaagttat tatatgtttt tttcaagtta atgcacattt tcatattccc ctcataaatt    480
agcatttata aaatgtattt tctcttgtta tttatgtttg gtaacacaca ttttttataga   540
accagaggca aaaatgtat tagggattta ggtgtgtgta tggtgtccat ttcttctga     599
```

<210> SEQ ID NO 40

```
<211> LENGTH: 599
<212> TYPE: DNA
<213> ORGANISM: Homo sapiens

<400> SEQUENCE: 40
ggaaaaccaa acattttatg ttctcactcg taagtgggag ctaagctatg aagatacaaa      60
ggcataagaa tgacacaatt gactttggag actcaagggt aagggtggga agagggcaag     120
agataaaaga ctacaaattg ggtgccgtgt atattgcttg ggtgacaggt gcaccaaaat     180
cttacaaatc accactaaag aacttactca tgtaaccaaa caccacctgt tccccaataa     240
cctatggaaa tgataaaatt ttttaaaaaa gaaataccac agaaaagatg ctgctctttr     300
tgaagcatca tatctaagaa cattccaaca catcccccca gtagtggtgg taaccttgat     360
cacctaatca agttgatgcc tgacagatct ctgcaatgta aagtcataat tttctttccc     420
ctgtgttttg gattgctgtt ttgtgggaag atattcagac atttcactaa catcctgttc     480
ttcatcatac cttcagccta cagctttagc attcaatcta catccatagc atccattgac     540
tgtttgtcac tgcttgtatt aactgactct gtgatagttg cccaagagta aatatccat     599

<210> SEQ ID NO 41
<211> LENGTH: 599
<212> TYPE: DNA
<213> ORGANISM: Homo sapiens

<400> SEQUENCE: 41
gtcaaaaggt tagcatctca cggcactaaa agaactctga tatattcatt caattctcag      60
cactagtgca gctgctctct gttttttcaat gttttttgat ttattattc cttaacaatc     120 ctaagtattt aggcatttca cttttttaggc taacactaac cagggtctct ctaatatttc     180
ctcatgacca aactcaggct ctacactttt gatataaatc ttcacaacct atgcatctga     240
caggactaat atccaaaatc tacaatgaac tcaaacaaac tagaagaaaa aaaacaatty     300
catcaaaagt gagctaagga tatgaataga caattctcaa aagaagatac acaaatggcc     360
aacaaacata tgaaaaaatg ctcgacatca ctaatgacca gggaaaatca aaaccacagt     420
gcagtaccac cttactcttg caagaatggc cataataaaa aaaatttaa aaatcgtaga     480 tgttggcatg gatttggtga acagggaaca cttctacact gcagtgggaa tgtaaactag     540
tacaaccatt atggaaaaca gtgtggagat tacttgaaga actaaaagta gaactagca     599

<210> SEQ ID NO 42
<211> LENGTH: 599
<212> TYPE: DNA
<213> ORGANISM: Homo sapiens

<400> SEQUENCE: 42
ttgtactcct gtaaagggta ctgaattttc tttcacccgg ttgattttat catttgctct      60
attaggtctg tttcaatttt gtccactgtc aaaggttaa gttcttacat tagagtgtgg     120
tccttactcc tacagtatgc cctttctgag gtctaaactg aatgtccaat gagctctgtg     180
gaatatctct actctgccta ggtcaaaagg ttagcatctc acggcactaa aagaactctg     240
atatattcat tcaattctca gcactagtgc agctgctctc tgttttttcaa tgttttttgr     300 tttattattt ccttaacaat cctaagtatt taggcatttc actttttagg ctaacactaa     360
ccagggtctc tctaatatttt cctcatgacc aaactcaggc tctacactttt tgatataaat     420 cttcacaacc tatgcatctg acaggactaa atccaaaaat ctacaatgaa ctcaaacaaa     480
ctagaaagaa aaaacaatt ccatcaaaag tgagctaagg atatgaatag acaattctca     540
```

```
aaagaagata cacaaatggc caacaaacat atgaaaaaat gctcgacatc actaatgac    599
```

<210> SEQ ID NO 43
<211> LENGTH: 599
<212> TYPE: DNA
<213> ORGANISM: Homo sapiens

<400> SEQUENCE: 43

```
atattaaaat tcaagaaaca ctaacttttc gagtatgtgt cttataaacc tcctactttg     60
tttgcacgtg ttgcacctac taacacacac aacactgaac tgttcaccgc ttgctttcct    120
ggcatgcact atagtaatag atttaattat cccaaaatat tctcattgaa aattatgtgt    180
aggttgtaga atcctggca atatcagtgg ttaactgttc atttgccaca tctcactgtg     240
taagatgtta gtgtcaccat ctgatactgc tctgtttgca cattcattgt tcagactttr    300
tagcctgttt gattttgag ctatctaata atttcactaa tttcagactc ttcctagacc     360
aatgatgtgt atgtcttcat tagcacagat cttagtactt gtccttatag aaagtcatgc    420
gcttagttac tttgaggcaa cagcttggta caggcaaata cattttaaag gtaaaattat    480
tcttcatttt caacattgtt ttggtattta agtactatgc attctcatat acatttaagg    540
tcagttttta attttttta aaagccagtt gggatattgg ttagaattgc agtagatct     599
```

<210> SEQ ID NO 44
<211> LENGTH: 599
<212> TYPE: DNA
<213> ORGANISM: Homo sapiens

<400> SEQUENCE: 44

```
cacatagaag gaggagaaag gattaaaaag gaaatatact gtaagcaagt atatcagttt     60
ggggatttat ttttagtgaa ggtatgaaag aagtgtgtga atgaaggcgg tttccattga    120
gggaaaaaaa tatttaggag cactcttatt gtgattttgt gaaccaatgg ggtaagagaa    180
gtaatagaat tagattcata tttgaatcag atgtgtagtg cttccatgat caaaattaga    240
ttatttaga catgttgaca tagaaatgcc agtaaaatgt gggatgcttt ttattgactr    300
tggaaagaac acagcataaa aaaagcaaat attttatct tacagcccaa ccgatcattg    360
ctcaaagaag ttataagcta aaaatgctat tttgctgcat tcaggtttag caaaaaatag    420
atacatgtag atttttgtt tgttttctat ggaatttcta ttgccctttt taaaaaaaat    480
tatcttccag ggaataaaaa atgagatatt aaggtagagt taagattgaa gtaaatgcaa    540
aatcaataac ccaaatagac aaaaaagcta tattttatgg tattcatgaa ctcatctttt   599
```

<210> SEQ ID NO 45
<211> LENGTH: 599
<212> TYPE: DNA
<213> ORGANISM: Homo sapiens

<400> SEQUENCE: 45

```
attgtttttt cagttacagt tctaggaatt gaatttctgt gtgaaaggca tattcaatat     60
taaacatttt cacactatta ccaaaatgct tttctgaaga tttaaacatc tttccatgag    120
ctttcttcac agctttccca ttcagctact gttcataaag ttttgcagt tatggctaga    180
tgataaacta gaaatatttt cattgtatat gaacaagtct aataaagata aagaactact    240
tcatagaaaa ataattcatg aatacataca tcagtttaca aaaagatga gttcatgaak    300
accataaaat atagcttttt tgtctatttg ggttattgat tttgcattta cttcaatctt    360
aactctacct taatatctca tttttattc cctggaagat aatttttttt aaaagggca    420
```

| | |
|---|---|
| atagaaattc catagaaaac aaacaaaaaa tctacatgta tctattttt gctaaacctg | 480 |
| aatgcagcaa aatagcattt ttagcttata acttctttga gcaatgatcg gttgggctgt | 540 |
| aagataaaaa tatttgcttt ttttatgctg tgttctttcc atagtcaata aaaagcatc | 599 |

<210> SEQ ID NO 46
<211> LENGTH: 599
<212> TYPE: DNA
<213> ORGANISM: Homo sapiens

<400> SEQUENCE: 46

| | |
|---|---|
| gaaatgtggg caaaggcata ttttttatat tcttaagagc catttggtat ttttagttaa | 60 |
| aaactgcaca tattacttca atacaaagtt ttaaaatcag gttattctat agtaaacttc | 120 |
| attgtagcta atctgcata ttatgtctgt cattgttttt tcagttacag ttctaggaat | 180 |
| tgaatttctg tgtgaaaggc atattcaata ttaaacattt tcacactatt accaaaatgc | 240 |
| ttttctgaag atttaaacat cttttccatga gctttcttca cagctttccc attcagctay | 300 |
| tgttcataaa gtttttgcag ttatggctag atgataaact agaaatattt tcattgtata | 360 |
| tgaacaagtc taataaagat aaagaactac ttcatgaaaa ataattcat gaatacatac | 420 |
| atcagtttac aaaaaagatg agttcatgaa taccataaaa tatagctttt ttgtctattt | 480 |
| gggttattga ttttgcattt acttcaatct taactctacc ttaatatctc attttttatt | 540 |
| ccctggaaga taatttttt taaaaagggc aatagaaatt ccatagaaaa caaacaaaa | 599 |

<210> SEQ ID NO 47
<211> LENGTH: 599
<212> TYPE: DNA
<213> ORGANISM: Homo sapiens

<400> SEQUENCE: 47

| | |
|---|---|
| tgtgtgcttc ttatgagaat ctaatgcctg atgatctgag gtggaacagt ttcacccca | 60 |
| agccatcccc tgccctgcct ccctgtctat ggaaacattt tcttccacaa aacctctctg | 120 |
| gtgccaaaaa gtctggggac cactactata gaggaacaag catgagaatt ataatgagtt | 180 |
| tcccataaga aactatgcaa gcaaaaaaag aatggagtga atatttaaa gtgttggaaa | 240 |
| gaagaaaaaa ataaatattt gactaaaatt ttatattcag tgaaattaac ctttagaaas | 300 |
| aaggaaataa ggactctacc aaacaaacaa aaactcatgg aatttattac cttaccaaca | 360 |
| ggtctgatct aaaagaaatt taaaagaaa ttttcagag acaaaaaaga ttatataggt | 420 |
| tagaaattca gatctatgtt aaaaaaaggc agtgtcagaa aaagaatgaa tgaaggtaag | 480 |
| gtaaattgtt ttattttaa ttaatctaaa aattatggat tatttttaaa ataacaatgt | 540 |
| atcgaatgat tataacatat aggtaagtaa aataaatgac aataagagat gggaaggag | 599 |

<210> SEQ ID NO 48
<211> LENGTH: 599
<212> TYPE: DNA
<213> ORGANISM: Homo sapiens

<400> SEQUENCE: 48

| | |
|---|---|
| tgcccgggtg actcagagtg actcctgcga gttggcactg agactttcaa tcagttgggc | 60 |
| tctctgcagc aggagatctg agtggtgtgt tcccatggct gccacataat gtgtatgtgt | 120 |
| ctgtgtgtgc atgcgcgcac gtttgcacat gggtgtgtgt ttatgcaata aatgttgctt | 180 |
| ttcaaattag tgaagaaagg aagacaagtt caataaatgg cactgaaaaa tattggctag | 240 |
| tataaatgct tcctgacagc agcaactgga tcatattttt acctgtattt ccaccacctr | 300 |

```
gaactatggc tagtacatta cagtagaaag taatgggaac agggtaatgt cctaatatcg      360
gttgtggcga tagactcaca actccataaa tatactaaaa actattcaat tttacactttt     420 aaatgggtga attgtgtgat atgaattata ccctaataac gctattaaaa atataatcta     480
aaacaatgtt atgtattttc tgtaatggca tatagatgca cataaattaa ctgaaaaagc     540
ttacacatca agtttataat gatgtatctg aggaaaaaga ggggtcagaa ttaacaata       599
```

<210> SEQ ID NO 49
<211> LENGTH: 599
<212> TYPE: DNA
<213> ORGANISM: Homo sapiens

<400> SEQUENCE: 49

```
gtgttgtttt atggtaattt gttacagagt agcagaaaat gaatataagg gtatttaaat      60
taaaattata actaaacagc aattctgtgc tcagttctat ataagcgaat aaaagcttgt     120
ttccaaattt atttagatac cttactaatc aaaacctgat atagattata acaataggc      180 taacagaaga ttcaatgatt gttaagtagt tatgtttgga attttaaaat aatatttct      240 tgaaatacat ctgtagattt aatgatatgt ggcaataata aaatacctta gatgcttccr     300
gattttgaaa attaaaacag aacagcagtg gatttgaggt ttctgcttag gttttagca     360 attgctatct ctaataactg cttggaatgg atgaaacatt gattgaaaaa ggaatgagga     420
gttggtagag gtcaactaaa catttgaaaa aaagtttgac ctgatttagg gcataagtaa     480
agcataatat gttataaccc ataatattta aatgcatgca attaatatat atggtgataa     540
ctgcatgaac atttgaaagg actcttgagg ggagaatacc caggaagaat gaaaataat      599
```

<210> SEQ ID NO 50
<211> LENGTH: 599
<212> TYPE: DNA
<213> ORGANISM: Homo sapiens

<400> SEQUENCE: 50

```
attcctctgt cagattggaa ataattttaa catgtgagaa ttatgtggca aggatataac      60
taaacatgca atccctaca ctgttagttt aaatagtta aattgttata attgcttttg     120
ggttttgttt tgtttcgttt tgttttattt tgtttttga gacgaagttt gctcttgtt      180 gcccaggctg gagtgcaata gcgaaatctc ggctcactgc aacttctgcc tcctggattc     240
aagcaattct cttgcctcac cctcccaagt agctgggatc acagacacac accacaacay     300
ccatttaatt ttgttttagt agagacgagg tttcaccata ttcatcaggc tggtctcgaa     360
ctcctgacct caagtgatca acccatctcg gcctcctaac atgctaggat tagaagcgtg     420
agccaccgtg cccagcctct tataattgct ttgaaggta acttttttttt ccactttat      480 tttaggttca aggtacacat gcaggtttgt tatataggta aacttgtgtc atggaggttt     540
gttgtacaga ttatttcatc actcagatac taagtctagt aacccagtag tccttttttt     599
```

<210> SEQ ID NO 51
<211> LENGTH: 599
<212> TYPE: DNA
<213> ORGANISM: Homo sapiens

<400> SEQUENCE: 51

```
aaaccatatc gccaagaatt ttccaaacat gtattcatct ttcatttgtc acctattaat     60
atcttacaaa tcatacttgt aaaatccatt tagaactgta ccagaggcaa tgaatgcaat   120
cattttagct atgtttaaga atggtgccaa atactcatt tcagactagg ctgtcagaaa    180
```

```
ttctgggagt aaggcagctt ggccacatcc ctagatgcca tggtccttct ctgtctctct    240
gggaagtaat ctaatactga gaggggtgtg ctgacctcac ctggaggatg tgtataaggm    300
tagaattctg agatctgtgc ttgagagagc agtagctgct acaggacttt tctctctttg    360
gtaacaagca aaaaccaaga tactttggt ggataaggat tacttttccc agaagctggg     420
caaaagtctt atttgaatac ttcaagttgc agaatccttt ggaaggggc tgccctatgg     480 acttgctttt ggtggcattg tttgttcatg ccagtgctgt tagaactagt gggtcactgc    540
tccactgatc tgaattgttc ccagctcctg cagttggaag agatgcagtt ggcatgcag     599

<210> SEQ ID NO 52
<211> LENGTH: 599
<212> TYPE: DNA
<213> ORGANISM: Homo sapiens

<400> SEQUENCE: 52
aatcacttta aattgttttg cattatcttc tatatttgac tactatatat cgcataacat     60
aacaatttca cactcaagta attattcagc acaaattcat gaacatgtac ctaaagcata    120
gatataaaaa tgtttatact cccaaagcaa aagcaaccca aagtctgtca attatagaat    180
aaataagtag tgttttagtc acacaataaa tactgtaaaa caattaaaat gaacaatcta    240
caactgtgtt caaccacatg gatgaatttt ataaaccaaa attttagtga aaggagccar    300
atacaaaaca acacatactc tatgattcat ttttgtatag ttgaaaacag acaaaacaag    360
tctattgtgt tagaagtcag tgtagtgagt aacatttgct ttggagtact ggggtgctga    420
tttggacagt gcaggaggag gtggtggtga tgctcaattt cttgagcaga ttgattgtta    480
ccttggttag ttcaatttgt gctcatgatt tatatacttt tctcttactt ttcatctaaa    540
aaattaaaag tggattaaaa cctaaatgaa tataataaat ctttaaaata tttaaaaga    599

<210> SEQ ID NO 53
<211> LENGTH: 599
<212> TYPE: DNA
<213> ORGANISM: Homo sapiens

<400> SEQUENCE: 53
tgttcagaag taaatgttga gcctacgctg agatcctgca gatggaatac aatctgtgag     60
attattcctg ttgttttct actactatgt caattatcat tctttgaagg gaaaaattaa    120
cagggcctct gttgggcatt gaggaaaaaa ctctggactc tgggtcagaa gaaaggaaac    180
aagccataac cacttggagc ctcacttctc atatgtataa aataatagca atagtggtta    240
gtatttattg agcagatgga acttctactt ctaatcctca caatagccca cttgagtttm    300
tggaataatt tatttagtca aatttatgtg aaaatgcctg ccatactata tactattgtt    360
ctgaaaatca aatggggcaa ttcatataaa actatctgaa aattaaagtt acaattttca    420
ataggaagga ctcttgtcta tcttttcttga aatcattttt atagctgttt tgcataactc    480
agttgctgtc agagaaaaag aagttgtata caaattccaa ataataattt gacactaata    540
agcaatgtca aaataagaac atagagttaa acacttttc ccttgagtaa caaacaact      599

<210> SEQ ID NO 54
<211> LENGTH: 599
<212> TYPE: DNA
<213> ORGANISM: Homo sapiens

<400> SEQUENCE: 54
tgtataaaat aatagcaata gtggttagta tttattgagc agatggaact tctacttcta     60
```

```
atcctcacaa tagcccactt gagtttctgg aataatttat ttagtcaaat ttatgtgaaa      120
atgcctgcca tactatatac tattgttctg aaaatcaaat ggggcaattc atataaaact      180
atctgaaaat taaagttaca atttcaata ggaaggactc ttgtctatct ttcttgaaat       240 cattttata gctgttttgc ataactcagt tgctgtcaga gaaaagaag ttgtatacar        300 attccaaata ataatttgac actaataagc aatgtcaaaa taagaacata gagttaaaca     360
ctttttccct tgagtaacaa acaacttga aaaagtcagt gtaatacttt tgacagatat     420
tattaacagg aaattgtgga attagtatac ttaaagtcta gggagaaaaa atttatattt     480
ttctcaggaa ctctaataaa tatatcatta taggaataaa tatgaatcta aaaataacc       540 tagttaatat gaccaataaa gagtaataat gggtgggaga taagtgtttt tctaaaata      599

<210> SEQ ID NO 55
<211> LENGTH: 599
<212> TYPE: DNA
<213> ORGANISM: Homo sapiens

<400> SEQUENCE: 55
cattgagggg gttaacaaag acaaatcagt gactagctgc tggcattatc atatttcagg      60
gcttaagttt tgatgtagaa atagcaaact atgaaacacg ttcatcgtca atctcttctg     120 ctttttttgaa gggacttcta agctctgtca gctaatagct ttagataaca gagttttaat   180
acaccgtatt gataacaact attattgtta tcaatcacga ggaccttcta ttcctttatc    240
aatatcaagg acctttatt ccttttacta aaaatgtcct aaacattcat cattgctgay    300
gttaagtatc ttctgagtga caaaaccggc agaggagggg tttacagtag tttctgttta    360
gtcctgtgaa ttagaaaaat taagaataac atgttcttt tataaagtca atatcactga    420
aattaaatta aattacagaa aacttaaaac ttaagaaaac ttaacaagta cttgctactt     480 acaaagtaa tttaagtatt acttgtcaag ctttaataat gagcagattc cttttaaagg     540 gaaaaatgc tctcacagac cagtgaataa gagattcatg aatccaaatt tgagagtcc     599

<210> SEQ ID NO 56
<211> LENGTH: 599
<212> TYPE: DNA
<213> ORGANISM: Homo sapiens

<400> SEQUENCE: 56
tatattttta attttttag gtacatacta gatgtatatg tttatggggt acatgagata      60
ttttggtaaa agcatgcaat gcataataat cacattgtgg aaaattggtg gatagccatc    120
ccctgaagca tttatctttt gtgtacagac aatccaatta tattctttta gttgttttaa    180
aatgtacaat ttaattatta ctgaccatag tcctcctgtt gtgctatcaa atactaggtc    240
ttattcattg tttctattt tttgtactca ttaaacatcc tcacctcctc ccattcccy     300 actatgcttc ctagcctctg gtaaccatcc ttccattctc tgtctctgtg agttcaattg    360
ttttgatttt taaatcctat gaatgagtga gaacacacaa tgtttgtctt tctgtgcctg   420
gtttatttca cttaaataat gacctccagt ttcatccatg ttattgcaaa taatcaaatc    480
tagttctttt ttatgactg tacatatgta ccacattttc tttatccatg tatctgttgg     540
tggacactta ggttgctcca aatcttggct attgtgaaca atactgcaac aaacatggg      599

<210> SEQ ID NO 57
<211> LENGTH: 599
<212> TYPE: DNA
<213> ORGANISM: Homo sapiens
```

<400> SEQUENCE: 57

```
ataatgtcga tttgtgaaat atttaaccag gttttttta atgagcaaaa cataaatatg     60
atcacattga agtttaagaa cttctcttta tcaaatgtaa tactgaagaa actgaaaagt    120
caagccacaa gctaggcaac atatttgcaa actatttta aaaagatga acaaatcctg     180
aacaggcatt tcacagcaga ggaaataaaa atgaccaata attgtactaa aacaagctca    240
aattcattag taggcatgga aatgcaaatt agaaccacaa aagatgtca tgttacccar    300
tgaatgaaaa cttaaaagtc tgacaataac aagtgttgct gataataaat tgctagtaag    360
tgaaagagct gttcaaaatt gacatataat agttaaaata aaacactttt agaaaacagt    420
ttgacatctt actagagttg aagatgattc agccactttt attccagcca ctccatttct    480
agcatacact acagagaagt gtatatttaa agaggcctgt ttaaaatagg tcaaaatgag    540
aagcaacgca aatgttaaac aataggagga ttatctactg agaactatcc atggaatgt     599
```

<210> SEQ ID NO 58
<211> LENGTH: 599
<212> TYPE: DNA
<213> ORGANISM: Homo sapiens

<400> SEQUENCE: 58

```
gccatgtttg gtgagcttct agtccttgac ctgggcaaaa ttaaacttt tccagagagt     60
agaaaagcaa cccactgtca ccattaaaag ttgagtgtgt gtgtgtgtgt gtgtgtgtgt    120
gtgtgtgtgt acttaatatg ttaaattata ttgagtcact ctgattgact tacaaatttt    180
ttcctcaggg tcagaagtaa tggacatttt aacagactga actatatcac caaaatactc    240
cccagaaaag tggtaacaat ttactttcca attgtgaata tcatactttt gatgcctatw    300
cataaattct ttaagactat tttaactact tgtgttattt tagaaaaata ttaatttag     360
gccaacttag atcaacataa atttgaagga aatatattga agaatgagag gaaaattatt    420
gtttttctcc tatgtcatct tacagacaag ttttcattaa actgggatga cttcacttgc    480
caaagacatt tgatatatca aatgcagcca tatgttctaa atataacgga ttactgccat    540
gtgcatgagt taaggaacat tgtattgtgt attgaaagaa cattgtattg aaagaacat     599
```

<210> SEQ ID NO 59
<211> LENGTH: 599
<212> TYPE: DNA
<213> ORGANISM: Homo sapiens

<400> SEQUENCE: 59

```
aatccatgtt ttcacaggaa tcaaaattga ataagtcaga agttatagga atattaagct     60
caatttggtg taatgaaaaa cactggattc acacactgct ttttatgtat tcttaatgta    120
gtacctatta cattgtattc aaattatctt ttcatgaaat ggtatttaca gctatgcttt    180
gcggtcctca agaacaggga caagtcatat ttctatgcct aacacttaac atacattaaa    240
cattaaataa atcattgatg agaacataaa tgaattaaca gagtagtcca aaaaataaay    300
agggatactc tggcagtagg tgacttcatc attcacttga taagatacaa gaaagaagtc    360
aggtattaaa atgggtgctg atacaaaata acctttacat atgcttccaa tactagatat    420
tttaaaaatg aaattgctat atcatgagaa taaattggtt tctagtgcta ataatgtact    480
tcctcttctt gtattaccac ccccaaataa taatattaat aagaacataa tgcttaaaga    540
gcattttatt tagtgaccct gtgagaaatc aggacaggca ataataatcc tacatagat     599
```

<210> SEQ ID NO 60

```
<211> LENGTH: 599
<212> TYPE: DNA
<213> ORGANISM: Homo sapiens

<400> SEQUENCE: 60
agtatcccat ttttattaaa gacaaatcac gataagactg atttgcttta ttatacttgg    60
cctgattatt tgtgtaaaat gtagcaagaa taattatttt tcacttagac tttttagatt   120
ggctttgatg gaactctctt ccatagaagg aatctcagat aagactttt  taaagtcaag   180
ccctgatatg ggattgtatc ctcaaatacc tatgagttgg gtaaatgtct ctccttttga   240
ggtcccaaga taacttaggg ctaatcagcc tgtcagaaag tgatattctt tacttaatay   300
aggtcaggaa tcctgtgcag ggactgtgta gacaaagtat gaggccagat ttcctaaggg   360
gcttttgtcg cctctatatg tcaagtttaa ttccttaaag gaaaacacac cattccagtc   420
aagtccttgg taaaataacc agtttctcca actgtgtatt gttgcaaaag aaaattgatt   480
cttattgcac ttacacaaat aattatactg acataaatta agaatactca caactagttc   540
caaattctgg agaaatcagt tagagagaaa caaatatgtt ccaaattttg ttcacagga    599

<210> SEQ ID NO 61
<211> LENGTH: 599
<212> TYPE: DNA
<213> ORGANISM: Homo sapiens

<400> SEQUENCE: 61
gcacagctag gggactgcac ccctctgcac cactgacaag agtgcagtgc agccgctgag    60
agactgcagc cccaataagc tagccctgct cgcatttatt tagtacagat ttaatgacaa   120
aggcttggag caaaaacaat ttgtggataa taaccattgt caactccccc acccccccaa   180
gtagagagca gtcctgcatg caaatgatca aaggttggtt tctggagaca ggaggaaaca   240
aatttatcta gataagtccc tttacattcc cttattattt acctttgct  ctcaggctcy   300
ggataagaga acttggctgt cttcaggcaa atttacttt  gaagcttttg caaaacctcc   360
tggccttcca agaaggtttg tgtctttccc tgtaacttt  ataccttttc ccaccacact   420
gactgatttc ctcagttttt gtaaatgtag ctctagtttt acattaagta aactaaaaat   480
ggaaatcata gatggtaaat tatgcgagtg gcttattaaa aaaaaaacat ggggatctta   540
attaggagac catatttgta gaggagggct tggtactaca tcaaaaactg gcagtagtt    599

<210> SEQ ID NO 62
<211> LENGTH: 599
<212> TYPE: DNA
<213> ORGANISM: Homo sapiens

<400> SEQUENCE: 62
cattccttgt gagtggccag ctctgtttat ctcacagagt cctggcaaat gcctgttttc    60
tctctgagag agtacagagt tgtgatcagt gcagtggatc ccagcaacca gaggtcgggc   120
cagatgtttg aaagacagct tatttatca  aaaagacatg gtttctcttg atttccttct   180
ggattaagtc tacttaactg aatacaatac aagctagaaa tgtttcaaaa tgccaaattg   240
ctattaaaat gaattcaagt ggaatattca taagaatata tgctctttaa ttaatgtcaw   300
attggctgaa tatttcctat cccaaatttt tctacccctt tctagtatct ctaactgaat   360
tatgatatgc atgaataaat aaatggcaga gaaaaaaagg accaaacttt ttctaatctt   420
ttatttctca aagattcaat tctctgtatt tcccaccatt atctgcttca cagcagaata   480
tctaaatatc tatgcttctt gttaaaagta ataggaagat taatgtgcac tcgaagacaa   540
```
cacagcctac aaggctcttt caaatgttca gctcaattaa cacttgaaat tctactaga    599

<210> SEQ ID NO 63
<211> LENGTH: 599
<212> TYPE: DNA
<213> ORGANISM: Homo sapiens

<400> SEQUENCE: 63
cagggaggac agctagacat tgctttcatc cccatcttga ttctggctgg tttctgccag     60
tttctttacc acatcctgtt atatcagtgt cgtctttgtg acctcttctt gagaaacaag    120
tcctaacaaa ctcctatctc agtttgtatg tgactatgta tacatttgat gtttcaggca    180
ttaataactc taaaattaat gtataggctc agtatggcta tatatcattt tacttgattt    240
cgtatggttc aacatcaact gcatgctgat ttttagtaaa tattggtctc aaattttgcy    300
tcggtatatg ttttgggtat atagataaaa tgcttcttcc aactgtcctt ttagttctgg    360
ctaccacaag tacattgcct ctgaccagca gcacaatgat gttggaactt gtgtcagaag    420
aatcatatcc ttctttttagc ttccatctac tttttgcact tttataaccct aaaccatgtc    480 ccactttgtc aatgtacaat tcaggataaa gtcattgatg tcacactgaa tattgtctaa    540
tggagagcat tcagattcac aactctcttc cactttaaag gcaatctgta ttaatgaca     599

<210> SEQ ID NO 64
<211> LENGTH: 599
<212> TYPE: DNA
<213> ORGANISM: Homo sapiens

<400> SEQUENCE: 64
tgggaattgc catagcatct gtaaactgtc atggcacttt tgggtgtttc tgttagcatg     60
ctaggcgtat aatgagcagg gaggacagct agacattgct ttcatcccca tcttgattct    120
ggctggtttc tgccagtttc tttaccacat cctgttatat cagtgtcgtc tttgtgacct    180
cttcttgaga aacaagtcct aacaaactcc tatctcagtt tgtatgtgac tatgtataca    240
tttgatgttt caggcattaa taactctaaa attaatgtat aggctcagta tggctatatw    300
tcattttact tgatttcgta tggttcaaca tcaactgcat gctgattttt agtaaatatt    360
ggtctcaaat tttgcctcgg tatatgtttt gggtatatag ataaaatgct tcttccaact    420
gtccttttag ttctggctac cacaagtaca ttgcctctga ccagcagcac aatgatgttg    480
gaacttgtgt cagaagaatc atatccttct tttagcttcc atctactttt tgcacttttta    540 taacctaaac catgtcccac tttgtcaatg tacaattcag gataaagtca ttgatgtca     599

<210> SEQ ID NO 65
<211> LENGTH: 599
<212> TYPE: DNA
<213> ORGANISM: Homo sapiens

<400> SEQUENCE: 65
tgatgttgaa ccatacgaaa tcaagtaaaa tgatatatag ccatactgag cctatacatt     60
aattttagag ttattaatgc ctgaaacatc aaatgtatac atagtcacat acaaactgag    120
ataggagttt gttaggactt gtttctcaag aagaggtcac aaagacgaca ctgatataac    180
aggatgtggt aaagaaactg gcagaaacca gccagaatca agatgggat gaaagcaatg    240 tctagctgtc ctccctgctc attatacgcc tagcatgcta acagaaacac ccaaaagtgy    300
catgacagtt tacagatgct atggcaattc ccagaaatta cactagataa tctaaaaagg    360
gcaggaaccc ttggttctgg gaactcccta ctcctttcct gaaaaactcg taattgaccc    420

```
cttgtttagc atattatcaa aaataaccat aaaaatagcc aaccagcagt ccttagggtg    480
actctgctat ggggtagcca ccattttatt ccttcacatt ttaatagact tgctttcact    540
tcactcttga attctttcct gctctaaccc aagaacccac atggcctccc aagctgaat     599
```

<210> SEQ ID NO 66
<211> LENGTH: 599
<212> TYPE: DNA
<213> ORGANISM: Homo sapiens

<400> SEQUENCE: 66

```
tatagattac acaaaatatc tgcaaccttt gtgacatatg taaggttaac aaaactaata     60
ttaacaatag acaaagaact tcaaggaaaa aggccccaaa ataaaagcga atgccaacaa    120
atacattaaa ataagagtcc tcaaacccca ggccacagac tggtagcagt ctgtgacctg    180
ttaggaacca gtctgcacag caggaggtga ctggtgggta agcaagcatt attgcctgag    240
ctctgcctcc tgaccttgt cagttcagcc aaggcattag attctcatag gagtgtgaam    300
cttattgtga attgtgcatg tgagggatct aggttgcaca ctccttatga aatctaatg     360 cctgatgatc tgagctggaa cagtttcaac acaaaaccat ccgcaacccc cacctcagtc    420
cgtggaaaaa ctgtcttcca taaaactggt ccctggtgcc aaaaaggttg aggactgctg    480
cattaaaaga tactcaatct cacttgtagt ctgataaata aaagttaaaa caattatcca    540
atatattaag ttaggctgaa attatataag atttttttta aaactgccaa tagtattgg     599
```

<210> SEQ ID NO 67
<211> LENGTH: 599
<212> TYPE: DNA
<213> ORGANISM: Homo sapiens

<400> SEQUENCE: 67

```
gaggggcaaa cagcctccac ttgtgaggtt tgtcatttta ttcagaacag agcgccctct     60
ccagggactc agtaagacaa aaggtgggga acgggtgat ttgattgctc aactatttgt    120
attgttataa aatgacaata catgccagtg ggtaatcaat gcccatacta gaaataaaaa    180
aatatgactc aaaatttaca ataggaaggg tgcagtggct cttgactaac tccagggctt    240
tgagaggtcg aggtggaagg atcacttgag gccaggagtt caagaccagt ctgagcgatr    300
taatgagatc tacccatgca aaaaataaat aattagccag gcatgatggt ttgtgcctat    360
agttctagct acttaggaag ctgagctggg aggattgctt gagcccagga gttcaaggct    420
gcagtgagct atgattgcac cactgcactc cagcctgggc atataaaat atttgattct     480 ttgatgattt atctaaaatg attttttataa agaatgcaga tgtatctctt tctctctctc    540
tttctctctc tatatatata cagatatata catatatcat atgtattgta tatattcct    599
```

<210> SEQ ID NO 68
<211> LENGTH: 599
<212> TYPE: DNA
<213> ORGANISM: Homo sapiens

<400> SEQUENCE: 68

```
tattggtgtt cagtaaatgt tattttgcat cattttacat atgcacctca ttaaatcccc     60
atagcaaact tgtaaagtgg gtactattag tctcctaatt aagaaaagcg aaagtggcag    120
agcctggctg gatctcagtt gagtttattg agctttcaaa ttagtacaga gactagttta    180
ggaaacacaa agagtatact tccgtggatg gatataagct gttacatgtt gaacctgtgg    240
gaaaataaca ttcatcttca ttttttcctc tctaactata aatgtaaact atattaaacr    300
```

| | | |
|---|---|---|
| ttcataatcc tatcagattc tatgccctct tttacaacag tagtttatag tttgcaacac | 360 | |
| tccctctaat atcccagaaa taaaatcttc agataacaga ctgaaaccat aaattcaaaa | 420 | |
| agtatatctt tatatgatac cccactgtaa tacaaaggat aaattttaaa atgtaattat | 480 | |
| taaagtaatt tgtagttcaa gataaaaatgc tcaggttccc ctatttgtac tatttgtaga | 540 | |
| atcactgtga ttgtgacagc taccgatgca gacctactga agactactta acctgaagc | 599 | |

<210> SEQ ID NO 69
<211> LENGTH: 599
<212> TYPE: DNA
<213> ORGANISM: Homo sapiens

<400> SEQUENCE: 69

| | | |
|---|---|---|
| tacatatgca cctcattaaa tccccatagc aaacttgtaa agtgggtact attagtctcc | 60 | |
| taattaagaa aagcgaaagt ggcagagcct ggctggatct cagttgagtt tattgagctt | 120 | |
| tcaaattagt acagagacta gtttaggaaa cacaaagagt atacttccgt ggatggatat | 180 | |
| aagctgttac atgttgaacc tgtgggaaaa taacattcat cttcattttt tcctctctaa | 240 | |
| ctataaatgt aaactatatt aaacgttcat aatcctatca gattctatgc cctcttttay | 300 | |
| aacagtagtt tatagtttgc aacactccct ctaatatccc agaaataaaa tcttcagata | 360 | |
| acagactgaa accataaatt caaaaagtat atctttatat gatacccacc tgtaatacaa | 420 | |
| aggataaatt ttaaaatgta attattaaag taatttgtag ttcaagataa aatgctcagg | 480 | |
| ttcccctatt tgtactattt gtagaatcac tgtgattgtg acagctaccg atgcagacct | 540 | |
| actgaagact acttaacctg aagcatataa tggtttctcc ctatgtccaa gaactctac | 599 | |

<210> SEQ ID NO 70
<211> LENGTH: 599
<212> TYPE: DNA
<213> ORGANISM: Homo sapiens

<400> SEQUENCE: 70

| | | |
|---|---|---|
| acaccaggat tgacattgat acagttaaga tagagaacat ttccattacc acaagaatcc | 60 | |
| cttatgttgc tcttttatag gaattttcac tgccttccca tctcactgac tccttaatct | 120 | |
| ctaccaacta ttaatctgtg ttccatttcg ataattttgt tacctcaaga gtgttatata | 180 | |
| aatgaaatct taccatatgt aacctttttgg tattggcttt ttgtaaatcc agtgtaattc | 240 | |
| tctagagatt tatccagatc taccgtatta attgtaacca tgcacctgtt caagaacaty | 300 | |
| tgcttgtttg tttccgatgc tgggctataa tgaataagac tgtatcatga agaggttttt | 360 | |
| gcttgaaaat aaattttcat ttatctggga taaatgcccc aagagtgcaa ttgctggtca | 420 | |
| aaacttacca agttttacgt ttatggatca tgcttttggt atcaactcta ggaactcttt | 480 | |
| gcctagtcct atatcctgca gtttttttct cttatttttt ggtaataatt ttatgcttac | 540 | |
| attgaaattt gtaatcattt taattttttcc aaaaggtgta agagatagat tgaagtttta | 599 | |

<210> SEQ ID NO 71
<211> LENGTH: 599
<212> TYPE: DNA
<213> ORGANISM: Homo sapiens

<400> SEQUENCE: 71

| | | |
|---|---|---|
| gctgtactgg cttccttgtt aatcctttat cccccttcagg tgttattcaa atgtcatctt | 60 | |
| ctcaagaagg ccttgtgtga ttagtttatt gaaattattc cactcaactc ctatgtctaa | 120 | |
| cactattcag tctcctttcc tgcttcaatt ttcttcttgg ctcctagcac catctaactt | 180 | |

```
ggaacatgta tatgtgacat atttggctag attatttcac ccattagcat gtaaactcca    240
cgaaggcttt tattttactg cagtattttc tgcacctaga acagtattgg tatatagcar    300
tcacttaaat atttgttgaa tgagtgatgt agagaaggtt caaaaagcca ctggagaatg    360
tcatggcttg accggtttga attgtaatac tttaaatcaa agatcaatgg aaacattaat    420
aggaaagatc ttaacatcaa ttttcttcca ggagaattta acataaaca catacaaata     480 gataagcaca tgctttagaa actctcccat tcccttctct aaacctcaac ccactctctc    540
taccacccTT ccctaaaaaa atgagagatt aaagaaaaag taaacacact gtgtccatg     599
```

<210> SEQ ID NO 72
<211> LENGTH: 599
<212> TYPE: DNA
<213> ORGANISM: Homo sapiens

<400> SEQUENCE: 72

```
ctaaaatcta tgctgtaata ctataagaat ttaaaaaata tcaacctagg atttctatga    60
tacattctca aacagcgtat ttattactta tttacacaaa aaactgtcac ttcaacttag   120
ataaaattga gcacctcact ttttaaatat tgaatatcgg tttaaagatc tcaagttttt   180
atatcctcct tttgttaaca atgtagaaag gatattttag attccactag caacttctca   240
cagaagatat tattaatgaa actgaagtat tgcattttat ttctaaaggt cagtttaatr   300
gacttgcaat ttcaaagttt aaccgtacca tctgttttaa cttaaaaata tagttataaa   360
ttctttttag caacatttgt gttttaatac cctgaagaat tattacaata aatccaaatt   420
aatattctgg tccctaatta cagaagagtg aatcaataaa ttagattacc cgaaatgaga   480
ctttggtgac ttcttagcag atatttagtg agcacccatt atgcacaagt attgatttgt   540
tgctgaagat taaaaattaa atcagtccct ttttaagagg ctcacagatt agtaagaac    599
```

<210> SEQ ID NO 73
<211> LENGTH: 599
<212> TYPE: DNA
<213> ORGANISM: Homo sapiens

<400> SEQUENCE: 73

```
tccttccatc tacaaacgca ggaaaccacg actggagaag ttatatgatt ggctaaacca    60
tgaatgacgc aacataaccc acgcccactg agaatcgtcc tttcccagac tggctcagat   120
tccgctttcc gattggtccc tacagcaaga gggcaaggac aattgcttaa gttgacctct   180
gggtccggaa tcgcgggcaa agatggcggc ggccaggtgt tggaggcctt tgctacgcgg   240
tccgaggctt tcattgcaca ccgcggctaa tgccgccgcc acggctacag aaacgacctb   300
ccaagacgtc gcggcgaccc ccgtcgcgcg gtacccgccg attgtggcct ccatgacagc   360
cgacagcaaa gctgcacggc tgcggcggat cgagcgctgg caggcgacgg tgcacgctgc   420
ggagtcggta gacgagaagc tgcgaatcct caccaagatg cagtttatga agtacatggt   480
ttacccgcag accttcgcgc tgaatgccga ccgctggtac cagtacttca ccaagaccgt   540
gttcctgtcg ggtctgccgc cgcccccagc ggagcccgag cccgagcccg aacccgaac    599
```

<210> SEQ ID NO 74
<211> LENGTH: 599
<212> TYPE: DNA
<213> ORGANISM: Homo sapiens

<400> SEQUENCE: 74

```
gaaccagggc ctagcacata aatactgagt aaacgttagg tatcttagtt aatacttcat    60
```

| | |
|---|---|
| ttaatcttca caattctaca acaaagaact actaccgtaa aacgcgaaaa attaagcaaa | 120 |
| aaagttacta aagaaaaaga aaagacatac taaatttaaa attaaggtaa aaagaagtta | 180 |
| ctactcagcc atgtgacaca tggtcacaca gctttgtggt ggaacagcca acaggaaacc | 240 |
| tggcccgccc cactctctta agtggcgttt ctcttcatca ccactgctct tccatttggs | 300 |
| tgaacactca caaagtagaa tccaggactg gaatcctgga gagctcaggc tttcagagtt | 360 |
| gaagagctgg taggtgttag cgcagccaca cacacctagt ctctagattc ctaacgcagt | 420 |
| gactgttaca aaaccaggcc accccagata ggaacgaaag gactaggaaa acatgaacga | 480 |
| agcagagaga aagaaatgac gaggggtaaa tctgcggcag agtaacccag tacaatcccc | 540 |
| atctctccct tccgccctgg ggcggaatcc aaggctcacc gagggcggca gcggccagg | 599 |

<210> SEQ ID NO 75
<211> LENGTH: 599
<212> TYPE: DNA
<213> ORGANISM: Homo sapiens

<400> SEQUENCE: 75

| | |
|---|---|
| tcagcagctt ccgtgtaact gttcagggcg gacatgaaaa gtaattaacg tataaataat | 60 |
| tttaaaaatt attgttttttg acgcattcat tattttatat cttctaccaa gtgtatgtct | 120 |
| taatatttat tgaagtaatg ttaggactgt agatgtgtgc tcaacctagc cttgttgtgt | 180 |
| gcatgttttt tcccttcccc agttgagaaa gaagtggtct tgaggaaagc gtcatggact | 240 |
| tagactactc ctgatggatg gcctagaaaa cctgtttaac tttgtcaaga cccaggttcy | 300 |
| tctcctataa aatagagata atgaaaagta tacataccct tgggagttat tgtgaaaatt | 360 |
| gaattggatg ttcataaaat agccctattt ttatttatgg tgaatgatat tcttgttaat | 420 |
| cttatttct tttattactc ctaatgagga atctctttgg ttactgttca ttgtaatgat | 480 |
| ggcacaagta gacaataaat gtttgaatgt tatatttaag tcataatagt taaattacca | 540 |
| cataacccag actcttacct caatcattcc taagttatca tttgctaagt tagtactct | 599 |

<210> SEQ ID NO 76
<211> LENGTH: 599
<212> TYPE: DNA
<213> ORGANISM: Homo sapiens

<400> SEQUENCE: 76

| | |
|---|---|
| ttattacaac atgcataaac actggaaaga aaatattaag ttcattattt gaaattttac | 60 |
| ttgtttctac caaatagaa gtatttaact ttagaaaata ggctttgttg acttattaga | 120 |
| tagaaaaatt agtgtttttt taaaagtaaa aacttttaga actggacttg agatagcaat | 180 |
| tggctttttt aagtgtccta tttgtgccat gcatggtggt aagataagga attcacaaat | 240 |
| tcataatgtc tgatgtctgc cctccctcat gcagcttatt tttttgcaat tttttcttcy | 300 |
| tttgttaatt cctacccaat gtgaagaagt cttaagaagg ttttatacca gccctccaga | 360 |
| cctatttat cagccttttc tcagtcactg tggtcttagg gagtgacctg caaggaactt | 420 |
| tttgttgaaa agactaccac tagaatcaag aatgtcagca tttcatgaaa tgttgctact | 480 |
| tatttttttt ttttttactt agaaaagtag tgtaaaaatg attttttaaa attaggagca | 540 |
| aagtgtgtaa ttatttcatt aaataagtta ttaaagtctt gaagtggctg tatcctctt | 599 |

<210> SEQ ID NO 77
<211> LENGTH: 599
<212> TYPE: DNA
<213> ORGANISM: Homo sapiens

<400> SEQUENCE: 77

```
ttgtggatta aatatttata ttacatcaat ggctatccta tataatttct ttaaaggtta      60
tatccaggat ttggattagg ggattgttca ttcattcagt aaacagtaac tgcttttta     120
tatgctatac tctgttcaag atgcagtgtt gagtgaaaca gatcctgctt tcttagagct    180
tatattatag tgggggtgtg gggtggtaaa agataataag catgtaatgt ttataactag    240
tggtaatact atgggaaaa  tactttagcc taaagagtag aatgatttat aggggggcar    300
gtataaatga ggtatggaga agaatctatt tttaaaaagt cattcaggag aggtccctaa    360
aaatgactta ctctaagacc tgaatggcga ggagctgcct atgcacaaat ctgggtaaag    420
acacttccag gcaaaaggat cagcaagtaa aagtccctga ggtgggaaca ggcctgaaat    480
atttaggaac aacatgaagg gtaatgaaga gtgggacaag gagaatgatg tagaaggaga    540
cagtggaagc cagaggctat atcttccagg actattagag ctcattgtgg ggcatttgg    599
```

<210> SEQ ID NO 78
<211> LENGTH: 599
<212> TYPE: DNA
<213> ORGANISM: Homo sapiens

<400> SEQUENCE: 78

```
atttggattt tattctaaaa cctgaagtaa tgtaatatga agtagattaa cactatgtga     60
atatccaaga ggaattttac tacatatttg attactaggc tcatcttttt ttaacatata    120
tatgtatttt aaccttatac tcaaaattga cttagattta tataatagaa ttaatagag     180
gaagtgggag taggagtaga tggaattaga caaagtaaga agtaactttc ttgaagatgg    240
tagaatggca ctgtttactt ttgaaagata aagtacttct ttttacaata aaataaattm    300
catatgtcaa cagtattact catttgctat ctccattaaa gatgacataa aatacgtgtg    360
gagaaataaa gttactactt ggccttggta attgggtaat gacatagtac cagatgtaga    420
aagcatctgt gtagataaag cttgctgctc ttagatgaag taaataagac tgatgttgtt    480
gaaaaagatt aatcatgaga ttgaggatac tagaagggag gaaaatatta tttgtgcaga    540
aataaaatat agggttagaa tagagatgat aaggaaactt tgaggtcttc agggattttt    599
```

<210> SEQ ID NO 79
<211> LENGTH: 599
<212> TYPE: DNA
<213> ORGANISM: Homo sapiens

<400> SEQUENCE: 79

```
gtgtaattgg aaatggactt tttctttcca attatatact tctttatagt ttttaaaagt     60
ggctttatat aggtgatact gatagctata tatttatctt gtaaaagacc aatttaagtt    120
gttcattaga gccaataatt tgtcagctga ttctcatgag gtgtatataa ccaatctgat    180
ttgcgttctt ctgaaactgc ttatcaaata gatggccatt agcccctaaa tggcaaaatc    240
cactggacag ttttctgtat tgtactcagt aaggtctgac atattttgca tgtttgaccr    300
ctccttcatt tttaaaatag tttttttatt gccttcagtg aaacatgctc ttggttttcc    360
tcctatctca tttgctgttc tgtcatattt ctgtttgctg ttcttcctct cacttttctt    420
caaatattgg tgtactttt  tttcttttct agactccatt tttgtttaac cacactctcc    480
ctagatgatt ttatcaaatt ccatggatttt aaatatattt gtaagcacat tcaaaattag    540
tttgatttca accttgtgtt ttgtatctga atgataagca tcagcattat aactaaaca     599
```

<210> SEQ ID NO 80

```
<211> LENGTH: 599
<212> TYPE: DNA
<213> ORGANISM: Homo sapiens

<400> SEQUENCE: 80
ttattgcctt cagtgaaaca tgctcttggt tttcctccta tctcatttgc tgttctgtca      60
tatttctgtt tgctgttctt cctctcactt ttcttcaaat attggtgtac ttttttttct     120
tttctagact ccattttgt ttaaccacac tctccctaga tgattttatc aaattccatg     180
gatttaaata tatttgtaag cacattcaaa attagtttga tttcaacctt gtgttttgta     240
tctgaatgat aagcatcagc attataacta aacagactgt gtggttaaga ttatggacar     300
tttttccctc tagttatcta attttcataa ttaccccag aacgtgagaa cattattttt     360
atgatcagaa agtattttaa gaaactagtt gagtggactc taatatggaa ccatcaacat     420
gtatcaaatt ccacttaatt ataagcaaat tcattatgaa attatattta aaaaggcatt     480
tcatgattac atttgttatt taagaaaatg ttatttaaag aaatttacat aagtttcatt     540
atacatgtat tttagcttac tcattctgga aatggaaaac ttagatacta ggcaagaag      599

<210> SEQ ID NO 81
<211> LENGTH: 599
<212> TYPE: DNA
<213> ORGANISM: Homo sapiens

<400> SEQUENCE: 81
caggggctgg aattaacctg ctctgagtcc ctttagatgt gcatactctc tccgatttgc      60
cacagttccc accaattctt atttctcctc tctttacttg gcccacatca ttgggcctat     120
ctcattaatt tctattaaat attttattac tgaggccatt agtttatgac ccctgaggcc     180
aagacagctg ttaagaactt gcattactgg tggcaaaatt acctttac gattacttac      240
taggttttag aaatctcact tttctaacaa gaggtattat ggtaatcata agttcaaaak     300
aattaaagtt catttgagat aattaaatca aaacctctag tctgggttgg agggtgataa     360
agttatctgg cgaaatatat gaacttctgt taccttcctc ttctgctaaa tgaatggtaa     420
aatgaatcct gatttgttta ggcagtttac ttatgaagtt gggagaattt tttttttct      480
ttaaaggact gagtctggct ctgttgccta ggctcaagta ctgtggatct tggctcactg     540
cagcctccac ctcttggatt caagcagttc tcctgcctca gcctcccgag tagctggga      599

<210> SEQ ID NO 82
<211> LENGTH: 599
<212> TYPE: DNA
<213> ORGANISM: Homo sapiens

<400> SEQUENCE: 82
tgctctggag gggggatttg ttagccaaga agaggctgaa acatgagta gtgtactttg      60
ggagactaga aggacgaacg ttaaaagtat acgacctcca aggttgtgac tctggtagaa     120
ttctttggtt agagatcctg aaggacagca tcctagggat aatggtgaaa cagaagtaga     180
ccattcacat agagtgtagt ttagcattaa atcatcaagg tggattagta aattgtgaga     240
ttttggaagt ggactaaggt gaccttaggt ttctaatgcc cctaggaacc tgaaagatas     300
aaacctggag gaagaatatt ttcctaggcc tcaaattatt tgggtacttt ttcaaataca     360
gtatctccac atacccctgga tacaggagga gaaaggcgga atgaaaactg gcagaaacag     420
tagacccaaa ggggcaccaa ataattgcat tgtgaggtag actttaagta tgtttactgt     480
attcaaggag ataaagatg gaaaatttcc atatagaatt ggaaactata aaaaagtcac     540
```

```
tgcagatttg ttaaaaaaaa aaaaaagcca aatataaatt tgaaaacttg aaaaaccaa      599
```

<210> SEQ ID NO 83
<211> LENGTH: 599
<212> TYPE: DNA
<213> ORGANISM: Homo sapiens

<400> SEQUENCE: 83

```
agttccttgt cccatggacc tctcctttag gacagcttac aacctggcag cttgccagag       60
ggaacctata gagcccatag agtgagtctg ctaacaagac aactgaagag agaaataacc      120
aaactgaaaa tgagaaaaaa atatttagaa ttaatgtctt tgtaaacttt gactctatta      180
ctctgccatc accagtaagg gggaattgaa atatacccat gctgggaaac aatggaagta      240
gtgtggagaa aagtattaag gatatatttt aattgaatgt aggagcttag aaataaggay      300
agtattaggg aagaatggat tattaaacta gatatttagg aatcctcttc atacttattc      360
aggacaccag tgggtaccca atctgtactg gttttactga tctttgtgca atttgctgct      420
cagcagatat tttcaatgct gattggtaat atgtcagtgg ataaccagtg gaaatgcatg      480
tctattaatt actattgcac ataatattta tcttgttttt atattttgca caggattttc      540
aaggtgctgg tatatttctg agcactgtaa agttttcttt gagaaataag tgtttatttt      599
```

<210> SEQ ID NO 84
<211> LENGTH: 599
<212> TYPE: DNA
<213> ORGANISM: Homo sapiens

<400> SEQUENCE: 84

```
tggtatattt ctgagcactg taaagttttc tttgagaaat aagtgtttat ttttaaattg       60
cgttgtctca tgggagggta acatttgtaa atatacttca aattagtgtt gttccctctg      120
cttttctttt cctgactcag aaacagagtg cttttgactgc tctatgttgg ggccatgttt      180
tccgcagact tgaacccaag ccaggccctt gaatgttccc aggcacggat aaacttgttt      240
agactggctg aaacaccaaa acatcaaacg tgttgctaaa catgtaaata ctagccccaw      300
ccctgaaccc aattccttaa gcccccatat aaactccata tccgattccc catatctagg      360
ttagaacgtc tcttttctcc ctgtcaatca tgaggactaa tgcagcacac aatgtataca      420
gtactaataa aggctttgga cttaccactt ccttctttga aatcccaact ggtcgcatct      480
taggttggtt tggggcagtc ccttgtggga actctcctgc tattctgtct ggttttgggc      540
cttactgcag ttgtggtttt gggtggttgg aacaagcata tatttcaata aatacgtttt      599
```

<210> SEQ ID NO 85
<211> LENGTH: 599
<212> TYPE: DNA
<213> ORGANISM: Homo sapiens

<400> SEQUENCE: 85

```
ccagttgaaa ctggactttc agatatagca atggtttttt tctaaagaaa tcctgtcaac       60
attaaagagg ttttctccat tgtaactaaa ctgaacaaag acagaaagct tatgggacaa      120
actaaaactg gctctcgacc cgcagttgtg tcatgttgtt ttttggacat ttaaaaaacg      180
tatttattga aatatatgct tgttccaacc acccaaaacc acaactgcag taaggcccaa      240
aaccagacag aatagcagga gagttcccac aagggactgc cccaaaccaa cctaagatgy      300
gaccagttgg gatttcaaag aaggaagtgg taagtccaaa gcctttatta gtactgtata      360
cattgtgtgc tgcattagtc ctcatgattg acagggagaa aagagacgtt ctaacctaga      420
```

```
tatgggaat  cggatatgga  gtttatatgg  gggcttaagg  aattgggttc  agggttgggg      480
ctagtattta  catgtttagc  aacacgtttg  atgttttggt  gtttcagcca  gtctaaacaa      540
gtttatccgt  gcctgggaac  attcaagggc  ctggcttggg  ttcaagtctg  cggaaaaca       599
```

<210> SEQ ID NO 86
<211> LENGTH: 599
<212> TYPE: DNA
<213> ORGANISM: Homo sapiens

<400> SEQUENCE: 86

```
atgagaacgt  tgagttactt  atcactgact  acttaagggg  acatttgcct  atttatttac       60
aatgctttgc  agaagtatcc  agtaacattt  atgaatttat  ttgtatatat  caaatattat      120
cttatgttct  aatgaatttt  atccatttca  ggtagagaat  ggattattct  gaaaactaga      180
ttttcatata  attttgtttt  tagtttcatt  ttcatttttta aaatataaga  ttttttgttat     240 tgctataaaa  tacatgatca  ttacaaaaaa  tctgaaaaac  agtagggaag  ataatctcay      300
gctgttaacg  ttttggtata  tcttttatct  atagattttt  gttgatattt  tgttttttcag    360 gtcatactat  agataaaggt  ttttacattt  gtatttcata  atcactttc  ctcattatac       420 atttcagtat  tccataagta  gtctttgggg  gtattttgta  gataattgaa  tataaaatta     480
ttgtaaaatt  aaacactaac  aaatacataa  acatgaaatt  ttcatcagtt  cacactcatt     540
acagggagaa  aaggaatcac  aactttttc  tattattaaa  aaaacccaag  catgataat       599
```

<210> SEQ ID NO 87
<211> LENGTH: 599
<212> TYPE: DNA
<213> ORGANISM: Homo sapiens

<400> SEQUENCE: 87

```
gtcatttaat  tttcaaaaca  actctccaaa  ggaagtgtca  ctctccttgt  ttgatttctt       60
gcttcccaaa  tggaaggtcc  tttgtattaa  tagtatctgt  caaatttcat  acaatactta      120
aatatgttct  tgatacgtac  ttcaatataa  ccaacagaat  gaggcagtat  tcgataaagt      180
aaaaaataag  atgaatattt  ctagtgattt  ataagttact  tgaggaaatc  atgctgttta      240
ttcttttcct  ttttaggtat  tcttttgtgaa tttgctattt  gtgtgtgaat  atatctgttk     300
cgataatgaa  taaccatatg  aaatggataa  ttgtatgaaa  attcatttgt  aattcaatag      360
attgccaggg  attttaggtt  ggttatgaag  gtttgttttt  tttttttttt  tcttttggag      420
agtggggaga  ttggcataca  gtttcaaatt  gtttatgtgg  aagttggaag  tgtgactaag      480
ctcgaagaaa  ggaagagagg  gacaaagaaa  gggaggaggt  accccctaagt gggaacctac    540 caggacattc  aaagcaagag  cagtaagttc  tgaatgttct  gggacaacct  gggtgatat      599
```

<210> SEQ ID NO 88
<211> LENGTH: 599
<212> TYPE: DNA
<213> ORGANISM: Homo sapiens

<400> SEQUENCE: 88

```
aggtttgttt  tttttttttt  tttcttttgg  agagtgggga  gattggcata  cagtttcaaa       60
ttgtttatgt  ggaagttgga  agtgtgacta  agctcgaaga  aaggaagaga  gggacaaaga     120
aagggaggag  gtaccctaa   gtgggaacct  accaggacat  tcaaagcaag  agcagtaagt     180
tctgaatgtt  ctgggacaac  ctgggtgata  tgcatggata  tgggctgtgg  aggctgagca     240
ttttaatgat  aacttaggga  aacgaggcat  ggccatggtg  taaaactctc  aaatcccaas     300
```

| | |
|---|---|
| ccctaatcca accttaaaat ccgagtcttc taaagggctg ttttaaccat gaaaggacca | 360 |
| taagaaaggc aattcacaga aaatgaagcc atgtggccaa gaaatataag aaaaacagta | 420 |
| aaagccctta atctcaatag caatagagtg gatgcaaatg aatataatga gttgccatgt | 480 |
| cgttcttact ggattgggaaa agaaattaga atgtctaaat aacatgtatc atccaggatg | 540 |
| tggggaaatg ggagctcttg taccctgcag gcaggcattt aaattggtgc aaccgctttt | 599 |

<210> SEQ ID NO 89
<211> LENGTH: 599
<212> TYPE: DNA
<213> ORGANISM: Homo sapiens

<400> SEQUENCE: 89

| | |
|---|---|
| atgtatcatc caggatgtgg ggaaatggga gctcttgtac cctgcaggca ggcatttaaa | 60 |
| ttggtgcaac cgctttggat tgctgctttg tagtatctgg tgcaactgaa gatgaacatg | 120 |
| ccctgtgaca cagcaaccgc acttctaggt caatacccta attatattct tactgtggtt | 180 |
| cacaagaagg tatgtaagag gtcattgcct gagcactgtt tagaataggg caaactgga | 240 |
| aatcctctaa atgtctgtca atgaaggaat agataaattg taatatgttc atataaaatr | 300 |
| ctgcataaat aagtgaaatt tataaatata ctaacgaatg aatcttgaaa acagagttgg | 360 |
| gagataaaag caagctgttg aagaacatgg tcagtatcct ctcacttatg taagttaaaa | 420 |
| actccaaaga acattatcta tattggtaat ggcatagaca tgtgtggtaa aatataaaaa | 480 |
| tattaactaa aagttctata cgcttcagga tattgttagt ataataaggc aggaagtgga | 540 |
| tagcattggg gtgagacagt ggtttggtgg ttatgtttgg ttactttagt tatgttagt | 599 |

<210> SEQ ID NO 90
<211> LENGTH: 599
<212> TYPE: DNA
<213> ORGANISM: Homo sapiens

<400> SEQUENCE: 90

| | |
|---|---|
| gagctcttgt accctgcagg caggcattta aattggtgca accgctttgg attgctgctt | 60 |
| tgtagtatct ggtgcaactg aagatgaaca tgccctgtga cacagcaacc gcacttctag | 120 |
| gtcaataccc taattatatt cttactgtgg ttcacaagaa ggtatgtaag aggtcattgc | 180 |
| ctgagcactg tttagaatag ggcaaactg gaaatcctct aaatgtctgt caatgaagga | 240 |
| atagataaat tgtaatatgt tcatataaaa tgctgcataa ataagtgaaa tttataaatr | 300 |
| tactaacgaa tgaatcttga aaacagagtt gggagataaa agcaagctgt tgaagaacat | 360 |
| ggtcagtatc ctctcactta tgtaagttaa aaactccaaa gaacattatc tatattggta | 420 |
| atggcataga catgtgtggt aaaatataaa aatattaact aaaagttcta tacgcttcag | 480 |
| gatattgtta gtataataag gcaggaagtg gatagcattg gggtgagaca gtggtttggt | 540 |
| ggttatgttt ggttacttta gttatgttag taacattttt tttttaaaga aggatctgg | 599 |

<210> SEQ ID NO 91
<211> LENGTH: 599
<212> TYPE: DNA
<213> ORGANISM: Homo sapiens

<400> SEQUENCE: 91

| | |
|---|---|
| cagtatcctc tcacttatgt aagttaaaaa ctccaaagaa cattatctat attggtaatg | 60 |
| gcatagacat gtgtggtaaa atataaaaat attaactaaa agttctatac gcttcaggat | 120 |
| attgttagta ataaggca ggaagtggat agcattgggg tgagacagtg gtttggtggt | 180 |

```
tatgtttggt tactttagtt atgttagtaa catttttttt ttaaagaagg atctggaata    240
attatggtaa aataatagta tttgctaaga ctagatgatt ggtgtactgg atttcatccr    300
ctatttctta agtttgttat gaacgcttaa aatatatatg tatgtagtaa aattaatgta    360
aatttgtaca aataaaaata aatggcatgt gatatatggc agaagctgtg tgtgtgtatg    420
aaaagcaaag gcaggcaggg caagtttctg ggtagcataa acatggaaca atcctaggaa    480
tatgaaattg acctaaatat accagctttc tggagattcc acagtcccag atgattgatg    540
atctaataca attttctagt tttattgata ataggagcaa gaagggttaa gtgactttc     599

<210> SEQ ID NO 92
<211> LENGTH: 599
<212> TYPE: DNA
<213> ORGANISM: Homo sapiens

<400> SEQUENCE: 92
aatattaact aaaagttcta tacgcttcag gatattgtta gtataataag gcaggaagtg     60
gatagcattg gggtgagaca gtggtttggt ggttatgttt ggttacttta gttatgttag    120
taacattttt tttttaaaga aggatctgga ataattatgg taaaataata gtatttgcta    180
agactagatg attggtgtac tggatttcat ccgctatttt ctaagtttgt tatgaacgct    240
taaaatatat atgtatgtag taaaattaat gtaaatttgt acaaataaaa ataaatggcm    300
tgtgatatat ggcagaagct gtgtgtgtgt atgaaaagca aaggcaggca gggcaagttt    360
ctgggtagca taaacatgga acaatcctag gaatatgaaa ttgacctaaa tataccagct    420
ttctggagat tccacagtcc cagatgattg atgatctaat acaattttct agttttattg    480
ataataggag caagaagggt taagtgactt tctccaagtt gcacatacat aagtggtaga    540
gctcagtcta gaatccaagt gttctgagtc ctgtccagtg ttgttcttcc tacattgct    599

<210> SEQ ID NO 93
<211> LENGTH: 599
<212> TYPE: DNA
<213> ORGANISM: Homo sapiens

<400> SEQUENCE: 93
aataaaaata aatggcatgt gatatatggc agaagctgtg tgtgtgtatg aaaagcaaag     60
gcaggcaggg caagtttctg ggtagcataa acatggaaca atcctaggaa tatgaaattg    120
acctaaatat accagctttc tggagattcc acagtcccag atgattgatg atctaataca    180
attttctagt tttattgata ataggagcaa gaagggttaa gtgactttct ccaagttgca    240
catacataag tggtagagct cagtctagaa tccaagtgtt ctgagtcctg tccagtgtts    300
ttcttcctac attgctgcaa atgagtcctt catgtatagc tcatgacttg cataaggtag    360
ataattttgt gagctgttct ttacagattc cctttattt tatattctac gaggtctatc    420
tatagcaaaa ggcatttaga agtggtgtta atattagcat gcccaaagta actctgagat    480
gatatcattt acttccatat gggaattttc cagttagtat caagcttgag attcaagtgg    540
aaattagctt tcaggaattt ttgcaatata aaatttatta tgtgttgacc tacttctgt     599

<210> SEQ ID NO 94
<211> LENGTH: 599
<212> TYPE: DNA
<213> ORGANISM: Homo sapiens

<400> SEQUENCE: 94
acatgtgtac ctgaacaata tttcagcctc tctcttcagc cagaatttgc tcctgagagg     60
```

-continued

```
caaattcata tctccagaca tctctacctg aacatcccaa atatgctcat aatcaacatg    120
ccccaaactg cattcatcag cttttttgtcc ttttcaatat tcccaaacca agggttggca    180
ctactacttg catagtcttt caatctagac acctgggagt catttttttac tttcattctt    240 cccttcccat actcagtcag tcaccaagtc ttgcagattc ccaaagatgt ttccaactcm    300
ccattcattt cttcccttat caatattttaa cttatttcag atccccatca tggctcccct    360
ggacaattcc aagggtcttc taaggttcct tactcacagt ctcattaccc tctagtcagc    420
cttcacaatg caatcagaaa gatccttgtg gcatacaaac cttttccccc tgaatgaaat    480
ccatgcttct aaccaagcca tgcaagactt cttgttttct ttctagccta aagtcttgtc    540
attctttacc tcctatgatt tagcaatcgt gatggagttg actttcacta aatgcacca    599

<210> SEQ ID NO 95
<211> LENGTH: 599
<212> TYPE: DNA
<213> ORGANISM: Homo sapiens

<400> SEQUENCE: 95
gtttactttg tgtcaattgg aaagtgttat atttactcat tgaatcccag ttttggaaag     60
aagatatgat gggctgccat aatttctcag taggattggg aaaaataaca atgcataaat    120
attcacattt tccttcactt ccctatcctt gcttggctct gagcaattca ttgcattggt    180
cattttacta gtcaggattt tgatataagt aggtatgaag tggcagagcc aacaaaaccc    240
ccacaaaact atattactta tatgaagacc ggcaaattct atgcttgggg ggaaaaagay    300
ttggaaaaaa atgaggaaaa ggagaaatag aaaagactaa gagtggtctg aattttcata    360
gaaagttttg cagagggaga acaatgaat gagaaagggg gaggggcaa attaaccaat    420 aactaggtgc gagatcccag gcaggggccc ttactgtgat gattgactat gggaggtggg    480
tgtgcacagc agattttttag gatattttgc agtgcatcat gcactaatca ctgttggcat    540
ttttgaagaa aatacagaaa aataagttga ttttcacttt tggattgagt tcctcctgc    599

<210> SEQ ID NO 96
<211> LENGTH: 599
<212> TYPE: DNA
<213> ORGANISM: Homo sapiens

<400> SEQUENCE: 96
gtcttgtgcc tttgcacact tttttacatg cacgtaacca aggatggctt caagatcatg     60
gcccaattat taatcgagaa aaagggatac ataaagtaag agcatgatgg tgcttatcct    120
agtggagact tctcccttgg ttgccatagt cattgactaa gcacttcgtg ggaataaatg    180
ttccaatagc agagacttcc accattagca gaaccatcag ctcatatttta tttcactgca    240 tatttcactc gattacttga aaagacatat ttttagagat aaactacact gggacagatm    300
tcataacacc gtagttttttt ttgctaattc acatatatta tttctggcct ttccagatat    360
aaaatagaat aattatggca aggataattg ccacaacttt aagaaaagg aaacccgaat    420 ttaagaggga ttaaataatt tgcttgaggc tacataataa ggggaaccca aacccaaaag    480
ggacacaaac ccaaatgttt ccagttctga gcccatcatt ttttctaaaa cgttacaata    540
aatcctaaat atattttgat taaaaattat aaatgtatat tttgacaaaa tgtggtcca    599

<210> SEQ ID NO 97
<211> LENGTH: 599
<212> TYPE: DNA
<213> ORGANISM: Homo sapiens
```

<400> SEQUENCE: 97

```
tcactgcata tttcactcga ttacttgaaa agacatattt ttagagataa actacactgg    60
gacagatatc ataacaccgt agtttttttt gctaattcac atatattatt tctggccttt   120
ccagatataa aatagaataa ttatggcaag gataattgcc acaactttaa agaaaaggaa   180
acccgaattt aagagggatt aaataatttg cttgaggcta cataataagg ggaacccaaa   240
cccaaaaggg acacaaaccc aaatgtttcc agttctgagc ccatcatttt ttctaaaacr   300
ttacaataaa tcctaaatat attttgatta aaaattataa atgtatattt tgacaaaatg   360
tggtccatca gaacagtgaa agaatgctgt gcacagtagg caaatacgtt aattttttcc   420
aaatctgtat tgatacatca gtcaaatgca tgtaggagac aaagcagcct ataatgttta   480
acacagccag tgtggaaaga ctacctaaaa atgctgggaa aattattatt ttactaggaa   540
acatactctt cacctccatt tgtctttgga gacatagcac aagaaatttg cctgaggag    599
```

<210> SEQ ID NO 98
<211> LENGTH: 599
<212> TYPE: DNA
<213> ORGANISM: Homo sapiens

<400> SEQUENCE: 98

```
taataagggg aacccaaacc caaaagggac acaaacccaa atgtttccag ttctgagccc    60
atcatttttt ctaaaacgtt acaataaatc ctaaatatat tttgattaaa aattataaat   120
gtatattttg acaaaatgtg gtccatcaga acagtgaaag aatgctgtgc acagtaggca   180
aatacgttaa ttttttccaa atctgtattg atacatcagt caaatgcatg taggagacaa   240
agcagcctat aatgtttaac acagccagtg tggaaagact acctaaaaat gctgggaaaw   300
ttattatttt actaggaaac atactcttca cctccatttg tctttggaga catagcacaa   360
gaaatttgcc tgaggagcaa ttttgtgaag caaagatgc agacaaattt taaggaagcc   420
acaagaggct agggaagaaa aatgcccaag gaaatgtcaa taaaacaaat gtatttaatc   480
tctgaatggt tatttaaatg gaacttttct tctactttga agcttaataa cagtttattg   540
ttttaaaaaa tctatcttga ttatgcataa tgacagggta tatatctttg ttcaatttc    599
```

<210> SEQ ID NO 99
<211> LENGTH: 599
<212> TYPE: DNA
<213> ORGANISM: Homo sapiens

<400> SEQUENCE: 99

```
tcttaacggt tctccatata ggaaaaatgt cttttgagga agtagcaatt tgagctggga    60
cctgaatgca aaagtagat ggattcattt ccagctgaga aaagaacata aggaaaggca   120
tgaagtctta cctggcacag cagagaattt tgtggataat ttttaaacat tgtcaatatc   180
tgggtcccca aagggaaagg atacaataaa gatattaaaa atagaatggg aatgtggatt   240
ttaacaggat ttgtgacaat catagctaac aatggcttcc ttgaaaaaat tgagtaatay   300
tgcagtttac ttaataatac attacctcat ttaatccaca tagatgcaat gaagtgtgtg   360
ctataattag cacaatttta tagtgaagga aactaatatt tagagagttg gaaatttgaa   420
tactgatctt cttcctcca gagcactagc ttttacatta aattgcttgg acaagccatg   480
acaccatctg gcatcctggg aatccaagtc ctatttctca cattgcttcc acaagaaaat   540
aggttataac ttccaaaaaa ttaactttca aataaacttc taaaacacaa cctatttaa    599
```

<210> SEQ ID NO 100

```
<211> LENGTH: 599
<212> TYPE: DNA
<213> ORGANISM: Homo sapiens

<400> SEQUENCE: 100
tgcgctgtaa ggaaatgaat attttggagg ttatggcagt aaagtaagca aaattctaca      60
aggttctgtt gtacgtttat gatatagggg aagaaaaaga tcgcaaagat gttaaggagg     120
gtgaattaat tggctgtaag agacaaggaa gatggagcta tgctttcaga ttaattttag     180
gtactacata aataaaggtg acattcgctg agataaggat atagcaaaag agccatgtta     240
ttgtgaaaac aaaaggagag gggagatatt gtatgtgtgt aatatataaa attctaacay     300
gttgagtttg agctgtctga tggaagttaa gatattaagg gacatttgga tattaataca     360
tgtatctgag tattcaggac agagatatgg ttggcaattt gaattgggca cctttggttc     420
atacagagat agcactagaa atcataggaa gaaaggaaac aaaccaaaga tcatcaagcg     480
tgaaaagaca tgaaggacaa gaactacatc tgaagatgta cgatcaaatt gatgttcaca     540
gaaacatgtg cagccacatg tgtgagggg tggctggctt agcaatcatg aaaggaaga      599

<210> SEQ ID NO 101
<211> LENGTH: 599
<212> TYPE: DNA
<213> ORGANISM: Homo sapiens

<400> SEQUENCE: 101
ccaattaatt caccctcctt aacatctttg cgatcttttt ctttccctat atcataaacg      60
tacaacagaa ccttgtagaa ttttgcttac tttactgcca taacctccaa aatattcatt     120
tccttacagc gcagctcttt tccaatttat tttcatactc tactcatcca cagtggtctt     180
tctaacacac aaaccttgga ttctaaattt agctaacatt cctctgattc agtaagttcc     240
ttgagtttac cacatttgat tcaactttgt atctctaatt tctagatgaa tacaggatam     300
gaggaagact tactaattca ttctcttatt cattcattct ctttctattg aacaccttct     360
gtgatccagg aaccatgacc tatacggggt atcagatgta aataacacag atgaagcccc     420
tgttttgtga aagatcatg tgatatgaca gaaagtaaac agaagtggct atttacata      480 gttttatcag agaaggatcc tctttttgaca aaacattggg gttggactct taagggtggg     540
aaggattcag tcttgaaaaa caaaaggag acagtgtatc tggagcatgg tgggctaga      599

<210> SEQ ID NO 102
<211> LENGTH: 599
<212> TYPE: DNA
<213> ORGANISM: Homo sapiens

<400> SEQUENCE: 102
aaaagtcaca tcttacatgg tggcaggaaa gagagcttgt gcagggaaac tcccatttat      60
aaaaccatca gatctcctga aacttattcg ctacatcaag aacactattg ggaaactgcc     120
caaatgattc cattgtctcc cactgggccc ctcccatgac atgtgggggat tatgggaact     180 acaatttaag atgagatttg ggtggggaca cagccaaacc atatcaacat ctaaggcatg     240
tcctactggg caaaagactt ctgtcagcac tgggtctctg gtagtattag aattgctagr     300
cctggccagt ggatagaact actatgatag gtgagagatc caagactgat ttgagcagta     360
gccaaaaaga gagggatgg gcattgcagg ttgttgagga ggatcagcct gttttgtaaa     420
tgcagcaggt gattcaacca aaagtcactg aatacttgat accatctaaa gatttcacta     480
aatgatgggc catagttttt gacaagttag caaggcacag agaaaggaa tttaagaaca     540
```

-continued

| | |
|---|---|
| ggtattaata gagtaaaaat cacaaggact gacgttcagc cttaaggcgc ctgcataca | 599 |

<210> SEQ ID NO 103
<211> LENGTH: 599
<212> TYPE: DNA
<213> ORGANISM: Homo sapiens

<400> SEQUENCE: 103

| | |
|---|---|
| ctagctagat tgtgtttgct tattgtgttt actggtttat cttttattta tgtatgtcat | 60 |
| tttgttttat gttttactt tattctttct ttccaaggat tactgttaga cgtatgctag | 120 |
| aacttctcaa ggtattgttt ttgacttgtt ttttaagatt tctattttat ctttttggcc | 180 |
| tatattctag atgatttttt tctatatcat ctttgagttt actaattttt tcttcacaat | 240 |
| acttcagatt ggagtttgtc tcatacttat gttctcaatt tcagtgaatt aattttatcr | 300 |
| tttcttagga tttccagttt gttctttaaa tttatccatt cttgaatcat tacttaaagt | 360 |
| tgattttata atttattgtt ctgttttaat gaatgctttc tttcaattttt gctctgtaag | 420 |
| aatgttaaac atacttattt taaaaataaa aatgttttca cgttgcatat ttttatctta | 480 |
| tttgagataa attagtcagc ttttttattta tttatttatt tttacaggga ggattgcact | 540 |
| ctgttgccca actggagcac agtggcacag tcatagctca ctacagcact gaactgctg | 599 |

<210> SEQ ID NO 104
<211> LENGTH: 599
<212> TYPE: DNA
<213> ORGANISM: Homo sapiens

<400> SEQUENCE: 104

| | |
|---|---|
| agttctgctg tgttactgtg ctagagatga tcatcttatt ctatttctca gttatttatt | 60 |
| ttttcatttt tttacacttg cattttccat ttactgtgag ttagaagaaa cagatctcaa | 120 |
| aacacagagg tatataatgc gatattgtct acagcagcac tgtccaatat gcaatccatt | 180 |
| agacacatgt ggcaatttaa attaaaatta ttcaaaatta aataatattg aaaatttagg | 240 |
| ttcttagtct tattagtcac atttaagttc tcaatagcca gttagggttg ttagctaccr | 300 |
| ttcagaataa tgcagatata taacactttt atcttcatag acagttctct tgggtagctc | 360 |
| tagttcatgg tatgaaacta aatactgaaa agataaaaaa agagtctgca ggtatttaac | 420 |
| cttttgtgag gctattagaa gccctgaagc tcactgaatt aatacatata gttcctatttt | 480 |
| ctgtgggatc ggtggtgata tcgcctactc atctgacaaa gggctaatat ccagaatcta | 540 |
| caatgaactc aaacagattt acaagaaaaa aacaaacaac cccatcaaaa agcgggtga | 599 |

<210> SEQ ID NO 105
<211> LENGTH: 599
<212> TYPE: DNA
<213> ORGANISM: Homo sapiens

<400> SEQUENCE: 105

| | |
|---|---|
| acatatgttt atagtggcac tattcacgat agcaaagact tggaaccaag ccaaatgtcc | 60 |
| aacaatgata gactggatta agaaaatgtg gcacatatat accatggaat actatgcagc | 120 |
| cataaaaaat gatgagttcc tgtcctttgt agggacatgg atgaagctgg aaaccatcat | 180 |
| tctcagcaaa ctatcgcaag acaaaaaac caaacactgc atgttctcac tcataggtgg | 240 |
| gaactgaaca atgagaacac acggacacag aaggggaac atcacacacc gggtcctgty | 300 |
| gtagagtggg ggaaggggg agggatagca ttagggcata tacctaatgt taaatgatga | 360 |
| gttgatgggt gcagcacacc aacattgcat gtgtatacat atgtaacaaa cctgcatgtt | 420 |

```
gtgcacatgc accctaaaac ttaaagtata taaaaaaaag aaagaaaaaa gaaaagaaa       480 aaaattaata catataacaa gatatacaca gactatgtaa taattggatt gtgaatctat      540
acgttttctt ttcaacatgt ctgtagtagc gtactatgaa ttttcccctg aaatataat      599
```

<210> SEQ ID NO 106
<211> LENGTH: 599
<212> TYPE: DNA
<213> ORGANISM: Homo sapiens

<400> SEQUENCE: 106

```
aggggaacat cacacaccgg gtcctgtcgt agagtgggggg aagggggggag ggatagcatt    60 agggcatata cctaatgtta aatgatgagt tgatgggtgc agcacaccaa cattgcatgt    120
gtatacatat gtaacaaacc tgcatgttgt gcacatgcac cctaaaactt aaagtatata   180 aaaaaagaa agaaaaaga aaagaaaaa aattaataca tataacaaga tatacacaga     240
ctatgtaata attggattgt gaatctatac gttttctttt caacatgtct gtagtagcgk   300
actatgaatt ttcccctgaa atataatctt atagttttgc agccagaaca tctgggtgca   360
aattctatcc cttcccctca ctaacaattt catcactggc tagacaccta acttctctga    420
acttccactg tctcatttga aaattaggat aagagccgtt ttgccaactt tgtgtgatcc    480
ttgaaacgta gtatgttcta ttaaagtggt tttctcgatt aattaaaagt gttcctttttt   540 gtatttaaaa cttttttttt tttgagacgg agtttcgctc tttgttgccc aggctagag     599
```

<210> SEQ ID NO 107
<211> LENGTH: 599
<212> TYPE: DNA
<213> ORGANISM: Homo sapiens

<400> SEQUENCE: 107

```
gaaaaaagaa aaagaaaaaa attaatacat ataacaagat atacacagac tatgtaataa    60
ttggattgtg aatctatacg ttttcttttc aacatgtctg tagtagcgta ctatgaattt    120 tccccctgaaa tataatctta tagttttgca gccagaacat ctgggtgcaa attctatccc   180 ttccccctcac taacaatttc atcactggct agacacctaa cttctctgaa cttccactgt    240
ctcatttgaa aattaggata agagccgttt tgccaacttt gtgtgatcct tgaaacgtar    300
tatgttctat taaagtggtt ttctcgatta attaaaagtg ttccttttg tatttaaaac    360 tttttttttt ttgagacgga gtttcgctct ttgttgccca ggctagagtg caatggcgca    420
atcttggctc actgcaacct ccgcctctca ggttcaagtg attctcctgc cttagcctcc   480
tgagtagccg agattacaga catgtgccac cacgcccggc taattttgta tttttagtgg   540
agatggggtt tctctatgtt ggtcaggcta gtcttgaact cctgttctcc ggtgatcct     599
```

<210> SEQ ID NO 108
<211> LENGTH: 599
<212> TYPE: DNA
<213> ORGANISM: Homo sapiens

<400> SEQUENCE: 108

```
taattctatt tgaatattgg gaatattcat gtttagctat tttaatagag acttaatttt    60
gagtaaatga gaaagtgta ataacttcat tccaaaacag gtatgcctat ggataacctg   120 gttcttttgga ctagagggta ctaatgaagg taatggtggt gataatgatg gcattccact   180
gcagaatctc ccaattgtag gcttagtgga tgaggtatat gtatttccaa ccctcagcct   240
aatcaattta aacctatagt ttttttttttt cacagtgttt agcacccatc acacaataas   300
```

```
taattcattt ttattagaca tagtaagcca aactatgaag ctgaaagctg aagccatcaa    360
aaggatttgg ctctaatagt tgtatttgtc tttataaatg tacagttttg tcagtctttt    420 ttttttttg gtaaaacagc ttaacataaa cattttatc aagacattta cattttaaaa      480
taataaattt gttaacatt gtgctctatg tcaccataac aaaatatcta tattcattcc     540
tgaatcattt tatttactta ctagaaaaga gaatctctaa ttgtgtaata aaatgctaa     599
```

<210> SEQ ID NO 109
<211> LENGTH: 599
<212> TYPE: DNA
<213> ORGANISM: Homo sapiens

<400> SEQUENCE: 109

```
agatcggcag aggttacttt gtcaattgta aagatcccctt ttagagcttg cttgataaat   60
ggttattcag ccggagctta aaagttcaat cttgtgaata ttccttttcca tatttgtcag   120 agagcacttt tatgttgaaa tagaaaactg tctcttttcc tggtaaaact tctacactca   180
gaaacaatat agagtaaatt tgcttttta tatgccagat cttcaaattt tgaagaagtc    240
tcaattggta gagtatcatt attatgccta attgcttggg tgttgataat gctgtttttk   300
ttgttggtca gttaatagtc gaaaaggtta agactcaagt aattattaga acaaaagtac   360
atatcttggg aagctttatt ggtttgtcaa ctgtttctat gcaaaacgga aattaaaggt    420
aagaataaaa tgtgcaagaa aaatgtgaat tcataaattg tgaagcatga ggtgaacaat   480
gcttgctttt taccaccaga ggtcttcaaa agacctataa tagctgcatc tctgccagat   540
gaggaggaaa aaatctctag ctaagctgac agagattctt agcaagtaat ttgcttaag    599
```

<210> SEQ ID NO 110
<211> LENGTH: 599
<212> TYPE: DNA
<213> ORGANISM: Homo sapiens

<400> SEQUENCE: 110

```
gcaagaaaaa tgtgaattca taaattgtga agcatgaggt gaacaatgct tgcttttac    60 caccagaggt cttcaaaaga cctataatag ctgcatctct gccagatgag gaggaaaaaa   120
tctctagcta agctgacaga gattcttagc aagtaatttg cttaagagct taagtaactt    180
tagtatgaat gttctatagt cttaatacta aacattctg ctagatagat ttcaggcaat   240
gaaaacaaac aaaaacccca aaacaatgca gaaccaacct tcaaaatgca gaacagttay   300
aatgtatcat tttacatttt attttaattt attacctaat tattttagtt tatattggga   360
agcttctgat gctaattata atgatttaaa aacataaat attacataga agtggaaatc    420
cactatcatt tacataaatt taatgaatat actctgtatg tagattataa acatattgtg   480
tgtatgtatg aaatatccta attttgctgt taaatttaaa gcttaggaga caatgtgggc   540
taattccttt gacttatcct aaactatgat gaagcaaaga cagccaaaga ttttctatc    599
```

<210> SEQ ID NO 111
<211> LENGTH: 599
<212> TYPE: DNA
<213> ORGANISM: Homo sapiens

<400> SEQUENCE: 111

```
tggaaatcca ctatcattta cataaattta atgaatatac tctgtatgta gattataaac    60
atattgtgtg tatgtatgaa atatcctaat tttgctgtta aatttaaagc ttaggagaca   120
atgtgggcta attcctttga cttatcctaa actatgatga agcaaagaca gccaaagatt    180
```

| | |
|---|---|
| ttctatcaac ttggatgaac agtttcccgt ttggacttaa aaaaacaata aaaggacttt | 240 |
| agatgaactg atactagaac ctataataat atgcataata atttgagtag taacaatctk | 300 |
| atttcattag tattttgtat ttttatgtta cttacttaat tcaatactta tggagggcct | 360 |
| actatgtgtc tgctatttta ccaagtgatg gaatacataa aaattgcaat cacacctgac | 420 |
| aaaattcagt ttactgcaag aaaaaagaca aaaaattgca attcaacttt ataaatacca | 480 |
| cattaggaaa atggcaatca tatgggctgt gggaacccag tgagtgagtc cctaacttag | 540 |
| ggagaatcag aagatttcac caaagaactg acctaagaat gagatgctga gagagacac | 599 |

<210> SEQ ID NO 112
<211> LENGTH: 599
<212> TYPE: DNA
<213> ORGANISM: Homo sapiens

<400> SEQUENCE: 112

| | |
|---|---|
| aaaggacttt agatgaactg atactagaac ctataataat atgcataata atttgagtag | 60 |
| taacaatctt atttcattag tattttgtat ttttatgtta cttacttaat tcaatactta | 120 |
| tggagggcct actatgtgtc tgctatttta ccaagtgatg gaatacataa aaattgcaat | 180 |
| cacacctgac aaaattcagt ttactgcaag aaaaaagaca aaaaattgca attcaacttt | 240 |
| ataaatacca cattaggaaa atggcaatca tatgggctgt gggaacccag tgagtgagty | 300 |
| cctaacttag ggagaatcag aagatttcac caaagaactg acctaagaat gagatgctga | 360 |
| gagagacaca aggcattcat gcagttgggc aggggaatgt tccacggagg ggagagaata | 420 |
| ctagaaaatg ctgggaagtg gatggataaa tgtgcctcct agacctctaa cacaagctgc | 480 |
| tttgcttgct ctgtgtaaaa tgagttcagg aagtacatcc ttggctgttt tatattaaga | 540 |
| gagaggaaag ggctaatgtt gaaatataga gtcagtatat cgtaattctt ttctttttct | 599 |

<210> SEQ ID NO 113
<211> LENGTH: 599
<212> TYPE: DNA
<213> ORGANISM: Homo sapiens

<400> SEQUENCE: 113

| | |
|---|---|
| aatagatctc tttcatttgt ctcatgagtc tttgaaatga actatattag tgactgttag | 60 |
| ctgagttact ccaaacagaa aaaacaattc agtaatctta tgcttttgat gtcaacttga | 120 |
| cataaagtta aaatgaaaga gattgttatt taagagaaga ctttaagcaa gtttctttga | 180 |
| agtgcatatt tatttgtaaa gaaaacttat tttaggtcaa ttggaagaaa ccacattcct | 240 |
| ctgaacattc tctaatgtta ctgcattgca tacctgcaaa tagtggtagt taggaaaaay | 300 |
| tgggggagaa aggagaaaag ataaaaatgt ttcagaacaa catgttcatt tgattttaag | 360 |
| catatgcaga atatgcagaa aaatcttagc aaatattgta catgtcccctt agatgatgcc | 420 |
| aagtttctgc tccttttttca taaccagaaa acattttttt tctaaaccag tgtataaata | 480 |
| tccagataag atatttcagt gcatgataga aaattatatt ttgtctgatt attcctaggt | 540 |
| ataaaatgtg taaactgttt atcaccatgt ttgagttctc acaaattctt ggcaatgtc | 599 |

<210> SEQ ID NO 114
<211> LENGTH: 599
<212> TYPE: DNA
<213> ORGANISM: Homo sapiens

<400> SEQUENCE: 114

| | |
|---|---|
| atgaaagaga ttgttattta agagaagact ttaagcaagt ttctttgaag tgcatattta | 60 |

```
tttgtaaaga aaacttattt taggtcaatt ggaagaaacc acattcctct gaacattctc    120
taatgttact gcattgcata cctgcaaata gtggtagtta ggaaaaattg ggggagaaag    180
gagaaaagat aaaaatgttt cagaacaaca tgttcatttg attttaagca tatgcagaat    240
atgcagaaaa atcttagcaa atattgtaca tgtcccttag atgatgccaa gtttctgcty    300 cttttttcata accagaaaaa cattttttc taaaccagtg tataaatatc cagataagat    360
atttcagtgc atgatagaaa attatatttt gtctgattat tcctaggtat aaaatgtgta    420
aactgtttat caccatgttt gagttctcac aaattcttgg caatgtccca agttctattt    480
gacaagtttc tgtattgaga actccaaggc tgccttggag atagatgtaa atctctttga    540
taatttacag atttccacac aggttatgaa ataatttcta tggtcctgtt cacctatat     599
```

<210> SEQ ID NO 115
<211> LENGTH: 599
<212> TYPE: DNA
<213> ORGANISM: Homo sapiens

<400> SEQUENCE: 115

```
aaaggagaaa agataaaaat gtttcagaac aacatgttca tttgatttta agcatatgca     60
gaatatgcag aaaaatctta gcaaatattg tacatgtccc ttagatgatg ccaagtttct    120
gctccttttt cataaccaga aaacatttt tttctaaacc agtgtataaa tatccagata    180
agatatttca gtgcatgata gaaaattata ttttgtctga ttattcctag gtataaaatg    240
tgtaaactgt ttatcaccat gtttgagttc tcacaaattc ttggcaatgt cccaagttcy    300
atttgacaag tttctgtatt gagaactcca aggctgcctt ggagatagat gtaaatctct    360
ttgataattt acagatttcc acacaggtta tgaaataatt tctatggtcc tgttcaccta    420
tattgcttac ctcttccct cctcaccatc tgtcaaaatc ctaccattca ttttgaactt    480
tgttcaagcc ctattatatt cgtgaagact gttttgatca tagagcctga caagatccct    540
ccttcctctg ctctcccata gcattgatta ccaagtccac tcatgtgctc tgtattttt     599
```

<210> SEQ ID NO 116
<211> LENGTH: 599
<212> TYPE: DNA
<213> ORGANISM: Homo sapiens

<400> SEQUENCE: 116

```
attcatggtg atagagagta gaatgatggt taccagaggc cagaaaggat agtgggaagg     60
cagcaataaa gagggatgg ttagtgggta caaaaataga gttagagaga agaaataaaa    120
tctagtgttc agtagcacaa tagggcaact agacttaaca atttattgga tatttcaaaa    180
taactaaaag agtggaattg gaatattctt accacaaaga agtaataggg tgatatgtat    240
cccaattacc ctgatttgat ccttagcaat catatgcttg tgtcaaaata acacatgtas    300
tccataaaca tgtactatta tgtaaccata taatcttaa aaaattaaag tcatggtgaa    360
atatattcct tctttggaac aaccacccaa atgtgagaaa aatcatgttt gcatctagaa    420
atgatggagg aatatccaga tcaatataca tatgtctcac aagcaaggaa ttaaaatcaa    480
tgtaagtata aatacctgta tgttctatga ttttatttta tttatttatt tttgagtaaa    540
aatggggaag gcagtaaaaa gaccttttta gtttatctct aaacttttca atactttta     599
```

<210> SEQ ID NO 117
<211> LENGTH: 599
<212> TYPE: DNA
<213> ORGANISM: Homo sapiens

```
<400> SEQUENCE: 117 ggatttctt  ttagggttga  aactcagttc  aacaggaaac  agactgactg  attcagaact    60
gcaagaaacc  ttgaggcaaa  aaaattcaac  tccatgccat  cattttactg  atgcataaaa   120
agctgacatt  cagtatagtt  acacggttta  tctagtctat  gggagagaca  caggtctcct   180
aattctcagg  gcggtggaat  tctgtgaccc  actgcatctt  aatgagatgc  tgaaatcaaa   240
cagttatgaa  gttgattgac  aatttttttt  tgtaatttag  tgaccaggtt  gatttggaay   300
tgtctttact  aattcatttt  ttgaaatgct  attattaata  tggagaccat  gaaaaattga   360
aaaatgccgt  ttaatatagg  agcacagata  ctgttgtaca  tcaatactgg  cttcagtctc   420
ccttaccagc  ttcacgctgg  ttcattctga  aacttgccat  acacatcatg  gctctacgac   480
ttagccccct  gtactccttt  atctggaatc  tttccacatc  ttgactgcct  ggaaaaaatc   540
ttacttatcc  tcccttttat  gtgtcttagc  cttacccaca  ccttccctcg  ctttggcag    599

<210> SEQ ID NO 118
<211> LENGTH: 599
<212> TYPE: DNA
<213> ORGANISM: Homo sapiens

<400> SEQUENCE: 118
tctaatttga  gaacttctaa  taagaaagcc  agtgactagt  ataaattata  aatctttata    60
tcactataat  tttggtagat  ccaaggttta  atatagtatt  acatatatgg  aacagatctg   120
tcataaataa  aatgtaactg  ctcctattta  tagaatgaat  tcacatgcaa  acacttcata   180
aagctgtttt  ctcttcacaa  ctaagaaaga  tggaaagcca  aacgtcagct  gtaggatatt   240
taattaaata  gattatattt  gttttcattg  gtacgctccc  aaaaattaag  cataattcaw   300
aacacattgg  gctttagag   atattgtctt  ctggtccta   catagagtta  tataatacc    360
agctgtttgt  tattaatcac  agtttgtaat  ggctcaagag  tttattctgt  actgcttaaa   420
acagcaaaaa  tgcaatgatt  ttttgttagt  ttgttttta   gagtgaacaa  attttggata   480
tctgaaactg  ataaatcagc  attacaattc  cttaatgggg  agcttttgct  ttcccaatgt   540
ctaaaatcag  tgaaacatct  gtaaatatgc  ttatattgag  cttgacagac  ccctttat    599

<210> SEQ ID NO 119
<211> LENGTH: 599
<212> TYPE: DNA
<213> ORGANISM: Homo sapiens

<400> SEQUENCE: 119
acataatcta  taactaaaat  gatgattagg  tggtatacat  gagctccttc  cttagagatt    60
tccaatggtg  caggagacag  gtgcagaagt  atcccagaat  ccaagattct  ttatatggaa   120
tttctaaaag  gtctgctatt  tttctttttt  cttttctttt  ttttttttt   ttttgccatt   180
tcagcattta  caaaaatgat  ctgtcatttc  agtagcccta  gtggagacca  cattgccaag   240
gaatggacct  caatattatt  ctctttatct  ttgcactgct  ttactcccag  aacccaagty   300
cttgtgtatt  tgtgcatttg  tgcatagcta  agttaaggtt  atcctatcct  aaatgtgctg   360
attaatatat  taaatatgat  atttctttcc  tccttttta   tttttgaag   gtgaagtatt   420
tctcaaacaa  atcatcacct  ttattcaggg  gaaatgcata  tactatagcc  aattaaatgc   480
tactacagat  gcaccatgaa  attttcagtt  catgtgaggc  atagctacat  tcctttagta   540
gacattctgc  cccttcccaa  gaaacaagt   ttctttgaat  gcttctaaga  cagaagagt    599

<210> SEQ ID NO 120
```

```
<211> LENGTH: 599
<212> TYPE: DNA
<213> ORGANISM: Homo sapiens

<400> SEQUENCE: 120
aggtggtata catgagctcc ttccttagag atttccaatg gtgcaggaga caggtgcaga      60
agtatcccag aatccaagat tctttatatg gaatttctaa aaggtctgct attttttcttt   120 tttcttttct ttttttttt ttttttgcc atttcagcat ttacaaaaat gatctgtcat      180
ttcagtagcc ctagtggaga ccacattgcc aaggaatgga cctcaatatt attctcttta    240
tctttgcact gctttactcc cagaacccaa gttcttgtgt atttgtgcat ttgtgcatar    300
ctaagttaag gttatcctat cctaaatgtg ctgattaata tattaaatat gatatttctt    360
tcctcctttt ttattttttg aaggtgaagt atttctcaaa caaatcatca cctttattca    420
ggggaaatgc atatactata gccaattaaa tgctactaca gatgcaccat gaaattttca    480
gttcatgtga ggcatagcta cattccttta gtagacattc tgccccttcc caagaaaaca    540
agtttctttg aatgcttcta agacagaaga gtaaaaacag atttgcacag ataactaaa    599

<210> SEQ ID NO 121
<211> LENGTH: 599
<212> TYPE: DNA
<213> ORGANISM: Homo sapiens

<400> SEQUENCE: 121
ttcctttagt agacattctg ccccttccca agaaaacaag tttctttgaa tgcttctaag     60
acagaagagt aaaaacagat ttgcacagat aactaaaagt gtgtttccaa atgtccacag   120
cttaccaggt tatagtacct aggtcattca attctttcct tgtagctact tcttgactgg    180
gaagtgggtt tttgtttttt gttttgtttt ttcatgtaga acataagatg ttacattgtt    240
ttactaaaac atcgcataag tcaatgaaaa ctaattccac gggacaagtt cccaaggaam    300
agatccggag actctgagat tttcatgtag gtttgttggg aatggctctt gggaacacct    360
aggaaaagtg atcgaggcaa tgttgagcag gagaagctga gctatgatgc agttgcagta    420
gtggtctcag acaatcctac aagaagtttt ccttctggga tggcccttca gagtttttat    480
gtcttgaggt aaggggccag gcttttacac tcctatatct accagtcatt tgatgcaagc    540
cacgcttggt ggggaccaga cagagtaact ttgagccact tgctctctg gctgaggcc     599

<210> SEQ ID NO 122
<211> LENGTH: 599
<212> TYPE: DNA
<213> ORGANISM: Homo sapiens

<400> SEQUENCE: 122
gctgtcaaca ctcccaacaa tggaaaaaaa agtccttaac tcctgaggag ggaatctgag     60
cagggcacta cagtgttcac tacaaggagg tgcttaactt ttgctacagt agtcttgtaa   120
tgctaatagt gaacgataat taacttgggt gttacataga atactaaaac ttttaagta   180 aactatgtat tatcagtcat ggctaacatc tgaattattc tgtagcatgg ttgtcttat    240 ctttagaaat ctaaaatgcc agcctctaat ttccagctga gaccctaggg aggttagagy   300
tcagattatc attagcttta atgagaataa tttgtatgga atcccatatg ttagtgaaag    360
aatataaaca tctccacata ttgagctttg aatatccctt tgtttacttc agcctttaaa    420
tgaatacaaa attgttttgt ttacagagtt tttatcaaaa taacgttgaa gattttttcat  480 gttttgtttt attcctaata gactttcaaa tatattagta taagatcagt attttaaaat   540
```

```
gttttttatta atctaagtta aaaattatag gtaaggaaga gttacacttt ctattatgt      599
```

<210> SEQ ID NO 123
<211> LENGTH: 599
<212> TYPE: DNA
<213> ORGANISM: Homo sapiens

<400> SEQUENCE: 123

```
aaaactttt aagtaaacta tgtattatca gtcatggcta acatctgaat tattctgtag      60
catggttgtc tttatcttta gaaatctaaa atgccagcct ctaatttcca gctgagaccc    120
tagggaggtt agagctcaga ttatcattag ctttaatgag aataaatttgt atggaatccc   180
atatgttagt gaaagaatat aaacatctcc acatattgag ctttgaatat ccctttgttt    240
acttcagcct ttaaatgaat acaaaattgt tttgtttaca gagttttat caaaataacr     300
ttgaagattt ttcatgtttt gttttattcc taatagactt tcaaatatat tagtataaga   360
tcagtatttt aaaatgtttt tattaatcta agttaaaaat tataggtaag gaagagttac   420
actttctatt atgtaataca gctaaaattc taaggtgaaa atggatgtat tttgaagata    480
tattcagagt gaaaagaag acagtaattg agtgatatac atcttgatgt ttattgacaa    540
agtgactgcc atggcaaaaa taatccaga tgtttgagta taaaagaatg gcaaagtgg     599
```

<210> SEQ ID NO 124
<211> LENGTH: 599
<212> TYPE: DNA
<213> ORGANISM: Homo sapiens

<400> SEQUENCE: 124

```
tatgttagtg aaagaatata aacatctcca catattgagc tttgaatatc cctttgttta     60
cttcagcctt taaatgaata caaaattgtt ttgtttacag agttttatc aaaataacgt    120
tgaagatttt tcatgttttg ttttattcct aatagacttt caaatatatt agtataagat   180
cagtatttta aaatgttttt attaatctaa gttaaaaatt ataggtaagg aagagttaca   240
cttttctatta tgtaatacag ctaaaattct aaggtgaaaa tggatgtatt ttgaagataw  300
attcagagtg aaaagaaga cagtaattga gtgatataca tcttgatgtt tattgacaaa   360
gtgactgcca tggcaaaaat aaatccagat gtttgagtat aaaagaatgg caaagtggta   420
taattaaatc aaacacatga aatttactag ttgaatgaac aggtcaattt gcatttaaca   480
ctaagggatc gattgatatt tggaatgagg gttggtgaca gatggcatag ttttgtagtc   540
ccatttcagt cagttaacaa gtaattgaca gatgtactca tggtgctgaa cattatttta   599
```

<210> SEQ ID NO 125
<211> LENGTH: 599
<212> TYPE: DNA
<213> ORGANISM: Homo sapiens

<400> SEQUENCE: 125

```
atgataactt acatactaat caaaaaaagc aaataatact tttatcagaa atatatagaa     60
ttcagacaaa agaatattat aaatgaagac attaagtaag ctaaaaataa tgtatttccc   120
cagatgatat aatagctgtg aacttgtatg gcaaccaaaa tgatcaatat atgaagtgaa   180
gtaggcataa cactaagaag aaactaaaaa acttataatg atagttgagt gtgttaaccc   240
atctcttttg gaaacagagt agcagacaag aatattatag gaagatgtgc acatgtaccm  300
caaagcttaa agtacaatta aaaaaaaaga atatttatagg aagatggtga aaaggaagag  360
gactaaaagt gagtggttgt tggtaatatc aattggtaag cacattttta agaacagtct    420
```

```
aggaacattc atttgaaagt gcacaagaag tatttcctaa taattctgct tctagatata    480
ccacttagaa aaatcactgc acgtctgtac aagaggatat gtccaaagat cccacggaa     540 gcattgcttt tagtagcaaa aattggaaac aacctaagtg ctatatgata gaatgctat    599
```

<210> SEQ ID NO 126
<211> LENGTH: 599
<212> TYPE: DNA
<213> ORGANISM: Homo sapiens

<400> SEQUENCE: 126

```
gtgaagagga ctggtttgga aaatctgtgt tcttaatcct gtcttccatc ccagagaaag    60 ggaggggga tgattgaccc ttcttctca aatctaggga gaaagtttca tgagggctgc     120
ttgcagagct tgatatatgt ttcttgtagt cgtggggcat tgtgaattgg tttctgattc   180
atgcctgtga aatttgagac aaaaagatca tggctggaag tttcgtgtga ctaggtgact   240
aagttccttc caataagaaa taatgaatgc agatgtcttg ttctcctttt ctctccttcy   300
tcctgtttct agttggccct ggaacagtgg cctccaggcc tgagataatc gaagcaactg   360
gagaagcttg aaggagtctg ggtccctgat cctgacaaag ccgctattcc acccctaaac   420
tggctacatc tggattttt ttctttggca tgagaaagga ataaacgatc ttactaattt    480
ttaaagttag tgttatttga ggtttagcag aagctaatcc tctcattaa tcatttttct    540 tatccaatct tcacaatttg agaggtttga agatgaagaa tacgtttaca gctaattaa    599
```

<210> SEQ ID NO 127
<211> LENGTH: 599
<212> TYPE: DNA
<213> ORGANISM: Homo sapiens

<400> SEQUENCE: 127

```
tttcattttt tgcatcatcc cagattctgg tgatagctgg gcacaggaag actgtgattt    60
atttgtgcag gagggtatg tgtttctaga tcatgagaaa ggcacacata gttctttttt    120
ctctttttgc tttccctcag tcccaccagc ccgactcctt tttcctaatt aggattccac   180
aagaaagctg tttctggatt atcagaaggt ggatcaccct aataaacaca ggatctgcta   240
ctggtatttg tttcctgtcc tgactgcatc gaactcatgt ccaaggtcag aggatatccr   300
gagaactgtg aaggacaact atgaacgtgg tttcattaaa acctcaataa gacttgaaac   360
acaagcaata atgcttgtaa tctcagttaa tgaagaggg aaaaccttct tccccactta    420
aaagcaaagc atagggattt tccatactgt ccctgaacca gtgagtttat tcctaactac   480
ttataacaca tatcctgggg ctcatagcaa tatttgagga acagtttaca tgtggctata   540
gcctgcactg atagatgttg gaaatagcca atattattta aattatcttc ctaatgtgt    599
```

<210> SEQ ID NO 128
<211> LENGTH: 599
<212> TYPE: DNA
<213> ORGANISM: Homo sapiens

<400> SEQUENCE: 128

```
tgtttaatta atactcatta gctaatgaca aatagagatc ctaggttaaa aaatatttca    60
ctgtctttca tatccattga tgaagcttct aggatataaa aaatggtgag actaacaata   120
ctgacctcag gtaattgctt tcagtagaaa atgacttaat gcatgtgaac tctgcatccc   180
cagatattat tatttttcac ccacttaact tcctcaaacc tcaattgatg tccttctcta    240
gaagtaatta cagagctaaa gatgactgca gctaaatcac tgcccttggg acttggcatk   300
```

| | |
|---|---|
| tatttataat aagagaatat ttttcccctt agcagtggta ataagtatac actgaccagt | 360 |
| ctccattcta ttacttcatt taatagctaa gcaggacatt tttttaaaaa agttttaaag | 420 |
| ccactttaaa attagaaaag ctttcaaatg gtgtatgaca tacactatac tgacaggcta | 480 |
| actggtatgc tttggagcac cactcagaat agctgtagtt ttattcctac agaaaatgat | 540 |
| gtcaaagagg cccaaccttc gtgaatgtgg gctggtgtgg gaccttcttt taaaaatag | 599 |

<210> SEQ ID NO 129
<211> LENGTH: 599
<212> TYPE: DNA
<213> ORGANISM: Homo sapiens

<400> SEQUENCE: 129

| | |
|---|---|
| actgcttaat ttctttctta aggagcaatt tgagaatata gtgaaagctg tggaccttct | 60 |
| tagaaaaatt ctgatgaatt gtattttcc acagaactct tgtgggccca tctagaattc | 120 |
| tatgaggttt ctgtagactc agtattaaga aactgtattc taaacatatt tgacgtcaaa | 180 |
| catttattga ataactaaat gccagagaat gtgctatttg tcactttttg gcatgcattc | 240 |
| actatgaggg ttatattgct cccaagggaa taacaaattt gttttggaa ggtgaaaaaw | 300 |
| acttactatt ttaatgtata atgcacagaa atacacacgg tacattgact gataatatac | 360 |
| ctgtggtatt aaaatttata gataaagcaa ttttaaaat gtctaaaatg cctccttata | 420 |
| gggcaattag gaaaaattga aagagctgc tcaacagcaa tttgcgtttg tgggacttta | 480 |
| acatcaatag atcagggaaa cttggagtgg aagaggatcc acatataaaa gagtttcctg | 540 |
| gatatattaa ttatatatcc agtacctagt atgatgtttg ccggcctaat acacagaac | 599 |

<210> SEQ ID NO 130
<211> LENGTH: 599
<212> TYPE: DNA
<213> ORGANISM: Homo sapiens

<400> SEQUENCE: 130

| | |
|---|---|
| tatcttgaaa acaacttctg ccttgagtga taccattaga tattctgagt aacaccatta | 60 |
| aacatcttgg cagcagctct ttacaggcat ttttaaatta atcagttcat gtccattatt | 120 |
| gtgtacattt ttctacttta tattcattga tttatttgag ggcatgtgtt tggatttatg | 180 |
| cctactcttt ttccacagac cttccatttt attttaaatt ttcttaaatt tttaattatt | 240 |
| aggagtatat aataggtata tatacatatt catggagtac atgtgatgtt ctaatacagr | 300 |
| catacaaagt gtgataatca catcagggta ctcagggtat ccatcacttc aagcatttat | 360 |
| cattttttgt gtgttaggaa cacgcaaatt ctactcttaa agttatttat aaatatataa | 420 |
| taattattca ctgtaatcat cctgtcatgc tatcaaatac tagaacttat tcattctgtc | 480 |
| tgtgtatttg cgcccattaa ctaattccac tccctgccca gttcctgacc tgctacttt | 540 |
| ctcaatcttt ggtaaccatc attctactct ctatctcaat gagttcaatt attttaatg | 599 |

<210> SEQ ID NO 131
<211> LENGTH: 599
<212> TYPE: DNA
<213> ORGANISM: Homo sapiens

<400> SEQUENCE: 131

| | |
|---|---|
| gatagatcac aaaattcaga aaatgtctaa gcttgaataa tatatttagc actgtgattt | 60 |
| gcagtggtct aataaaaatg ctgattatat acgtttcact gttcatggga aaatatagca | 120 |
| tgttctcaat gaatgtaatt ttttctaga catttaatta tgaacaaatt ttttacatga | 180 |

-continued
agtgtttata gaagccctca ggtgatatta tagagacaat gtaggaacaa acatcatgac 240
agattttatt agagctaata attagtttta agaaaagtac ctactatgaa ttatttttgk 300

agagaaatag attttcatct tatattcaag tttcttcctt tttcctatat tgaaatacac 360
agaaattagt cccagggaag ttctaattat aaatgtcttt gttcattgat tttcgttttg 420
tacacttttt tttctctttt tttctgtaac aaggaagaca tcatctatgt ttttgaaatc 480
catggcccaa acacagagta ttgtgagggc cacattggca catgtatttc aatttctgca 540
aaaccaaagc ctaaaatcct cacttacaga gaatctttgt gatatccatt catgataac 599

<210> SEQ ID NO 132
<211> LENGTH: 599
<212> TYPE: DNA
<213> ORGANISM: Homo sapiens

<400> SEQUENCE: 132
tatctgtcca gttagaggga atcagttggt gatgtgcatg tcacacaatc acaaaagtgt 60
cataatggaa aattcagaag tgacacagaa acttcagcaa tctgctcatc ttctgaaagt 120
ctattgcaca ttagctgaac aactgacaca ttcttacctg gtcttactga cattttcgca 180
ccctgaaggg taaaggaaga gattacagaa gctaatattt tcaacctaat ttggaccaat 240
gaggataatt tggttcatga agtgcaattg acagtagcct ttggaaaaat tgaccatcty 300
attttagaat taggagcata atgggaagga ttttcattgg acggttactc tagattttaa 360
gaaggaagac ttcaaaaatt tcaggtataa aaaactcaga agaaagctca gaaaagtagc 420
aaactgctat tgatataact ctgacaatgt aaatctcaaa ttatattaat gaggaagaaa 480
agaaggatgg tagcagtaga aaatggcata actgtagaga gaactttatt gtgtgttcag 540
attataaaaa atgcatgcac ggaagataag aaggaagaca cataaccaga aggaagaca 599

<210> SEQ ID NO 133
<211> LENGTH: 599
<212> TYPE: DNA
<213> ORGANISM: Homo sapiens

<400> SEQUENCE: 133
agaagctaat attttcaacc taatttggac caatgaggat aatttggttc atgaagtgca 60
attgacagta gcctttggaa aaattgacca tctcatttta gaattaggag cataatggga 120
aggattttca ttggacggtt actctagatt ttaagaagga agacttcaaa aatttcaggt 180
ataaaaaact cagaagaaag ctcagaaaag tagcaaactg ctattgatat aactctgaca 240
atgtaaatct caaattatat taatgaggaa gaaaagaagg atggtagcag tagaaaatgr 300
cataactgta gagagaactt tattgtgtgt tcagattata aaaaatgcat gcacggaaga 360
taagaaggaa gacacataac cagaaggaag acaaattact ctaaatatag aaatgcagca 420
tagaccagca agaatattgc aggaaggtca acatacataa tgagctgagg tttgcaaaat 480
ttgctactga ctgttgagtt tggcttcaat tggaatgaac aaggctattt tggatgtaaa 540
gtcaaaactg ctctggttga tacatttcct tcactgctct cttgttctct ggtattcct 599

<210> SEQ ID NO 134
<211> LENGTH: 599
<212> TYPE: DNA
<213> ORGANISM: Homo sapiens

<400> SEQUENCE: 134
actcacaaga ggaatttttc tgccttctgg aaacttttct gtaactagct gtgatagaat 60

```
tattattaag atattccagg agaatgaaaa ctagcagcag aaatagaaga tgagctttgt    120
tatcattttg tgagagagct gcatagaaag aaactggaga tggcttccta gatctgaaag    180
tggctcccat tcaagagcct gtaagaaaca gagacttcac tcttaccact ataaggaagc    240
aaattctgtc attaactcaa gggtgcttgg aagtagatct ttccacagac cagcttccaw    300
atgagaatgt agccaggctg acaccttgat tgcagccttg tgtgcccag  agtagaagat    360 aagctgtgtc cagacccaca aaaactgtga gataataaac atgcatagtt ttaagctacc    420
aagctggtag taatttgtta cataacaata gaagacaaat gcaggaggaa agtagatcaa    480
ggtagtaaca tggtatgatg agagtaggag ccagcttact gaagacaagt caaagtaagg    540
tcttcagctt ttactgtgag tgtggtggga aaccagtgca tggttccagt ggagaggtg     599
```

```
<210> SEQ ID NO 135
<211> LENGTH: 599
<212> TYPE: DNA
<213> ORGANISM: Homo sapiens

<400> SEQUENCE: 135
```

```
aagtggctcc cattcaagag cctgtaagaa acagagactt cactcttacc actataagga     60
agcaaattct gtcattaact caagggtgct tggaagtaga tctttccaca gaccagcttc    120
catatgagaa tgtagccagg ctgacaccct tgattgcagcc ttgtgtggcc cagagtagaa    180
gataagctgt gtccagaccc acaaaaactg tgagataata acatgcata  gttttaagct    240 accaagctgg tagtaatttg ttacataaca atagaagaca aatgcaggag gaaagtagay    300
caaggtagta acatggtatg atgagagtag gagccagctt actgaagaca agtcaaagta    360
aggtcttcag cttttactgt gagtgtggtg ggaaaccagt gcatggttcc agtggagagg    420
tgatacaatc aaacttacat ttcaaaagga tcactctggc agttatatga agaaaggtag    480
aagcagacag cctacttaag aaactatttt actaatcaga gtgtactggc ttgaataagg    540
cagcagagta atgagaaaag tggttgggtt ttgaaagtta tttgaaaggt gagtctaca     599
```

```
<210> SEQ ID NO 136
<211> LENGTH: 599
<212> TYPE: DNA
<213> ORGANISM: Homo sapiens

<400> SEQUENCE: 136
```

```
tggtgtttct gaggtccctc aggatcctag tcaagactag gtctgactcc ctatatatta     60
aaagagtgtg ctccactcta ctaagaggaa gtcttgtttg atcgaatttc atcacgggcg    120
caaatcccat caccttttgca tctttgttac ataatgtaac ctagtcaagg gaatgtcatg    180
ccatgccata acctttgctc tattcttttg ttagaagcaa aaatcccacc catattcaag    240
ggaaggaacc atactgggtg taacaccagg ggctgagact atgaaagcta tcttagaaty    300
cttcccatca tacctcctaa tgtctccatc acttactctg ccccacctat ttaggcctcc    360
cttttgtcct ccaggcatgc ctctatgtta gggcctctac ctgttgtttc ctctggtttg    420
aatattctac ctctagatat tcacaaaaat ctgtctcata tttctttctg tcttttctca    480
agtgtaacta taacaaacag gccttccacc ctgatcatcc tatttaaagt agcatttcca    540
acaatattcc cctatactcc tgtcttcatt atgtttcttt atctagcacc atagcactt     599
```

```
<210> SEQ ID NO 137
<211> LENGTH: 599
<212> TYPE: DNA
<213> ORGANISM: Homo sapiens
```

```
<400> SEQUENCE: 137
gaacccggga ggcggagctt gcagtaagct gagatcagcc actgcactcc agcctgggag      60
acagagcgag actctgtctc aaaaaaaaaa aaaaaaaacc cagactatat catatgtttg     120
ttttacatca gaaaattgcc acaaatcaac tttaaaaaag gaaacttaga gtatcttctt     180
aacctaaaat aaaattaaat agtatcatta gttttgaaat gatttgtaat tagcttttct     240
ttctaataat aataaatgaa acttaccaag tacaaggttt gtcattttt aaaagcttcy      300 ttcattaaat aaattaatat tgtcaataat aggaaataaa acaaatgtcc aaatcagcta     360
aaaataaatc tatttaaaag agaaaatgtc acaaaaagat aaaatgatca agatctaatt     420
tttagattgt gatggatatt ggaggactaa ttgcttatat gttgaatacc ctgtccaggc     480
aaaattaaaa tgaactgaaa ttagcatact tgaaaattgc ttatgtcata cattcagcca     540
ttcaaatttc agacattatg tcttcagcaa ttctcctgct aaatccattg ccctcacat      599

<210> SEQ ID NO 138
<211> LENGTH: 599
<212> TYPE: DNA
<213> ORGANISM: Homo sapiens

<400> SEQUENCE: 138
agtaggaaat taaagaaacc aacaaaaat attaaatcta gaaaatattt tgtactttaa      60
tgacattagt actaatagga cttcttcagg cactgtttcc aaatttgttt gaatcttttt     120
tatgatacct catttcctga aagcacagcc cactttggag tagtgttctt aactggtctt     180 attctatttta tgctgttact tcacaacagt gttagtctgg tagctgcata ttttcttaga     240
actattattg caggctttat ggattttaag gactatgctg ctttaaagac aataattgtr     300
taagttccaa acatgttggg tagcaccagc attcaaaaat ttctcaggcg tgtgaagttc     360 atttttaac gaagaataaa cccaggcaca gccaagtgta agatattgga ataaccatt      420 tccaaagtac atcagagaaa tttaaaaggt cacagaactc cttataacat taatatttga     480
catttgaatt attttccagt ttagcaagct ggataaagag cttcatcttc agatgaactg     540
aaacaactaa aaatacaaaa actttgtctt cagttcagtc aagataagtt actgagaat      599

<210> SEQ ID NO 139
<211> LENGTH: 599
<212> TYPE: DNA
<213> ORGANISM: Homo sapiens

<400> SEQUENCE: 139
atcgcaccac tgcactctag cctgggcaat acagtgaaac tctgtctcaa aaaaaaaaa      60 attctcttcc tccccagttt atctgcatct tgttattggg ccacaagaaa tagcagcccg     120
gccctcagtt tggtccagga acactccttc tctttcctca ttcatatgga cataataggt     180
ggaggaacag cagccatttt ggatcaaacc ctagaaatgg attggttaga aagctgagaa     240
aacctgtgta tttttagtga cacatggctc aaacttaggt gtgttgtctg accccacay      300 ctgagactgt taagttattt ggataaaatc ttatgcattt aagccactct tgatttcagt     360
tttctttccc aagtagcaaa attaaatcct aactaaaatc tgtcccaaat tatctttggg     420
aatacaagca gaatcaagat gttattcata tattcttcta gtttaaatat tttttgatag     480
cacttttgct agggtcactt tttacataaa ggtctcagaa atacttaaat tatatttatg     540
gtatacatac aaacaaattc tataagagcc agataaatag gcatgaagtt aaaaacaac     599

<210> SEQ ID NO 140
```

```
<211> LENGTH: 599
<212> TYPE: DNA
<213> ORGANISM: Homo sapiens

<400> SEQUENCE: 140
tgaggacaca gagccaaacc atttcaccag agggctgagt aactctaatc tggcaggatg     60
attatcctac acaggttgca atggcccctg aaatttggac gcactttgtg agagaccagt    120
gtctagataa ctaggaacta ggtaaatgtt ggagagctgc ttcccttcat ttctgtcatt    180
gtctgtttca tttcctttgc attgtttgtt gatctgtatt aaacaaaaat gaaagcaaac    240
cttgtatctg agtctccatt tttaccaatc ctcacattta tggttcagtg tcttagtctr    300
gtttcgaata caagaacct tttgtacttg gaagtataaa acttgatagc agcaacatta    360
ttgatattta gagctcagta cctgtctaat tacaggcagg cagaaagaag tgtcaaggta    420
ttcttgctta tcaggtcaca ggtaatttct tcctctaaga attcataaac tgatagacta    480
atattggaga aagaaatgca atttaattgc tgaaagtctg tttcagttta ctggtcttgt    540
aatagaggta aaattctaaa caacttgggg agctttggtg agaattaaaa taggtgggt     599

<210> SEQ ID NO 141
<211> LENGTH: 599
<212> TYPE: DNA
<213> ORGANISM: Homo sapiens

<400> SEQUENCE: 141
gctaccgtgc ccagcccaaa agaactttt tttctttata aattacctac tctctggtat     60
tcctttacag aaatgcaata aagactaaga gaaatgatat gcacaagtga tataaaacag    120
ttttttttca cattctttt tattttaatt gaaattttaa taataataga ttacatgcag    180
ttttgagaaa taatactgag aggtactctt tacccagttt ccccaaatgt tactatcatg    240
caaaactata atgccatact gcaaactggt tattgatgat acaattcagc tatcttatty    300 agatttttc aattgtgctt gtagtcacat gtgtgtatat gtatttaatt acatacattt    360
ttatcatgtg taggttttgtg catcttcaat cacagtcaag atacagaata cagcactttg    420
ggaggctgag gtgggtggat catctgaggt taggagttcg agatcagcct gaccaagatg    480
gtgaaacctc gtctgtagta aaaatacaaa aattagctgg atgtggttgc gggtgcctgt    540
aatcccagct actcaggagg ctgaggcagg aaaattgctt gaacctggga ggtggaggt     599

<210> SEQ ID NO 142
<211> LENGTH: 599
<212> TYPE: DNA
<213> ORGANISM: Homo sapiens

<400> SEQUENCE: 142
gttaagtgaa agcagtcagt cacagaagac tatatactgt aggattctat ttatctgaga     60
tgtgaagaat aagcaaatga aaacactact ttaaaattat ggtcttgaaa caaagtgtgt    120
taaagccgaa tggacagccc aatatactac atgatacaac cagaatgcac cttcaaagta    180
aagcaacaaa tttacattaa caaagcagga tgtggtctct cttagtcatg aaaaagaaaa    240
gacagagatt ttttcctttt gtgaataaat tgatagcatg aactctgtat tagccttctr    300
ttgctgctga aacaaataac cacaaacttg atggcttaag acaatacagt ttttaaattt    360
cacagttctg gaggtcacac atgcaaaata ggtctcactg ggataaaatc aaggtgtctg    420
cagggctgca ttccttctgg atgcactaag agaaaatcca ttgccttagt ttctttgcct    480
tgtgcagatt ttatgggctg cctgaattcc ttggcctgtc gtccatttcc accttcaaaa    540
```
ccagcaatgg ctttctctcac atcatatgac tctgatactg actcttctgc ctccgttat    599

<210> SEQ ID NO 143
<211> LENGTH: 599
<212> TYPE: DNA
<213> ORGANISM: Homo sapiens

<400> SEQUENCE: 143
cagaaagagg ttatgtaacc tgtcctgtcc aatgtcacag agatatgaag tgttggaatc     60
cagattttac ataggaattt tctttagagc tggcactata taacactagg ctcatagcct    120
agcaaagcaa tgtagttatt cctaaggatt tgctgaattg aaatgattac tacagtttat    180
ctgtagtcat catcatcacc atctttgata cccaaactag ctctcagtat tttacaaaat    240
atggcaagat aaattattct tctccaggag tagtagttag tgaatcatac tgttaaatcr    300
cctgattttc cagatgtcaa ttgttaaatt gcctaataca ttctgtcagt ggtattttgt    360
ttcccttgaa gaagtaaaca aacaaaactt ttatctcagc aattataggc taaggcttct    420
ttccaagcaa agcttttgca tgggtgatgt taaaatattt ttaagcattt aaaaggcaaa    480
ttgctttata catgacaatt atattgtgtt agaaaaactt aactagagaa taaggtcctt    540
gccctctcac tttgatgtct gtggtaacat tgaagtcaat tatctgtgtt aaccagcat    599

<210> SEQ ID NO 144
<211> LENGTH: 599
<212> TYPE: DNA
<213> ORGANISM: Homo sapiens

<400> SEQUENCE: 144
tcatactgtt aaatcgcctg attttccaga tgtcaattgt taaattgcct aatacattct     60
gtcagtggta ttttgtttcc cttgaagaag taaacaaaca aactttta ctcagcaatt    120 ataggctaag gcttctttcc aagcaaagct tttgcatggg tgatgttaaa atatttttaa    180
gcatttaaaa ggcaaattgc tttatacatg acaattatat tgtgttagaa aaacttaact    240
agagaataag gtccttgccc tctcactttg atgtctgtgg taacattgaa gtcaattaty    300
tgtgttaacc agcatttaaa aattaaggtt catattttag cagaaattca gcttgcaaca    360
taataaaaaa tgagattgtt aattttttatt tgtggtttaa tatttactca gtgcaaaata    420
tctataagga ggtaaattgc acaggaaaaa aattatttga ggaaaagaa attacacaca    480 cacacacgta catatttgta aataatatat tttccagtta gaaattagtt catgctggct    540
gggcacagtg gctcacactt gtaatcccag cactttggga agccgaggca ggtggatca    599

<210> SEQ ID NO 145
<211> LENGTH: 599
<212> TYPE: DNA
<213> ORGANISM: Homo sapiens

<400> SEQUENCE: 145
cattaaagtt cagaaaattt gcagcctgat gatgtgatag aaaagaaaaa ctcattttct     60
gaggcgaaat tcaagccacc tgtagaaatt tacataagta atgaggaact aaatgttaat    120
caccatgacg ataggtaaaa tgtctccaga gcatgtcaga gaactttgtg caccccct    180 cccatcacag gcccagaggc ctggaaggaa gaaacagttt cacgtgatgg gcccaaggct    240
ccctactctg tgcagccttg ggacatggtg ttctgcatcc aagttgctct agccgtggcy    300
aaaagggaac aagatgcagc ttgaccagtg gctacaaagg gtgcaagccc caggccttgg    360
cagcttccat atggtgttga gcctgcaggt gcacagaagt caagaattga ggtttggaaa    420

```
cctccaccta gatttcagag gaggtatgga aatgcctaca tgtctaggca gaagtttgct    480
gccagggctg gtccctcatg gagtatctct gccagggcag tgtggaaggg aaatgtgggg    540
ttgaaacccc cacacagagt ctccagtggg gcactaccta gtggagctgt gagaggagg     599
```

<210> SEQ ID NO 146
<211> LENGTH: 599
<212> TYPE: DNA
<213> ORGANISM: Homo sapiens

<400> SEQUENCE: 146

```
ctgatgatgt gatagaaaag aaaaactcat tttctgaggc gaaattcaag ccacctgtag     60
aaatttacat aagtaatgag gaactaaatg ttaatcacca tgacgatagg taaaatgtct    120
ccagagcatg tcagagaact ttgtggcacc ccctcccat cacaggccca gaggcctgga    180
aggaagaaac agtttcacgt gatgggccca aggctccta ctctgtgcag ccttgggaca    240
tggtgttctg catccaagtt gctctagccg tggctaaaag gaacaagat gcagcttgas    300
cagtggctac aaagggtgca agccccaggc cttggcagct tccatatggt gttgagcctg    360
caggtgcaca gaagtcaaga attgaggttt ggaaacctcc acctagattt cagaggaggt    420
atggaaatgc ctacatgtct aggcagaagt ttgctgccag ggctggtccc tcatggagta    480
tctctgccag ggcagtgtgg aagggaaatg tggggttgaa accccacac agagtctcca    540
gtggggcact acctagtgga gctgtgagag gagggccaga gtcatccaga ccccagaaa    599
```

<210> SEQ ID NO 147
<211> LENGTH: 599
<212> TYPE: DNA
<213> ORGANISM: Homo sapiens

<400> SEQUENCE: 147

```
agttgactca ggttgtctag taacattctg aaacagaatt cagaatgata atctgctcac     60
ttaaaactga tgcaggtaaa aattctgtgt ccaaatctaa agagatcatg gacaatagta    120
atatgtgtta aggaaagaaa ttctcagaag tcattaaaaa catttatttt gaattgggta    180
aaagaatgtg aaagtggagc tatccctgaa gatctctaag aaaaagctca cactttctt    240
atggattatt aattataaaa tcatatttta tttatgtatt aatgagtttt aaataaaacw    300
tcattggagg gcctcaagca aaaaagggac ttatagatac tttattagtg ctaatttcta    360
taaatatttt aaattagagt aaatgttaaa ttacatgata ttgaggaatg ggatgaatct    420
acatctacag agggtgaaga atgtgatcaa ggaggtaaat aacatgaaaa tttaaaaaga    480
gaaaactgac cacataacag atgatggaaa tatataatat gggagaatga gacatgcaac    540
aaatgtaggc cagtgactgg gtaagggagt ggttaccatt tacattagat tgttaggga    599
```

<210> SEQ ID NO 148
<211> LENGTH: 599
<212> TYPE: DNA
<213> ORGANISM: Homo sapiens

<400> SEQUENCE: 148

```
ctcctaaaga tccaacttct aaaacatcac attgctgatt aggtttcaac atatgaaatt     60
gggaaggtgg ggacacaaac tttcagacca tagcagctcc ctggcccttt ctgccatgtg    120
aggaaacaac tgtatgtcca tcaatgaacc aggaagcggt ctgtcattag acactgaatt    180
tgctggtgcc ttgagcttgg acttctcaac tccagaactg tgagaaataa atttctgttg    240
tttataagca aaccagtcta cagtattctg taatagcaac cccacagtac taagaaaaaw    300
```

```
ccagtctctc tttatccat cttttcaga acaatgtaa tgaacagcaa ttcatagaat      360
caaagtaaaa tttgaaaata atgtagttgc cttgattcaa aataaagctt tgtcatatga   420
ggaacatgtg atattattgt aaatgttgtt ataattttag ttgaaatgtt caactggaca   480
actgttatgg gttgaattgt gttcttcccc aaattccaaa tgtgggagtc ctaactttag   540
gtaactgtga atatgacttt ttttggaatg gagtcttggt agatgtcatt gagttatga    599

<210> SEQ ID NO 149
<211> LENGTH: 599
<212> TYPE: DNA
<213> ORGANISM: Homo sapiens

<400> SEQUENCE: 149
tgagttatga tgagatcatt aagatggttc taataataat tcagtatgac tggtgttctt    60
gtaagaagaa gagagcagaa gcaaagcaaa aaacatcctg taaagatgga gacagaaaat   120
gatctgctgc cacaaacaaa ggtatttctg ggactcagga gggggaagag gcaagaaagg   180
aagacgtcag caggagcatg gtcctgccaa caccttaatt ttggacttct agcctctagg   240
gctgtgaaag aataaatttc tgttgtttta agtcactgac tttattacag taacctcagr   300
aaactaatat agcaaccttc cagcttggga gtgtgattct ttcctgtgtt gaataagagc   360
cacactccct cctttcctca gaccaataat gccctatgtc aaaggttttc ttcaatagtc   420
tttcgtattt atagactttt tctatatagc tgggaggcga gtgatgaagc ttgacagatt   480
ctagaataat ttctgctatc ttttttaagt cctataagga ggaccctaag ataatcctta   540
gcacataatt acctgctatt ctcagtatta tggttttagc caaagctatg agtcaggat    599

<210> SEQ ID NO 150
<211> LENGTH: 599
<212> TYPE: DNA
<213> ORGANISM: Homo sapiens

<400> SEQUENCE: 150
tctgttgttt taagtcactg actttattac agtaacctca ggaaactaat atagcaacct    60
tccagcttgg gagtgtgatt cttcctgtg ttgaataaga gccacactcc ctcctttcct   120
cagaccaata atgccctatg tcaaaggttt tcttcaatag tctttcgtat ttatagactt   180
tttctatata gctgggaggc gagtgatgaa gcttgacaga ttctagaata atttctgcta   240
tcttttttaa gtcctataag gaggacccta agataatcct tagcacataa ttacctgctm   300
ttctcagtat tatggtttta gccaaagcta tgagtcagga tggaaattct cattcaacat   360
tctgttaaac atacatatat tcatgtaagt caaaatttat gctgagatag tcatacaaaa   420
tgtgagaagg ggttaggtaa aagataactt gtaattgttt gatttatgca aattaatggg   480
gaaaaaccct ccgtctttgt cattagagtg aaattctttt aaaatattgt aatgcaaagt   540
gctagggcca agaaaactgc catagtcatc attataacta gggcagcatt ttgtatcta    599

<210> SEQ ID NO 151
<211> LENGTH: 599
<212> TYPE: DNA
<213> ORGANISM: Homo sapiens

<400> SEQUENCE: 151
gaaactaata tagcaaccttt ccagcttggg agtgtgattc tttcctgtgt tgaataagag    60
ccacactccc tcctttcctc agaccaataa tgccctatgt caaaggtttt cttcaatagt   120
ctttcgtatt tatagacttt ttctatatag ctgggaggcg agtgatgaag cttgacagat   180
```

```
tctagaataa tttctgctat cttttttaag tcctataagg aggaccctaa gataatcctt    240
agcacataat tacctgctat tctcagtatt atggttttag ccaaagctat gagtcaggay    300
ggaaattctc attcaacatt ctgttaaaca tacatatatt catgtaagtc aaaatttatg    360
ctgagatagt catacaaaat gtgagaaggg gttaggtaaa agataacttg taattgtttg    420
atttatgcaa attaatgggg aaaaaccctc cgtctttgtc attagagtga aattcttttα    480 aaatattgta atgcaaagtg ctagggccaa gaaaactgcc atagtcatca ttataactag    540
ggcagcattt tgtatctagc ataaagaact gtagaccaaa taaataactg agaaatatg     599
```

<210> SEQ ID NO 152
<211> LENGTH: 599
<212> TYPE: DNA
<213> ORGANISM: Homo sapiens

<400> SEQUENCE: 152

```
acaattaatt caattttttct tttatattct gcattccaca taaagcgata acaggaaaac     60
ataaaattcc actaacttca ttattatttg tgtgtgtgta ggtgtgaggt tttcaattttt   120 aaaaattttt cttttttttct tgtcatgtta tttcatcttg gtttcatttt tattcttcag   180
gattataata atccccccttg tttgcagaag cagttataac tcactgcagt tcttttccat   240
gaaaagattt tcctatcttc agtcaggttt ctcatgatgt acaaagaaat atctgggctr   300
tctctgctct tgatgaattt cactcaatct ttgagagtta gaaagctctc ttccttaacc   360
gtgtgttaag tatttgctca catgcacagt cagtgacaca cttatacaaa acacatgtgc   420
acacacacac tgtatttaca ttcatctact ttgcaatgct tttaacgtgc ttcattggat   480
atttcataat acctaggtgt gatgactaat attaagtgtc aacttgattg aaggatgcct   540
agatagctgg taaagtattg tttctgggtg tgtctgtgag ggtgttgcca gagaagatt    599
```

<210> SEQ ID NO 153
<211> LENGTH: 599
<212> TYPE: DNA
<213> ORGANISM: Homo sapiens

<400> SEQUENCE: 153

```
tgtctgttga ggacccattt tctggttcac agatggtgcc ttctggctgt gtcctcacat     60
ggcctttctc aggcctcttt tgtcggagca cttagcccat tcacgaggct ccaccctcat   120
gacctaatca cctccaaaag acctcatctc ctaatattag ccccttagag gttagaattt   180
taacatgtaa attggcgggg cggggtgggg gagacataaa tattcagttt attgcaacat   240
gtgtttaaaa tgtgaaatta ttattgcatg ataggctata tatcatcttg gtattaatty   300
ggctaggctt aattatctag gattttaagt tgatttatg aaaattaact atgaagtgtt    360
gcatagtgag cctatcaggg taattagcat atacaccatc tcaaacacat attatttctt   420
tgaattggaa atgttcaata ttctccctct agctattaga agctatataa tatattattg   480
ctaactatag ttgtcctaac taagttttga atgtccttac tgtaaaaata ttaatcacaa   540
catctgacca gtcaacattg attaactgtg gttagtcctt gatccctgaa gatcatgaa    599
```

<210> SEQ ID NO 154
<211> LENGTH: 599
<212> TYPE: DNA
<213> ORGANISM: Homo sapiens

<400> SEQUENCE: 154

```
aaagtgcaaa gtaaataaga gattatacac agtatctgtt gcaaaccatg atagggtatc    60
```

-continued

```
agttctctct ctctcttttt tttttgcatc ttgtttcaat acacaagaaa aggataagca    120
ccacactggc cccagatggt tatataggaa ataggaacat acttctcaaa ggctcaccct    180
ttttccctaa gacttttaga gaaaataaaa taatattaac tcaattgctt cattatgctt    240
aaaaaaaacc cctaaaattt atctaacatt caaggattaa aattattttg tggccagats    300
tcgctaacac aaatttattt cttatctggg gcgcatttta aatcataact catttctcat    360
aggaacctgc atagtattac ttgatttttc tcatcatggt aaatgtaatc ataacaatac    420
tatttgaaaa gtcttccctg cacaaactga caccagttta ttttacttcc ctgtcatact    480
taaatatttg caaataggac tttaagaaat ttcccttaaa actatgaagt agttaaatga    540
tctgaggtga gttgtagaat ttgcttcgat gttttatggt tatactttat gaagtaaaa     599
```

<210> SEQ ID NO 155
<211> LENGTH: 599
<212> TYPE: DNA
<213> ORGANISM: Homo sapiens

<400> SEQUENCE: 155

```
aagatataaa tgaagcaact ggattaacat acatatcttg agcaaaagag tatatagctt     60
tcaggctctt ttaacctttt ttatcaaatt tatccagaaa actctcgcaa tattatagca    120
tctatgtatc acagctgaag aataaatatt ggctaatttg tctttgcagg gaagaacact    180
tacctaatca taatttatag ttttgtttac ctttccattg tgaaagctaa ttatttgtct    240
gaacaagagt ttctccccta ttaagccact ggtgagtaaa gacgcaattt aaattttacw    300
tgtgtattca gttcacaagc tttataactc ccattaggga atcaaatccc ttcaggattt    360
ttgtgaatgt ttaccccctag cagaggtaaa tgaccagtct tcaattttaa atcatggcta    420
gcagaagcta tagtaaagca tcaaagaaga ccaaaaccca agtcacttgg ttttcaacac    480
tcagttgtgt gaccatgaca gcaaattatt agccttgtca tttaaatagc tttatttgaa    540
atgaatatag aaaaaaaacc tccttcttat tctattacca tattgctgtg gattatctc     599
```

<210> SEQ ID NO 156
<211> LENGTH: 599
<212> TYPE: DNA
<213> ORGANISM: Homo sapiens

<400> SEQUENCE: 156

```
gaagtttccc atgaaacaaa gagccagaga aaacagaatg aattttgtgg ttgaagtaag     60
aaagacttaa agtgaatttg catgggccaa agagaagaga ccagttggga atgtgaattt    120
agatgccagg atacatcaat gccaattagg catctttatc cttccctata cattgacatt    180
atttaaacat cttggaattt agaaaatatg ggaaattata aattgagtaa gatcagtctg    240
aattgatgaa gacttcccag aaatgactgg gattgcattt ttaccacaga gtagaattgr    300
gaactaagaa aaaaggtatg ttttaactta aaaaaaaaga aataacaaaa ttcttagaag    360
ttatacttct cacttatcca aatttgtaga atacgaaatt gtacccacgc acttatgttc    420
gaagaaaact cctgttttg cagaaaaaaa aatgtaaaaa acagaaaatt acttctagcc    480
tggaagctcc aaaatggaat aggggctgtt tttaattacc ggagataatc cacagcaata    540
tggtaataga ataagaagga ggttttttttt ctatattcat ttcaaataaa gctatttaa     599
```

<210> SEQ ID NO 157
<211> LENGTH: 599
<212> TYPE: DNA
<213> ORGANISM: Homo sapiens

<400> SEQUENCE: 157

```
aaagagccct gtcctttgca caggacctgt ctaaagctga ggctggatca agataaaaga      60
caaacccacc ctcatgacaa atctaggtcc tacaacaaac aacaatccac cactggggta     120
ggtagaagag cgtagaaaga ccagaaaaag agcagagaag gacctcctct gtatcaaggg     180
tgtgcaggaa tagctgaagg ggaagccaga aagctaaaac ctccagcatc ttagctgtca     240
ctgtaagcac aaggtaagta agtggtcaat tagtccatca gactcaggaa gaaatggaaw     300
cctgtggtct cctgaaggta acaacagaaa caacaacagg caaacactaa cactgatgaa     360
atctcaaagg cattatgcaa atggaagaag tcaggcacaa aagactctac attttattct     420
ttcattttca tgacattttg aaagggtaaa agtatacagg gtcaaaaatc agattcatgt     480
tcaccagtga ctgggatgat ttggaaagga ctgtgtaaaa aatgcataag ggaatttttt     540
gtggcaatga atatttattc tatgtcttca ctgtgatggt ggctacatga ctatggaca     599
```

<210> SEQ ID NO 158
<211> LENGTH: 599
<212> TYPE: DNA
<213> ORGANISM: Homo sapiens

<400> SEQUENCE: 158

```
ccacatatttt ttcctgccgg ttgccttgga acacagcagg gaatgtctct cccaagcaga     60
agaactgctt ctaaactgct atgaaaccaa gaatgcacta gaatattagc agattatcag    120
ttcaggcttt atagtaatct tcaaaatgcc cagaatgcta ttaaggatat caggtaattc    180
taggttattg ttttatatgt tggtatataat tttaatgagc tatatctctg gggagaagtg    240
tctaatcaac aaagtatggg catttttaatc aagtttttact ttttacttgt ctgagattas    300
taaaattatt tgtagaaagg ccaacagtca gaagatcaga atgtaaccaa ttgcactaca    360
acagttcccc catctgtgct gggactagtt ttctgcatct ggtctagatt atctcatctt    420
ccttcccagg tctaaaatcc aatgcatctg ttacacagca gaagaacttt tttgtgtgat    480
aaaaacataa tttatatagt aaaaccttca ttttagaatc aataggaaac tctcaacaag    540
ggattaacta ccagaatata caaggaactc caacaactca atagcagaaa agcaaacaa     599
```

<210> SEQ ID NO 159
<211> LENGTH: 599
<212> TYPE: DNA
<213> ORGANISM: Homo sapiens

<400> SEQUENCE: 159

```
aagtactcca tggtgaaaag aagcaataca gatgctgctt tttattcttt tagtctctgt      60
ggaatcaaag atggcccaaa tctgatcgtt ttcatgaatc gaagcctgat ttggaaaatt     120
taagtgagtg gtatctgaaa ataataatcc atgtcgaaac atataaatag aaaaaattac     180
tatccacata gcataattgt aatcattgat cagcaaaccc ataatcttat caatgacttg     240
ctaccttact cactagatga ctagatgttg accaaaattt taacttaagt gcatcatgcy     300
cttatattaa ggctttgatg tattttttaaa attaaattag ccaatgagag gtattttaag    360
ctgttttaag ccattgacat cttactgtga ctgagattac aagtttaggt tttggtagag    420
gagagaaaac caaaaatatt ttgtatctaa gtgataggaa atgggcaaga gaaggataaa    480
gaatagagag acagagctcc aggaaatcaa gctttactct atccacaatt aatattcgaa    540
gtagtccttt tgggcttttg aaaatgataa aagtggaacc tttagtttca tttgcttca     599
```

<210> SEQ ID NO 160

<211> LENGTH: 599
<212> TYPE: DNA
<213> ORGANISM: Homo sapiens

<400> SEQUENCE: 160

```
aatatgacgt catataggca ttaatttcca tgttatgaat tcaccagtaa aattgtttaa    60
acagagaagt aaacaagacg gtaatgttat tcaggtaaaa gtagagaggg aaaagaaata   120
ttggaaccag ttcagcaacc aaaatggtgc cagagcccaa gcatgagtta ttaaaggctg   180
gtggttcctc tctcctgacc cattaccatt cttatctctg atgctccagg ctgtcagttt   240
ctttcttttt tgaccatata caggtaagga aagcccattt atgagctatt ttatttccar   300
gttttaaaaa tgtcaattga tataggctat gatctacagt aatgcttaat ctattgaagt   360
ttttgcatca aattccatct taagatgcaa gcctgaagcc catttaatgc caaatgtaaa   420
tacaagtgct agtttcaaag ggcaagattc aaagaaagac aaacagaaga aaagtatttt   480
aattgctatc taaagaagg ctgtgttctt gggtgaatac tttgttgatg tatttggggt    540
agaaacagag ggagaaataa ttatgtaatg ttaagctgtt ttctaaaatt ccagggctc    599
```

<210> SEQ ID NO 161
<211> LENGTH: 599
<212> TYPE: DNA
<213> ORGANISM: Homo sapiens

<400> SEQUENCE: 161

```
cacctgggtc tgggctttgc ctactactgc ctttgggatg agtcagccta atatagaaag    60
cttgttttc tctttttaa ttttgttttt cttctttctc taatttctgc ctcattataa   120
caatctgccc tctgtgcccc accccaaatt caagtctttc ctatgtgcaa aatatattca   180
tcccaaaaaa aatcttaatc attccagcat tgactctctt gggccaaaag tctcatcaag   240
acttcatcat ctcaacatct caaatctcat tatctaaaca attgaaatca attgtggtaw   300
gattctggga aaaaaacttg aaatcatctg tttccaaaat acagtggaac aggtatagaa   360
tacatatgtc tattccaaaa gggaaaaata gaaaaaagag acacagagag agaaagagag   420
agagagagaa agagagagag agagagatta tggtgtccca agaaaattcc aaacctagca   480
atctaatcaa atttcattag attctaaggc tagggaataa ttctctttgg cttgatgctc   540
tgtcctctag gccccaccagg gtgacagcac catcctgagg atcagttttt gcttttctt    599
```

<210> SEQ ID NO 162
<211> LENGTH: 599
<212> TYPE: DNA
<213> ORGANISM: Homo sapiens

<400> SEQUENCE: 162

```
acttgatctc tatctccaag attatttgag ctgtgtttat acacatttta ccttttagat    60
catatattgt aaaatagata ttattattat tccaatctta tagactgagc atctaaaccc   120
agtgtaacac acctcccaag tgttaaaact gggttctaaa cctcatattt caatgatact   180
tctagaactc tttctactac atccggtaat aatattaaaa acaaaatgta tataatttca   240
gtgaacatta ttgaaagttt tgtgatactt atcttaattc ctcccattat gtggcaaatr   300
taatatccca gatggttttg taaaattaga gaaatcttgt ttgaacagca gtgttgagaa   360
aatgagactg ctaaaaattt tagagaacca aactcctcat tatttttctt tgaaggtaca   420
tgataaatta cctatcctta aattctcatg tagtcatttt ataccaga aagatatta   480
atattatatt gttatgccat cgcacactga acagttgaaa attggtgtaa tttagttcat   540
```

```
gtaggaagct gttaagaccc ttaaagtaaa aaccttttaa actgaaaatc tttcctgga      599
```

<210> SEQ ID NO 163
<211> LENGTH: 599
<212> TYPE: DNA
<213> ORGANISM: Homo sapiens

<400> SEQUENCE: 163

```
tgtaatccca tctactcggt aggctgccgt gggagaaccg cttgacccg ggaggcggag       60 gttgcagtaa gccgagatca caccattgca ctccagcctg ggcgacagag caagactcca      120
tctcaaaata taatagtaa taataataat aataaattta aaaatcagca acaaaaaag        180 aaatacaaca taagaagtga atatcaagtg gtggtaggag ctactccttt acctctgcag      240
gtgacattgg gacagaaacc tgaataataa tatatagga aggaagaaac ttcaagaacr       300
cttgtggaag aatgctccag gcagagggaa agccccaaga aggaagcctg cctgttgtgt     360
gtttatggga acagaaaata ggacagtggg actgaaacac aatagagaga gaaagagtag     420
taggatctgg gaacagagac ctaaccagag aacagatact taagggctgt gcatgtcatg     480
gtaaaatctt tgaattgtct ttgaagtgtg atgtaaggcc atcaaaaagg ttttgaacag     540 attttaaaagg cttacgctgg tagtaagagg catataggct ctaagctggc gagagagcc     599
```

<210> SEQ ID NO 164
<211> LENGTH: 599
<212> TYPE: DNA
<213> ORGANISM: Homo sapiens

<400> SEQUENCE: 164

```
aagcaaggtt tcgtttatga atagcctaga cccattgggg tagtaggaat ctaaaatgta      60
cctcactgat agtcctgtgt gtagctggct taagcaagga tattttgtgt gtgtgtgtgt     120
gtgtgtgtgt gtgtgtgtgt gtgtattgta ataaccattg aaaggtatgg ataacataaa     180
tttacttgaa aattccaaca tcagagatag tattgttttt catagaacta cctcccacca     240
ccagaagttt aagatgcata tattaacgta cctattagca ttattatcac acctgcttgr     300
ggtgttttat catgtttgct tgaattacca gaagtcaggg actcttgata ggctgagttg     360
ggaccttcta gatagagcaa aagctgtgaa aagggaaggt acatgcagaa gagtgattcc     420
atggaagcct tgagccagga ggaagtagaa tgaggacaca acaactagag gaagaaaaga     480
tcctggaact gaagagtaga gagccacatc tacatttgcc aacaagcatt tttagaacaa     540
catattttca gttttacagg gattggtgaa ttggaaaaaa acattcctat aacaaatgc     599
```

<210> SEQ ID NO 165
<211> LENGTH: 599
<212> TYPE: DNA
<213> ORGANISM: Homo sapiens

<400> SEQUENCE: 165

```
actacctcat tagaaattag gatttcacca tatacatttt agggacatat aaacattctg      60
tccatagcaa ttaagatgct cattcccatt ttcaatatat ttctaaattt gattttgcta     120
aatttttaaa tcaatgcctc aggtatttat tgctgatcta caaatgttca aattatggca    180 taattttttat ttttaattta gattgaaata aaatgtcatt ttaattgact ttaggtatta    240
tagttactaa aatttgaact gtaaatttta ttagctaaat agggaaattc attacaaggr    300
aagtaattcc tataaatata gtccaacagg gtacatttac atagtcaaaa tatcttgagg    360
aagagctatt gattatttaa atctaggatc aatcaaatat ggcatattat ttgctttcaa    420
```

```
atatttgtgt tgcatcgaa tttcactaat ttttaatagg attgactttc aacaaagact      480
tccagtcaaa aattgtcctg aggccaggct caatggctca tgcctgtaat cccagcactt      540
tgggaggccg aggcgagggg atcaccaggt caggagatcc agacaatcct ggctaatat      599
```

<210> SEQ ID NO 166
<211> LENGTH: 599
<212> TYPE: DNA
<213> ORGANISM: Homo sapiens

<400> SEQUENCE: 166

```
tattgtcata ttttaagaaa ttgccacagc caccccaacc ttcagcaacc acaaccctga       60
atagtcagca gccattaaca tcgaggcaag actctccatt ggcaaatttg ctgaaggttc      120
agatgattct tagaatcttt tcagcaataa agtggttttt agctaagtta tttataattt      180
tttacacata atgctattca caatagatta cagcacagtg taaacataac tgttacatgc      240
attgggagac cacaaaattt gtatgactca ctatatagca atattcattt tattgcatts      300
gtatggaact aaacctgcaa taaatcccag gtatgcctgt atttgactgg ttacagttat      360
acagttgcca tatttggtct atctagtcag gaagtttcca gttaaatagt tacacgggtt      420
tttttggctc cttctaattg gctgagctta agttctcttt ttatttgata taggcattta      480
gaagaaatag ctaaagttaa gttttgctta tgttggcaaa tcaagcaaga tttaggtcac      540
ttatgaggcc taacttgctt tctctgctca gggattttc aggctagctc ttctttcta      599
```

<210> SEQ ID NO 167
<211> LENGTH: 599
<212> TYPE: DNA
<213> ORGANISM: Homo sapiens

<400> SEQUENCE: 167

```
gataaaactt cttgattcaa acttaaggtt tgtccagacc agtttcacat cagacatggt       60
ttccttttca acaataaaaa tcttttctaa tataatcaca tcgacagaaa tattggtcag      120
actgaaagca agtcgactag ttatttcttt atgatgacct atttcagttc tctttaagct      180
acttacaaat gttccaaaat agtttagact ttcaactgcc atttttataa aaagttttca      240
aagacaaatt ttaactagca aaatatatga agtatttttt ttactaagct acagatgtar      300
tttccaattc ctgtaacttt gggcctcctt ctacaggctt gatagctata aaataaaacc      360
agttattatt taattcagtg gttaactaca ctctttttaga acgttcgaag gtcatgaaat      420
taatgttcta cccttgtgaa atgaaagcct gaaagctgag aagttaactc agcatatttt      480
agtaagactt aactgcaggc tatatataca cttggaatag aagtgttcgg atctctgtat      540
taaggatgtc agcatttcca ttaaaaatag cctaggtaag gagtttaact agattcagt      599
```

<210> SEQ ID NO 168
<211> LENGTH: 599
<212> TYPE: DNA
<213> ORGANISM: Homo sapiens

<400> SEQUENCE: 168

```
aaatgaccat gtttctttt tggcttaatt atgttccttt tcaaaatgta ttgttaactg       60
ttattttgta ggatgaagat gactaagcaa tttctggaca ttcacccctc tggaggctta      120
gatttcatag tgtgaaaatg aatgtgctat gtgttgcatt atactctctg aataaaatcc      180
tgattaccta tgcaacaagg accacagggg gcacgggata gaattatgaa atcagttatg      240
gaatatgcat ttagaacaga agtaactctg cccaaataac ccaggaggaa gaaaaggacw      300
```

```
tctccacaag ggcaagtaca catagaataa ctgcaaagca accaagaact tcaatgcaca      360
ctaaattggc catcattatt ttaatgagct ggctgtaatt tttaaaagca tttgcttttg      420
taggcagatg cataaaatct gttctaatgg ggtcatttat taatttgcct aaagattatt      480
tcttgtgacg aaagcctaat ggatttaata gaatgcatct ttaagtagca gggcctaaaa      540
tttgtgtgtg tgtgtctgtg tgtttaattt caaatctttc tattgtgcat gcaccaaa       599

<210> SEQ ID NO 169
<211> LENGTH: 599
<212> TYPE: DNA
<213> ORGANISM: Homo sapiens

<400> SEQUENCE: 169
ttctggttct tggttatttc ttccccttttt tcctactcgt gaacattatt ctaccaatta     60
tcctcttcct cttgcaccat tatttttattt cttactactg gataattcca aaaattatac   120
aaactttcct atattaacac agaaaagcaa aacacacaca cacacacaca cacacacaca    180
cacacacaca caataaaaccc tctcttgacc caacatttcc cttaagctcc atactttatt   240
ctctgctctc catttaaagg aataatcttt gaaagaattt tctattcttg atacccacaw   300
atactactct ttctttccct ctaaaactcat cttagttcta ccacttcacc atttcttttt    360
tgtatagatc actaataact tacatgttgc tgaattcaat ccagtttta atcttcatat    420 cacctgtctt gtcatcagca tttaacagaa atcactccat tttccttgac agaccttctt   480
cacttggttt ccaggacatc actctcttag gttttctcct acctcactgg gtggcccttc    540
gtggtcccca ttgttagatt ccactcatct cccaaatctc tcacattgga gtgtacaat    599

<210> SEQ ID NO 170
<211> LENGTH: 599
<212> TYPE: DNA
<213> ORGANISM: Homo sapiens

<400> SEQUENCE: 170
tatatatttt acttactgtc tgtcatccca agtagagcat gaactattgt attagttttcc    60 caggggtgtg ataacaaatc acacaaactt tgtggtttaa tatcaaagaa atttattctc   120
tcacagttct ggaagccaga agtctgaaat caaggtgtca gtagtgccac acatccccctt   180 aaggctctag aggagaatcc tttctttttt tcttttttt ctcttttttg agatggagtc    240
tttcccctcc gcccaggagt gccctggtgc aatctcggct cactgcaatc tccgcctccr    300
ggattcaagt gattcctcctg cctcagtctc ccgagcagct gggattatag cacccacca    360 ccacacctgg ctaatttttt gtatctttag tagagacaga gtttcaccat gttggccagg    420
ctggtctcga actcatgacc tcgtgatcca cttgccttgg cctcccaaag tgctgggatt   480
acaagcatga gccaccacgc ccggccagag agaatccttt cttgtctctt ctagctctgg   540
tggctcaagg aggcattcct tggcctatgt ctacataact acaatctcta tcttcacat    599

<210> SEQ ID NO 171
<211> LENGTH: 599
<212> TYPE: DNA
<213> ORGANISM: Homo sapiens

<400> SEQUENCE: 171
agtttcccag gggtgtgata acaaatcaca caaactttgt ggtttaatat caaagaaatt    60
tattctctca cagttctgga agccagaagt ctgaaatcaa ggtgtcagta gtgccacaca   120
tccccttaag gctctagagg agaatccttt cttttttttct ttttttctc ttttttgaga  180
```

```
tggagtcttt ccctccgcc caggagtgcc ctggtgcaat ctcggctcac tgcaatctcc      240
gcctccagga ttcaagtgat tctcctgcct cagtctcccg agcagctggg attataggcr      300
cccaccacca cacctggcta attttttgta tctttagtag agacagagtt tcaccatgtt      360
ggccaggctg gtctcgaact catgacctcg tgatccactt gccttggcct cccaaagtgc      420
tgggattaca agcatgagcc accacgcccg gccagagaga atcctttctt gtctcttcta      480
gctctggtgg ctcaaggagg cattccttgg cctatgtcta cataactaca atctctatct      540
tcacatggcc ttttcctctt ttctctgtgc cttctcttcc atctcttata aggatgtgt       599
```

<210> SEQ ID NO 172
<211> LENGTH: 599
<212> TYPE: DNA
<213> ORGANISM: Homo sapiens

<400> SEQUENCE: 172

```
gtatgaatat tcaactttca tgaaaaacta tttcaagagt atttactcac agacaagatg       60
gggaatcatt cagcgggggg atccctagtg tgggacaagt ttaccatggt ccaaagttaa      120
ttccatagaa tactttctat ctatctatct atctatctat ctatctatct atctatctac      180
ctatcatcta tctatcatct atctatctat catctatcat ctatgtatgt atgtaggtat      240
gtatgtatgt atgtatgcat gtatatacgt atatatctgt ctctctgtat ctaccgcatr      300
tattgtgtgt gtatacatat atgtaataaa ggtaaataac atctacttgt atataaaaag      360
aaaagataaa gggcagaatg tctcagatca tttaatagac aaatctacat tgtgaatctc      420
agagaatgaa atattgtagg cataatttcc cagatttatt tgactttcca cctcagagac      480
ccctttcctt gcttttctca tcacagcatc tcatgaaact agtgtttatt gaacctgtaa      540
gtactgaatt agaccttaat caattatgct cctgacagag atgactactt ccttcgca       599
```

<210> SEQ ID NO 173
<211> LENGTH: 599
<212> TYPE: DNA
<213> ORGANISM: Homo sapiens

<400> SEQUENCE: 173

```
agaccattta aaaactgttc ttggcttaaa atatcaggga ataggaatag ggggtgacca       60
aattcaggaa aaattatttt tatatttatt ggcaaaatta gcacgtgttg actagcattt      120
gtctgagtgg cttattcctg ataaacagca tcatgtgtta aattgagttt gggtcctcat      180
ggatgactgg gctaaatttt ttttaagctt gaaagctttc taattgtctg tataaccata      240
tagcataatt gatgttgtat attaaaaata accaacttga acacattgag tgattttty       300 ctcctagtaa cataaagtca tctgagtatt tatggaaata aatttgaata gccataggta      360
taataattaa gaatatagta tctatgtttt tcagcacaaa tgatttagtc atttcatcag      420
ttccaagcag tgcaatgtct attatagtac ttgaagtaat ataatttta tgacttacat       480 gcaaatgtta agttttgatt gcatcctttt catattatca tcatgaaaag taaaattcta      540
ctaattcgta aacaccatcc tctgtacgaa gcgtttccta gctagaactc attttatt       599
```

<210> SEQ ID NO 174
<211> LENGTH: 599
<212> TYPE: DNA
<213> ORGANISM: Homo sapiens

<400> SEQUENCE: 174

```
tagtttcgtc tcttgttcat tggtttattt cattcagaag gattatgatg acttcttttg       60
```

```
tttcttttca atttcctact cactttcagt cataaatcaa cctgtaaggt cccaactgac    120
aactaggtga gtattagaca agcctgggta ctgtgaattt ggagtgactt aagtatctgc    180
ttttcatcag agatagggac tcatttccaa tgtagtagaa gatggctctc ttagaaaaaa    240
catatttcta cttttataca tcaaacatgt ctatctactt gcaaacaaaa aatatcaagr    300
ctattgccca atccctgtga atctaccata gggtattcta aaattgaagt taaattttat    360
gatgctatta agcacgttac ttttttttctt cccaaatgca tgcataaaat gttattttgt    420
agaattcaaa aatttggagg aggttatata ttgttcgtgt gtgtctgtgc ttgtgtgctt    480
gaacgcatct aatttaacca ctttaattta gtcaagtttg ctaacaactt tattcatagg    540
gaaagggaaa atatctcata ttatagataa ggaaactgag gcttgaagag ttaataaac    599
```

<210> SEQ ID NO 175
<211> LENGTH: 599
<212> TYPE: DNA
<213> ORGANISM: Homo sapiens

<400> SEQUENCE: 175

```
atcttataaa tattaaatat taagatattt ataatttatg tcatacctgt ttctaaaagt     60
aatgaggcag ctttaaaatg tacctgagca aatatatatc acaaacccaa gactaggtaa    120
ctaaatgata ttttatggat ctcaattagt tgccattaac tttgtcagct ttgaatgtgt    180
gaaattatta attggacatt aaaccttaat gtgaaattat ttgaaagtca tcttttgtct    240
tatattatac aggagagagt gtgttatcag tattttggaa tttagcataa caatgtcatr    300
taccaaatgt atggggacca attgaataac attacaacat cacagcagga agtaattctt    360
gtcacaaata tttccagagg taattcttga tttagttatt ttgccagtgg atgtgtcaag    420
ttccatataa atgaatgttg gttcccttgt ggaaagagaa aattagtaac taaaagagga    480
gcctttaaag gggcaaaatc ttttaaagt gatccatttc tatatattcc tacatggaag    540
aatatggctg gaaaccttaa tttattatga agaggccaac acatattatt tttgattttt     599
```

<210> SEQ ID NO 176
<211> LENGTH: 599
<212> TYPE: DNA
<213> ORGANISM: Homo sapiens

<400> SEQUENCE: 176

```
taaaaatcaa ggcatcttaa aattttcatt tttgatttct gaccctctca atgtagtcct     60
ttcaaactct cttgaaactc tctctctctc tttgccattt gcccacataa attctaagac    120
atcctacctc tgtcttttg aactccttga tcccaacact ttctctctcc aacttttttg    180
ttttttcttt tgagatcaac tcttgctctg tggcccaggc tagattgcag tggtgcgatc    240
ttggctcact gcatcctctg cctcctaggt tccagcaatt cttctgccac caccagaatr    300
gctgggacta caggcatggg ccaccatgtc tggctacttt ttgaattttt agtagacatg    360
gggtttcgcc atattggcca ggctggtttt gaactcctgg cctcaagtga tcagcctact    420
tctgcatctc aaagtgctgg gaccacacgc gtgacctatc atgcctggcc tctccacctt    480
ctttgtgctc ttatttttct cttgtgaata atttttcttg tttcaaaaag taagcaaaat    540
ttctataatt caaagaaggc atattattga ttcttgacat attttgttaa attgtcttc     599
```

<210> SEQ ID NO 177
<211> LENGTH: 599
<212> TYPE: DNA
<213> ORGANISM: Homo sapiens

<400> SEQUENCE: 177

```
cattcctaga atgtgtttaa tctctagctc acaaggcttc ctgcttcctg gcttactgct     60
gcttgcctga cttcacttcc cacttcttct ccacttacct gacactccat ctatggaaaa    120
ccattgctgc ttcctttacc tgcaataata tctctggcct ctggagcatc tcctcacact    180
gtcacctcac ccagaaggcc attgagctaa aagggatct tgtcagtgat ttcaatgatc      240
caacattatg atttagcaca tgataaatgt tttcatgatg gtcagatatt aaataaacak    300
aaggttttag acagtgaatt tttctttttaa ataaagatg aaaacaaaca tgaaaatggg    360
gttacgtcca ataggaaata gacccagaaa ttaagacttt gtggaattta gttttttccta   420
gcttttttcta tgtgggctta ccattaccct cttgacacct tttactgtca ttgtacaggc   480
tctccagagt gactatcaat agtgacaaga ataataaatc tatattgaaa tatcctcaca    540
gttttactac ctaaaggagc ttgttttttca taatatgagg gaccaaatga gctgtctgc    599
```

<210> SEQ ID NO 178
<211> LENGTH: 599
<212> TYPE: DNA
<213> ORGANISM: Homo sapiens

<400> SEQUENCE: 178

```
aagacaataa aaacaaaaag agggaggaaa tatggcaatg ttaatatatt ctgttaggct     60
taaaaggga agtaattctg tcttttccaaa cagaagccat taaccacaaa ctgattgtaa    120
ttagataata ttctttgctt tgtaaagctt aaaaaaagat agcatctcag cgctgagtaa    180
aatatttatg acttgaactt gtgtatacat cacaatttaa taatgatctt ttatatgaaa    240
agtagtagtt tcttaaagaa agtctctcga taaaatgacg cataaataat tgtccaggam   300
ttcagtaaaa aacattttttc tcttttctga aagtttaaaa tatagatatt gcttatttta   360
ggaaacagtt tcaatttgtc acatatcttt atcctgtaga gcaataaagc ttaatgtatt   420
atttctacag tcatgtgcta aataacaatg ttttggtcaa taactgatag catatatgtt   480
tgtggtccca taagattata atggagctga aaaattccta ttgcctggtg atatcatcct    540
agccaacata atgtcatagc acaacatatt actcacctgt ttgttgtgat gttggtgtt    599
```

<210> SEQ ID NO 179
<211> LENGTH: 599
<212> TYPE: DNA
<213> ORGANISM: Homo sapiens

<400> SEQUENCE: 179

```
tgctttaagt ctgaactttt acagaaaatt ctggcaccct tattttcagt gtttccccta     60
atgataataa taattggcac aaaagaaagg gacccagttg tattgcaaaa tacatatgta    120
ttacaaaatg ttggcagtgg agaaatgcat ttatgcaggc tagatagggg aagcaatgat    180
ttgtgtacta tttttgtctt tgtctttgtc tttgacagcc agtatctcta taagaataag    240
tcagttgata tgttttgggt ggagatttca gggtagataa tcccattagc tctttgagar   300
gatgaactac agaaacacga gatttggcct ctattgtgtg aaatacttat atattacaca   360
tgtgcacaat ttgaggcaga acacattatt cagaaagaac caattttcct ttgaacaaga    420
aaagaactta caaattatgt cggaatgtta atatagcatg tcatcatttt ctgttattga   480
ggaaatgtta aatctgggt gaacatagaa gctacaattt atgaagtatt tcttccatga    540
agtgacccac caaagtcagc atattctaca aatgacttag ctgttttgct gtacaccaa    599
```

<210> SEQ ID NO 180

```
<211> LENGTH: 599
<212> TYPE: DNA
<213> ORGANISM: Homo sapiens

<400> SEQUENCE: 180
gatttggcct ctattgtgtg aaatacttat atattacaca tgtgcacaat ttgaggcaga      60
acacattatt cagaaagaac caatttttcct ttgaacaaga aaagaactta caaattatgt    120
cggaatgtta atatagcatg tcatcatttt ctgttattga ggaaatgtta taatctgggt    180
gaacatagaa gctacaattt atgaagtatt tcttccatga agtgacccac caaagtcagc    240
atattctaca aatgacttag ctgttttgct gtacaccaaa tagtcatcag gaattatcay    300
tgtggcccaa atggcacacc attaaaaatc caaggtcact tagatttgac tgagggcgta    360 cttttcagaaa caggcaatta tgcttttgat tttaaaggca aagaaacaac tgtacttaag    420
gttagcattt taattgctta gcaacacagg taactgacaa aggaagatag ttttttattta    480 tgcttcatca agttctttcc tcacagaata ctttttctac ctagagtttc tttattttaa    540
agtttaattt tatatatatt ttaaatcctg ctgctgagaa ttactttcct ccaagactg    599

<210> SEQ ID NO 181
<211> LENGTH: 599
<212> TYPE: DNA
<213> ORGANISM: Homo sapiens
<220> FEATURE:
<221> NAME/KEY: variant
<222> LOCATION: 300
<223> OTHER INFORMATION: a,c,g or t (any base)

<400> SEQUENCE: 181
atatgcagcc ctcaattgta cagctaggtg ctaaagctag gtaaagcacc aaaaacccca      60
agatgaaata catttgcaga taatttttgtg tattgctcac tgtctagaca gtttcacaaa    120
tttcataaac aaatgacttc ttatagaaat caatatagcc tagagtctat gaagcccaga    180
tcagggctta gtctttcatc ttctaatctt ataaccctga gaatttatag aattttgtat    240
ctttatagct agaaaatact ttaactctct tagttctact gcccttactt tacaggtggn    300
aaaaaaaaaa aagagagatc tgggatcacg aagtgagctg cccaggatga cagggccgat    360
agtgacaagc tgcttcctgt gcactaaact agtgaatggc aagcacttca gccttacata    420
cttacagata taatgcactt ccaagaataa cagtggcccc ttctgaggct gtggggcaag    480
aaggaagaga gggaacattt cagaatctct ggggcatttg gcacgtgatg tttggaaaat    540
tctcaaggtg tattgcaatg tttgccttcg gaaggttctg accttgtggt tgaaaactt    599

<210> SEQ ID NO 182
<211> LENGTH: 599
<212> TYPE: DNA
<213> ORGANISM: Homo sapiens

<400> SEQUENCE: 182
atccatgtaa gatgtgactt gctcctcctt tccctctgcc atgattgtga ggcctcccca      60
gccatgtgaa actgtaagtc caattgaacc tctttcttct gtaaattgcc cagtctaggt    120
tatgtcttta tcagcagcat gaaaacagac taatacattc agttatcagc agaagtttgg    180
ctattttaat ttgacatttg aattatattg gcagagggag aaagaactta gaaatatttc    240
ttcggccaac ttctgagaaa gaaacattct tttgctttac accattgtag ccatgttcaw    300
ctgtgggtga attaaggtag agtcttccta cctacagca ctagatagta atgtttattt    360
atttagctgg tatgttttca gtgtttcgcc tatacttgct gttttatata ttttttccct    420
```

| aaaaatagga aaatatatat aaatatataa tttcctaaaa tatatatgag aaatatttta | 480 |
| atcatgtatt ttctacaatt tgaaacttag ttgtgggaaa tcacccaact cattcctgtc | 540 |
| attttataaa cacacacaca cacacacaca cacacacaca cacacacacc ccttcaagg | 599 |

```
<210> SEQ ID NO 183
<211> LENGTH: 599
<212> TYPE: DNA
<213> ORGANISM: Homo sapiens

<400> SEQUENCE: 183
```

| ttgatactac aacagtagca gtaaagagag cccttgtcct tgacttggga ccctgctctg | 60 |
| tgtcaagtta acccttcttc tttcctttgg gggcagatac ctaacttctg ggctactttt | 120 |
| ccaccaagat gaaaagaaa ttgattattt tgcctagaaa tctaaggctg atagtgcac | 180 |
| atccattcta cataattagt ggagaaaaaa aactttgcaa gctagctgag gatgttccct | 240 |
| gagagcattt gaagcttact ttagtgaaga ttcttaaaat gacctcaagg ggggctatgr | 300 |
| ggaaaaaaaa tccctatttta ctcattactt aagagttaga atttagctaa caaactctgc | 360 |
| tgccattctc acctctgttt tggtattttg agtgtgtcag ttgaattta gctactgcat | 420 |
| ttttaaaata agtaaaactt taagtagta aaatgagtct taacctaaag acaggatctc | 480 |
| ctattatcaa agtccaaaat gaattgttt gtaaggttaa aaaaattata actaagcaaa | 540 |
| gccaggggaa aaagtgacta gtttatcttt tggtaaagaa gcaagggaaa tgaaataca | 599 |

```
<210> SEQ ID NO 184
<211> LENGTH: 599
<212> TYPE: DNA
<213> ORGANISM: Homo sapiens

<400> SEQUENCE: 184
```

| cacgagggca ggttttttct gtgctgttct tgtaatagtg aattagtctc atgagatctg | 60 |
| atggttttat aaaggggaga tccctgcac atgctctc ttgcctgcca ccatgcaaga | 120 |
| cgtgactttg ctcctccttt gtcatctgca atgattgtga ggcctcccca gccatgtgga | 180 |
| actgtgagcc attaaacctc tttcctttat aaattactca gtctcaggta tgtcttaca | 240 |
| agcagtgtga gaacagacta atacaggccc cttacctaag ttaacctctt ttttataak | 300 |
| gtttaatttc tagcactatt gtataggtat taaagttagt acaagtaaca tgattttatt | 360 |
| tgggaatgag tcttcaacta atagattttt aaatgatttt tcatgataaa atgacctaaa | 420 |
| atacatagag tatggaagta atgtgttttt agttggacaa tattttgaaa cagatcagtg | 480 |
| ttttcctcag tggatgtgtg tgctgtgtgt tgttgaatat tattctggat ttattctcca | 540 |
| acaaagtgta tttcctggaa ctgtttcttg tagaaaaata tacagtttct tagtttca | 599 |

```
<210> SEQ ID NO 185
<211> LENGTH: 599
<212> TYPE: DNA
<213> ORGANISM: Homo sapiens

<400> SEQUENCE: 185
```

| acccacaggt ccacctgcag ctctttacca gacctttgac ctgatctcct gttactctac | 60 |
| accttgctca ttctgttcca gctaactgac ctccatgttc tctcttgaat gtgctagata | 120 |
| tggtccacct cagggtcttt gcacttgtca cccttaacta taacaagctt cctccaaatt | 180 |
| gctgcttact taatttcctc accttcttta attctgaact tgggcataat ttcagagtg | 240 |
| aagactgtaa caaccctatt taaaatttta ggcacctccc atatcccaat ccatccagtm | 300 |

```
ctctctgtgt tattgctatg cagcacttac tgctcttaaa taaaatgtat aatttccaca    360
ttctagatca gtttagatat ttcataattg taaatcattt ttattagtgt ttaaatatta    420
ttgtattcac ttgtctttat attgtccaag atttccttat ggaaaaagtt taacatacaa    480
cttagtggaa caaattttgt aataaacatc ctaatactca tcacctatat ttgaccatat    540
acattttact gtacttgctt tattgcatac atctctatgt caccatcatc ctgtttagc     599
```

<210> SEQ ID NO 186
<211> LENGTH: 599
<212> TYPE: DNA
<213> ORGANISM: Homo sapiens

<400> SEQUENCE: 186

```
aggtagaagc aaagagacca ttttgacaac tagagcagta atccaggact ttagctggac    60
ttaaggttat aacattaaaa gtggtgaaat gtgattgtat cctggttaca tcttagagta    120
taatcaaact gatttgctga tgtgttgtat gttcagcatg agagaaagaa tagtggagga    180
tagcaccaag atttttgtc ttgataaagt ggaaatactg agtttgtgta agagacagaa    240
gaaaagggga gaagtgttgg agtgaaacta tctttgagta ggcaagagag aatgaaatay    300
ggtgtataga tgaagggatt agatttaggg gaataaacag ttaattttac catgggtgag    360
agaacatggt atatgatata gatcctgtca agtggcaaat ttgtctcagg tagcttgtga    420
gagttccctt ttgattgctt cttatgttct tagtgaaata aaaatacttg gtcatcaact    480
gaattttatt tttatcttta cattaaaaaa tgtacatact cttttgaccca gacgttccac    540 ttctgggaat ctatcctttg gaaataaaac actggcatac aaggacatag gtacaaaat    599
```

<210> SEQ ID NO 187
<211> LENGTH: 599
<212> TYPE: DNA
<213> ORGANISM: Homo sapiens

<400> SEQUENCE: 187

```
aaattatgtt actaggttac catcatccca gatcactttt attacacttc ctatttgtat    60
ttttattata tctctcggtt tatgggttta ttttgcttat gattgagaag taaacagatt    120 ttcactttt gttgtagttg atttaaatat tttcttataa cagtttaat aaaatactat    180 tttcctataa aagaatactt aatcatatga ttatgtaaaa tgtattttaa tggaacagag    240
tttatatact gctatggtct gaatattggt gtccccaaa attcatatgt tagagcttam    300
tacccaatgt gatagtagta agaaggtgag ccttcaggaa gtgattaagg cctgagggct    360
tcatcttcgt gaatgggtta ctatcccaac taaaagagg ttcaagggaa ctccctgtgc    420
cctctgctat gtaaagactt agcaacaatg caccatctat taagtaatga gtgagcccctt    480 actaaacacc agatctattg gcatcttgat tttggacttc ccagcctcca gaaatgtgag    540
taatacgttt ctgctgtttg taagttactc agcctaaagt attttgttat agcagccca     599
```

<210> SEQ ID NO 188
<211> LENGTH: 599
<212> TYPE: DNA
<213> ORGANISM: Homo sapiens

<400> SEQUENCE: 188

```
ctctcggttt atgggtttat tttgcttatg attgagaagt aaacagattt tcacttttg    60 ttgtagttga tttaaatatt ttcttataac agttttaata aaatactatt ttcctataaa    120
agaatactta atcatatgat tatgtaaaat gtattttaat ggaacagagt ttatatactg    180
```

```
ctatggtctg aatattggtg tccccaaaa ttcatatgtt agagcttact acccaatgtg        240
atagtagtaa gaaggtgagc cttcaggaag tgattaaggc ctgagggctt catcttcgtk        300
aatgggttac tatcccaact aaaaagaggt tcaagggaac tccctgtgcc ctctgctatg        360
taaagactta gcaacaatgc accatctatt aagtaatgag tgagcccctta ctaaacacca      420 gatctattgg catcttgatt ttggacttcc cagcctccag aaatgtgagt aatacgtttc        480
tgctgtttgt aagttactca gcctaaagta ttttgttata gcagcccaaa aggagtgaga       540
cacatataca tattaaaatt acttctaaca ccaccacagt tatcaatctt ctgtccggc        599

<210> SEQ ID NO 189
<211> LENGTH: 599
<212> TYPE: DNA
<213> ORGANISM: Homo sapiens

<400> SEQUENCE: 189
caagccagct aggctaggcc tgtccagctt tccttcacaa agaaggattg gagagttgcc         60
gcttactggc tttctcaaat gtcattactt agccagtctt ctgaagattg agattcatga       120
acattggact cttgcctgta attacaattc ttaagtatat taaccttatt ttcagctgta      180 ttttagttg ctttctgact tcatcttgaa atacctata ctctttctgc atttattcta         240
atcttacttc tgatcttgat tttaaaaaga tctttatcaa tgaaatcacc tccaagaacy      300 attttttgaac tttaagatgt attcttaaat ttttagtaaa ataggattta gaatcaactt     360
tgtgaagatt actaacagaa aaatgaatag ctccctaccat gaggcagttt atagttaatg    420
taaagaatat tatacttgtt tatacatgaa aaagccattt tctttctcta aacctcagag        480
agctatatat atttaatgaa taatgaatg tatgatgaat gaattcctgt cagtctttag       540
cgaagtctta tctcttattt ggaattcttt ctttatcccc tatgtcttca taaattcca        599

<210> SEQ ID NO 190
<211> LENGTH: 599
<212> TYPE: DNA
<213> ORGANISM: Homo sapiens

<400> SEQUENCE: 190
ataacagatg cccaatgaat atttctgaat gtctaagtga ttgaaccagt acttcaattt         60
tgacatttta atacatctat aaataattga gtgatctgaa tgcctaaatt tggctaagag       120
gataggttat atggcaacgt gctgatctat ttgagtactc tctcaataaa tgctttcagt      180
tgtcatcagc acagttctca ttcatctttg atttaagcat ttgtcattgt gccccattgt       240
agaatagcat aatacaatgc atacatgcct caccaatctg acacatctaa ggtcacactr       300
ttagtagtac ttgaatattg ctatttccaa cttctcattt tctcattcag aaactccaat      360
gccttaacac ttcccacccc ttcagcaaca aaaaggatct tatatgcact tcaatatcag       420
tttgaactgt aattacccac catcctctgc tactccaagc tctatcttca ccatcattcc       480
ttgcctcaca caggcccctc atttcattaa ggtgcatatt cctaccttt tatttgcaac       540 attaatgttc tcagtgctca aacagtatgt caggagtctt tgcaatgttc catcccact         599

<210> SEQ ID NO 191
<211> LENGTH: 599
<212> TYPE: DNA
<213> ORGANISM: Homo sapiens

<400> SEQUENCE: 191
tttttatttt actcacaata acaatttcaa gatttaccat cttatttatt cattttatgc         60
```

```
tgtatatttt ctctaccagc aaataatccc caggaagaaa cagagacctt gtctgtccta      120
atccaccatt tcatcaccat tgcctaggac catgccacag acataacaga tgcccaatga      180
atatttctga atgtctaagt gattgaacca gtacttcaat tttgacattt taatacatct      240
ataaataatt gagtgatctg aatgcctaaa tttggctaag aggataggtt atatggcaam      300
gtgctgatct atttgagtac tctctcaata aatgctttca gttgtcatca gcacagttct      360
cattcatctt tgatttaagc atttgtcatt gtgccccatt gtagaatagc ataatacaat      420
gcatacatgc ctcaccaatc tgacacatct aaggtcacac tgttagtagt acttgaatat      480
tgctatttcc aacttctcat tttctcattc agaaactcca atgccttaac acttcccacc      540
ccttcagcaa caaaaaggat cttatatgca cttcaatatc agtttgaact gtaattacc      599

<210> SEQ ID NO 192
<211> LENGTH: 599
<212> TYPE: DNA
<213> ORGANISM: Homo sapiens

<400> SEQUENCE: 192
agtgtggctg aacatggta tgtaaacagt gaagctgcta gatataagat tgcagatgct       60
gatagaggct aaatcattca cgacctaata ggtcctggtg aggacattga gtttttaacc      120
taaaggtaat gggaaaaaag gaagagtttt tgtttttgtt ctggggtttt atttatttat      180
ttttagtagc gacaaggttt cactatgtta cccaggctgg tctcaaattc ctcagttcaa      240
gtgatcctcc tgcctcagcc tcccaaagtg ctgggcttac agacgtgagc caccatacck      300
ggcaaaagga aggttttaag cagagcagtg aaatgaaaga gaagtaacca gttaggaggc      360
tattaccaga aaccaagcaa ggaataatag tgacctggga aggcaatggt agagatgcag      420
agtagtaaat gaatttgagg aatatttttga aggtagactt aacaggatttt actgtgctga      480 ttaatatgaa tttctttctt tcttttttct ttttttaaag acacaggatt ccactatgtt      540
gtccaggttg gggtgcagtt tgactaatca cagacacagt cattgtgcac tatagcctg       599

<210> SEQ ID NO 193
<211> LENGTH: 599
<212> TYPE: DNA
<213> ORGANISM: Homo sapiens

<400> SEQUENCE: 193
tcacgaccta ataggtcctg gtgaggacat tgagttttta acctaaaggt aatgggaaaa       60
aaggaagagt ttttgttttt gttctggggt tttattttatt tatttttagt agcgacaagg      120
tttcactatg ttacccaggc tggtctcaaa ttcctcagtt caagtgatcc tcctgcctca      180
gcctcccaaa gtgctgggct tacagacgtg agccaccata cctggcaaaa ggaaggtttt      240
aagcagagca gtgaaatgaa agagaagtaa ccagttagga ggctattacc agaaaccaar      300
caaggaataa tagtgacctg ggaaggcaat ggtagagatg cagagtagta aatgaatttg      360
aggaatattt tgaaggtaga cttaacagga tttactgtgc tgattaatat gaatttcttt      420
ctttcttttt tctttttttta aagacacagg attccactat gttgtccagg ttggggtgca      480
gtttgactaa tcacagacac agtcattgtg cactatagcc tggaatttct agtctcaagt      540
gatctttcct cctcagcatc ttgagtgctc tgtatttctt gcattacaga tgagtgaat      599

<210> SEQ ID NO 194
<211> LENGTH: 599
<212> TYPE: DNA
<213> ORGANISM: Homo sapiens
```

<400> SEQUENCE: 194

```
tacagacgtg agccaccata cctggcaaaa ggaaggtttt aagcagagca gtgaaatgaa      60
agagaagtaa ccagttagga ggctattacc agaaaccaag caaggaataa tagtgacctg     120
ggaaggcaat ggtagagatg cagagtagta aatgaatttg aggaatattt tgaaggtaga    180
cttaacagga tttactgtgc tgattaatat gaatttcttt cttctttttt tctttttttta   240
aagcacagat tccactat gttgtccagg ttggggtgca gtttgactaa tcacagacay     300
agtcattgtg cactatagcc tggaatttct agtctcaagt gatctttcct cctcagcatc    360
ttgagtgctc tgtatttctt gcattacaga tgagtgaata caggattact ggagattaat    420
caggtttaag atttaaagtc aagaagtctt caatatacat atttttgaag taccttcatt    480
atatcacagc tattaagtag gcatcagaac acaatgatag tatcatcagc cttgtgctag    540
cctttccaga gaagatttag ctttctgaca gtctgcattg tgtatcagct tcactcatg     599
```

<210> SEQ ID NO 195
<211> LENGTH: 599
<212> TYPE: DNA
<213> ORGANISM: Homo sapiens

<400> SEQUENCE: 195

```
caagatttgg aagtgctata gtttgaaggt gtcccagaaa gcatgtgttg gaaacttaat     60
ccccaatgca acagttttgg gagatgggtc ctaatgggag gtgtctagat aaatagatta   120
atgtttatta taaagggat cgagactgta tgcttgatct cttgcactct ctcttgccta    180
tgatcacttg ttcttctacc ttctgccatt gagtgatgta gcaagaaagc cctagccaga    240
tgcagcccct caaccttgga cttctcagtc tctagaactg taagaaataa atctgtgttm    300
tttagaaatt acccagtctc acatattctg ttacagcagc acagagtcaa gtaagaaatg    360
tgtttataat agtgtggcag ttttttaaaaa tggttacaat ttttttgtat cttcttgcat    420
ctagaagtag agtttatgtc ccttttctg agtctgagaa tccttgtgct cttcaacca    480
gtagaggcaa aagaagggat gttctatgac ttccaagact aggctacaaa aggtcttgca   540
gtctctgtcg agttttcttg agatgatctg agggaggcta acctccatat aagaagtgt    599
```

<210> SEQ ID NO 196
<211> LENGTH: 599
<212> TYPE: DNA
<213> ORGANISM: Homo sapiens

<400> SEQUENCE: 196

```
aagtcataga acatcccttc ttttgcctct actggttgaa agagcacaag gattctcaga     60
ctcagaaaaa gggacataaa ctctacttct agatgcaaga agatacaaaa aaattgtaac    120
cattttaaa aactgccaca ctattataaa cacatttctt acttgactct gtgctgctgt    180
aacagaatat gtgagactgg gtaatttcta aagaacacag atttatttct tacagttcta    240
gagactgaga agtccaaggt tgagggctg catctggcta gggctttctt gctacatcay    300
tcaatggcag aaggtagaag aacaagtgat cataggcaag agagtgca agagatcaag    360
catacagtct cgatcccttt tataataaac attaatctat ttatctagac acctcccatt    420
aggacccatc tcccaaaact gttgcattgg ggattaagtt tccaacacat gcttctggg    480
acaccttcaa actatagcac ttccaaatct tgtatgttct agtacaatag ttatttaagt   540
tgttttagt ttctgagctc cttagaaaaa ggcaagttca ttactttgaa gtgtacatt     599
```

<210> SEQ ID NO 197

<211> LENGTH: 599
<212> TYPE: DNA
<213> ORGANISM: Homo sapiens

<400> SEQUENCE: 197

```
ctttagagtc acaacttttg ttgttgttgt tgttgttgtt gtttcactta aatgctctag      60
ttacaacgtc cagagaactt tggtaattgt tgatttgggc catgatgtca ttgacatttt     120
atagctgagg ttcttttttt aaataatagc taactctaga cttttaagtat tattttttgtt   180
ggggtaatag agctataaaa gaggcaaaac acatctctaa tttcagtaca ctaacattaa     240
aagaagaatt gccagaataa ggattttaaa aatcaaacat tttaggagta gtccagactk    300
tattggacaa ttgtcacaga tgttttctag gattaagttg gtccaagcaa taaaatttag    360
ctggtaagtg acctattttt gagttttttcc ttccatctca taagcaagct attgccattc   420
tactattgtt tccatggaag aatgcttttct aggaggtagt atagcattgt atcgttcaca   480
agtaaatatc ttgggtgaaa ttaactaaag tataagagac tgcaagatag tttaaagtaa   540
cttttttagtg tacataaatc agtgccataa aggctttggt tttctgataa tgaagatgt   599
```

<210> SEQ ID NO 198
<211> LENGTH: 599
<212> TYPE: DNA
<213> ORGANISM: Homo sapiens

<400> SEQUENCE: 198

```
cccttttccta gatctactgt tggcaaaaat cctatctgct gtatttcatt acaaactaaa      60
atctcatggg aattcttgga gggttcactt tacgttgttg ttcaataatc catatggaaa     120
gagtcttaga aatactgaag catttttgctt tgactcttcc ttaatttaaa agttattcca    180
ttttgtaact aatgcctctt ttccacgttt aaatatctta taaacactgt catcaggttc    240
tggagcttta ctattctctt gccccctgaca gctataataa cctcttcaaa acaaaagaar   300
taaataattc ataacctgga aaatggacct ctgagtaatt gagttattcg tgtatatttg    360
aatagatatt aggaattatt agaccacatt ctatttttaag ggatcattat gatatataga    420
aataaatgta cattatatga ctcagagacc aagtaacagt tacttaaact taggagtaca   480
accttttccat gaaaggctat ttctccttaa ctgagagttt tatgaaaatt tggctacaaa   540
actacttggg aatttatctg tttaatcatg atgcatattg attagcaaat tttctgaat    599
```

<210> SEQ ID NO 199
<211> LENGTH: 599
<212> TYPE: DNA
<213> ORGANISM: Homo sapiens

<400> SEQUENCE: 199

```
atctcataaa aatgcttata tttgagtgcc tgcctataaa agtcatacat ggctgcctgt      60
caagaacgta gacatataag actgttggcc ttttttcctct aacattcttt tctttcctca    120
acattcaact gaaaaagag atctagaggc agaggagtga gccagaaaca agaatgaaa    180
gtcgtagaaa gtcagaaaca agaataaaa ggtggaaaga gcacaagatc acaccattct    240
cctctcctta gcagggtggt ccaggcctga agttggaaag cagagaaata tgttatttgr   300
atttgaaata agaattgaca tttgaattgg attggactaa actttgtaaa agaaaattga   360
gtcttggtga cgaaaatgaa actcttcata taatataaaa tctagacagc aaagagttct   420
cttcaaaata tgattgatca gtgtagaata gagatccggg tagaggttgg aaaaagcatt   480
aaagcatttt ttcaatctta ccctacaggg taaacccatt atagttagac agcttgttgg   540
```

```
tgacagaagc tacaaatcct aactctaagt acaatactat ttagaacatt tatttctta        599
```

<210> SEQ ID NO 200
<211> LENGTH: 599
<212> TYPE: DNA
<213> ORGANISM: Homo sapiens

<400> SEQUENCE: 200

```
atctaacaga gaaagcataa tcctgtttca acaaacccag gcaaaaatgt ctaaattaac         60
ttttgaagaa atttttattt tatttttacca acagttttca aaccagcttt atttaccaaa       120
gaccactaaa gttacatgaa cttgaaagca ttttagctag ccatttagtt tatgggcact        180
catttattta taagtcagtt tagtacctgt agacaatgta gacatacatg catagacaca        240
tacatactta gacataacat acagcacaca catacacaca cacacacaca cacacacacy        300
tgtccaaaga ttattattta atgttagacc tgagagaaac ctgcccatga ctcttggggt        360
ctctgtgaga aagacaggaa gtcccaaaag atggggtcag tggtgccttt gtgtgtgtgt        420
gtgtgtgtgt gtgtgtgtgt gtgtgtgtgt gtgtgttcct aaagggatct cagagtcatt        480
agaagtcccc tctctccctt catgtggtat caaagatggc aaaaggaagg aggagctgaa        540
gtagaaggaa atggaagagc aagtcttaga gccaatttag gagagatttt taagtttca        599
```

<210> SEQ ID NO 201
<211> LENGTH: 599
<212> TYPE: DNA
<213> ORGANISM: Homo sapiens

<400> SEQUENCE: 201

```
gtctttacca agaatttaca ttacatttat ataagctatt cattggctat acattgttaa         60
gttataaggt gtaggttgta gtatcaggtg tggcattatt ggttaattta tagctacttc        120
tggcaactac aagcagtttg caagagatga atacatggct caaagagggg aaaccaggac        180
agaattgttc tctcgtttta acatctctct gaacctggta atttagaagg actcgcatta        240
cttagataaa agttcttttc tcatttcccc ccttttgatc aaaaatcttt cttcttgaam        300
gcattgatga acaaaatctg agtgtcaagg tatccctcat cactgggaag gctcgatcct        360
cgatcgtcct gtcaaagtgg ttgatctata gctgctgtca tctctacatg ttgtagtagc        420
atgaatttac ttttctcaga agtaaaacag atgcatagta gaagtattct atacataaga        480
attttggtaa aaagcaaatt tgtatttcag aagtaaaaaa aaaaattccc ttggggcagt        540
caactaaaaa catcatgaat aaaattaaaa agctggtcct tttttagaga tttgttgta         599
```

<210> SEQ ID NO 202
<211> LENGTH: 599
<212> TYPE: DNA
<213> ORGANISM: Homo sapiens

<400> SEQUENCE: 202

```
atgtatcttg gactatctct aaccactagg tgatagcaga gtgctcaaga tatgggggac         60
ccagactctc atattatacc tgtctgaaag agcaaaaggc ggtacacttc agttagaaac        120
taacaaagat tggtcacaaa taaagtctaa gtctgaattt tcaagtcata gaaaacagtt        180
gcaatcttaa aagtatgctg tgcaactgct attgtagtcc ctgactgcca atcctttgat        240
accaacttct actatgagat agaggtggaa aaaccttgat cagacttgac tagaacctcy        300
gctgtgagag aaaggttgga aaaaaggca gtcctctgta gagctctttc cctgaatatc        360
atatccagag aaagaaatca aagccttcac tcttaaagga aagatggggt ttgaaaacag        420
```

| | |
|---|---|
| cccaagtaaa aagtctagag tcagaattcc gaattcagga gaacttaccc ctaacaccca | 480 |
| atgggacttt tgaagacaga gtttatgagg ttactgagta atactttcag aggcaaacac | 540 |
| caggggggcta aagggagtca ctccgaatcc tgtcaacgta tgccagatgt gttgacctg | 599 |

<210> SEQ ID NO 203
<211> LENGTH: 599
<212> TYPE: DNA
<213> ORGANISM: Homo sapiens

<400> SEQUENCE: 203

| | |
|---|---|
| agtgagcgat ggtagttgta gtgatggtgt gttaaatcaa ggaagaaatg ttagcaaagc | 60 |
| aaaaactgtc aggagcatct ccttcagaaa caacaaatac agtgggcttc ctgagcactt | 120 |
| tcttactgca ttttttgtca tgcatttata tgattaccat agattttatg aaattttatt | 180 |
| ttataataat ttgtattcat tcattttcca gcctgcttat tccagtttag ggtcaccagt | 240 |
| gtcagatcct ctcccagcag ctcagggtgc aaggtgggaa ctgccctgga caggaagctr | 300 |
| tctcactgca gggggcaccc acacacaccc caacactcac tcacattgga accatttaga | 360 |
| cacaccagtg aacctcatgt gaacttcctt gggatgtgga aggaaaccaa actacccaga | 420 |
| gaaaacccat gtacacatgc agagaacatg tagactccac acagacagtg gccatgacca | 480 |
| agaattagtg attttcttct catcaaagtg atcataaaat gactttgaat gaaatggtgt | 540 |
| tatttgagga cttgccctat ctcacagcta agtctatttg aattgtgaga gaaataggt | 599 |

<210> SEQ ID NO 204
<211> LENGTH: 599
<212> TYPE: DNA
<213> ORGANISM: Homo sapiens

<400> SEQUENCE: 204

| | |
|---|---|
| ctgagctagc tggatggagg aagatatggt agatgatgct cataataata aaatgatgca | 60 |
| ggaaatatat agttcctaga ttctagtaaa tataactgaa ctcttcaaga aaaggaattg | 120 |
| tattttgccg ggtttgattt tccagcaaac agctaagtgc ataacacttg ttgctgaaag | 180 |
| gaatagtgga ggttttcttt ctgcttctga tccaattgtc atttgatgat tatttctac | 240 |
| ctgtcatgcc ctgtgccttg actctcatct atattaatct catttaattc ccactaaaar | 300 |
| agaacaaaac aaaatcacga gcacaaaatc cccaaaaaac cttttgagat aagtatcatt | 360 |
| ctcatttcac agataaggat gcagatgtag agatggtaat tttcagtacc cgcaattagt | 420 |
| aaaacagatg ctaaaataca tgattcaaat tccagaacgc tttatgttac actgcttcct | 480 |
| ctctcacact gtctgttaaa agtacttgta tttgaagctg tttgagcaaa catcatgtca | 540 |
| ttgatcctaa tattgtatgt ttgttacagt gaatacaatg ttatgaccat cttagcagg | 599 |

<210> SEQ ID NO 205
<211> LENGTH: 599
<212> TYPE: DNA
<213> ORGANISM: Homo sapiens

<400> SEQUENCE: 205

| | |
|---|---|
| atttcactct tcttttgacat agctgtgttt tcagtgatta actttagtct tttccttaaa | 60 |
| ttaattagct atcttagtaa atgttaatga aaaaatgaaa ataacttgat tagacagcta | 120 |
| tagagatcta tgtaacatac tatgcgtcct gacttttgag agtagataca aaagcagcac | 180 |
| aaattgggtt aatttaaact caaacaaaag gtcagtttgc agaaagtaaa gacctgtgtg | 240 |
| acctcttgtt caaatcctgg aagctataaa tcctactaaa ttacttaggg ctttgttaar | 300 |

```
caggcccaac aaaagataac caacattgta attattgttc agtgatggac tgaataataa      360
gcctggtttc tatttgtcaa agcaacagac cttaagtcat ttgtagagct attctaatga      420
atagtggaag gctgtgggtt acataagcaa ttaaagaaaa atcataaaaa ccaaacacct      480
agaattgcta aaaccttaaa agtatccatc aagcgttgtg aaagtcaagc ttgcaagggt      540
aaataaaatg caaaatacaa gaacaaaatc tatttaggtt tcacaatctc cagtgtctc      599
```

<210> SEQ ID NO 206
<211> LENGTH: 599
<212> TYPE: DNA
<213> ORGANISM: Homo sapiens

<400> SEQUENCE: 206

```
actcaatata gaactgataa tgagagtgaa tatatattga gcattttcta ttggtctgac       60
cctgagctaa acccttttgta agtattagct catttatctc tcacaaaata cctatgaagt     120
aggtataagt tactatctta cgttctcagg gtcaagaagc tagtaagggg taaagtcaga      180
gtttgaaccc aggattggcc cttttccaagg cctgtgctct tcatctcaat gaaattagtg     240
tgtcaaagaa tgtttgaact attttaaggt ttaaatactga gtggctgtgc caaaaagctr     300
tgccaatttg aacatcttgt aagaatcagt agtgttaatt ggtttgacag aaaaataaaa      360
atgtaaatgt ttataacata catgaaaata ttttaacttc tatatctttc tcattaaggc      420
agctgaatat tgctgtttat atatttattt ccatttccat ttctgtaaaa tcttttttcgg     480 cttttgcttt ttagaaaaac tcacagtcct tttctttatt gatttaaaaa aacttcattt      540
tttccatttt ggcatttgtc tttaatttg catatatttt tgatttacag aagaattca       599
```

<210> SEQ ID NO 207
<211> LENGTH: 599
<212> TYPE: DNA
<213> ORGANISM: Homo sapiens

<400> SEQUENCE: 207

```
aaaccatatg ctgaagtcct tctctcaata tccttctact agaaactgat cttgatactc       60
aactctattc cagtgctttg gttttaaatc acactgctgc ttctgagaag cactcataga     120
tactctagaa tcctttctgc ttttgatcta gtatggcatc ttattttggc agttaaagaa      180
cttaaagtgt cccatgagag actgtttgct ttcttatcta atctttagta catctagcag     240
caaaacaggc catttcatgg tattattctt cagggagaag gttgttcaag gatacacaay     300
tcctgttgct tttattgtgt ggtcaaataa ataacttgag gcatctccag ctcctgacta      360
cgtcatgtat ttgttagttt cttttttgcag ctccagtttg catccctcct atagggatag    420
gttccaactc aagatccggc aaatattttc tgaataggag tggcctttct ctgcttaggc     480
aacacataat gaagcctcgc aaaagcgatt tgatgttgtt ttctgaattc tgtgctacct     540
cctgagttgt gaaagactta cttggcccga acctttctct tgcttcctct tttctcatc      599
```

<210> SEQ ID NO 208
<211> LENGTH: 599
<212> TYPE: DNA
<213> ORGANISM: Homo sapiens

<400> SEQUENCE: 208

```
cctttctctg cttaggcaac acataatgaa gcctcgcaaa agcgatttga tgttgttttc       60
tgaattctgt gctacctcct gagttgtgaa agacttactt ggcccgaacc tttctcttgc     120
ttcctctttt ctcatcgcta acatgacttg taaaagtaac tttaaagaaa aggatcctgt      180
```

```
tgccatgctg tatccttgct ggatcacaca cgaggtgttt agatgaagct ttatgcccta      240
cgggcctgtc tgccctgtac aaacattaca gtgcccatga ggctctgtaa tattagaags      300
gctgatacca attttggaac ctggttaaac cctgggggag atccaagacc atgagttctt      360
tttggcaggc caggccacct gctcacaaac aagaaacatg cagggggttt gcaaccaact      420
attcagaaag aaaataaagt tatggatgcc agaagcttca taaattacta cacaatctca      480
ggaaaggggg agtaagagg ctaggaagcg acaactgca agaacacctg aatctaataa        540
cattctgaaa cagtttcaac tggcagagaa cgtgggcatg gaaaagaag aacaattct        599

<210> SEQ ID NO 209
<211> LENGTH: 599
<212> TYPE: DNA
<213> ORGANISM: Homo sapiens

<400> SEQUENCE: 209
tatactatat tgtatttaat gtatttataa gtactcttta aatacaattc tttggaagat       60
aatgccttaa attaaggctg ttcctctctc tatttctggt aaaactagca ctgtattgct      120
ggccagtgga ggagatatat attactatag gagaaaggca agagatcagg caacccaaga     180
ggatatgaaa ggtaaacatg ggatggagta agtcatgaaa gtggctattt ttttttcattg     240 aataaatacc tattaattct ctgctggaat ctaagacagt catgtttgta gaaaacagay     300
attttgagat taactcctca tataattcct tgtatttctg cttagaagac agccattctt     360
tttttctgag agctctaaag cttaatagtc tgttgaaaaa ttatattgtg tcaaaaatat     420
gtatactcat atttttacc cattgccact actttatct tccatagtca ttatagcacc      480
aatttgctgt ttcttgcata tatcattat tccagtagat tttagtacat cttttgtatt     540
ctcttacgcc cactttctag gggtttcata tatatttgat acgttttgt tttggaaat      599

<210> SEQ ID NO 210
<211> LENGTH: 599
<212> TYPE: DNA
<213> ORGANISM: Homo sapiens

<400> SEQUENCE: 210
tttagtagtg actgactaca gtaattgaat caatttgaaa ttaattattt gtatcatgat       60 ttttttttcag tttcacagca aagcaatcct gttgcaattt gttttggtg ttatatacaa     120 gcatagtgcc cccatggaga tcccaaatat atgtgaattg ataataaagt ggatattgct     180 cttctggca cctgttatag attttcaaag aaatatcact agtatattat catagaattt      240
attaaacctg gaagcatttc caaatatat gtttatagtt ttatatttta aactattccr     300
agaaagaact ctactcattc gtattcaaac ctcctgactg tctcccctcc aattcattct     360
tgtagtactg ttgagttaca ttccctcatt gtgactccaa tcaagccatt tttctgctgg    420
aaccatattg atggctccct actgaatgcc aaataagtc cacattcatc aatatatgtg      480
tgaagtgatg agctcaatag ctattccata gtttatattc aatattgctc aaactatgtt    540
ttgtcaaata cttgagtcac actggaggtt aatcatgttt tagtggaaaa actattaga     599

<210> SEQ ID NO 211
<211> LENGTH: 599
<212> TYPE: DNA
<213> ORGANISM: Homo sapiens

<400> SEQUENCE: 211
ccatggaccc tggttgtaat gatcatgcag gtcctctatc tatgcatgcc agagattctg       60
```

```
gacagacaag tatggggaca tcccttctt tatttgattc ttttgtcaat ttttataaa    120 agttttattg ctttcagtcc tttggagaaa tggaagctga atgctaaccc caaggacttc    180
tgtggcctat catgaactgg gcgtgaaata agagtttctt ggagaagtag attccttgaa    240
gtttctgaga caaaaactgg acttcttgtg atgaaaagaa agcacagtca gaatacaaam    300
tgataatgga ttgggtccaa gtggccagca tcttagacta tggaaatttg ctgttggaca    360
ttaaagcatg acacaagtta ccgaagaaga gagaagctgc tacagtccgt aacaaaaaag    420
gctgtactgt tagctagcca aacacataca cagaaacctg aaaagagtt agttttcttt    480 cttttcatgt tcaaatgaca tagtctacct gatgcagaaa ctctcacatg gcaaggtta    540 attagaggtt tccatggact atatcccttg ctcctgggct acaacaggac atgaggctt    599

<210> SEQ ID NO 212
<211> LENGTH: 599
<212> TYPE: DNA
<213> ORGANISM: Homo sapiens

<400> SEQUENCE: 212
cttgtttggc aaaaagcttt gcttcttttg gaccttctcg ccttcatcct ctctatagtt     60
ccagcggttc aacttccttt cattcagctt ctagtgtatg cattctctac tccatatgaa    120
ggcaaccgct gaagtgaggc agtgggagat gagaggagga gaatctaaaa ggctcagatt    180
ctgaagggca agaagagaa gacttaggga tggtctaacc tcaggacaga atagctaaaa    240
gccacctgag cattaaccct gaggaaatta acatcaagct caagcttatt attaaaaaar    300
tctatatctg tggagcatct tttctggatt taagttaaat aataaaaaaa agacaggact    360
gcatttgaga atccagtagg cagtacgaga gaaagaaaa agagggacat cacatttgca    420
gtggtgtgca caaaattgca ttgcctgtat tacacagtaa tgtaaatatt ttgaaatagg    480
ctgtgtattt gtaagcatac tctctacctt ctaaattatt aagagccaag tgatatacta    540
gtatgatttt aaaataaagc aaaaggaagg gctgaggcct ctgtattagt ctgttaggg    599

<210> SEQ ID NO 213
<211> LENGTH: 599
<212> TYPE: DNA
<212> TYPE: DNA
<213> ORGANISM: Homo sapiens

<400> SEQUENCE: 213
attctagaca tgcttggaga tcacaatccc tacatataaa agaccagagg aagaaaaaga     60
aaaggaaagc ttctcgagtt acatgaaatt tcatgtacag agtatcatga ggtaatttaa    120
aagcaaagac tcaagggtac ataccttcac caggtaaagc ccataccccca aaacaatggg    180 agagaaatta actgtgaaaa tctccgctgg aagagagcag gtgttggtga aaagagacat    240
gggaaatatg tttagcattt gagagggaaa ggaaatgaaa gtggggaaag gaaaatatgk    300
ggagaggaaa ttcaaattca cactgtagtc tgcccgtgtt ttattggtaa aatttaaaag    360
ctgggaaact ggccatcaca ttgcaaagtc agaaaatcat ttatgcgcct tatgggatcc    420
aatgactcct tgccaaaata ataacaaatc tatttttatc ttctctcggg gactgtcaac    480
cacttgctgt ttaatcacct tctaactaat gttagtattc taaaaggggt agtgctgttt    540
gctagatagc aatattaata tcatcacatg taccctaaaa cttaataata aaatttaaa    599

<210> SEQ ID NO 214
<211> LENGTH: 599
<212> TYPE: DNA
<213> ORGANISM: Homo sapiens
```

```
<400> SEQUENCE: 214
gatcacaatc cctacatata aaagaccaga ggaagaaaaa gaaaaggaaa gcttctcgag      60
ttacatgaaa tttcatgtac agagtatcat gaggtaattt aaaagcaaag actcaagggt     120
acataccttc accaggtaaa gcccataccc caaaacaatg ggagagaaat taactgtgaa     180
aatctccgct ggaagagagc aggtgttggt gaaaagagac atgggaaata tgtttagcat     240
ttgagaggga aggaaatgaa agtggggaa aggaaaatat ggggagagga aattcaaaty      300
cacactgtag tctgcccgtg ttttattggt aaaatttaaa agctgggaaa ctggccatca     360
cattgcaaag tcagaaaatc atttatgcgc cttatgggat ccaatgactc cttgccaaaa     420
taataacaaa tctattttta tcttctctcg gggactgtca accacttgct gtttaatcac     480
cttctaacta atgttagtat tctaaaaggg gtagtgctgt ttgctagata gcaatattaa     540
tatcatcaca tgtaccctaa aacttaataa taaaatttaa aaaaaaagaa taggctagt      599

<210> SEQ ID NO 215
<211> LENGTH: 599
<212> TYPE: DNA
<213> ORGANISM: Homo sapiens

<400> SEQUENCE: 215
tttttggatt aaatatacgt gagaatcagt gaatattata tacctggaga cctacaatgt      60
tcatttgtat attaaaggct ataaaaagtt ctatcataaa ttacatttaa tttcttaaaa     120
tacagtgttt ctcaagccca ctggaacact ggaagctttt cttatgctac atgcgctaat     180
atcttatagg acataatttg ggaaacgcga agttgtttca taataatata attaaggaac     240
ctaatatgat ccccaggaag gttaagcagc tggctcattg tggtgccact ggtttatgcs     300
aagatccaga ataatccata catctcccaa ctaccaatta ttgacaatgt gtgttactgt     360
tggcatagtg acattatgat tcttcatttt tagaagtgtt ttgtaactta cttttaaatc     420
tcctgatagc tgatgaatta aggtgatatc atacatttct ctttctactt tttccatgtc     480
ataaatgata tgataaatatg gctaagagac aaaaaataat ggaagattta acactaagcc     540
ctggtttatc tgatctaatt taaaatgccc ccttctcatc cacataccac acttactca     599

<210> SEQ ID NO 216
<211> LENGTH: 599
<212> TYPE: DNA
<213> ORGANISM: Homo sapiens

<400> SEQUENCE: 216
gatataccct caacaacacta tttttacttt acaattgatc aaattaacag agattattaa      60
ctacctacgg ttttatagaa aatgtaattc aaaataaagt ctcaagatta tttctaaaat     120
accatgtaga agtccatgat atgataggaa attagttctc tattaaaaag ataagacatt     180
tctagctcct ttaagttagt gactagttag tcccttcttg tgtgctttaa aataatttat     240
aaatcatatt attgacattg taggtgctgt atcaaaggac tcactattat agagcttgty     300
tcccaaacat gtttctactt tatattaccct ctacttaaag taacactttt tcctggaaaa     360
tgctgcttcc aaattttaca ttttacattt taaatcccctt caaatttatg tatttaatga     420
cttttagtaa agccttggca tcagcaatgt tgtctgttgg gcaaagacac atctataacc     480
caaagtatct tttatcaaag gtgatcaaga tgcagaaaag aaaaacaagt ttcactggca     540
atcaagacag gaacactgga gggtccattg tgccactgga atcagcctaa aaccataac     599

<210> SEQ ID NO 217
```

<211> LENGTH: 599
<212> TYPE: DNA
<213> ORGANISM: Homo sapiens

<400> SEQUENCE: 217

| tgctagctgt gctagatgtt gaagatacag tgatgaaaag atacacattt ttcatggcac | 60 |
| tggagggcat aattaggtaa atgaatacta tggttgatgt ttgtgtactc ccaaaatgta | 120 |
| tttgttgaaa tcctaattcc gaatgtgatg atattaggag gtgggacctt tggctgctga | 180 |
| ttaggtcatg atggtgaagc tttcataaat gggattagtg cccttataaa agaggttcaa | 240 |
| gagagacctc tttccccttt caccatgtga gtaagccagt gccatctaca gagaaagtgk | 300 |
| agtcctcaca agatgctgaa tctgtcagca ccttgatctt tgacttgcca gcatccggaa | 360 |
| ttgtgagaaa taaatttcta ttgtttaagc cacctaattt attgtatttg ttatagcagc | 420 |
| ccaaacaggc caagacaatg aataattaac aataaaaata atatttataa gattagaaag | 480 |
| taaaatgttt tggagttaga ttgaagagat atccaaccca gccttgttga tcatagaggt | 540 |
| gatgatgaat tgtatctcag aacaaattat gagtatatgt gtttgtgtgt atgcataaa | 599 |

<210> SEQ ID NO 218
<211> LENGTH: 599
<212> TYPE: DNA
<213> ORGANISM: Homo sapiens

<400> SEQUENCE: 218

| agaaggagga gtcagtttca ggttgacttg aggtagtttg aacttgttga ggtgttcttg | 60 |
| aaatagtttg aacttgttga cttttgaggta tacatgggaa ctctggtggc tggttctaag | 120 |
| ttatatatga agttttgcaa ttcaaggaga gaatctggat taagataggt attttgaaag | 180 |
| gatagtcatt gaagccatgg gagttgaagg ataatggcaa gaaagaacat gtagactgac | 240 |
| atcattaaag ggcttagcat accctgaaga tcagcaataa ttgaaagatg aacacaagar | 300 |
| gaggagaata caaactagta tgagacacag ctactagaca gagtgaactt ttagaaaact | 360 |
| ggttgatata ctgaaaggtt agaaagcagt attaggcaca gctatagctc ctgaaataat | 420 |
| ttttataatc ccaaatttga aaaacagaaa gaaaaattag tcattttttct ggttttatgt | 480 |
| agtgctatag ctgtatagct gtataatcct agaactataa taattattaa agaatatcta | 540 |
| tgtcgatttt ataaattact ttcaataatc caggttttag cttaacatac atggaatta | 599 |

<210> SEQ ID NO 219
<211> LENGTH: 599
<212> TYPE: DNA
<213> ORGANISM: Homo sapiens

<400> SEQUENCE: 219

| aggttatgct acttccctgg aggacctctc aaaaggaagc tgtttgttct atttctttct | 60 |
| catctgtccc aggactaggt attgcattag gagatcccctt gcttcccact gctgctttta | 120 |
| aatcatttca tttccttctt cccttcattc ttcccaaatg caaggtcttt caactttcat | 180 |
| ttcgtgctac actctgccct ttattgctgc tctctggaat ttgtggtcac tgtccctcat | 240 |
| acactgaaaa ctcacatacc tctacctcta gccctgttgt attcctgatg acttgagcay | 300 |
| ccaagggagt gatacataca gcactggtca atcatttctt tacctgccac acatacagca | 360 |
| atctttaatt tcaatagcct tagccactca ttcccaaata atgcttggat catgcacatt | 420 |
| atcatgagta aatacaccca tgtctgaaat cctgatttca agtacttccc aattttttctg | 480 |
| tcttttcttt actttcagct cacagaaaca attcttccac catattaaaa actctaatcc | 540 | aattcacttg ttccaccact ttttttattc attattctct cctgtcttta ctttcttcc    599

<210> SEQ ID NO 220
<211> LENGTH: 599
<212> TYPE: DNA
<213> ORGANISM: Homo sapiens

<400> SEQUENCE: 220
ctggggagag agagaaactg aggcaggggc tgcctgactc tccgagcccc tcagcagacc     60
atttgacatc acacagagtg ccactagcca caagctgcat gaatttacct ctctataagt    120
aaacagagag aaaaaaatcc tcgctgtgtg tgaagatagc cccaggaggg ggaaatcttg    180
taaaagtcaa aaaaggctgt gacttatgtg acttcactgc acacatccag ctggacttct    240
cacccatctc agcgggaggg ttgtcttgag acagttgaaa cagcaaaagg gtttggaaay    300
ggtaagctat ttcaggtaac actttacgtt gccaaaccag cgatagcagc acttcagact    360 gtcactttt ataatgtttg cctataaact ttcccgtgt ggttttgaa atggcgccca       420 aatgcaaaca gagaacagat gggaaacctg agtcttgccc cgtccaatca cttcacggag    480
aatggacgac agatttaaac tgttaaggaa gaaaaaagca gtttctacca acggcacagc    540
tccctccatt acttttcaca aattaagcct tttctggggt ttcccaggga tggtgtctt     599

<210> SEQ ID NO 221
<211> LENGTH: 599
<212> TYPE: DNA
<213> ORGANISM: Homo sapiens

<400> SEQUENCE: 221
ttaaaaatta tatatttagg cacacccctc atatcattta agtctgcctt tgagaaacat     60
gctggatggc tcttcatgtt tgaaagaaat tatattgttg cccatgagaa aataaaaatg    120
cacacagagt aaaagagccta agaatgcact tactgaggag tgagtcaccg tgtctcccaa   180
tgtccccacc cacagtggaa atccgcactc cctgttttgt cagtatccct cttgcttttg    240
atctgatgtt ttcggctgtt catgacagtt ttctccaaaa aaagatgcac agagggaagr    300
ttttctctct ggtcccaaca cgtgtattaa agtcatattt catgagtgaa aaattcctga    360
tggaccacta agacgcaggt attgaatcag tactgtgtgc ataaactcct agatatgggc    420
agctttgctt gcataagaac ttcaaaattg agtcctggcc gagtgcggtg gctcatgcct    480
gtaatcccag cactttggca ggccgaggcg ggtggatcac ctgaggtcag gagttcaaga    540
gcagcctggc caacatggtg aaaccccatc tctactaaaa atacaaaaat taagccagg     599

<210> SEQ ID NO 222
<211> LENGTH: 599
<212> TYPE: DNA
<213> ORGANISM: Homo sapiens

<400> SEQUENCE: 222
ctcccttcat cgtgtaagag aagaggctgg tggaggagga ggaggttgaa ggtcacttgc     60
ttgttttgga tacgacctct gtagacatcc aggttatgta tttcctcccc ccgggcaggt    120
ggaaatatga acctacaagc agggacttga gtggcatctg cggggaggag gtgggaaaag    180
ccacacgtgc ccaggagact ggaatgcagg gaaaggacca aagagccag aggtagaatt     240 ctgggtatat ccatggatac aggagggtg gcagggaagg agaaatttcc tagaaaggcr    300
agaagtcctc cttgacatgt tcctgtccat aagaacacat acgcacatgt acgcaccagc    360
aggaagcaga atgctaaccg aagataatta acccccaatt ctgtgttagg gattgagaaa    420

```
tagaccagga gccctgcccc ctcctctctc atttcctgac cttccacact gagaagacct    480
ggctaggcag ccttgctttt tttcctgttt agcggaggag tgaggatttc agccggaagg    540
tctttctgat ggcagatgtg taagtgccag acattgtgct gggtgccttc tgtgtccta     599
```

<210> SEQ ID NO 223
<211> LENGTH: 599
<212> TYPE: DNA
<213> ORGANISM: Homo sapiens

<400> SEQUENCE: 223

```
accatgggtg atgggttagg cgcattgcag aggtcttgtg gaggactgga ggagacctgt     60
gggatgcagt tttgcctgta cttctttca gagctaagct ttctatcagg gataggccta    120
ataggtgaag gggtgtgggg actgatcaga ggaagggcca gaggaaaaga ggggcttcag    180
ggccgacttg gagcttgggc ggcagttcag tggtgtgact cccttcatcg tgtaagagaa    240
gaggctggtg gaggaggagg aggttgaagg tcacttgctt gttttggata cgacctctgy    300
agacatccag gttatgtatt cctccccccc gggcaggtgg aaatatgaac ctacaagcag    360
ggacttgagt ggcatctgcg gggaggaggt gggaaaagcc acacgtgccc aggagactgg    420
aatgcaggga aaggaccaga agagccagag gtagaattct gggtatatcc atggatacag    480
gaggggtggc agggaaggag aaatttccta gaaaggcgag aagtcctcct tgacatgttc    540
ctgtccataa gaacacatac gcacatgtac gcaccagcag gaagcagaat gctaaccga     599
```

<210> SEQ ID NO 224
<211> LENGTH: 599
<212> TYPE: DNA
<213> ORGANISM: Homo sapiens

<400> SEQUENCE: 224

```
gtgtttgcag ggttattctc ggcatgctgt ggggctaggg taagttatcc ggctcctgag     60
ccctgctggg gttctcatct caagggaatt ctgtggtgtg ttactgtgcc ccacatgcaa    120
atatcagcta ctctcaaatg tgttggatgg atgaatagta gaaggtattt taagaagcca    180
caggcctctt tgtaaattaa acaggcatca tacatgggtt ttgataatga tgaatctcac    240
aaaatcttca gatgtttagt ctctgggaac attccaggaa tcctcattta ggtaacttay    300
atgtgatgag acctatttgt tcacttgaaa gaaaacctgt tttgaagtca gaggaatgcg    360
aatagaggct ctcacatggt tggaaaaagc aatctgcagg ccagttacgc cccgtaaaca    420
ggaacccagg actgccctcc tggccagggc tgagttgcag gatggggacc ccccactacc    480
tccaaccgcc cgccaggatg aggagtgctt gctctcagac gtgcccctca ctttaaatat    540
acagaggcct tcctaggcag cctttgattg tgtccttgtg gtgaccttgc cctgcagca     599
```

<210> SEQ ID NO 225
<211> LENGTH: 599
<212> TYPE: DNA
<213> ORGANISM: Homo sapiens

<400> SEQUENCE: 225

```
tttctgttac tacctctaat tggcagagtt tcttgccagg tcaatgtgga ggcagagaga     60
tggccggagg gcggccaggg gagtcaggcc aggtgtgggc aggatgggat tctgcctcct    120
cccaggtgcc tcgcctgggg gatgccctgt cccagaaagc ctacattcgt gggagccggc    180
gcacagccct tctgagatct aaagcttccc tctgaatgct gctttggagg attgtgagag    240
gtagtgactc ttcaaagttt gtttgttttc ttgaagcttt tacctctatg caaatatgcr    300
```

```
gtttggagca gggaagaaag gttaactgtg atggcgccgg ctcttaacgt ggaatgtcct    360
gaattaatgt gggttttcagt cctctggctc aggatcccct gagggagagt ttttcttttcc   420 tctgcaaaac acaggagaaa agtgatcccct gtggctccga cctgccttcc ttgggtcctg    480
cggtgcaaaa ccagctggga ccgtgtcccg cccacccgaa ggcagtgtgg ggaacctttc    540
ctccaggtca ttcccattca gctgattgct gccggctccc caggccacaa ctctgtgcc    599
```

<210> SEQ ID NO 226
<211> LENGTH: 599
<212> TYPE: DNA
<213> ORGANISM: Homo sapiens

<400> SEQUENCE: 226

```
aggaaatata gctggtgtgc tactctccac tgtactggtc cgattctcgc caggggaca      60 tctctgtagg cagttcagaa attatttttt ggaagttttt taggctattc cacagataat    120
tctgatccag taggttttat gcaactgtgc aaaatgctta tggtctctat tttttttcc    180 ttgagagatg attttagcct ttggttttt gtttgttttt gttttttgag acagagtctt    240
gatctgccac ccaggctgga gtacaatggt gcaattgtac cctcactgca ttgtcaaack   300
tggctcactg taccctcgga ctcctgggct gaaggggtcc tccaacctcc tgagtagctg    360
ggactacagg cctggataat ttttaaaaat atttcgtaga tatggggttt cgccatgttg    420
ctcaggctgg tctccaactc ctggcagcct tggcctccca aagtgctggg attacaagtg    480
tgagccacca cacctgtcct agccttaagt tttgcatttt tttccatctt tttgctgtat    540
cccatatgat ttagagattt tgctgtatc ccatgagatt tagagatggc tctacttttt    599
```

<210> SEQ ID NO 227
<211> LENGTH: 599
<212> TYPE: DNA
<213> ORGANISM: Homo sapiens

<400> SEQUENCE: 227

```
tcacaaaacc acagcaatcc aatatgagat gttttttaata tcagacttaa caaataatta    60
catggctatg aaataactgg ggtcgtgttt aaactggaag tgttttgttt aatgttcgta    120
gtttcaataa aatgtatcca ctagtcttcc agtttgcaga ctgttgttta ggtgtttgtt    180
tagccagggt aattgttaaa aactccctct aatctagctt acccttacat ttccatggaa    240
gcgaatttta gtcattaaag gaaaacatgg gaaattgatt tttgggtgcc tggctgttam    300
gctaggtagg aaatatagct ggtgtgctac tctccactgt actggtccga ttctcgccag    360
ggggacatct ctgtaggcag ttcagaaatt atttttttgga agtttttag gctattccac     420 agataattct gatccagtag gttttatgca actgtgcaaa atgcttatgg tctctatttt    480 ttttccttg agagatgatt ttagcctttg gtttttttgtt tgtttttgtt ttttgagaca    540
gagtcttgat ctgccaccca ggctggagta caatggtgca attgtaccct cactgcatt    599
```

<210> SEQ ID NO 228
<211> LENGTH: 599
<212> TYPE: DNA
<213> ORGANISM: Homo sapiens

<400> SEQUENCE: 228

```
tggcgagaat cggaccagta cagtggagag tagcacacca gctatatttc ctacctagct     60
taacagccag gcacccaaaa atcaattttc catgttttcc tttaatgact aaaattcgct    120
tccatggaaa tgtaagggta agctagatta gagggagttt ttaacaatta ccctggctaa    180
```

| acaaacacct aaacaacagt ctgcaaactg aagactagt ggatacattt tattgaaact | 240 |
|---|---|
| acgaacatta aacaaacac ttccagttta aacacgaccc cagttatttc atagccatgy | 300 |
| aattatttgt taagtctgat attaaaaaca tctcatattg gattgctgtg gttttgtgaa | 360 |
| ttctcaccct caactgggtc agaaagactt gaaaggaata aagtctttac ttatggcttg | 420 |
| atgcggggcc attggcatag taagtgctct gtcttttaac tggttgaaat aaacagacaa | 480 |
| aacagaaaca cacacatata ccccaaattt gaatcagaga gagccagtat aaaatgatac | 540 |
| aagtaccagt tctctgggct tgccagattt ctgctctata agtaatatta aacatggct | 599 |

<210> SEQ ID NO 229
<211> LENGTH: 599
<212> TYPE: DNA
<213> ORGANISM: Homo sapiens

<400> SEQUENCE: 229

| gacttcaaat atttataatg ttaatcaaca gaatagtact tggcattgag gactgccccc | 60 |
|---|---|
| cttcgagtca ataaccatgt tttcactcct ctgctggtgc cctataacaa tgaatgacca | 120 |
| aaaggaaatt aacaatgaat gaccaactgg aaaactcata tttaatctga atattaaaa | 180 |
| actaaaatct tctagagatt atttttcttaa gtcaattgag tgggcccaac cccactgcta | 240 |
| ctatttcaga acgtgtccag aagacaaatg atatatatga tatatgatat gacatatgay | 300 |
| atgatacgat attgcacaaa gccaagatga ctaaacataa ccttccctg aggggccaaa | 360 |
| agaaaaggac cctctagtgt tagggcccag gcttcttcct ggaacttctc agtcacattt | 420 |
| ttctcctatc caatagacat tatctaaact gagcttccaa ataaattagc aaaccaaaaa | 480 |
| gtcttacaag ataagacctt ggtgcacaga aggtcaaggt ggaacttact gctaaccaaa | 540 |
| gctatagtag ttctaatcat ggagaactga tggacagggg cacaggcacg cacgcacgc | 599 |

<210> SEQ ID NO 230
<211> LENGTH: 599
<212> TYPE: DNA
<213> ORGANISM: Homo sapiens

<400> SEQUENCE: 230

| tggtggaaga gtcagaagac ttctgaggac attaatattc aatgactatt aatgaagaga | 60 |
|---|---|
| ccctaaagat catcttctta agccctcaga cgacagaaag ggaaactgag gcctgggact | 120 |
| tgtatacttt tccaaagcct cttctttgcc aggttttgca ccttcctcta agacatcttt | 180 |
| tcttttccat ctcataattc tggatgcaaa tgaactcata gctcatggaa actataaacc | 240 |
| cataaaaatg cacaaaagga cattaacaaa atattaccta aaatttccag aacttcatcr | 300 |
| acctccttcc tgatccataa gtgcatccac agatcccagg ttgagcaggc ctgcttccaa | 360 |
| caatacccac attgttggat gtaaattctt acacaaagac tcactcgggg aacttcgtcc | 420 |
| cttccacga tttcttccct ctgcctcacc tgtccctccc tgcatgtata cacaatttta | 480 |
| aacttccttc aagaattaaa tacagtaaaa caaatcctct gggaccattt tacactttat | 540 |
| gttgaaataa actcacaata acgctgccct gaaaagccaa aatgaaaaat gacagttttt | 599 |

<210> SEQ ID NO 231
<211> LENGTH: 599
<212> TYPE: DNA
<213> ORGANISM: Homo sapiens

<400> SEQUENCE: 231

| ctgaggacat taatattcaa tgactattaa tgaagagacc ctaaagatca tcttcttaag | 60 |

```
cccctcagacg acagaaaggg aaactgaggc ctgggacttg tatactttc caaagcctct      120 tctttgccag gttttgcacc ttcctctaag acatctttc ttttccatct cataattctg      180
gatgcaaatg aactcatagc tcatggaaac tataaaccca taaaaatgca caaaggaca      240 ttaacaaaat attacctaaa atttccagaa cttcatcgac ctccttcctg atccataagy     300
gcatccacag atcccaggtt gagcaggcct gcttccaaca atacccacat tgttggatgt      360
aaattcttac acaaagactc actcggggaa cttcgtccct ttccacgatt tcttccctct      420
gcctcacctg tccctccctg catgtataca caattttaaa cttccttcaa gaattaaata      480
cagtaaaaca atcctctggg gaccatttta cactttatgt tgaaataaac tcacaataac      540
gctgccctga aaagccaaaa tgaaaaatga cagttttcc ctaacctggg ttgctccta       599

<210> SEQ ID NO 232
<211> LENGTH: 599
<212> TYPE: DNA
<213> ORGANISM: Homo sapiens

<400> SEQUENCE: 232
ctccagctcc gagaacctcc aagtatcaca gggcatgcgc cggtgtcaca gctttggaaa       60
tttaattttc aaggtgtaag tccaattacg aggactacat gaggctgaat tattcagctt      120
agcagatttg gaacctctct cccagcccctt tggagacaac gtgagccaag cctctacttg     180
gtgctgcact gaaatctgtc atcagtaggg aatattggta gctgagttat tttcgagtg      240 gtaatccgag aataaaacgg cagatcccag cactcatcgc cacttaatga acctgtttgy     300
ggagagtcca cctggtgcct gcctggcttt aggaacccgc agcagtccga gtggtgtctg      360
gggtaagctg agctgctctg gaacacatc tcgtgcgtgg ggtgaatgaa cagcacactt      420
acccagtggg gtaggctggg agaggacaga gagcccagcc tccttagctg gatcaggaca      480
gtttaggaag gagggttgcg tccatctgag atgagagttc tgagagacat gggctcccca      540
ggaagacccc aggcacttgt cattgaagga tgaggaccga agcacttatc acctgaagc      599

<210> SEQ ID NO 233
<211> LENGTH: 599
<212> TYPE: DNA
<213> ORGANISM: Homo sapiens

<400> SEQUENCE: 233
tgcacgcaca caccatgtac acacacacac cgtgcataca cacacaccat gcacgcacac       60
acaccgtgta cacacacaca cactgcacac atactttct tgcttttgct gtgaatcaca      120
ccgtttcacc tgtgctatct ttgaagcaga ggttttcttt attcctcctt tggaaatgat      180
gtggcatatt cttttccctc ctccatttt gtcctcagtc aaagctaaaa ggagcagttt      240
ttatgatgag atttggggag gctccagcag tgttgaaatc ctatgacata acttgaaacm     300
tcgagtgggt acataaaaaa tgtagagttt agagattttt gtattaaagg cctccctgcc      360 accccagtc ttagaaaatg tggttcattc ctgtggttca cagaatctga agcctgagat      420
tgatgagccc cttcttgtga ttgttttaat cattctctaa agtttgtgca ttttactgta      480
cccttagtca cagagagtac tgagtgaatt taaagttgct tggaatatat taagctttct      540
tggaaaattc tctttccctt ggatcaaatg ggtgaacaga atattaagtt gagtgtcct      599

<210> SEQ ID NO 234
<211> LENGTH: 599
<212> TYPE: DNA
<213> ORGANISM: Homo sapiens
```

<400> SEQUENCE: 234

```
gcggcgtacc tggcccggcg cggcgactgc tctccgggct ggcggggggcc ggccgcgagc    60
cccgggggcc ccgaggccgc agcttgcctg cgcgctctga gccttcgcaa ctcgcgagca   120
aagtttggtg gaggcaacgc caagcctgag tcctttcttc ctctcgttcc ccaaatccga   180
gggcagcccg cgggcgtcat gcccgcgctc ctccgcagcc tggggtacgc gtgaagcccg   240
ggaggcttgg cgccggcgaa gacccaagga ccactcttct gcgtttggag ttgctccccv   300
caacccgggg ctcgtcgctt tctccatccc gacccacgcg gggcgcgggg acaacacagg   360
tcgcggagga gcgttgccat tcaaggtaat cgccgcgcaa gacgcctcgg ggagcttcgc   420
cagccgggga cgtgggcgcc acgggagccc gggacgccgg gtgcaccgtc ctccgggcgg   480
ggggcgcgga aggactagca ttgtggagga cgctccgtgt cctccctctg tggctgcata   540
ggtgatgggg gaggtgggtg cgtgctgacg gccggcgttc tggaagttct gcctctgct   599
```

<210> SEQ ID NO 235
<211> LENGTH: 599
<212> TYPE: DNA
<213> ORGANISM: Homo sapiens

<400> SEQUENCE: 235

```
aggttatgct acttccctgg aggacctctc aaaaggaagc tgtttgttct atttcttttct   60
catctgtccc aggactaggt attgcattag gagatccctt gcttcccact gctgctttta   120
aatcatttca tttccttctt cccttcattc ttcccaaatg caaggtcttt caactttcat   180
ttcgtgctac actctgccct ttattgctgc tctctggaat ttgtggtcac tgtccctcat   240
acactgaaaa ctcacatacc tctacctcta gccctgttgt attcctgatg acttgagcay   300
ccaagggagt gatacataca gcactggtca atcatttctt tacctgccac acatacagca   360
atctttaatt tcaatagcct tagccactca ttcccaaata atgcttggat catgcacatt   420
atcatgagta aatacaccca tgtctgaaat cctgatttca agtacttccc aattttctg   480
tcttttcttt actttcagct cacagaaaca attcttccac catattaaaa actctaatcc   540
aattcacttg ttccaccact ttttttattc attattctct cctgtcttta ctttcttcc   599
```

<210> SEQ ID NO 236
<211> LENGTH: 599
<212> TYPE: DNA
<213> ORGANISM: Homo sapiens

<400> SEQUENCE: 236

```
ctttttgatc ttatttttt ttagattttg aagcatactt agctctttgc agctcagaga    60
ttgttgacct gatgttactt ctgtttgaaa gattcccctc ctcctctccc atttgcttgt   120
tttatttctt aatgttttag cctaaatgtt atgtttaaca gaactttag ggtgtttaac   180
agacacccctt cctaaaataa atctcgccca cctcatacta ttaactttt ctacaccagc   240
actttgtttt cttctttata atattgttat aacattgtta taagtgatta tataagatay   300
gtaaacacta tcaatagt ttattcactt gtcatttatt tttgcatcta gaatgcaaac   360
tccatatggt tagattatac ctgtactaaa ctcatttcct agctggaagt agctgcaaat   420
aagcattttc tttttttgaa tattgaataa agaattatc ttgcaaagag tgtggagttt   480
tcatcctgaa gtgaagcaac tgtgatgttt gtatctgact atgtgggatt cagtgttgga   540
tgtgtaacct aagggctgct gtttgccacc ccagaagaca agggatagat ggtaactta   599
```

<210> SEQ ID NO 237

```
<211> LENGTH: 599
<212> TYPE: DNA
<213> ORGANISM: Homo sapiens

<400> SEQUENCE: 237
actctatatg tgtgcattcc attctgaaat gaattggaat ttaccattct ttagttagac      60
aaggggttaa aggaaagaat atacaacagc ttagccccct gacttggtac tgtcaaaaag     120
aatcagaagt ttttgagagt ggcatgatgt ggccaaagtc cacaatggcg cagaattact     180
tacagtattc caaagtggag taaattacac attcagcatc tgaaagctct tccatggtac     240
cggtttccca aaaccaaaat tactgaaaat ctaaagcacg cctattttac ttgacacacr     300
ctcttcaagg atggccatgg cttgtcccaa tgattcatac ttgtgtataa atatttaaat     360
ggtaagagct tgaagttata taaatagaag tcagctacca catacaaatc acagtgagga     420
aagagaaact tgtaaaaagt gtgacttttg tctattacag aaggagacat cttcaagacg     480
tgaaggatca ccacaatgac ctgtccagca tcttgttcaa tcagacctct ccttaaaaga     540
acttagcctc tgaatagcca aggcaatcct aagcaaaaat aacaaagctg ggggcatca     599
```

GENETIC VARIANTS ON CHR 5P12 AND 10Q26 AS MARKERS FOR USE IN BREAST CANCER RISK ASSESSMENT, DIAGNOSIS, PROGNOSIS AND TREATMENT

This application is the U.S. national phase of International Application No. PCT/IS2008/000012, filed May 21, 2008, which claims priority benefit of Iceland Application No. 8647 filed May 25, 2007, and Iceland Application No. 8700 filed Dec. 21, 2007.

BACKGROUND OF THE INVENTION

Breast cancer is by far the most common cancer in women worldwide. Current global incidence is in excess of 1,151,000 new cases diagnosed each year [Parkin, et al., (2005), CA Cancer) Clin, 55, 74-108]. Breast cancer incidence is highest in developed countries, particularly amongst populations of Northern European ethnic origin, and is increasing. In the United States the annual age-standardized incidence rate is approximately 125 cases per 100,000 population, more than three times the world average. Rates in Northern European countries are similarly high. In the year 2008 it is estimated that 184,450 new cases of invasive breast cancer will be diagnosed in the U.S.A. and 40,930 people will die from the disease [Jemal, et al., (2008), CA Cancer J Clin, 58, 71-96]. To this figure must be added a further 67,770 ductal and lobular carcinoma in-situ diagnoses expected in 2008. From an individual perspective, the lifetime probability of developing breast cancer is 12.3% in U.S. women (i.e., 1 in 8 women will develop breast cancer during their lives). As with most cancers, early detection and appropriate treatment are important factors. Overall, the 5-year survival rate for breast cancer is 89%. However, in individuals presenting with regionally invasive or metastatic disease, the rate declines to 84% and 27%, respectively [Jemal, et al., (2008), CA Cancer J Clin, 58, 71-96].

Increasingly, emphasis is falling on the identification individuals who are at high risk for primary or recurrent breast cancer. Such individuals can be managed by more intensive screening, preventative chemotherapies, hormonal therapies and, in cases of individuals at extremely high risk, prophylactic surgery. Mass screening programs constitute a huge economic burden on health services, while preventative therapies have associated risks and quality of life consequences.

Genetic Predisposition to Breast Cancer

The two primary classes of known risk factors for breast cancer are endocrine factors and genetics. Regarding the latter, approximately 12% of breast cancer patients have one or more first degree relatives with breast cancer [(2001), Lancet, 358, 1389-99]. The well known, dominant breast cancer predisposition genes BRCA1 and BRCA2 confer greatly increased breast cancer risk to carriers, with lifetime penetrance estimates ranging from 40-80%. The presence of BRCA1 and BRCA2 mutations can account for the majority of families with 6 or more cases of breast cancer and for a large proportion of families comprising breast and ovarian or male breast cancer. However such families are very rare indeed. BRCA1 and BRCA2 mutations are found much less frequently in families with fewer cases or in families characterized by breast cancer cases only. Together, mutations in BRCA1 and BRCA2 can account for 15-20% of the risk for familial breast cancer. In non-founder populations, if all common BRCA mutations could be detected, between 2-3% of incident breast cancer patients would be expected to harbor a mutation [Gorski, et al., (2005), Breast Cancer Res Treat, 92, 19-24; (2000), Br J Cancer, 83, 1301-8]. This low "chance to find" statistic precludes the responsible use of BRCA mutation testing outside families with an obvious hereditary predisposition (Anon[(2003), J Clin Oncol, 21, 2397-406]). Rare, high penetrance mutations are known to occur in the TP53 and PTEN genes, however, these together account for no more than 5% of the total genetic risk for breast cancer [Easton, (1999), Breast Cancer Res, 1, 14-7]. Linkage studies have been largely unsuccessful in identifying any more, widespread mutations conferring high risk for breast cancer [Smith, et al., (2006), Genes Chromosomes Cancer, 45, 646-55].

Recent epidemiological studies have indicated that the majority of breast cancer cases arise in a predisposed, susceptible minority of the population [Antoniou, et al., (2002), Br Cancer, 86, 76-83; Pharoah, et al., (2002), Nat Genet, 31, 33-6]. Data from twin studies and observations of the constant, high incidence of cancer in the contralateral breast of patients surviving primary breast cancer indicate that a substantial portion of the uncharacterized risk for breast cancer is related to endogenous factors, most probably genetic [Lichtenstein, et al., (2000), N Engl J Med, 343, 78-85; Peto and Mack, (2000), Nat Genet, 26, 411-4]. Knowledge of the genetic factors that underpin this widespread risk is very limited. Segregation analyses predict that the uncharacterized genetic risk for breast cancer is most likely to be polygenic in nature, with risk alleles that confer low to moderate risk and which may interact with each other and with hormonal risk factors. Nevertheless, these studies predict as much as 40-fold differences in relative risk between the highest and lowest quintiles of a distribution that could be defined by genetic profiling that captures these low to moderate risk alleles [Antoniou, et al., (2002), Br Cancer, 86, 76-83; Pharoah, et al., (2002), Nat Genet, 31, 33-6]. 88% of all breast cancer cases are expected to arise amongst a predisposed 50% of the population and the 12% of the population at highest risk accounts for 50% of all breast cancer cases [Pharoah, et al., (2002), Nat Genet, 31, 33-6; Pharoah, (2003), Recent Results Cancer Res, 163, 7-18; discussion 264-6]. Much focus is therefore directed towards the identification of such genetically predisposed individuals and developing personalized medical management strategies for them.

We and others have shown that there is a significant familial risk of breast cancer in Iceland which extends to at least 5$^{th}$ degree relatives [Amundadottir, et al., (2004), PLoS Med, 1, e65; Tulinius, et al., (2002), J Med Genet, 39, 457-62]. The contribution of BRCA1 mutations to familial risk in Iceland is thought to be minimal [Arason, et al., (1998), J Med Genet, 35, 446-9; Bergthorsson, et al., (1998), Hum Mutat, Suppl 1, S195-7]. A single founder mutation in the BRCA2 gene (999-del5) is present at a carrier frequency of 0.6-0.8% in the general Icelandic population and 7.7-8.6% in female breast cancer patients [Thorlacius, et al., (1997), Am J Hum Genet, 60, 1079-84; Gudmundsson, et al., (1996), Am J Hum Genet, 58, 749-56]. This single mutation is estimated to account for approximately 40% of the inherited breast cancer risk to first through third degree relatives [Tulinius, et al., (2002), J Med Genet, 39, 457-62]. Although this estimate is higher than the 15-25% of familial risk attributed to all BRCA 1 and 2 mutations combined in non-founder populations, there is still some 60% of Icelandic familial breast cancer risk to be explained. First degree relatives of patients who test negative for BRCA2 999del5 remain at a 1.72 fold the population risk for breast cancer (95% CI 1.49-1.96) [Tulinius, et al., (2002), J Med Genet, 39, 457-62].

Genetic risk is conferred by subtle differences in the genome among individuals within a population. Genes differ between individuals most frequently due to single nucleotide polymorphisms (SNP), although other variations are also important. SNP are located on average every 1000 base pairs in the human genome. Accordingly, a typical human gene containing 250,000 base pairs may contain 250 different SNP. Only a minor number of SNPs are located in exons and alter the amino acid sequence of the protein encoded by the gene. Most SNPs may have little or no effect on gene function, while others may alter transcription, splicing, translation, or stability of the mRNA encoded by the gene. Additional genetic polymorphism in the human genome is caused by insertion, deletion, translocation, or inversion of either short or long stretches of DNA. Genetic polymorphisms conferring disease risk may therefore directly alter the amino acid sequence of proteins, may increase the amount of protein produced from the gene, or may decrease the amount of protein produced by the gene.

As genetic polymorphisms conferring risk of common disease are uncovered, genetic testing for such risk factors becomes important for clinical medicine. Recent examples are apolipoprotein E testing to identify genetic carriers of the apoE4 polymorphism in dementia patients for the differential diagnosis of Alzheimer's disease, and of Factor V Leiden testing for predisposition to deep venous thrombosis. More importantly, in the treatment of cancer, diagnosis of genetic variants in tumor cells is used for the selection of the most appropriate treatment regime for the individual patient. In breast cancer, genetic variation in estrogen receptor expression or heregulin type 2 (Her2) receptor tyrosine kinase expression determine if anti-estrogenic drugs (tamoxifen) or anti-Her2 antibody (Herceptin) will be incorporated into the treatment plan. In chronic myeloid leukemia (CML) diagnosis of the Philadelphia chromosome genetic translocation fusing the genes encoding the Bcr and Abl receptor tyrosine kinases indicates that Gleevec (STI571), a specific inhibitor of the Bcr-Abl kinase should be used for treatment of the cancer. For CML patients with such a genetic alteration, inhibition of the Bcr-Abl kinase leads to rapid elimination of the tumor cells and remission from leukemia.

Understanding of the genetic factors contributing to the residual genetic risk for breast cancer is limited. Variants in two genes have been rigorously confirmed as low penetrance breast cancer risk genes; CHEK2 and ATM [Renwick, et al., (2006), Nat Genet, 38, 873-5; (2004), Am J Hum Genet, 74, 1175-82]. Furthermore, a recent report establishes a link between variants on chromosomes 2q35 and 16q12 and increased risk of estrogen receptor positive breast cancer (Simon, S N. et al. *Nat Genet*. 39:865-9 (2007)). Many other genes have been implicated however their contribution to breast cancer risk has not been confirmed in analyses employing very large sample sets [Breast Cancer Association, (2006), J Natl Cancer Inst, 98, 1382-96].

No universally successful method for the prevention or treatment of breast cancer is currently available. Management of breast cancer currently relies on a combination of primary prevention, early diagnosis, appropriate treatments and secondary prevention. There are clear clinical imperatives for integrating genetic testing into all aspects of these management areas. Identification of cancer susceptibility genes may also reveal key molecular pathways that may be manipulated (e.g., using small or large molecular weight drugs) and may lead to more effective treatments.

SUMMARY OF THE INVENTION

The present invention relates to methods of assessing a susceptibility to breast cancer. The invention includes methods of diagnosing an increased susceptibility to breast cancer, as well as methods of diagnosing a decreased susceptibility to breast cancer or diagnosing a protection against cancer, by evaluating certain markers or haplotypes that have been found to be associated with increased or decreased susceptibility of breast cancer. The invention also relates to methods of assessing prognosis of individuals diagnosed with breast cancer, methods of assessing the probability of response to a breast cancer therapeutic agent or breast cancer therapy, as well as methods of monitoring progress of treatment of an individual diagnosed with breast cancer.

In one aspect, the present invention relates to a method of diagnosing a susceptibility to breast cancer in a human individual, the method comprising determining the presence or absence of at least one allele of at least one polymorphic marker on chromosome 5p12 or on chromosome 10q26 in a nucleic acid sample obtained from the individual, wherein the presence of the at least one allele is indicative of a susceptibility to breast cancer. The invention also relates to a method of determining a susceptibility to breast cancer, by determining the presence or absence of at least one allele of at least one polymorphic marker on chromosome 5p12 or on chromosome 10q26 in a nucleic acid sample from the individual, wherein the determination of the presence of the at least one allele is indicative of a susceptibility to breast cancer.

In another aspect, the invention relates to a method of determining a susceptibility to breast cancer in a human individual, comprising determining whether at least one at-risk allele in at least one polymorphic marker is present in a genotype dataset derived from the individual, wherein the at least one polymorphic marker is selected from markers within chromosome 5p12, and wherein determination of the presence of the at least one at-risk allele is indicative of increased susceptibility to breast cancer in the individual.

The invention furthermore relates to a method for determining a susceptibility to breast cancer in a human individual, comprising determining whether at least one allele of at least one polymorphic marker is present in a nucleic acid sample obtained from the individual or in a genotype dataset derived from the individual, wherein the at least one polymorphic marker is selected from rs10941679 (SEQ ID NO:236), rs4415084 (SEQ ID NO:235), and rs1219648 (SEQ ID NO:237), and markers in linkage disequilibrium therewith, and wherein the presence of the at least one allele is indicative of a susceptibility to breast cancer for the individual.

The genotype dataset comprises in one embodiment information about marker identity, and the allelic status of the individual, i.e. information about the identity of the two alleles carried by the individual for the marker. The genotype dataset may comprise allelic information about one or more marker, including two or more markers, three or more markers, five or more markers, one hundred or more markers, etc. In some embodiments, the genotype dataset comprises genotype information from a whole-genome assessment of the individual, that may include hundreds of thousands of markers, or even one million or more markers.

In certain embodiments, the at least one polymorphic marker is associated with the FGF10 gene, the HCN1 gene, the MRPS30 gene, and/or the FGFR2 gene. In certain such embodiments, the at least one polymorphic marker is in linkage disequilibrium with the FGF10 gene, the HCN1 gene, the MRPS30 gene, and/or the FGFR2 gene. In certain other embodiments, the at least one polymorphic marker is selected from the group of markers located within the chromosomal segment spanning position 44,666,047 and 44,976,797, in NCBI Build 34, and markers in linkage disequilibrium therewith. In another embodiment, the at least one polymorphic marker is selected from the group consisting of the polymorphic markers listed in Table 1 and Table 3, and markers in linkage disequilibrium therewith.

In certain embodiments, the at least one polymorphic marker is selected from the markers set forth in Table 12, Table 13 and Table 14. In one embodiment, the at least one polymorphic marker is selected from the markers as set forth in SEQ ID NO:1-237. In one embodiment, the markers in linkage disequilibrium with marker rs4415084 are selected from the markers set forth in Table 12. In another embodiment, the markers in linkage disequilibrium with marker rs10941679 are selected from the markers set forth in Table 13. In another embodiment, the markers in linkage disequilibrium with marker rs1219648 are selected from the markers set forth in Table 14.

In certain embodiments, a further step of assessing the frequency of at least one haplotype in the individual is performed. In such embodiments, two or more markers, including three, four, five, six, seven, eight, nine or ten or more markers can be included in the haplotype. In one embodiment, the haplotype comprises markers in the chromosome 5p12 region. In another embodiment, the haplotype comprises markers in the chromosome 10q26 region. In certain embodiments, the haplotype comprises markers in linkage disequilibrium with rs4415084. In certain other embodiments, the haplotype comprises markers in linkage disequilibrium with rs10941679. In certain other embodiments, the haplotype comprises markers in linkage disequilibrium with rs1219648.

The markers conferring risk of breast cancer, as described herein, can be combined with other genetic markers for breast cancer. Thus, in certain embodiments, a further step is included, comprising determining whether at least one at-risk allele of at least one at-risk variant for breast cancer not in linkage disequilibrium with any one of the markers set forth in Table 12, Table 13 and Table 14 is present in a sample comprising genomic DNA from a human individual or a genotype dataset derived from a human individual. In other words, genetic markers in other locations in the genome can be useful in combination with the markers of the present invention, so as to determine overall risk of breast cancer based on multiple genetic factors. Selection of markers that are not in linkage disequilibrium (not in LD) can be based on a suitable measure for linkage disequilibrium, as described further herein. In certain embodiments, markers that are not in linkage disequilibrium have values for the LD measure $r^2$ between the markers of less than 0.2. In certain other embodiments, markers that are not in LD have values for $r^2$ between the markers of less than 0.15, including less than 0.10, less than 0.05, less than 0.02 and less than 0.01. Other suitable cutoff values for establishing that markers are not in LD are contemplated, including values bridging any of these values.

In certain embodiments, multiple markers as described herein are determined to determine overall risk of breast cancer. Thus, in certain embodiments, an additional step is included, the step comprising determining whether at least one allele in each of at least two polymorphic markers is present in a sample comprising genomic DNA from a human individual or a genotype dataset derived from a human individual, wherein the presence of the at least one allele in the at least two polymorphic markers is indicative of an increased susceptibility to breast cancer. In one embodiment, the markers are selected from rs4415084 (SEQ ID NO:235), rs10941679 (SEQ ID NO:236) and rs1219648 (SEQ ID NO:237), and markers in linkage disequilibrium therewith. Risk assessment based on the markers of the present invention can also be combined with assessment for the presence of absence of at least one high penetrant genetic factor for breast cancer in a nucleic acid sample obtained from the individual or in a genotype dataset derived from the individual. The high penetrant genetic factor for breast cancer can for example be a BRCA1 mutation, a BRCA2 mutation, a TP53 mutation or a PTEN mutation. Together, mutations in BRCA1 and BRCA2 can account for 15-20% of the risk for familial breast cancer, and these can account for between 2-3% of incident breast cancer patients [Gorski, et al., (2005), Breast Cancer Res Treat, 92, 19-24; (2000), Br J Cancer, 83, 1301-8]. Known mutations in the TP53 and PTEN genes account for about 5% of the total genetic risk for breast cancer [Easton, (1999), Breast Cancer Res, 1, 14-7]. In one embodiment, the high penetrant genetic factor is BRCA2 999del5.

The genetic markers of the invention can also be combined with non-genetic information to establish overall risk for an individual. Thus, in certain embodiments, a further step is included, comprising analyzing non-genetic information to make risk assessment, diagnosis, or prognosis of the individual. The non-genetic information can be any information pertaining to the disease status of the individual or other information that can influence the estimate of overall risk of breast cancer for the individual. In one embodiment, the non-genetic information is selected from age, gender; ethnicity, socioeconomic status, previous disease diagnosis, medical history of subject, family history of breast cancer, biochemical measurements, and clinical measurements.

In another aspect, the invention relates to a method of assessing risk of developing at least a second primary tumor in an individual previously diagnosed with breast cancer, the method comprising determining the presence or absence of at least one allele of at least one polymorphic marker in a nucleic acid sample obtained from the individual, wherein the at least one polymorphic marker is selected from the group consisting of the polymorphic markers listed in Tables 12, 13 and 14, and markers in linkage disequilibrium therewith, wherein the presence of the at least one allele is indicative of risk of developing at least a second primary tumor. Alternatively, the invention relates to a method of determining risk of developing at least a second primary tumor in an individual previously diagnosed with breast cancer, the method comprising determining whether at least one allele of at least one polymorphic marker is present in a nucleic acid sample obtained from the individual, or in a genotype dataset derived from the individual, wherein the at least one polymorphic marker is selected from rs10941679 (SEQ ID NO:236), rs4415084 (SEQ ID NO:235), and rs1219648 (SEQ ID NO:237, and markers in linkage disequilibrium therewith, and wherein the presence of the at least one allele is indicative of risk of developing at least a second primary tumor. In one such embodiment, the at least one polymorphic marker is selected from the markers set forth in Table 12, Table 13 and Table 14.

The invention also relates to an apparatus for determining a genetic indicator for breast cancer in a human individual, comprising: a computer readable memory; and a routine stored on the computer readable memory; wherein the routine is adapted to be executed on a processor to analyze marker and/or haplotype information for at least one human individual with respect to at least one polymorphic marker selected from rs10941679 (SEQ ID NO:236), rs4415084 (SEQ ID NO:235), and rs1219648 (SEQ ID NO:237, and markers in linkage disequilibrium therewith, and generate an output based on the marker or haplotype information, wherein the output comprises an individual risk measure of the at least one marker or haplotype as a genetic indicator of breast cancer for the human individual. In one embodiment, the at least one polymorphic marker is selected from the markers set forth in Table 12, Table 13 and Table 14. In one embodiment, the routine further comprises a risk measure for breast cancer associated with the at least one marker allele and/or haplotype, wherein the risk measure is based on a comparison of the frequency of at least one allele of at least one polymorphic marker and/or haplotype in a plurality of individuals diagnosed with breast cancer and an indicator of the frequency of the at least one allele of at least one polymorphic marker and/or haplotype in a plurality of reference individuals, and wherein the individual risk for the human individual is based on a comparison of the carrier status of the individual for the at least one marker allele and/or haplotype and the risk measure for the at least one marker allele and/or haplotype. For example, the risk measure may in certain embodiments be a measure of risk conferred by each copy of an at-risk variant for breast cancer in a population of individuals with breast cancer, compared with controls. Based on such reference data, risk for a particular individual can be estimated, by determining his/her genotype status at the particular marker and calculate a risk for the individual based thereupon. If the individual carries one copy of the genetic risk variant in his/her genome, the calculated risk can be based on the risk conferred by a single copy of the risk variant. If the individual carries two copies of the genetic risk variants, i.e. the individual is homozygous for the at-risk variant, then the risk estimate for the individual can be based on the risk based on a group of individuals, compared with controls. Normally, risk for homozygous carriers will be the risk for a single copy of the variant squared. Other methods for reporting or estimating risk for the individual based on genotype status at particular markers are also possible, and within the scope of the present invention.

In another aspect, the invention relates to a method of identification of a marker for use in assessing susceptibility to breast cancer, the method comprising: identifying at least one polymorphic marker in linkage disequilibrium with at least one of rs10941679 (SEQ ID NO:236), rs4415084 (SEQ ID NO:235), and rs1219648 (SEQ ID NO:237); determining the genotype status of a sample of individuals diagnosed with, or having a susceptibility to, breast cancer; and determining the genotype status of a sample of control individuals; wherein a significant difference in frequency of at least one allele in at least one polymorphism in individuals diagnosed with, or having a susceptibility to, breast cancer, as compared with the frequency of the at least one allele in the control sample is indicative of the at least one polymorphism being useful for assessing susceptibility to breast cancer. Significant difference can be estimated on statistical analysis of allelic counts at certain polymorphic markers in breast cancer patients and controls. In one embodiment, a significant difference is based on a calculated P-value between breast cancer patients and controls of less than 0.05. In one embodiment, an increase in frequency of the at least one allele in the at least one polymorphism in individuals diagnosed with, or having a susceptibility to, breast cancer, as compared with the frequency of the at least one allele in the control sample is indicative of the at least one polymorphism being useful for assessing increased susceptibility to breast cancer. In another embodiment, a decrease in frequency of the at least one allele in the at least one polymorphism in individuals diagnosed with, or having a susceptibility to, breast cancer, as compared with the frequency of the at least one allele in the control sample is indicative of the at least one polymorphism being useful for assessing decreased susceptibility to, or protection against, breast cancer.

The invention also relates to a method of genotyping a nucleic acid sample obtained from a human individual comprising determining whether at least one allele of at least one polymorphic marker is present in a nucleic acid sample from the individual sample, wherein the at least one marker is selected from rs10941679 (SEQ ID NO:236), rs4415084 (SEQ ID NO:235), and rs1219648 (SEQ ID NO:237, and markers in linkage disequilibrium therewith, and wherein determination of the presence of the at least one allele in the sample is indicative of a susceptibility to breast cancer in the individual. In one embodiment, determination of the presence of allele T in rs4415084 (SEQ ID NO:235), allele G in rs10941679 (SEQ ID NO:236) and/or allele G in rs1219648 (SEQ ID NO:237) is indicative of increased susceptibility of breast cancer in the individual. In one embodiment, genotyping comprises amplifying a segment of a nucleic acid that comprises the at least one polymorphic marker by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology. In one embodiment, the microarray technology is Molecular Inversion Probe array technology or BeadArray Technologies. In one embodiment, the process comprises allele-specific probe hybridization. In another embodiment, the process comprises microarray technology. One preferred embodiment comprises the steps of (1) contacting copies of the nucleic acid with a detection oligonucleotide probe and an enhancer oligonucleotide probe under conditions for specific hybridization of the oligonucleotide probe with the nucleic acid; wherein (a) the detection oligonucleotide probe is from 5-100 nucleotides in length and specifically hybridizes to a first segment of a nucleic acid whose nucleotide sequence is given by any one of SEQ ID NO:1-237; (b) the detection oligonucleotide probe comprises a detectable label at its 3' terminus and a quenching moiety at its 5' terminus; (c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and (d) a single base gap exists between the first segment and the second segment, such that when the oligonucleotide probe and the enhancer oligonucleotide probe are both hybridized to the nucleic acid, a single base gap exists between the oligonucleotides; (2) treating the nucleic acid with an endonuclease that will cleave the detectable label from the 3' terminus of the detection probe to release free detectable label when the detection probe is hybridized to the nucleic acid; and (3) measuring free detectable label, wherein the presence of the free detectable label indicates that the detection probe specifically hybridizes to the first segment of the nucleic acid, and indicates the sequence of the polymorphic site as the complement of the detection probe.

A further aspect of the invention pertains to a method of assessing an individual for probability of response to a breast cancer therapeutic agent, comprising: determining whether at least one allele of at least one polymorphic marker is present in a nucleic acid sample obtained from the individual, or in a genotype dataset derived from the individual, wherein the at least one polymorphic marker is selected from rs10941679 (SEQ ID NO:236), rs4415084 (SEQ ID NO:235), and rs1219648 (SEQ ID NO:237, and markers in linkage disequilibrium therewith, wherein the presence of the at least one allele of the at least one marker is indicative of a probability of a positive response to the therapeutic agent The invention in another aspect relates to a method of predicting prognosis of an individual diagnosed with breast cancer, the method comprising determining whether at least one allele of at least one polymorphic marker is present in a nucleic acid sample obtained from the individual, or in a genotype dataset derived from the individual, wherein the at least one polymorphic marker is selected from rs10941679 (SEQ ID NO:236), rs4415084 (SEQ ID NO:235), and rs1219648 (SEQ ID NO:237, and markers in linkage disequilibrium therewith, wherein the presence of the at least one allele is indicative of a worse prognosis of the breast cancer in the individual.

Yet another aspect of the invention relates to a method of monitoring progress of treatment of an individual undergoing treatment for breast cancer, the method comprising determining whether at least one allele of at least one polymorphic marker is present in a nucleic acid sample obtained from the individual, or in a genotype dataset derived from the individual, wherein the at least one polymorphic marker is selected from rs10941679 (SEQ ID NO:236), rs4415084 (SEQ ID NO:235), and rs1219648 (SEQ ID NO:237), and markers in linkage disequilibrium therewith, wherein the presence of the at least one allele is indicative of the treatment outcome of the individual. In one embodiment, the treatment is treatment by surgery, treatment by radiation therapy, or treatment by drug administration.

The invention also relates to the use of an oligonucleotide probe in the manufacture of a reagent for diagnosing and/or assessing susceptibility to breast cancer in a human individual, wherein the probe hybridizes to a segment of a nucleic acid with nucleotide sequence as set forth in any one of SEQ ID NO:1-237, wherein the probe is 15-500 nucleotides in length. In certain embodiments, the probe is about 16 to about 100 nucleotides in length. In certain other embodiments, the probe is about 20 to about 50 nucleotides in length. In certain other embodiments, the probe is about 20 to about 30 nucleotides in length.

The invention also relates to computer-readable media. In one aspect, the invention relates to a medium on which is stored: an identifier for at least one polymorphic marker; an indicator of the frequency of at least one allele of said at least one polymorphic marker in a plurality of individuals diagnosed with breast cancer; and an indicator of the frequency of the least one allele of said at least one polymorphic markers in a plurality of reference individuals; wherein the at least one polymorphic marker is selected rs10941679 (SEQ ID NO:236), rs4415084 (SEQ ID NO:235), and rs1219648 (SEQ ID NO:237, and polymorphic markers in linkage disequilibrium therewith. In one embodiment, the polymorphic marker is selected from the markers set forth in Table 12, Table 13 and Table 14. In another embodiment, the medium further comprises information about the ancestry of the plurality of individuals.

Various diagnoses and categories of the breast cancer phenotype are within scope of the present invention. In its broadest sense, the invention relates to any breast cancer phenotype. Breast cancer, in certain embodiments, includes any clinical diagnosis of breast cancer, including, but not limited to: invasive ductal, invasive lobular, tubular, or as otherwise invasive or mixed invasive, medullary, DCIS (Ductal Carcinoma In-Situ), LCIS (Lobular Carcinoma In-Situ), or otherwise non-invasive; Invasive breast cancer, including stage 0, stage 1, stage 2 (including stage 2a and stage 2b), stage 3 (including stage 3a, stage 3b and stage 3c) and stage 4 breast cancer. In certain embodiments, the breast cancer phenotype is selected from All Breast Cancer, Multiple Primary Breast Cancer, and early onset Breast Cancer. In some embodiments, the markers of the invention are associated with risk of breast cancer in individuals with a family history of breast cancer. In one such embodiment, the summed family history (FHS) is the phenotype associated with breast cancer. In another embodiment, the breast cancer associated with the variants of the invention is estrogen receptor (ER) positive and/or progesterone receptor (PR) positive breast cancer. In one embodiment, the breast cancer associated with the variants of the invention is estrogen receptor (ER) positive. In another embodiment, the breast cancer associated with the variants of the invention is progesterone receptor (ER) positive. In one such embodiment, the markers described herein to be associated with increased risk or susceptibility of breast cancer confer increased risk or susceptibility of ER-positive and/or PR-positive breast cancer. Thus, in certain embodiments, presence of at least one of the at-risk variants of the invention is predictive of ER positive or PR positive breast cancer in the individual.

In some embodiments of the methods of the invention, the susceptibility determined in the method is increased susceptibility. In one such embodiment, the increased susceptibility is characterized by a relative risk (RR) of at least 1.10. In another embodiment, the increased susceptibility is characterized by a relative risk of at least 1.20. In another embodiment, the increased susceptibility is characterized by a relative risk of at least 1.30. In another embodiment, the increased susceptibility is characterized by a relative risk of at least 1.40. In yet another embodiment, the increased susceptibility is characterized by a relative risk of at least 1.50. In a further embodiment, the increased susceptibility is characterized by a relative risk of at least 1.70. In yet another embodiment, the increased susceptibility is characterized by a relative risk of at least 2.0. Other embodiments are characterized by relative risk of at least 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35. Other numberic values for risk bridging any of these above-mentioned values are also possible, and these are also within scope of the invention.

In some embodiments of the methods of the invention, the susceptibility determined in the method is decreased susceptibility. In one such embodiment, the decreased susceptibility is characterized by a relative risk (RR) of less than 0.9. In another embodiment, the decreased susceptibility is characterized by a relative risk (RR) of less than 0.8. In another embodiment, the decreased susceptibility is characterized by a relative risk (RR) of less than 0.7. In yet another embodiment, the decreased susceptibility is characterized by a relative risk (RR) of less than 0.5. Other cutoffs, such as relative risk of less than 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, and so on, are within scope of the invention.

The invention also relates to kits. In one such aspect, the invention relates to a kit for assessing susceptibility to breast cancer in a human individual, the kit comprising reagents necessary for selectively detecting at least one allele of at least one polymorphic marker on chromosome 5p12 or 10q26 in the genome of the individual, wherein the presence of the at least one allele is indicative of increased susceptibility to breast cancer. In another aspect, the invention relates to a kit for assessing susceptibility to breast cancer in a human individual, the kit comprising reagents for selectively detecting at least one allele of at least one polymorphic marker in the genome of the individual, wherein the polymorphic marker is selected from rs10941679 (SEQ ID NO:236), rs4415084 (SEQ ID NO:235), and rs1219648 (SEQ ID NO:237, and markers in linkage disequilibrium therewith, and wherein the presence of the at least one allele is indicative of a susceptibility to breast cancer. In one embodiment, the at least one polymorphic marker is selected from the markers set forth in Table 12, Table 13 and Table 14.

Kit reagents may in one embodiment comprise at least one contiguous oligonucleotide that hybridizes to a fragment of the genome of the individual comprising the at least one polymorphic marker. In another embodiment, the kit comprises at least one pair of oligonucleotides that hybridize to opposite strands of a genomic segment obtained from the subject, wherein each oligonucleotide primer pair is designed to selectively amplify a fragment of the genome of the individual that includes one polymorphism, wherein the polymorphism is selected from the group consisting of the polymorphisms as defined in Tables 12, 13 and 14, and wherein the fragment is at least 20 base pairs in size. In one embodiment, the oligonucleotide is completely complementary to the genome of the individual. In another embodiment, the kit further contains buffer and enzyme for amplifying said segment. In another embodiment, the reagents further comprise a label for detecting said fragment.

In one preferred embodiment, the kit comprises: a detection oligonucleotide probe that is from 5-100 nucleotides in length; an enhancer oligonucleotide probe that is from 5-100 nucleotides in length; and an endonuclease enzyme; wherein the detection oligonucleotide probe specifically hybridizes to a first segment of the nucleic acid whose nucleotide sequence is set forth in any one of SEQ ID NO:1-237, and wherein the detection oligonucleotide probe comprises a detectable label at its 3' terminus and a quenching moiety at its 5' terminus; wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

Kits according to the present invention may also be used in the other methods of the invention, including methods of assessing risk of developing at least a second primary tumor in an individual previously diagnosed with breast cancer, methods of assessing an individual for probability of response to a breast cancer therapeutic agent, and methods of monitoring progress of a treatment of an individual diagnosed with breast cancer and given a treatment for the disease.

The markers that are described herein to be associated with breast cancer can all be used in the various aspects of the invention, including the methods, kits, uses, apparatus, procedures described herein. In certain embodiments, the invention relates to use of markers within chromosome 5p12. In certain other embodiments, the invention relates to markers within chromosome 10q26. In certain embodiments, the invention relates to the markers set forth in Table 1 or Table 3, and markers in linkage disequilibrium therewith. In certain other embodiments, the invention relates to the markers set forth in Table 3. In certain other embodiments, the invention relates marker rs10941679, rs7703618, rs4415084, rs2067980, rs10035564, rs11743392, rs7716600, and rs1219648, and markers in linkage disequilibrium therewith.

In some preferred embodiments, the invention relates to markers rs4415084, rs10941679 and rs1219648, and markers in linkage disequilibrium therewith. In some other preferred embodiments, the invention relates to markers as set forth in Table 12, Table 13 and Table 14 herein. In other preferred embodiments, the invention relates to rs4415084 and markers in linkage disequilibrium therewith (e.g., markers as set forth in Table 12). In other preferred embodiments, the invention relates to rs10941679 and markers in linkage disequilibrium therewith (e.g., markers as set forth in Table 13). In other preferred embodiments, the invention relates to rs1219648 and markers in linkage disequilibrium therewith (e.g., markers as set forth in Table 14). In one embodiment, the invention relates to marker rs4415084. In another embodiment, the invention relates to rs10941679. In another embodiment, the invention relates to rs1219648.

In certain embodiments, the at least one marker allele conferring increased risk of breast cancer is selected from of rs10941679 allele G, rs7703618 allele T, rs4415084 allele G, rs2067980 allele G, rs10035564 allele G, rs11743392 allele T, rs7716600 allele A, and rs1219648 allele G. In these embodiments, the presence of the allele (the at-risk allele) is indicative of increased risk of breast cancer.

In certain embodiments of the invention, linkage disequilibrium is determined using the linkage disequilibrium measures $r^2$ and $|D'|$, which give a quantitative measure of the extent of linkage disequilibrium (LD) between two genetic element (e.g., polymorphic markers). Certain numerical values of these measures for particular markers are indicative of the markers being in linkage disequilibrium, as described further herein. In one embodiment of the invention, linkage disequilibrium between marker (i.e., LD values indicative of the markers being in linkage disequilibrium) is defined as $r^2>0.1$. In another embodiment, linkage disequilibrium is defined as $r^2>0.2$. Other embodiments can include other definitions of linkage disequilibrium, such as $r^2>0.25$, $r^2>0.3$, $r^2>0.35$, $r^2>0.4$, $r^2>0.45$, $r^2>0.5$, $r^2>0.55$, $r^2>0.6$, $r^2>0.65$, $r^2>0.7$, $r^2>0.75$, $r^2>0.8$, $r^2>0.85$, $r^2>0.9$, $r^2>0.95$, $r^2>0.96$, $r^2>0.97$, $r^2>0.98$, or $r^2>0.99$. Linkage disequilibrium can in certain embodiments also be defined as $|D'|>0.2$, or as $|D'|>0.3$, $|D'|>0.4$, $|D'|>0.5$, $|D'|>0.6$, $|D'|>0.7$, $|D'|>0.8$, $|D'|>0.9$, $|D'|>0.95$, $|D'|>0.98$ or $|D'|>0.99$. In certain embodiments, linkage disequilibrium is defined as fulfilling two criteria of $r^2$ and $|D'|$, such as $r^2>0.2$ and $|D'|>0.8$. Other combinations of values for $r^2$ and are also possible and within scope of the present invention, including but not limited to the values for these parameters set forth in the above.

BRIEF DESCRIPTION OF THE DRAWINGS

The foregoing and other objects, features and advantages of the invention will be apparent from the following more particular description of preferred embodiments of the invention.

FIG. 1 shows a map of Association Data on 5p12 from the Iceland 1 Cohort. The upper panel shows the P-values for the association signals derived from the Illumina Hap300 data form the Iceland 1 cohort of 1660 breast cancer patients and 11,563 controls, plotted according to their physical location (NCBI Build 34). The signals from the key SNPs defining the 6 equivalence classes in the region are labelled A-F. In the lower panel are shown the locations of recombination hotspots, chromosome bands, exons of known genes and recombination rates. At the bottom are plotted pairwise $r^2$ values derived from HapMap Phase II data (release 19). The intensity of the dots is proportional to the magnitude of the pairwise r² value. Recombination hotspots and recombination rates are derived using methods described by McVean et al. 2004 (see text).

DETAILED DESCRIPTION OF THE INVENTION

The present invention discloses polymorphic variants and haplotypes that have been found to be associated with breast cancer. Particular alleles at polymorphic markers on chromosome 5p12 have been found to be associated with breast cancer. Such markers and haplotypes are useful for diagnostic purposes, for methods of predicting drug response, and methods for predicting treatment progress, as described in further detail herein. Further applications of the present invention includes methods for assessing response to breast cancer therapy by surgery or radiation utilizing the polymorphic markers of the invention, as well as kits for use in the methods of the invention.

DEFINITIONS

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometimes referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including single nucleotide polymorphisms (SNPs), mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNVs). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

Sequence conucleotide ambiguity as described herein is as proposed by IUPAC-IUB. These codes are compatible with the codes used by the EMBL, GenBank, and PIR databases.

| IUB code | Meaning |
| --- | --- |
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C G or T |
| D | A G or T |
| H | A C or T |
| V | A C or G |
| N | A C G or T (Any base) |

A nucleotide position at which more than one sequence is possible in a population (either a natural population or a synthetic population, e.g., a library of synthetic molecules) is referred to herein as a "polymorphic site".

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population.

An "indel" is a common form of polymorphism comprising a small insertion or deletion that is typically only a few nucleotides long.

A "haplotype," as described herein, refers to a segment of genomic DNA within one strand of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles.

The term "susceptibility", as described herein, encompasses both increased susceptibility and decreased susceptibility. Thus, particular polymorphic markers and/or haplotypes of the invention may be characteristic of increased susceptibility (i.e., increased risk) of breast cancer, as characterized by a relative risk (RR) of greater than one, or as an odds ratio (OR) of greater than one. Alternatively, the markers and/or haplotypes of the invention are characteristic of decreased susceptibility (i.e., decreased risk) of breast cancer, as characterized by a relative risk of less than one, or an odds ratio of less than one. Haplotypes are described herein in the context of the marker name and the allele of the marker in that haplotype, e.g., "T rs4415084" refers to the T allele of marker rs4415084 being in the haplotype, and this nomenclature is equivalent to "rs4415084 allele T" and "T-rs4415084". Furthermore, allelic codes in haplotypes are as for individual markers, i.e. 1=A, 2=C, 3=G and 4=T.

The term "susceptibility", as described herein, refers to the proneness of an individual towards the development of a certain state (e.g., a certain trait, phenotype or disease, e.g., breast cancer), or towards being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of breast cancer, as characterized by a relative risk (RR) or odds ratio (OR) of greater than one for the particular allele or haplotype. Alternatively, the markers and/or haplotypes of the invention are characteristic of decreased susceptibility (i.e., decreased risk) of breast cancer, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or the can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" is a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "breast cancer therapeutic agent" refers to an agent that can be used to ameliorate or prevent symptoms associated with breast cancer.

The term "breast cancer-associated nucleic acid", as described herein, refers to a nucleic acid that has been found to be associated to breast cancer. This includes, but is not limited to, the markers and haplotypes described herein and markers and haplotypes in strong linkage disequilibrium (LD) therewith.

The term "Breast Cancer", as described herein, refers to any clinical diagnosis of breast cancer, and includes any and all particular subphenotypes of breast cancer. For example, breast cancer is sometimes categorized as estrogen receptor (ER) positive breast or estrogen receptor negative breast cancer; breast cancer is sometimes also categorized as progesterone receptor (PR) positive or negative. Breast cancer is furthermore sometimes diagnosed as invasive ductal, as invasive lobular, as tubular, or as otherwise invasive or mixed invasive. Breast cancer can also be categorized as medullary DCIS (Ductal Carcinoma In-Situ) or LCIS (Lobular Carcinoma In-Situ, or otherwise non-invasive. Invasive breast cancer can also be defined as stage 0, stage 1, stage 2 (including stage 2a and stage 2b), stage 3 (including stage 3a, stage 3b and stage 3c) or stage 4 breast cancer. In the present context, "breast cancer" can include any of these subphenotypes of breast cancer, and also includes any other clinically applicable subphenotypes of breast cancer.

The term "All Breast Cancer", or "All BC", refers to all individuals diagnosed with breast cancer.

The term "Medium Predisposition" breast cancer or "Med-Pre" breast cancer, refers to a sub-phenotype of breast cancer. The definition of this phenotype requires that the proband fulfills at least one of the following criteria:
  The proband is a member of a cluster of breast cancer cases containing 3 or more affected relatives within a genetic distance of 3 meiotic events (3M).
  The proband is a member of an affected pair related within 3M, one of whom was diagnosed when aged 50 or younger.
  The proband is a member of an affected pair related within 3M, one of whom was diagnosed with a second primary tumor of any type.
  The proband has been diagnosed with a second primary tumor of any type.

The term "Multiple Primary Breast Tumor", or "MPBC", as described herein, refers to cases where at least one Primary tumor is diagnosed in addition to the first breast cancer diagnosis, and the two tumors confirmed both clinically and by histology to be independent primary tumors, arising simultaneously or subsequently to the first breast cancer and occurring in the contralateral or ipsilateral breast.

The term "family history score" or "FHS", as described herein, is defined based on the number of relatives affected with breast cancer for a proband with the disease. For each proband, a score of 1 is assigned for each affected first-degree relative, 0.5 for each affected second degree relative, and 0.25 for each third-degree relative. The total sum thus obtained over all affected relatives represents the summed family history score or FHS.

The term "estrogen receptor positive breast cancer", or "ER-positive breast cancer", as described herein, refers to tumors determined to be positive for estrogen receptor. In the present context, ER levels of greater than or equal to 10 fmol/mg and/or an immunohistochemical observation of greater than or equal to 10% positive nuclei is considered to be ER positive. Breast cancer that does not fulfill the criteria of being ER positive is defined herein as "ER negative" or "estrogen receptor negative".

The term "progesterone receptor positive breast cancer", or "PR-positive breast cancer", as described herein, refers to tumors determined to be positive for progesterone receptor. In the present context, PR levels of greater than or equal to 10 fmol/mg and/or an immunohistochemical observation of greater than or equal to 10% positive nuclei is considered to be PR positive. Breast cancer that does not fulfill the criteria of being PR positive is defined herein as "PR negative" or "progesterone receptor negative".

The term "chromosome 5p12", as described herein, refers to the region on Chromosome 5 between positions 44,094,392 and 46,393,984 of NCBI (National Center for Biotechnology Information) Build 34.

The term "FGF10" or "FGF10 gene", as described herein, refers to the Fibroblast Growth Factor 10 gene on human chromosome 5p.

The term "MRPS30" or "MRPS30 gene", as described herein, refers to the Mitochondrial Ribosomal Protein S30 gene on human chromosome 5p. This gene is also called programmed cell death protein 9 (PDCD9), and encodes a mitochondrial 28S subunit.

The term "FGFR2" or "FGFR2 gene", as described herein, refers to the Fibroblast Growth Factor Receptor 2 gene on human chromosome 10q26. This gene is also called Protein Tyrosine Kinase Receptor Like 14 (TK14), Keratinocyte Growth Factor Receptor (KGFR), and Fibroblast Growth Factor Receptor BEK.

Through association analysis of a population of individuals diagnosed with breast cancer according to the present invention, it has been discovered that certain alleles at certain polymorphic markers on chromosome 5p12 are associated with breast cancer. A genome-wide analysis for variants associated with cancer revealed association of breast cancer to a region of chromosome 5, between positions 44,094,392 and 46,393,984 (NCBI Build 34 coordinates), referred to herein as chromosome 5p12 region. Particular markers were found to be associated with an increased risk of breast cancer in this region.

Through genotyping of approximately 1,600 Icelandic breast cancer patients and 11,563 controls using the Illumina HumanHap300 microarray technology, a large number of markers on chromosome 5p were found to show association to breast cancer (Table 1). In particular, the T allele of marker rs4415084 and the G allele of marker rs7703618 were found to be associated with an increased risk of breast cancer. The association of marker rs7703618 was replicated in a second Icelandic cohort, showing that the association signal is indeed significant.

A comparison of the Iceland discovery cohort with the public CGEMS data set revealed that association to rs4415084 is also replicated in this cohort. In fact, the association signal to this marker (p-value 9.02E-06 in the Icelandic discovery cohort) is significant at the genome-wide level (after Bonferroni correction), with a nominal p-value of 1.38E-07 when the two data sets are merged. This SNP had an unremarkable P-value of 2.21E-03 in the CGEMS data set alone, but does replicate the original finding in the Icelandic population.

Marker rs10941679, which is correlated with marker rs4415084 (D'=0.99, r2=0.51), has an even stronger correlation with breast cancer (OR=1.19, p-value 2.2E-06). Follow-up analysis has shown that the signal due to rs4415084 and rs10941679 in cohorts from Sweden, Holland, Spain and the US (see Table 6).

The present invention also shows evidence of allelic heterogeneity in the Chr5p12 region, and six equivalence classes, represented by the key markers rs7703618, rs4415084, rs2067980, rs10035564, rs11743392 and rs7716600, have been identified. Further analysis has established that the observed association signal is mostly accounted for by markers rs4415084 and rs10941679.

There are three known genes of note in the region identified by the present invention as harboring markers and haplotypes associating with breast cancer. These genes are FGF10, MRPS30, and HCN1, along with the poorly characterized gene LOC441070. Two of these genes, FGF10 and MRPS30, are compelling candidates for an involvement in breast cancer predisposition.

Thus, FGF10 is required for normal embryonic development of the breast [Howard and Ashworth, (2006), PLoS Genet, 2, e112], and FGF10 has been implicated as an oncogene in mouse models of breast cancer by MMTV insertional mutagenesis and FGF10 is over expressed in around 10% of human breast cancers [Theodorou, et al., (2004), Oncogene, 23, 6047-55]. The FGF10 gene is separated from the main clusters of association signals by a recombination hotspot. However key elements controlling regulation of FGF10 may be present in the region where the strong association signals occur. Alternatively, the association signals may be in linkage disequilibrium with pathogenic mutations within the FGF10 gene itself.

The MRPS30 gene, also known as programmed cell death protein 9 (PDCD9), encodes a mitochondrial 28S ribosomal subunit. This gene is the mammalian counterpart of the *Gallus gallus* pro-apoptotic protein p52. It has been shown to induce apoptosis and activate the stress-responsive JNK1 pathway in mammalian cells. The protein appears to function in apoptosis at least in part through the Bcl-2 pathway [Sun, et al., (1998), Gene, 208, 157-66; Carim, et al., (1999), Cytogenet Cell Genet, 87, 85-8; Cavdar Koc, et al., (2001), FEBS Lett, 492, 166-70]. Although it has not been implicated previously in breast cancer, its involvement in the above pathways suggest that genetic variants in MRPS30 may be involved in modifying breast cancer risk.

It has also been discovered that marker rs1219648 at the FGFR2 locus on chromosome 10 confers risk of breast cancer (Table 6), which is particularly associated with ER positive tumours (Table 10). It was also discovered that association to rs1219648 was more significant in node positive than node negative tumours, and that the association is stronger for individuals with a family history of breast cancer.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have arisen by a single mutational event, and therefore there are usually two possible alleles possible at each SNP site; the original allele and the mutated (alternate) allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions, inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. All sequence variants can be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

Due to their abundance, SNPs account for a majority of sequence variation in the human genome. Over 6 million SNPs have been validated to date (http colon-slash-slash www.ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs cover over 15% of the human genome sequence (Estivill, X Armengol; L., PloS Genetics 3: 1787-99 (2007). A http colon-slash-slash projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. Nature 23:444-454 (2006)). It is thus possible that either previously described or unknown CNVs represent causative variants in linkage disequilibrium with the markers described herein to be associated with breast cancer. Methods for detecting CNVs include comparative genomic hybridization (CGH) and genotyping, including use of genotyping arrays, as described by Carter (Nature Genetics 39:S16-S21 (2007)). The Database of Genomic Variants (http colon-slash-slash projects.tcag.ca/variation/) contains updated information about the location, type and size of described CNVs. The database currently contains data for over 15,000 CNVs.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realize that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e. A and G. Alternatively, by designing an assay that is designed to detect the opposite strand on the DNA template, the presence of the complementary bases T and C can be measured. Quantitatively (for example, in terms of relative risk), identical results would be obtained from measurement of either DNA strand (+strand or −strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., Genome Res. 9(5): 492-98

(1999)), utilizing PCR, LCR, Nested PCR and other techniques for nucleic acid amplification. Specific commercial methodologies available for SNP genotyping include, but are not limited to, TaqMan genotyping assays and SNPIex platforms (Applied Biosystems), gel electrophoresis (Applied Biosystems), mass spectrometry (e.g., MassARRAY system from Sequenom), minisequencing methods, real-time PCR, Bio-Plex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader; Third Wave). Some of the available array platforms, including Affymetrix SNP Array 6.0 and Illumina CNV370-Duo and 1M BeadChips, include SNPs that tag certain CNVs. This allows detection of CNVs via surrogate SNPs included in these platforms. Thus, by use of these or other methods available to the person skilled in the art, one or more alleles at polymorphic markers, including microsatellites, SNPs or other types of polymorphic markers, can be identified.

In certain methods described herein, an individual who is at an increased susceptibility (i.e., increased risk) for breast cancer, is an individual in whom at least one specific allele at one or more polymorphic marker or haplotype conferring increased susceptibility for breast cancer is identified (i.e., at-risk marker alleles or haplotypes). In one aspect, the at-risk marker or haplotype is one that confers a significant increased risk (or susceptibility) of breast cancer. In one embodiment, significance associated with a marker or haplotype is measured by a relative risk (RR). In another embodiment, significance associated with a marker or haplotye is measured by an odds ratio (OR). In a further embodiment, the significance is measured by a percentage. In one embodiment, a significant increased risk is measured as a risk (relative risk and/or odds ratio) of at least 1.10, including but not limited to: at least 1.11, at least 1.12, at least 1.13, at least 1.14, at least 1.15, at least 1.16, at least 1.17, at least 1.18, at least 1.19, at least 1.20, at least 1.21, at least 1.22, at least 1.23, at least 1.24, at least 1.25, at least 1.30, at least 1.35, at least 1.40, at least 1.50, at least 1.60, at least 1.70, 1.80, at least 1.90, at least 2.0, at least 2.5, at least 3.0, at least 4.0, and at least 5.0. In a particular embodiment, a risk (relative risk and/or odds ratio) of at least 1.15 is significant. In another particular embodiment, a risk of at least 1.17 is significant. In yet another embodiment, a risk of at least 1.20 is significant. In a further embodiment, a relative risk of at least about 1.25 is significant. In another further embodiment, a significant increase in risk is at least about 1.30 is significant. However, other cutoffs are also contemplated, e.g. at least 1.16, 1.18, 1.19, 1.21, 1.22, and so on, and such cutoffs are also within scope of the present invention. In other embodiments, a significant increase in risk is at least about 10%, including but not limited to about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. In one particular embodiment, a significant increase in risk is at least 15%. In other embodiments, a significant increase in risk is at least 17%, at least 20%, at least 22%, at least 24%, at least 25%, at least 30%, at least 32% and at least 35%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than $1 \times 10^{-3}$ (0.001), less than $1 \times 10^{-4}$ (0.0001), less than $1 \times 10^{-4}$ (0.00001), less than $1 \times 10^{-5}$ (0.000001), less than $1 \times 10^{-6}$ (0.0000001), less than $1 \times 10^{-7}$ (0.00000001), or less than $1 \times 10^{-8}$ (0.000000001).

An at-risk polymorphic marker or haplotype of the present invention is one where at least one allele of at least one marker or haplotype is more frequently present in an individual at risk for the disease or trait (affected), or diagnosed with the disease or trait, compared to the frequency of its presence in a comparison group (control), such that the presence of the marker or haplotype is indicative of susceptibility to the disease or trait (e.g., breast cancer). The control group may in one embodiment be a population sample, i.e. a random sample from the general population. In another embodiment, the control group is represented by a group of individuals who are disease-free, i.e. individuals who have not been diagnosed with breast cancer. Such disease-free control may in one embodiment be characterized by the absence of one or more specific disease-associated symptoms. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors are at least one genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

In other embodiments of the invention, an individual who is at a decreased susceptibility (i.e., at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk of less than 0.90, including but not limited to less than 0.85, less than 0.80, less than 0.75, less than 0.7, less than 0.6, less than 0.5, less than 0.4, less than 0.3, less than 0.2 and less than 0.1. In one particular embodiment, significant decreased risk is less than 0.90. In another embodiment, significant decreased risk is less than 0.85. In yet another embodiment, significant decreased risk is less than 0.80. In another embodiment, the decrease in risk (or susceptibility) is at least 10%, including but not limited to at least 15%, at least 20%, at least 25%, at least 30%, at least 35%, at least 40%, at least 45%, at least 50%, at least 55%, at least 60%, at least 65%, at least 70%, at least 80%, at least 85%, at least 90%, at least 95% and at least 98%. In one particular embodiment, a significant decrease in risk is at least about 15%. In another embodiment, a significant decrease in risk at least about 20%. In another embodiment, the decrease in risk is at least about 25%. Other cutoffs or ranges as deemed suitable by the person skilled in the art to characterize the invention are however also contemplated, and those are also within scope of the present invention.

The person skilled in the art will appreciate that for polymorphic markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

A genetic variant associated with a disease or a trait (e.g. breast cancer) can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^p$ where n is the number autosomal loci and p the number of gonosomal (sex chromosomal) loci. Overall risk assessment calculations usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider a total of eight variants that have been described to associate with prostate cancer (Gudmundsson, J., et al., *Nat Genet.* 39:631-7 (2007), Gudmundsson, 3., et al., *Nat Genet.* 39:977-83 (2007); Yeager, M., et al, *Nat Genet.* 39:645-49 (2007), Amundadottir, L., et al., *Nat Genet.* 38:652-8 (2006); Haiman, C. A., et al., *Nat Genet.* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with breast cancer may be assessed.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet.* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrence of a person's having both elements is 0.25 (25%), assuming a random distribution of the elements. However, if it is discovered that the two elements occur together at a frequency higher than 0.125, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g., human populations, individuals will typically have two alleles for each genetic element (e.g., a marker, haplotype or gene).

Many different measures have been proposed for assessing the strength of linkage disequilibrium (LD; reviewed in Devlin, B. & Risch, N., *Genomics* 29:311-22 (1995)). Most capture the strength of association between pairs of biallelic sites. Two important pairwise measures of LD are $r^2$ (sometimes denoted $\Delta^2$) and |D'|(Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and particular SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value between genetic segments (such as SNP markers) can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, 0.99 or 1.0. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, 0.99. Thus, linkage disequilibrium represents a correlation between alleles of distinct markers. It is measured by correlation coefficient or |D'| ($r^2$ up to 1.0 and |D'| up to 1.0). Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http colon-slash-slash www.hapmap.org). In one such embodiment, LD is determined in the CEU population of the HapMap samples. In another embodiment, LD is determined in the YRI population. In another embodiment, LD is determined in a European population. In yet another embodiment, LD is determined in the Icelandic population.

If all polymorphisms in the genome were identical at the population level, then every single one of them would need to be investigated in association studies. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al, *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294: 1719-1723 (2001); Dawson, E. et al., *Nature* 418:544-548 (2002); Phillips, M. S. et al., *Nature Genet.* 33: 382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310: 321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait. One or more causative (functional) variants or mutations may reside within the region found to be associating to the disease or trait. The functional variant may be another SNP, a tandem repeat polymorphism (such as a minisatellite or a microsatellite), a transposable element, or a copy number variation, such as an inversion, deletion or insertion. Such variants in LD with the variants described herein may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (<10° A) allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a susceptibility region, for example, within an LD block region, association of all possible combinations of genotyped markers within the region is studied. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of an significant marker and/or haplotype association.

Haplotype Analysis

One general approach to haplotype analysis involves using likelihood-based inference applied to NEsted MOdels (Gretarsdottir S., et al., Nat. Genet. 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; Biometrics, 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families, first and second-degree relatives can be eliminated from the patient list. Furthermore, the test can be repeated for association correcting for any remaining relatedness among the patients, by extending a variance adjustment procedure previously described (Risch, N. & Teng, J. (*Genome Res.*, 8:1273-1288 (1998)) for sibships so that it can be applied to general familial relationships, and present both adjusted and unadjusted p-values for comparison. The method of genomic controls (Devlin, B. & Roeder, K. *Biometrics* 55:997 (1999)) can also be used to adjust for the relatedness of the individuals and possible stratification. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., Hum. Hered. 42:337-46 (1992) and Falk, C. T. & Rubinstein, P, Ann. Hum. Genet. 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study, and hence the less stringent the statistical measure that is applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300,000=1.7\times10^{-7}$ for the signal to be considered significant applying this conservative test on results from a single study cohort. Obviously, signals found in a genome-wide association study with P-values less than this conservative threshold are a measure of a true genetic effect, and replication in additional cohorts is not necessarily from a statistical point of view. However, since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, J Natl Cancer Inst 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies in individual studies, for example due to unequal matching of cases and controls or population stratification will tend to balance out when results from multiple cohorts are combined, again providing a better estimate of the true underlying genetic effect.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different geno-type. For a disease, a relative risk of 2 means that one group has twice the chance of developing a disease as the other group. The Risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

As described herein, certain polymorphic markers and haplotypes comprising such markers are found to be useful for risk assessment of breast cancer. Risk assessment can involve the use of the markers for diagnosing a susceptibility to breast cancer. Particular alleles of polymorphic markers are found more frequently in individuals with breast cancer, than in individuals without diagnosis of breast cancer. Therefore, these marker alleles have predictive value for detecting breast cancer, or a susceptibility to breast cancer, in an individual. Tagging markers within haplotype blocks or LD blocks comprising at-risk markers, such as the markers of the present invention, can be used as surrogates for other markers and/or haplotypes within the haplotype block or LD block. Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high or possibly even higher than the at-risk variant. The at-risk variant identified may not be the functional variant itself, but is in this instance in linkage disequilibrium with the true functional variant. The functional variant may for example be a tandem repeat, such as a minisatellite or a microsatellite, a transposable element (e.g., an Alu element), or a structural alteration, such as a deletion, insertion or inversion (sometimes also called copy number variations, or CNVs). The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the at-risk variants detected, also have predictive value for detecting association to breast cancer, or a susceptibility to breast cancer, in an individual. These tagging or surrogate markers that are in LD with the markers of the present invention can also include other markers that distinguish among haplotypes, as these similarly have predictive value for detecting susceptibility to breast cancer.

The present invention can in certain embodiments be practiced by assessing a sample comprising genomic DNA from an individual for the presence of variants described herein to be associated with breast cancer. Such assessment includes steps of detecting the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of breast cancer. Alternatively, the invention can be practiced utilizing a dataset comprising information about the genotype status of at least one polymorphic marker described herein to be associated with breast cancer (or markers in linkage disequilibrium with at least one marker shown herein to be associated with breast cancer). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with breast cancer. A positive result for a variant (e.g., marker allele) associated with increased risk of breast cancer, as shown herein, is indicative of the individual from which the dataset is derived is at increased susceptibility (increased risk) of breast cancer.

In certain embodiments of the invention, a polymorphic marker is correlated to breast cancer by referencing genotype data for the polymorphic marker to a look-up table that comprises correlations between at least one allele of the polymorphism and breast cancer. In some embodiments, the table comprises a correlation for one polymorphism. In other embodiments, the table comprises a correlation for a plurality of polymorphisms. In both scenarios, by referencing to a look-up table that gives an indication of a correlation between a marker and breast cancer, a risk for breast cancer, or a susceptibility to breast cancer, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers of the invention, e.g., polymorphic markers on Chromosome 5p12 and Chromosome 10q26, e.g., the markers presented in Tables 12, 13 and 14, e.g., markers marker rs7703618, rs4415084, rs2067980, rs10035564, rs11743392, rs7716600, rs10941679, rs1219648, may be useful for risk assessment and diagnostic purposes for, either alone or in combination. Thus, even in cases where the increase in risk by individual markers is relatively modest, i.e. on the order of 10-30%, the association may have significant implications. Thus, relatively common variants may have significant contribution, to the overall risk (Population Attributable Risk is high), or combination of markers can be used to define groups of individual who, based on the combined risk of the markers, is at significant combined risk of developing the disease.

For example, combined risk can be assessed based on genotype results for markers on chromosome 5p12 and chromosome 10q26, such as marker rs10941679 and marker rs1219648. Alternatively, markers in LD with either of these markers could be assessed. Other markers known to confer risk of breast cancer can also be assessed together with the markers described herein, such as markers on chromosome 2q14 (e.g., marker rs4848543 or markers in linkage disequilibrium therewith), 2q35 (e.g., marker rs13387042, or markers in linkage disequilibrium therewith), and chromosome 16 (e.g., marker rs3803662, or markers in linkage disequilibrium therewith).

Thus, in one embodiment of the invention, a plurality of variants (markers and/or haplotypes) is used for overall risk assessment. These variants are in one embodiment selected from the variants as disclosed herein. Other embodiments include the use of the variants of the present invention in combination with other variants known to be useful for diagnosing a susceptibility to breast cancer. Results for any two or more markers can be combined in such analysis, such as results for three markers, four markers, five markers, six markers, seven markers, eight markers, nine markers, or ten or more markers. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses, may subsequently be used to determine the overall risk conferred based on the genotype status at the multiple loci. Assessment of risk based on such analysis may subsequently be used in the methods and kits of the invention, as described herein.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined. This includes markers that are described herein (e.g., Table 1 and Table 3, e.g. rs4415084, rs10941679, rs1219648), but may also include other markers that are in strong LD (characterized by $r^2$ greater than 0.1 or 0.2 and/or |D'|>0.8) with one or more of the markers listed in Table 1 and Table 3.

For the SNP markers described herein, the opposite allele to the allele found to be in excess in patients (at-risk allele) is found in decreased frequency in breast cancer. These markers and haplotypes in LD and/or comprising such markers, are thus protective for breast cancer, i.e. they confer a decreased risk or susceptibility of individuals carrying these markers and/or haplotypes developing breast cancer.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype found to be associated with breast cancer, (e.g., marker alleles as listed in Table 1 and Table 3, the markers as listed in Tables 12, 13 and 14, SEQ ID NO:1-237) is one in which the marker allele or haplotype is more frequently present in an individual at risk for breast cancer (affected), compared to the frequency of its presence in a healthy individual (control), wherein the presence of the marker allele or haplotype is indicative of breast cancer or a susceptibility to breast cancer. In other embodiments, at-risk markers in linkage disequilibrium with one or more markers found to be associated with breast cancer are tagging markers that are more frequently present in an individual at risk for breast cancer (affected), compared to the frequency of their presence in a healthy individual (control), wherein the presence of the tagging markers is indicative of increased susceptibility to breast cancer. In a further embodiment, at-risk markers alleles (i.e. conferring increased susceptibility) in linkage disequilibrium with one or more markers found to be associated with breast cancer, are markers comprising one or more allele that is more frequently present in an individual at risk for breast cancer, compared to the frequency of their presence in a healthy individual (control), wherein the presence of the markers is indicative of increased susceptibility to breast cancer.

Study Population

In a general sense, the methods and kits of the invention can be utilized from samples containing genomic DNA from any source, i.e. any individual. In preferred embodiments, the individual is a human individual. The individual can be an adult, child, or fetus. The present invention also provides for assessing markers and/or haplotypes in individuals who are members of a target population. Such a target population is in one embodiment a population or group of individuals at risk of developing the disease, based on other genetic factors, biomarkers, biophysical parameters (e.g., weight, BMD, blood pressure), or general health and/or lifestyle parameters (e.g., history of cancer, history of breast cancer, previous diagnosis of disease, family history of cancer, family history of breast cancer).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of the disease in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either sex, males or females. In some embodiments, it relates to assessment of male subjects. In preferred embodiments, it relates to assessment of female subjects.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Styrkarsdottir, U., et al. *N Engl J Med* Apr. 29, 2008 (Epub ahead of print); Thorgeirsson, T., et al. *Nature* 452:638-42 (2008); Gudmundsson, J., et al. *Nat. Genet.* 40:281-3 (2008); Stacey, S, N., et al., *Nat. Genet.* 39:865-69 (2007); Helgadottir, A., et al., *Science* 316:1491-93 (2007); Steinthorsdottir, V., et al., *Nat. Genet.* 39:770-75 (2007); Gudmundsson, J., et al., *Nat. Genet.* 39:631-37 (2007); Frayling, T M, *Nature Reviews Genet.* 8:657-662 (2007); Amundadottir, L. T., et al., *Nat. Genet.* 38:652-58 (2006); Grant, S. F., et al., *Nat. Genet.* 38:320-23 (2006)). Thus, genetic findings in the Icelandic population have in general been replicated in other populations, including populations from Africa and Asia.

The markers of the present invention found to be associated with breast cancer are believed to show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portugues, Italian, Polish, Bulgarian, Slavic, Serbian, Bosnian, Czech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Orogen, She, Tujia, Tu, Xibo, Yi, Mongolan, Naxi, Cambodian, Japanese, Yakut, Melanesian, Papuan, Karitianan, Surui, Colmbian, Maya and Pima.

In certain embodiments, the invention relates to populations that include black African ancestry such as populations comprising persons of African descent or lineage. Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry.

The racial contribution in individual subjects may also be determined by genetic analysis. Genetic analysis of ancestry may be carried out using unlinked microsatellite markers such as those set out in Smith et al. (*Am J Hum Genet.* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, are polymorphic in one population but not in another. The person skilled in the art will however apply the methods available and as taught herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Models to Predict Inherited Risk for Breast Cancer

The goal of breast cancer risk assessment is to provide a rational framework for the development of personalized medical management strategies for all women with the aim of increasing survival and quality of life in high-risk women while minimizing costs, unnecessary interventions and anxiety in women at lower risk. Risk prediction models attempt to estimate the risk for breast cancer in an individual who has a given set of congenital risk characteristics (e.g., family history, prior benign breast lesion, previous breast tumor). The breast cancer risk assessment models most commonly employed in clinical practice estimate inherited risk factors by considering family history. The risk estimates are based on the observations of increased risk to individuals with one or more close relatives previously diagnosed with breast cancer. They do not take into account complex pedigree structures. These models have the further disadvantage of not being able to differentiate between carriers and non-carriers of genes with breast cancer predisposing mutations.

More sophisticated risk models have better mechanisms to deal with specific family histories and have an ability to take into account carrier status for BRCA1 and BRCA2 mutations. For example, the Breast and Ovarian Analysis of Disease Incidence and Carrier Estimation Algorithm (BOADICEA) (Antoniou et al., 2004) takes into account family history based on individual pedigree structures through the pedigree analysis program MENDEL. Information on known BRCA1 and BRCA2 status is also taken into account. The main limitations of the BOADICEA and all other breast cancer risk models currently in use are that they do not incorporate genotypic information from other predisposition genes. Current models depend strongly on family history to act as a surrogate to compensate for the lack of knowledge of non-BRCA genetic determinants of risk. Therefore the available models are limited to situations where there is a known family history of disease. Lower penetrance breast cancer predisposition genes may be relatively common in the population and may not show such strong tendencies to drive familial clustering as do the BRCA1 and BRCA2 genes. Patients with a relatively high genetic load of predisposition alleles may show little or no family history of disease. There is a need therefore to construct models which incorporate inherited susceptibility data obtained directly through gene-based testing. In addition to making the models more precise, this will reduce the dependency on family history parameters and assist in the extension of the risk profiling into the wider at-risk population where family history is not such a key factor.

Integration of Improved Genetic Risk Models into Clinical Management of Breast Cancer Primary Prevention Clinical primary prevention options currently can be classified as chemopreventative (or hormonal) treatments and prophylactic surgery. Patients identified as high risk can be prescribed long-term courses of chemopreventative therapies. This concept is well accepted in the field of cardiovascular medicine, but is only now beginning to make an impact in clinical oncology. The most widely used oncology chemopreventative is Tamoxifen, a Selective Estrogen Receptor Modulator (SERM). Initially used as an adjuvant therapy directed against breast cancer recurrence, Tamoxifen now has proven efficacy as a breast cancer preventative agent [Cuzick, et al., (2003), Lancet, 361, 296-300][Martino, et al., (2004), Oncologist, 9, 116-25]. The FDA has approved the use of Tamoxifen as a chemopreventative agent in certain high risk women.

Unfortunately, long term Tamoxifen use increases risks for endometrial cancer approximately 2.5-fold, the risk of venous thrombosis approximately 2.0-fold. Risks for pulmonary embolism, stroke, and cataracts are also increased [Cuzick, et al., (2003), Lancet, 361, 296-300]. Accordingly, the benefits in Tamoxifen use for reducing breast cancer incidence may not be easily translated into corresponding decreases in overall mortality. Another SERM called Raloxifene may be more efficacious in a preventative mode, and does not carry the same risks for endometrial cancer. However risk for thrombosis is still elevated in patients treated long-term with Raloxifene [Cuzick, et al., (2003), Lancet, 361, 296-300; Martino, et al., (2004), Oncologist, 9, 116-25]. Moreover, both Tamoxifen and Raloxifene have quality of life issues associated with them. To make a rational risk: benefit analysis of SERM therapy in a chemopreventative mode, there is a clinical need to identify individuals who are most at risk for breast cancer. Given that a substantial proportion of risk for breast cancer is genetic, there is a clear clinical need for genetic tests to quantify individuals' risks in this context. One can anticipate similar issues arising from any future cancer chemo-preventative therapies that may become available, such as the aromatase inhibitors. Moreover, as chemopreventative therapies become safer, there is an increased need to identify patients who are genetically predisposed, but do not have massively elevated risks associated with BRCA1 & 2 mutation carriers.

Patients who are identified as being at high risk for breast cancer are considered for prophylactic surgery; either bilateral mastectomy or oophorectomy or both. Clearly such drastic treatments are recommended only for patients who are perceived to be at extremely high risk. In practice, such risks can currently be identified only in individuals who carry mutations in BRCA1, BRCA2 or genes known to be involved in rare breast cancer predisposition syndromes like p53 in Li-Fraumeni Syndrome, PTEN in Cowden's Syndrome.

Estimates of the penetrance of BRCA1 and BRCA2 mutations tend to be higher when they are derived from multiple-case families than when they are derived from population-based estimates. This is because different mutation-carrying families exhibit different penetrances for breast cancer (see [Thorlacius, et al., (1997), Am J Hum Genet, 60, 1079-84] for example). One of the major factors contributing to this variation is the action of as yet unknown predisposition genes whose effects modify the penetrance of BRCA1 and BRCA2 mutations. Therefore the absolute risk to an individual who carries a mutation in the BRCA1 or BRCA2 genes cannot be accurately quantified in the absence of knowledge of the existence and action of modifying genes. Since the treatment options for BRCA1 and BRCA2 carriers can be severe, it is important in this context to quantify the risks to individual BRCA carriers with the greatest accuracy possible. There is a need, therefore, to identify predisposition genes whose effects modify the penetrance of breast cancer in BRCA1 and BRCA2 carriers and to develop improved risk assessment models based on these genes.

Furthermore, there are individuals who are perceived to be at very high risk for breast cancer, perhaps because of a strong family history of breast cancer, but in whom no mutations in known predisposition genes can be identified. Consideration of prophylactic surgery is difficult in such cases because one cannot test the individual to discover whether or not she has inherited a high penetrance predisposition gene. Accordingly, the individual's risk cannot be assessed accurately. There is a clear clinical need, therefore, to identify any high penetrance predisposition genes that remain undiscovered and to develop associated genetic tests for use in primary prevention strategies. Such genes may for example be the genes disclosed herein to be associated with risk of breast cancer (e.g., the FGF10, MRPS30 and/or FGFR2 genes). Although the variants shown herein to be associated with risk of breast cancer are fairly common, and conferring a relatively low risk of breast cancer, it is quite possible that higher risk variants exist within one or more of these genes. It is thus contemplated that high-risk genetic variants within, or associated with, one or more of the FGF10, MRPS30 and/or FGFR2 genes could be useful for determining whether an individual is a carrier of a high risk (and high penetrance) genetic factor for breast cancer.

Early Diagnosis

Clinical screening for breast cancer in most western countries consists of periodic clinical breast examination (CBE) and X-ray mammography. There is good evidence to indicate that CBE has little added benefit when used in the context of a good mammographic screening program. In the United Kingdom, women between the ages of 50 and 70 are invited to undergo screening mammography every three years. The situation in the United States varies depending on healthcare provider, however the American Cancer Society recommends annual mammographic screening from age 40. Mammographic screening has proven effectiveness in reducing mortality amongst screened women over the age of 50.

It is unlikely that genetic testing would ever be employed as a means of reducing access to existing mammographic screening programs. However, mammographic screening is not without shortcomings and it is conceivable that genetic testing should be used to select people for augmented screening programs. One of the drawbacks of mammographic screening is that is has thus far not been possible to demonstrate a significant effect on improved survival for women screened under 50 years of age.

One reason that mammography is less effective in women under 50 may be that the density of breast tissue is higher in younger women, making mammographic detection of tumors more difficult. However, breast cancers in predisposed individuals tend to occur at early ages groups and there is a clear association between high breast density and breast cancer risk. Therefore there is a problem with simple increases in mammographic screening for individuals with high predisposition because they would be managed by a technique that performs sub-optimally in the group at highest risk. Recent studies have shown that contrast-enhanced magnetic resonance imaging (CE-MRI) is more sensitive and detects tumors at an earlier stage in this high-risk group than mammographic screening does [Warner, et al., (2004), Jama, 292, 1317-25; Leach, et al., (2005), Lancet, 365, 1769-78]. CE-MRI strategies work particularly well when used in combination with routine X-ray mammography [Leach, et al., (2005), Lancet, 365, 1769-78]. Because CE-MRI requires specialist centers that incur high costs, screening of under-50's must be restricted to those individuals at the highest risk. Present CE-MRI trials restrict entry to those individuals with BRCA1, BRCA2 or p53 mutations or very strong family histories of disease. The extension of this screening modality to a wider range of high-risk patients would be greatly assisted by the provision of gene-based risk profiling tools.

There is good evidence to support the notion that early-onset breast cancers and cancers occurring in genetically predisposed women grow faster than cancers in older, less strongly predisposed women. This comes from observations of higher rates of interval cancers in younger women, that is, cancers that arise in the intervals between screening visits in a well-screened population are higher amongst younger women. Therefore there are suggestions that screening intervals, by whatever method, should be reduced for younger women. There is a paradox here in that more frequent screening using more expensive methodologies seems to be required for an age group in which the overall rates of breast cancer are comparatively low. There is a clear clinical need here to identify those young individuals who are most strongly predisposed to develop the disease early, and channel them into more expensive and extensive screening regimes. The variants disclosed herein to confer risk of breast cancer can be useful for identification of individuals who are at particularly high risk of developing breast cancer. Such individuals are likely to most benefit from early and aggressive screening programs, so as to maximizing the likelihood of early identification of the cancer.

Treatment

Currently, primary breast cancer is treated by surgery, adjuvant chemotherapy, radiotherapy, followed by long term hormonal therapy. Often combinations of three or four therapies are used. Breast cancer patients with the same stage of disease can have very different responses to adjuvant chemotherapy resulting in a broad variation in overall treatment outcomes. Consensus guidelines (the St Galen and NIH criteria) have been developed for determining the eligibility of breast cancer patients for adjuvant chemotherapy treatment. However, even the strongest clinical and histological predictors of metastasis fail to predict accurately the clinical responses of breast tumors [Goldhirsch, et al., (1998), J Natl Cancer Inst, 90, 1601-8; Eifel, et al., (2001), Natl Cancer Inst, 93, 979-89]. Chemotherapy or hormonal therapy reduces the risk of metastasis only by approximately ⅓, however 70-80% of patients receiving this treatment would have survived without it. Therefore the majority of breast cancer patients are currently offered treatment that is either ineffective or unnecessary. There is a clear clinical need for improvements in the development of prognostic measures which will allow clinicians to tailor treatments more appropriately to those who will best benefit. It is reasonable to expect that profiling individuals for genetic predisposition may reveal information relevant to their treatment outcome and thereby aid in rational treatment planning. The markers of the present invention, conferring risk of breast cancer, are contemplated to be useful in this context.

Several previous studies exemplify this concept: Breast cancer patients who are BRCA mutation carriers appear to show better clinical response rates and survival when treated with adjuvant chemotherapies [Chappuis, et al., (2002), J Med Genet, 39, 608-10; Goffin, et al., (2003), Cancer, 97, 527-36]. BRCA mutation carriers demonstrate improved responses to platinum chemotherapy for ovarian cancer than non-carriers [Cass, et al., (2003), Cancer, 97, 2187-95]. Similar considerations may apply to predisposed patients in whom the genes involved are not known. For example, infiltrating lobular breast carcinoma (ILBC) is known to have a strong familial component but the genetic variants involved have not yet been identified. Patients with ILBC demonstrate poorer responses to common chemotherapy regimes [Mathieu, et al., (2004), Eur J Cancer, 40, 342-51].

Genetic predisposition models may not only aid in the individualization of treatment strategies, but may play an integral role in the design of these strategies. For example, BRCA1 and BRCA2 mutant tumor cells have been found to be profoundly sensitive to poly (ADP-ribose) polymerase (PARP) inhibitors as a result of their defective DNA repair pathway [Farmer, et al., (2005), Nature, 434, 917-21]. This has stimulated development of small molecule drugs targeted on PARP with a view to their use specifically in BRCA carrier patients. From this example it is clear that knowledge of genetic predisposition may identify drug targets that lead to the development of personalized chemotherapy regimes to be used in combination with genetic risk profiling. Similarly, the markers of the present invention may aid in the identification of novel drugs that target, for example, one or more of the FGF10, MRPS30 and/or FGFR2 genes.

Cancer chemotherapy has well known, dose-limiting side effects on normal tissues particularly the highly proliferative hemopoetic and gut epithelial cell compartments. It can be anticipated that genetically-based individual differences exist in sensitivities of normal tissues to cytotoxic drugs. An understanding of these factors might aid in rational treatment planning and in the development of drugs designed to protect normal tissues from the adverse effects of chemotherapy.

Genetic profiling may also contribute to improved radiotherapy approaches: Within groups of breast cancer patients undergoing standard radiotherapy regimes, a proportion of patients will experience adverse reactions to doses of radiation that are normally tolerated. Acute reactions include erythema, moist desquamation, edema and radiation pneumatitis. Long term reactions including telangiectasia, edema, pulmonary fibrosis and breast fibrosis may arise many years after radiotherapy. Both acute and long-term reactions are considerable sources of morbidity and can be fatal. In one study, 87% of patients were found to have some adverse side effects to radiotherapy while 11% had serious adverse reactions (LENT/SOMA Grade 3-4); [Hoeller, et al., (2003), Int J Radiat Oncol Biol Phys, 55, 1013-8]. The probability of experiencing an adverse reaction to radiotherapy is due primarily to constitutive individual differences in normal tissue reactions and there is a suspicion that these have a strong genetic component. Several of the known breast cancer predisposition genes (e.g. BRCA1, BRCA2, ATM) affect pathways of DNA double strand break repair. DNA double strand breaks are the primary cytotoxic lesion induced by radiotherapy. This has led to concern that individuals who are genetically predisposed to breast cancer through carriage of variants in genes belonging to these pathways might also be at higher risk of suffering excessive normal tissue damage from radiotherapy. It is contemplated that the genetic variants described herein to confer risk of breast cancer, for example through one or more of the FGF10, MRPS30 and/or FGFR2 genes, may be useful for identifying individuals at particular risk of adverse reaction to radiotherapy.

The existence of constitutively radiosensitive individuals in the population means that radiotherapy dose rates for the majority of the patient population must be restricted, in order to keep the frequency of adverse reactions to an acceptable level. There is a clinical need, therefore, for reliable tests that can identify individuals who are at elevated risk for adverse reactions to radiotherapy. Such tests would indicate conservative or alternative treatments for individuals who are radiosensitive, while permitting escalation of radiotherapeutic doses for the majority of patients who are relatively radioresistant. It has been estimated that the dose escalations made possible by a test to triage breast cancer patients simply into radiosensitive, intermediate and radioresistant categories would result in an approximately 35% increase in local tumor control and consequent improvements in survival rates [Burnet, et al., (1996), Clin Oncol (R Coll Radiol), 8, 25-34].

Exposure to ionizing radiation is a proven factor contributing to oncogenesis in the breast [Dumitrescu and Cotarla, (2005), J Cell Mol Med, 9, 208-21]. Known breast cancer predisposition genes encode pathway components of the cellular response to radiation-induced DNA damage [Narod and Foulkes, (2004), Nat Rev Cancer, 4, 665-76]. Accordingly, there is concern that the risk for second primary breast tumors may be increased by irradiation of normal tissues within the radiotherapy field. There does not appear to be any measurable increased risk for BRCA carriers from radiotherapy, however their risk for second primary tumors is already exceptionally high. There is evidence to suggest that risk for second primary tumors is increased in carriers in breast cancer predisposing alleles of the ATM and CHEK2 genes who are treated with radiotherapy [Bernstein, et al., (2004), Breast Cancer Res, 6, R199-214; Broeks, et al., (2004), Breast Cancer Res Treat, 83, 91-3]. It is expected that the risk of second primary tumors from radiotherapy (and, possibly, from intensive mammographic screening) will be better defined by obtaining accurate genetic risk profiles from patients during the treatment planning stage.

Secondary Prevention

Approximately 30% of patients who are diagnosed with a stage 1 or 2 breast cancer will experience either a loco-regional or distant metastatic recurrence of their original tumor. Patients who have had a primary breast cancer are also at greatly increased risk for being diagnosed with a second primary tumor, either in the contralateral breast or in the ipsilateral breast when breast-conserving surgery has been carried out. Secondary prevention refers to methods used to prevent recurrences or second primary tumors from developing. Methods currently in use comprise; long-term treatment with Tamoxifen or another SERM either alone or alternated with an aromatase inhibitor, risk-reducing mastectomy of the contralateral breast, and risk-reducing oophorectomy (in patients who are at risk for familial breast-ovarian cancer). Considerations regarding the use of Tamoxifen have been discussed above. With risk-reducing surgical options, it is clear that the risk needs to be quantified as well as possible in order to make an informed cost: benefit analysis.

There are some indications that patients with known genetic predispositions to breast cancer fare worse than the majority of patients. Patients carrying the CHEK2 gene 1100delC variant have an estimated 2.8-fold increased risk of distant metastasis and a 3.9-fold increased risk of disease recurrence compared to non-carriers [de Bock, et al., (2004), Med Genet, 41, 731-5]. Patients with BRCA1 node-negative tumors have a greater risk of metastasis than similar patients who do not carry a BRCA1 mutation [Goffin, et al., (2003), Cancer, 97, 527-36; Moller, et al., (2002), Int 3 Cancer, 101, 555-9; Eerola, et al., (2001), Int J Cancer, 93, 368-72]. Genetic profiling can therefore be used to help assess the risk of local recurrence and metastatsis, thereby guiding the choice of secondary preventative treatment. Genetic profiling based on the variants described herein may be useful in this context. In certain embodiments, such profiling may be based on one or more of the variants described herein. In other embodiments, such profiling may include one or several other known genetic risk factors for breast cancer. Such risk factors may be well established high-penetrant risk factors, or they may be one or more of the common, lower penetrance risk factors that have been previously described (e.g., markers on chromosome 2q14 (e.g., marker rs4848543 or markers in linkage disequilibrium therewith), 2q35 (e.g., marker rs13387042, or markers in linkage disequilibrium therewith), and chromosome 16 (e.g., marker rs3803662, or markers in linkage disequilibrium therewith).

In general, patients with a primary tumor diagnosis are at risk for second primary tumors at a constant annual incidence of 0.7% [Peto and Mack, (2000), Nat Genet, 26, 411-4]. Patients with BRCA mutations are at significantly greater risks for second primary tumors than most breast cancer patients, with absolute risks in the range 40-60%[Easton, (1999), Breast Cancer Res, 1, 14-7]. Carriers of BRCA mutations have a greatly increased risk for second primary tumors [Stacey, et al., (2006), PLoS Med, 3, e217; Metcalfe, et al., (2004), J Clin Oncol, 22, 2328-35]. Patients with mutations in the CHEK2 gene have an estimated 5.7-fold increased risk of contralateral breast cancer [de Bock, et al., (2004), J Med Genet, 41, 731-5]. Carriers of the BARD1 Cys557Ser variant are 2.7 fold more likely to be diagnosed with a second primary tumor [Stacey, et al., (2006), PLoS Med, 3, e217]. Genetic risk profiling can be used to assess the risk of second primary tumors in patients and will inform decisions on how aggressive the preventative measures should be.

METHODS OF THE INVENTION

Diagnostic and Screening Methods

In certain embodiments, the present invention pertains to methods of diagnosing, or aiding in the diagnosis of, breast cancer or a susceptibility to breast cancer, by detecting particular alleles at genetic markers that appear more frequently in breast cancer subjects or subjects who are susceptible to breast cancer. In particular embodiments, the invention is a method of determining a susceptibility to breast cancer by detecting at least one allele of at least one polymorphic marker (e.g., the markers described herein). In other embodiments, the invention relates to a method of diagnosing a susceptibility to breast cancer by detecting at least one allele of at least one polymorphic marker. The present invention describes methods whereby detection of particular alleles of particular markers or haplotypes is indicative of a susceptibility to breast cancer. Such prognostic or predictive assays can also be used to determine prophylactic treatment of a subject prior to the onset of symptoms associated with breast cancer. The present invention pertains in some embodiments to methods of clinical applications of diagnosis, e.g., diagnosis performed by a medical professional. In other embodiments, the invention pertains to methods of diagnosis or determination of a susceptibility performed by a layman. The layman can be the customer of a genotyping service. The layman may also be a genotype service provider, who performs genotype analysis on a DNA sample from an individual, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for up to one million SNPs simultaneously, at relatively little cost. The resulting genotype information, which can be made available to the individual, can be compared to information about disease or trait risk associated with various SNPs, including information from public literature and scientific publications. The diagnostic application of disease-associated alleles as described herein, can thus for example be performed by the individual, through analysis of his/her genotype data, by a health professional based on results of a clinical test, or by a third party, including the genotype service provider. The third party may also be service provider who interprets genotype information from the customer to provide service related to specific genetic risk factors, including the genetic markers described herein. In other words, the diagnosis or determination of a susceptibility of genetic risk can be made by health professionals, genetic counselors, third parties providing genotyping service, third parties providing risk assessment service or by the layman (e.g., the individual), based on information about the genotype status of an individual and knowledge about the risk conferred by particular genetic risk factors (e.g., particular SNPs). In the present context, the term "diagnosing", "diagnose a susceptibility" and "determine a susceptibility" is meant to refer to any available diagnostic method, including those mentioned above.

In certain embodiments, a sample containing genomic DNA from an individual is collected. Such sample can for example be a buccal swab, a saliva sample, a blood sample, or other suitable samples containing genomic DNA, as described further herein. The genomic DNA is then analyzed using any common technique available to the skilled person, such as high-throughput array technologies. Results from such genotyping are stored in a convenient data storage unit, such as a data carrier, including computer databases, data storage disks, or by other convenient data storage means. In certain embodiments, the computer database is an object database, a relational database or a post-relational database. The genotype-data is subsequently analyzed for the presence of certain variants known to be susceptibility variants for a particular human conditions, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for an heterozygous carrier of an at-risk variant for a particular disease or trait (such as breast cancer). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

In addition, in certain other embodiments, the present invention pertains to methods of diagnosing, or aiding in the diagnosis of, a decreased susceptibility to breast cancer, by detecting particular genetic marker alleles or haplotypes that appear less frequently in breast cancer patients than in individual not diagnosed with breast cancer or in the general population.

As described and exemplified herein, particular marker alleles or haplotypes (e.g., markers on Chromosome 5p12 and 10q26, e.g. the markers and haplotypes as listed in Tables 12, 13 and 14, e.g. markers rs4415084, rs10941679 and rs1219648, and markers in linkage disequilibrium therewith) are associated with breast cancer. In one embodiment, the marker allele or haplotype is one that confers a significant risk or susceptibility to breast cancer. In another embodiment, the invention relates to a method of diagnosing a susceptibility to breast cancer in a human individual, the method comprising determining the presence or absence of at least one allele of at least one polymorphic marker in a nucleic acid sample obtained from the individual, wherein the at least one polymorphic marker is selected from the group consisting of the polymorphic markers listed in Tables 12, 13 and 14, and markers in linkage disequilibrium therewith. In another embodiment, the invention pertains to methods of diagnosing a susceptibility to breast cancer in a human individual, by screening for at least one marker allele or haplotype as listed in Table 12, 13 or 14, or markers in linkage disequilibrium therewith. In another embodiment, the marker allele or haplotype is more frequently present in a subject having, or who is susceptible to, breast cancer (affected), as compared to the frequency of its presence in a healthy subject (control, such as population controls). In certain embodiments, the significance of association of the at least one marker allele or haplotype is characterized by a p value <0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to breast cancer. These diagnostic methods involve detecting the presence or absence of at least one marker allele or haplotype that is associated with breast cancer. The haplotypes described herein include combinations of alleles at various genetic markers (e.g., SNPs, microsatellites, or other genetic variants). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a breast cancer—associated nucleic acid (e.g., by protein sequencing or by immunoassays using antibodies that recognize such a protein). The marker alleles or haplotypes of the present invention correspond to fragments of a genomic DNA sequence associated with breast cancer. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype (as determined by a value of $r^2$ greater than 0.1 and/or $|D'|>0.8$).

In one embodiment, diagnosis of a susceptibility to breast cancer can be accomplished using hybridization methods (see Current Protocols in Molecular Biology, Ausubel, F. et al., eds., John Wiley & Sons, including all supplements). A biological sample from a test subject or individual (a "test sample") of genomic DNA, RNA, or cDNA is obtained from a subject suspected of having, being susceptible to, or predisposed for breast cancer (the "test subject"). The subject can be an adult, child, or fetus. The test sample can be from any source that contains genomic DNA, such as a blood sample, sample of amniotic fluid, sample of cerebrospinal fluid, or tissue sample from skin, muscle, buccal or conjunctival mucosa, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined. The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample. The invention can also be reduced to practice using any convenient genotyping method, including commercially available technologies and methods for genotyping particular polymorphic markers.

To diagnose a susceptibility to breast cancer, a hybridization sample can be formed by contacting the test sample containing a breast cancer-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of a nucleotide sequence comprising the markers set forth in Tables 12, 13 and 14 (SEQ ID NO:1-237), or a nucleotide sequence comprising the FGF10, MRPS30, HCN1 or FGFR2 genes or fragments thereof, as described herein, optionally comprising at least one allele of a marker described herein, or at least one haplotype described herein, or the probe can be the complementary sequence of such a sequence. In a particular embodiment, the nucleic acid probe is a portion of the nucleotide sequence of a nucleotide sequence comprising the markers listed in any one of Tables 12, 13 and 14 (SEQ ID NO:1-237), or a nucleotide sequence comprising the FGF10, MRPS30, HCN1 and FGFR2 genes or fragments thereof, as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to breast cancer.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (Nucleic Acid Res. 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., Bioconjug. Chem. 5:3-7 (1994)). The PNA probe can be designed to specifically hybridize to a molecule in a sample suspected of containing one or more of the marker alleles or haplotypes that are associated with breast cancer. Hybridization of the PNA probe is thus diagnostic for breast cancer or a susceptibility to breast cancer.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with breast cancer, can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with breast cancer. Further, the expression of the variant(s) can be quantified as physically or functionally different.

In another method of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes associated with breast cancer (e.g. the polymorphic markers of Tables 12, 13 and 14 (SEQ ID NO:1-237) and markers in linkage disequilibrium therewith). Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid associated with breast cancer, and the presence of a specific allele can then be detected directly by sequencing the polymorphic site (or multiple polymorphic sites in a haplotype) of the genomic DNA in the sample.

Allele-specific oligonucleotides can also be used to detect the presence of a particular allele in a nucleic acid associated with breast cancer (e.g. the polymorphic markers of Tables 12, 13 and 14, and markers in linkage disequilibrium therewith), through the use of dot-blot hybridization of amplified oligonucleotides with allele-specific oligonucleotide (ASO) probes (see, for example, Saiki, R. et al., Nature, 324:163-166 (1986)). An "allele-specific oligonucleotide" (also referred to herein as an "allele-specific oligonucleotide probe") is an oligonucleotide of approximately 10-50 base pairs or approximately 15-30 base pairs, that specifically hybridizes to a nucleic acid associated with breast cancer, and which contains a specific allele at a polymorphic site (e.g., a marker or haplotype as described herein). An allele-specific oligonucleotide probe that is specific for one or more particular a nucleic acid associated with breast cancer can be prepared using standard methods (see, e.g., Current Protocols in Molecular Biology, supra). PCR can be used to amplify the desired region. The DNA containing the amplified region can be dot-blotted using standard methods (see, e.g., Current Protocols in Molecular Biology, supra), and the blot can be contacted with the oligonucleotide probe. The presence of specific hybridization of the probe to the amplified region can then be detected. Specific hybridization of an allele-specific oligonucleotide probe to DNA from the subject is indicative of a specific allele at a polymorphic site associated with cancer, including breast cancer (see, e.g., Gibbs, R. et al., Nucleic Acids Res., 17:2437-2448 (1989) and WO 93/22456).

With the addition of such analogs as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures ($T_m$) of 64° C. and 74° C. when in complex with complementary DNA or RNA, respectively, as opposed to 28° C. for both DNA and RNA for the corresponding DNA nonamer. Substantial increases in $T_m$ are also obtained when LNA monomers are used in combination with standard DNA or RNA monomers. For primers and probes, depending on where the LNA monomers are included (e.g., the 3' end, the 5' end, or in the middle), the $T_m$ could be increased considerably.

In another embodiment, arrays of oligonucleotide probes that are complementary to target nucleic acid sequence segments from a subject, can be used to identify polymorphisms in a nucleic acid associated with breast cancer (e.g. the polymorphic markers of Table 12, 13 and 14 (SEQ ID NO:1-237), and markers in linkage disequilibrium therewith). For example, an oligonucleotide array can be used. Oligonucleotide arrays typically comprise a plurality of different oligonucleotide probes that are coupled to a surface of a substrate in different known locations. These oligonucleotide arrays, also described as "Genechips™," have been generally described in the art (see, e.g., U.S. Pat. No. 5,143,854, PCT Patent Publication Nos. WO 90/15070 and 92/10092). These arrays can generally be produced using mechanical synthesis methods or light directed synthesis methods that incorporate a combination of photolithographic methods and solid phase oligonucleotide synthesis methods, or by other methods known to the person skilled in the art (see, e.g., . . . , Bier, F. F., et al. *Adv Biochem Eng Biotechnol* 109:433-53 (2008); Hoheisel, J. D., *Nat Rev Genet.* 7:200-10 (2006); Fan, J. B., et al. Methods Enzymol 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300,063, U.S. Pat. No. 6,733,977, U.S. Pat. No. 7,364,858, EP 619 321, and EP 373 203, the entire teachings of which are incorporated by reference herein.

Other methods of nucleic acid analysis that are available to those skilled in the art can be used to detect a particular allele at a polymorphic site associated with breast cancer. Representative methods include, for example, direct manual sequencing (Church and Gilbert, *Proc. Natl. Acad. Sci. USA*, 81: 1991-1995 (1988); Sanger, F., et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the invention, diagnosis of breast cancer or a susceptibility to breast cancer can be made by examining expression and/or composition of a polypeptide encoded by a nucleic acid associated with breast cancer in those instances where the genetic marker(s) or haplotype(s) of the present invention result in a change in the composition or expression of the polypeptide. Thus, diagnosis of a susceptibility to breast cancer can be made by examining expression and/or composition of one of these polypeptides, or another polypeptide encoded by a nucleic acid associated with breast cancer, in those instances where the genetic marker or haplotype of the present invention results in a change in the composition or expression of the polypeptide (e.g., one or more of the FGF10, MRPS30, HCN1 and FGFR2 genes). The haplotypes and markers of the present invention that show association to breast cancer may play a role through their effect on one or more of these nearby genes. Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to breast cancer affect the expression of a nearby gene. It is well known that regulatory element affecting gene expression may be located tenths or even hundreds of kilobases away from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more of the FGF10, MRPS30, HCN1 and FGFR2 genes.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with breast cancer. An alteration in expression of a polypeptide encoded by a nucleic acid associated with breast cancer can be, for example, an alteration in the quantitative polypeptide expression (i.e., the amount of polypeptide produced). An alteration in the composition of a polypeptide encoded by a nucleic acid associated with breast cancer is an alteration in the qualitative polypeptide expression (e.g., expression of a mutant polypeptide or of a different splicing variant). In one embodiment, diagnosis of a susceptibility to breast cancer is made by detecting a particular splicing variant encoded by a nucleic acid associated with breast cancer, or a particular pattern of splicing variants (e.g., the nucleic acids encoding the FGF10, MRPS30, and HCN1 genes).

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, breast cancer. In one embodiment, the control sample is from a subject that does not possess a marker allele or haplotype as described herein. Similarly, the presence of one or more different splicing variants in the test sample, or the presence of significantly different amounts of different splicing variants in the test sample, as compared with the control sample, can be indicative of a susceptibility to breast cancer. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with breast cancer can be used. Antibodies can be polyclonal or monoclonal. An intact antibody, or a fragment thereof (e.g., Fv, Fab, Fab', F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with breast cancer (e.g., FGF10, MRPS30, and HCN1) in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, the diagnosis of a susceptibility to breast cancer is made by detecting at least one marker or haplotypes of the present invention (e.g., associated alleles of the markers listed in Tables 12, 13 and 14 (SEQ ID NO:1-237), and markers in linkage disequilibrium therewith), in combination with an additional protein-based, RNA-based or DNA-based assay. The methods of the invention can also be used in combination with an analysis of a subject's family history and risk factors (e.g., environmental risk factors, lifestyle risk factors).

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with breast cancer, means for analyzing the nucleic acid sequence of a nucleic acid associated with breast cancer, means for analyzing the amino acid sequence of a polypeptide encoded by a nucleic acid associated with breast cancer, etc. The kits can for example include necessary buffers, nucleic acid primers for amplifying nucleic acids of the invention (e.g., one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with breast cancer diagnostic assays.

In one embodiment, the invention is a kit for assaying a sample from a subject to detect the presence of a breast cancer or a susceptibility breast cancer in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism, wherein the polymorphism is selected from the group consisting of the polymorphisms as listed in Table 12, 13 and 14 (SEQ ID NO:1-237), and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are indicative of breast cancer. In another embodiment, the kit comprises one or more labeled nucleic acids capable of allele-specific detection of one or more specific polymorphic markers or haplotypes associated with breast cancer, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers in Tables 12, 13 and 14. In another embodiment, the marker to be detected is selected from marker rs10941679, rs7703618, rs4415084, rs2067980, rs10035564, rs11743392, rs7716600 and rs1219648. In another embodiment, the marker or haplotype to be detected comprises at least one marker from the group of markers in strong linkage disequilibrium, as defined by values of $r^2$ greater than 0.2, to at least one of the group of markers consisting of the markers listed in Tables 12, 13 and 14. In yet another embodiment, the marker or haplotype to be detected comprises at least one marker selected from the group of markers consisting of markers rs10941679, rs7703618, rs4415084, rs2067980, rs10035564, rs11743392, rs7716600 and rs1219648, and markers in linkage disequilibrium therewith.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. The detection oligonucleotide probe comprises a fluorescent moiety or group at its 3' terminus and a quencher at its 5' terminus, and an enhancer oligonucleotide is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one of such embodiments, the presence of the marker or haplotype is indicative of a susceptibility (increased susceptibility or decreased susceptibility) to breast cancer. In another embodiment, the presence of the marker or haplotype is indicative of response to a breast cancer therapeutic agent. In another embodiment, the presence of the marker or haplotype is indicative of breast cancer prognosis. In yet another embodiment, the presence of the marker or haplotype is indicative of progress of breast cancer treatment. Such treatment may include intervention by surgery, medication or by other means (e.g., lifestyle changes).

Therapeutic Agents

Variants of the present invention (e.g., the markers and/or haplotypes of the invention, e.g., the markers listed in Tables 12, 13 and 14, e.g., rs4415084, rs10941679, rs1219648) can be used to identify novel therapeutic targets for breast cancer. For example, genes containing, or in linkage disequilibrium with, variants (markers and/or haplotypes) associated with breast cancer (e.g., one or more of the FGF10, MRPS30, HCN1 and FGFR2 genes, or their products, as well as genes or their products that are directly or indirectly regulated by or interact with these variant genes or their products, can be targeted for the development of therapeutic agents to treat breast cancer, or prevent or delay onset of symptoms associated with breast cancer. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, nucleic acids comprising one or more variant of the invention (e.g., nucleic acids with sequence as set forth in any one of SEQ ID NO:1-237, or fragments thereof) or nucleic acids comprising their complementary sequence, may be used as antisense constructs to control gene expression in cells, tissues or organs. The methodology associated with antisense techniques is well known to the skilled artisan, and is described and reviewed in *AntisenseDrug Technology: Principles, Strategies, and Applications*, Crooke, ed., Marcel Dekker Inc., New York (2001). In general, antisense nucleic acid molecules are designed to be complementary to a region of mRNA expressed by a gene, so that the antisense molecule hybridizes to the mRNA, thus blocking translation of the mRNA into protein. Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002)

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, such as breast cancer. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today,* 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor mmRNA (pre-miRNA). These miRNA molecules are exported from the nucleus to the cytoplasm, where they undergo processing to generate mature mmRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants of the present invention (e.g., the markers and haplotypes set forth in Tables 12, 13 and 14) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Layery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of breast cancer, or a defect causing breast cancer, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the adminstered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat breast cancer. Thus, the variants of the invention are useful as targets for the identification and/or development of therapeutic agents. In certain embodiments, such methods include assaying the ability of an agent or compound to modulate the activity and/or expression of a nucleic acid that includes at least one of the variants (markers and/or haplotypes) of the present invention, or the encoded product of the nucleic acid. This includes, for example, one or more of the FGF10, MRPS30, HCN1 and FGFR2 genes, and their gene products. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating breast cancer can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods for Treating Breast Cancer As is known in the art, individuals can have differential responses to a particular therapy (e.g., a therapeutic agent or therapeutic method). The basis of the differential response may be genetically determined in part. Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different response rate to a particular treatment modality. This means that a patient diagnosed with breast cancer, and carrying a certain allele at a polymorphic or haplotype of the present invention (e.g., the at-risk and protective alleles and/or haplotypes of the invention) would respond better to, or worse to, a specific therapeutic, drug and/or other therapy used to treat the disease. Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample, as described herein). If the patient is positive for a marker allele or haplotype (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

As described further herein, current clinical preventive options for breast cancer are mainly chemopreventive (chemotherapy, or hormonal therapy) and prophylactic surgery. The most common chemopreventive is Tamoxifen and Raloxifene; other options include other Selective Estrogen Receptor Modulator (SERM) and aromatase inhibitors. Treatment options also include radiation therapy, for which a proportion of patients experience adverse symptoms. The markers of the invention, as described herein, may be used to assess response to these therapeutic options, or to predict the progress of therapy using any one of these treatment options. Thus, genetic profiling can be used to select the appropriate treatment strategy based on the genetic status of the individual, or it may be used to predict the outcome of the particular treatment option, and thus be useful in the strategic selection of treatment options or a combination of available treatment options.

The present invention also relates to methods of monitoring progress or effectiveness of a treatment for a breast cancer. This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for breast cancer as presented herein is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of the at-risk variants of the present invention, i.e. individuals who are carriers of at least one allele of at least one polymorphic marker conferring increased risk of developing breast cancer may be more likely to respond to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

The present invention also relates to computer-implemented applications of the polymorphic markers and haplotypes described herein to be associated with breast cancer. Such applications can be useful for storing, manipulating or otherwise analyzing genotype data that is useful in the methods of the invention. One example pertains to storing genotype information derived from an individual on readable media, so as to be able to provide the genotype information to a third party The third party may be the individual from which the genotype data is derived. The third party may also be a service provider for analyzing the genotype information, for example a service provider who calculates genetic risk based on the genotype of the individual at particular genetic markers. In one such embodiment, the service provider receives genotype information from a genotype service provider, and stores the genotype information on a readable medium for subsequent analysis. In another embodiment, the genotype provider is also the service provider, i.e. the same party generates genotypes from a DNA sample from an individual, stores the genotype data on a readable medium, and providers service relating to the risk assessment or other interpretation of the genotype data. The additional interpretation may for example include assessment or prediction of the ancestry of the individual, or the genealogical relationship between the individual and a reference individual. The reference individual may for example be a friend, relative or any other person to whom the individual wishes to compare his/her genotypes to. In one particular embodiment, the genotype data is used to derive information about genetic risk factors contributing to increased susceptibility to breast cancer, and report results based on such comparison.

In one aspect, the invention relates to computer-readable media. In general terms, such medium has capabilities of storing (i) identifier information for at least one polymorphic marker or a haplotye; (ii) an indicator of the frequency of at least one allele of said at least one marker, or the frequency of a haplotype, in individuals with breast cancer; and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

Additional information about the individual can be stored on the medium, such as ancestry information, information about sex, physical attributes or characteristics (including height and weight), biochemical measurements (such as blood pressure, blood lipid levels, etc.), or other useful information that is desirable to store or manipulate in the context of the genotype status of a particular individual.

The invention furthermore relates to an apparatus that is suitable for determination or manipulation of genetic data useful for determining a susceptibility to breast cancer in a human individual. Such an apparatus can include a computer-readable memory, a routine for manipulating data stored on the computer-readable memory, and a routine for generating an output that includes a measure of the genetic data. Such measure can include values such as allelic or haplotype frequencies, genotype counts, sex, age, phenotype information, values for odds ratio (OR) or relative risk (RR), population attributable risk (PAR), or other useful information that is either a direct statistic of the original genotype data or based on calculations based on the genetic data.

The markers and haplotypes shown herein to be associated with increased susceptibility (e.g., increased risk) of breast cancer, are in certain embodiments useful for interpretation and/or analysis of genotype data. Thus in certain embodiments, an identification of an at-risk allele for breast cancer, as shown herein, or an allele at a polymorphic marker in LD with any one of the markers shown herein to be associated with breast cancer, is indicative of the individual from whom the genotype data originates is at increased risk of breast cancer. In one such embodiment, genotype data is generated for at least one polymorphic marker shown herein to be associated with breast cancer, or a marker in linkage disequilibrium therewith. The genotype data is subsequently made available to the individual from whom the data originates, for example via a user interface accessible over the internet, together with an interpretation of the genotype data, e.g., in the form of a risk measure (such as an absolute risk (AR), risk ratio (RR) or odds ration (OR)) for the disease (e.g., breast cancer). In another embodiment, at-risk markers identified in a genotype dataset derived from an individual are assessed and results from the assessment of the risk conferred by the presence of such at-risk variants in the dataset are made available to the individual, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived. In particular embodiments, the results of risk assessment is made available to a third party, e.g., a physician, other healthcare worker or genetic counselor.

Markers Useful in Various Aspects of the Invention

The above-described applications can all be practiced with the markers and haplotypes of the invention that have in more detail been described with respect to methods of assessing susceptibility to breast cancer. Thus, these applications can in general be reduced to practice using markers within the Chr5p12 and Chr10q26 genomic regions as defined herein, including markers as listed in Tables 12, 13 and 14, and markers in linkage disequilibrium therewith. In one embodiment, a marker useful in the various aspects and embodiments of the invention is selected from the markers set forth in Tables 12, 13 and 14 (SEQ ID NO:1-237). In one embodiment, the marker is selected from marker rs10941679, rs7703618, rs4415084, rs2067980, rs10035564, rs11743392, rs7716600, and rs1219648, and markers in linkage disequilibrium therewith. In another embodiment, the marker is selected from marker rs10941679, rs7703618, rs4415084, rs2067980, rs10035564, rs11743392, rs7716600 and rs1219648. In another embodiment, the marker is selected from rs10941679, and markers in linkage disequilibrium therewith. In one embodiment, the marker is selected from the markers set forth in Table 13. In another embodiment, the marker is selected from marker rs4415084, and markers in linkage disequilibrium therewith. In another embodiment, the marker is selected from the markers set forth in Table 12. In another embodiment, the marker is selected from marker rs1219648, and markers in linkage disequilibrium therewith. In another embodiment, the marker is selected from the markers set forth in Table 14. In another embodiment, the marker is rs4415084. In another embodiment, the marker is rs10941679. In another embodiment, the marker is rs1219648. In another embodiment, the marker is rs4415084 or rs10941679. In another embodiment, marker alleles conferring increased risk or susceptibility of breast cancer are selected from rs10941679 allele G, rs7703618 allele T, rs4415084 allele G, rs2067980 allele G, rs10035564 allele G, rs11743392 allele T, rs7716600 allele A, and rs1219648 allele G.

Nucleic Acids and Polypeptides

The nucleic acids and polypeptides described herein can be used in methods and kits of the present invention, as described in the above. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present.

With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.*, 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions× 100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S, and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA*, 85:2444-48 (1988).

In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, a nucleotide sequence comprising the polymorphic markers listed in Table 12, Table 13 and Table 14 (SEQ ID NO:1-237), and the nucleotide sequence of the FGF10, MRPS30, HCN1 and FGFR2 genes; or a nucleotide sequence comprising, or consisting of, the complement of the nucleotide sequence of a nucleotide sequence comprising the polymorphic markers listed in Table 12, Table 13 and Table 14 (SEQ ID NO:1-237), and the nucleotide sequence of the FGF10, MRPS30, HCN1 and FGFR2 genes, wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In general, the isolated nucleic acid sequences of the invention can be used as molecular weight markers on Southern gels, and as chromosome markers that are labeled to map related gene positions. The nucleic acid sequences can also be used to compare with endogenous DNA sequences in patients to identify breast cancer or a susceptibility to breast cancer, and as probes, such as to hybridize and discover related DNA sequences or to subtract out known sequences from a sample (e.g., subtractive hybridization). The nucleic acid sequences can further be used to derive primers for genetic fingerprinting, to raise anti-polypeptide antibodies using immunization techniques, and/or as an antigen to raise anti-DNA antibodies or elicit immune responses.

Antibodies

Polyclonal antibodies and/or monoclonal antibodies that specifically bind one form of the gene product but not to the other form of the gene product are also provided. Antibodies are also provided which bind a portion of either the variant or the reference gene product that contains the polymorphic site or sites. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., Nature 266:55052 (1977); R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9: 1370-1372 (1991); Hay et al., Hum. Antibod. Hybridomas 3:81-85 (1992); Huse et al., Science 246: 1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies may also be useful in pharmacogenomic analysis. In such embodiments, antibodies against variant proteins encoded by nucleic acids according to the invention, such as variant proteins that are encoded by nucleic acids that contain at least one polymorpic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein, in particular breast cancer. Antibodies specific for a variant protein of the present invention that is encoded by a nucleic acid that comprises at least one polymorphic marker or haplotype as described herein can be used to screen for the presence of the variant protein, for example to screen for a predisposition to breast cancer as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

EXAMPLE 1

Identification of Variants on Chromosome 5p12 that Associate with Risk of Breast Cancer Introduction Mutations in breast cancer susceptibility genes BRCA1 and BRCA2 account for 15-25% of the familial component of breast cancer risk [Easton, (1999), Breast Cancer Res, 1, 14-7; Balmain, et al., (2003), Nat Genet, 33 Suppl, 238-44]. Much of the genetic component of risk of breast cancer remains uncharacterized and is thought to arise from combinations of less penetrant variants that, individually, may be quite common [Pharoah, et al., (2002), Nat Genet, 31, 33-6]. Many searches for less penetrant breast cancer risk variants have been carried out using a candidate gene, case-control association approach. Findings from these studies have often proven difficult to replicate [Breast Cancer Association, (2006), J Natl Cancer Inst, 98, 1382-96]. Recently common missense variants in two genes, CASP8 and TGFB1, have been shown to be associated with breast cancer risk by using well-powered, multi-center analyses [Cox, et al., (2007), Nat Genet, 39, 352-8]. These reports emphasize the importance of large scale studies with adequate replication when the goal is to identify common variants conferring modest increases in the risk of breast cancer.

Results

Numerous Illumina SNPs in a Region on Chromosome 5p12 are Associated with an Increased Risk for Breast Cancer in Iceland In order to search widely for alleles of common SNPs associating to breast cancer susceptibility, we carried out a genome-wide SNP association study using Illumina HumanHap300 microarray technology. Genotyping was carried out on approximately 1,600 Icelandic breast cancer patients and 11,563 controls. This discovery sample set was designated "Iceland 1". After removing SNPs that failed quality control checks, 311,524 SNPs remained and were tested for association with breast cancer. The results were adjusted for relatedness among individuals and potential population stratification using the method of genomic control [Devlin and Roeder, (1999), Biometrics, 55, 997-1004] (see Methods). Signals were ranked by P-value. A set of SNPs from the same area on chromosome 5p12 occupied 39 of the top 50 ranks. The highest ranks occupied by SNPs located in 5p12 were ranks 5 through 9. The region of interest containing these SNPs extended from approximately chromosome 5 co-ordinate 44,094,392 bp (position of marker rs7704166; all co-ordinates herein are from NCBI Build 34) to the position of the last Illumina SNP before the centromere; namely rs10941803 at 46,393,984 bp. Results from genotyping of the Illumina SNPs in this region are presented in Table 1 and are presented graphically in FIG. 1.

In order to further investigate the signals related to one of the highly ranked SNPs, marker rs7703618 on chr5p12, we generated and validated Centaurus assays for this SNP. The Centaurus assay was designated SG05S3065.c1. This SNP assay was used to genotype an independent sample of approximately 591 Icelandic Breast Cancer patients and 1314 controls. This independent sample was designated Iceland 2. As shown in Table 2, the SNP showed a significant association with breast cancer in the Iceland 2 sample, confirming the original observations with Iceland 1. We have thus replicated the original finding observed in the Iceland 1 sample in the independent Iceland 2 sample. The joint P-value for Iceland 1 & Iceland 2 approached a level that would be considered genome-wide significant after applying the conservative Bonferroni correction for the 311,524 SNPs tested [Skol, et al., (2006), Nat Genet, 38, 209-13].

Association to Chromosome 5p12, Confirmed in CGEMS Data, is Genome-Wide Significant Following Joint Analysis with CGEMS The Cancer Genetics Markers of Susceptibility (CGEMS) project of the U.S. National Cancer Institute has released data to the public domain on a genome-wide SNP association study for breast cancer susceptibility based on 1145 patients and 1142 controls genotyped with approximately 530,000 SNPs using the Illumina platform. These data are available at: https colon-slash-slash caintegrator.nci.nih.gov/cgems/. The CGEMS project found no genome-wide significant signals in the 5p12 region. However, we noted that one SNP, namely rs4415084, had a P-value of 1.38E-07 when data from Iceland (Iceland 1 cohort) and the CGEMS data set was analyzed jointly, that is genome-wide significant after Bonferroni correction. This SNP had an unremarkable P-value of 2.21E-03 in the CGEMS data set, the genome wide significance of the joint value being mostly carried by the Iceland 1 P-value of 9.02E-06. Thus, the CGEMS data, while nowhere significant on its own, provides confirmation of our original observation of association to chromosome 5p12.

Numerous HapMap (Non Illumina) SNP Markers could Show BC Risk Associations Through their Correlation with the Illumina SNPs that Showed an Association in the 5p12 Region We contemplated that there may be allelic heterogeneity at this locus, that is there may be more than one underlying at-risk variant present in the 5p12 region that is correlated to different degrees with the Illumina SNP set tested and exist at different frequencies in different populations. This is based on the observation that there appear to be significant signals distal to the cluster of most significant markers (see FIG. 1). Furthermore, we have noted that in some cases association signals are very strong in the Iceland 1 material but are not strong in the CGEMS data: for example the rs4415084 SNP described above gave a very strong signal in Iceland 1 but not in the CGEMS data. Similarly, the SNP that was tested successfully for replication in Iceland, rs7703618, gave a P-value of 6.93E-06 and only 2.37E-02 in the CGEMS data set. Given that there may be alleleic heterogeneity in the 5p12 region, we define a set of HapMap SNPs that, through their correlations with signals that we observed in the Iceland 1 data set, could be used to detect all pathogenic mutations in the 5p12 region. In order to identify such a set of HapMap SNPs, we first identified a class of SNPs that gave P-values of 10E-3 or less in the Iceland 1 data set. We then split this set into equivalence classes, membership of a particular equivalence class being defined as two SNPs that have an $r^2$ value of >0.8 between them. This resulted in a set of 6 equivalence classes which we designated A to F. For each equivalence class we started with the SNP that gave the most significant signal in the class (which we denoted the "key" SNP), then by reference to HapMap data we identified all HapMap SNPs that were correlated with the key SNP by an $r^2$ value of 0.2 or greater and were not themselves represented on the Illumina Hap300 chip. Thus, using the Iceland 1 data we observed signals in several different equivalence classes and that fact, in itself, provides evidence for allelic heterogeneity. These HapMap SNPs could, through their correlations with SNPs in one or more of the equivalence classes we identified, also be used to detect the same breast cancer risk associations we originally observed. The list of the key SNPs and their correlations with HapMap SNPs is shown in Table 4.

FGF10 and MRPS30 are the Most Likely Candidate Genes in the 5p12 Region

FIG. 1 shows a plot of the association signals obtained in the 5p12 region superimposed on a map of recombination hotspots, chromosome bands, known genes, and recombination rates. Recombination hotspots and recombination rates were determined as described by McVean et al. [McVean, et al., (2004), Science, 304, 581-4]. A representation of $r^2$ values between HapMap SNPs in the region is also shown. It can be seen that there are three known genes of note in the region; FGF10, MRPS30, and HCN1, along with one poorly characterized gene LOC441070. Two of these, FGF10 and MRPS30 are compelling candidates for an involvement in breast cancer predisposition.

As reviewed by Howard and Ashworth [Howard and Ashworth, (2006), PLoS Genet, 2, e112], FGF10 is required for normal embryonic development of the breast. FGF10 has been implicated as an oncogene in mouse models of breast cancer by MMTV insertional mutagenesis and FGF10 is over expressed in around 10% of human breast cancers [Theodorou, et al., (2004), Oncogene, 23, 6047-55]. As can be seen in FIG. 1, the FGF10 gene is separated from the main clusters of association signals by a recombination hotspot. However key elements controlling regulation of FGF10 may be present in the region where the strong association signals occur. Alternatively, the association signals may be in linkage disequilibrium with pathogenic mutations within the FGF10 gene itself.

MRPS30 encodes the mitochondrial 28S ribosomal subunit. It is also known as programmed cell death protein 9 (PDCD9). This is the mammalian counterpart of the *Gallus gallus* pro-apoptotic protein p52. It has been shown to induce apoptosis and activate the stress-responsive JNK1 pathway in mammalian cells. The protein appears to function in apoptosis at least in part through the Bcl-2 pathway [Sun, et al., (1998), Gene, 208, 157-66; Carim, et al., (1999), Cytogenet Cell Genet, 87, 85-8; Cavdar Koc, et al., (2001), FEBS Lett, 492, 166-70]. Although it has not been implicated previously in breast cancer, its involvement in the above pathways suggest that genetic variants in MRPS30 may be involved in modifying breast cancer risk.

Methods

Patient and Control Selection

Approval for this study was granted by the National Bioethics Committee of Iceland and the Icelandic Data Protection Authority. Records of breast cancer diagnoses were obtained from the Icelandic Cancer Registry (ICR). The ICR contains all cases of invasive breast tumors and ductal or lobular carcinoma in-situ diagnosed in Iceland from Jan. 1, 1955. All people living in Iceland who had a diagnosis entered into the ICR up to the end of December 2005 were eligible to participate in the study. The ICR contained records of 4603 individuals diagnosed during this period. A prevalence cohort comprised of all living patients (approximately 2840) were eligible for recruitment into the study. We obtained informed consent, a blood sample, and diagnostic information from 2210 patients, a participation rate of approximately 78%. Genotyping was successful on a total of 2190 patients for rs7703618. Further details of the recruitment of this patient group have been reported previously [Stacey, et al., (2006), PLoS Med, 3, e217].

The 12,904 Icelandic controls consisted of 846 individuals randomly selected from the Icelandic Genealogical Database and 12,058 individuals from other ongoing genome-wide association studies at deCODE. Individuals with a diagnosis of breast cancer in the ICR were excluded. Both male and female genders were included.

Illumina Genotyping

DNA samples were genotyped according to the manufacturer's instructions on Illumina Infinium HumanHap300 SNP bead microarrays (Illumina, San Diego, Calif., USA), containing 317,503 SNPs derived from Phase I of the International HapMap project. This chip provides about 75% genomic coverage in the Utah CEPH (CEU) HapMap samples for common SNPs at $r^2 \geq 0.8$ [Barrett and Cardon, (2006), Nat Genet, 38, 659-62]. Of the total number of SNPs on the chip, 5979 were deemed unsuitable either because they were monomorphic (i.e. the minor allele frequency in the combined patients and control set was less than 0.001), or had low (<95%) yield or showed a very significant distortion from Hardy-Weinberg equilibrium in the controls (P<1×10$^{-10}$). All of these problematic SNPs were removed from the analysis. Thus 311,524 SNPs were used in the association analysis. Any chips with an overall call rate below 98% of the SNPs were also excluded from the genome-wide association analysis.

Centaurus SNP Genotyping

A Centaurus assay [Kutyavin, et al., (2006), Nucleic Acids Res, 34, e128] was designed for rs7703618 and validated by genotyping the HapMap CEU sample and comparing the genotypes with published data. The assays gave <1.5% mismatches with HapMap data. Table 5 shows the sequence context for the key SNPs discussed herein. Table 6 shows the description of the Centaurus Assay for marker rs7703618 that was developed for genotyping in this study.

Statistical Methods

We calculated the odds ratio (OR) of a SNP allele assuming the multiplicative model, i.e. assuming that the relative risk of the two alleles that a person carries multiplies. Allelic frequencies rather than carrier frequencies are presented for the markers. The associated P-values were calculated with a standard likelihood ratio Chi-squared statistic as implemented in the NEMO software package [Gretarsdottir, et al., (2003), Nat Genet, 35, 131-8]. Confidence intervals were calculated assuming that the estimate of the OR has a log-normal distribution. Some Icelandic patients and controls are related, both within and between groups, causing the Chi-squared test statistic to have a mean greater than one and a median larger than 0.675$^2$. We estimated the inflation factor for Iceland 1 using a method of genomic control [Devlin and Roeder, (1999), Biometrics, 55, 997-1004] by calculating the average of the observed Chi-squared statistics for the genome-wide SNP set, which accounts for relatedness and for potential population stratification. For Iceland 2, which was not typed with a genome-wide set of markers, the inflation factor was estimated by simulating genotypes through the Icelandic genealogy [Grant, et al., (2006), Nat Genet, 38, 320-3]. The estimated inflation factors were 1.105 for Iceland 1 and 1.11 for Iceland 2. The estimated inflation factor for the joint analyses of the Iceland 1 and Iceland 2 sample sets was 1.08, obtained by simulation.

All P-values are reported as two-sided.

TABLE 1

Association results for Illumina SNPs in the 5p12 region:

| SNP | Allele | Position bld34 | P-value | OR | Cases | Frq. Cases | Controls | Frq. Controls |
|---|---|---|---|---|---|---|---|---|
| rs7704166 | A | 44094392 | 1.15E−01 | 1.063 | 1660 | 0.492 | 11561 | 0.477 |
| rs6879107 | A | 44096806 | 6.07E−01 | 1.029 | 1659 | 0.856 | 11554 | 0.852 |
| rs4334895 | G | 44105438 | 4.12E−01 | 1.037 | 1658 | 0.273 | 11555 | 0.266 |
| rs6859263 | G | 44111594 | 9.65E−01 | 1.002 | 1628 | 0.170 | 10803 | 0.169 |
| rs4242104 | T | 44122873 | 6.22E−01 | 1.028 | 1660 | 0.858 | 11563 | 0.854 |
| rs4502833 | C | 44144266 | 6.53E−01 | 1.020 | 1625 | 0.304 | 11379 | 0.300 |
| rs6871975 | T | 44166026 | 5.11E−01 | 1.029 | 1618 | 0.295 | 11263 | 0.289 |
| rs4242107 | A | 44174584 | 7.26E−01 | 1.015 | 1660 | 0.278 | 11562 | 0.275 |
| rs4242108 | T | 44174787 | 6.53E−01 | 1.025 | 1660 | 0.858 | 11563 | 0.854 |
| rs4492117 | C | 44174878 | 3.54E−01 | 1.055 | 1660 | 0.136 | 11563 | 0.130 |
| rs4596388 | G | 44194286 | 3.91E−01 | 1.053 | 1660 | 0.121 | 11562 | 0.116 |
| rs4866869 | G | 44195892 | 7.44E−01 | 1.014 | 1660 | 0.309 | 11555 | 0.306 |
| rs4296809 | A | 44232169 | 6.18E−01 | 1.028 | 1660 | 0.152 | 11552 | 0.149 |
| rs4866880 | A | 44237263 | 8.77E−01 | 1.007 | 1660 | 0.302 | 11562 | 0.301 |
| rs4866773 | A | 44264014 | 7.86E−01 | 1.015 | 1659 | 0.850 | 11537 | 0.848 |
| rs1550939 | G | 44267213 | 7.20E−01 | 1.015 | 1660 | 0.299 | 11563 | 0.296 |
| rs4643965 | C | 44270309 | 8.24E−01 | 1.010 | 1660 | 0.259 | 11562 | 0.257 |
| rs10512836 | T | 44273926 | 6.14E−01 | 1.025 | 1660 | 0.794 | 11563 | 0.790 |
| rs726941 | C | 44279279 | 9.02E−02 | 1.078 | 1660 | 0.271 | 11563 | 0.257 |
| rs2053784 | C | 44286984 | 6.31E−01 | 1.021 | 1660 | 0.287 | 11562 | 0.283 |
| rs7713769 | G | 44314707 | 3.23E−01 | 1.062 | 1660 | 0.884 | 11561 | 0.878 |
| rs1011814 | G | 44381321 | 2.23E−01 | 1.051 | 1660 | 0.660 | 11563 | 0.649 |
| rs11743802 | T | 44396655 | 2.16E−02 | 1.134 | 1656 | 0.857 | 11533 | 0.840 |
| rs2121875 | T | 44411046 | 2.14E−01 | 1.052 | 1660 | 0.660 | 11563 | 0.649 |
| rs1384449 | A | 44422561 | 7.95E−01 | 1.012 | 1649 | 0.763 | 11202 | 0.761 |
| rs2973644 | C | 44429684 | 9.54E−01 | 1.003 | 1660 | 0.232 | 11562 | 0.232 |
| rs10512852 | C | 44439070 | 1.82E−01 | 1.101 | 1660 | 0.923 | 11562 | 0.915 |
| rs723166 | C | 44441516 | 8.00E−02 | 1.081 | 1658 | 0.740 | 11537 | 0.725 |
| rs16901843 | T | 44448618 | 4.81E−01 | 1.036 | 1660 | 0.819 | 11561 | 0.814 |
| rs4866898 | A | 44449132 | 1.00E+00 | 1.000 | 1660 | 0.146 | 11553 | 0.146 |
| rs13357659 | G | 44478386 | 1.53E−01 | 1.059 | 1660 | 0.406 | 11562 | 0.392 |
| rs1351637 | G | 44487204 | 8.87E−01 | 1.007 | 1660 | 0.197 | 11563 | 0.196 |
| rs922853 | G | 44497553 | 9.46E−01 | 1.004 | 1660 | 0.108 | 11562 | 0.108 |
| rs1120718 | T | 44512079 | 6.10E−02 | 1.089 | 1660 | 0.761 | 11563 | 0.746 |
| rs1384450 | C | 44525645 | 3.55E−01 | 1.037 | 1660 | 0.585 | 11562 | 0.576 |
| rs2062140 | T | 44541916 | 1.84E−01 | 1.112 | 1660 | 0.066 | 11563 | 0.060 |
| rs17320222 | A | 44544792 | 1.76E−01 | 1.142 | 1657 | 0.960 | 11552 | 0.955 |
| rs6866555 | C | 44584014 | 3.26E−01 | 1.052 | 1659 | 0.176 | 11553 | 0.169 |
| rs4463187 | G | 44614156 | 1.43E−02 | 1.100 | 1660 | 0.532 | 11561 | 0.508 |
| rs7708449 | A | 44614727 | 5.00E−02 | 1.084 | 1660 | 0.355 | 11561 | 0.337 |
| rs6889804 | T | 44618310 | 3.31E−01 | 1.051 | 1660 | 0.176 | 11561 | 0.169 |
| rs4642379 | T | 44620489 | 3.27E−01 | 1.052 | 1660 | 0.176 | 11562 | 0.169 |
| rs6896299 | G | 44655907 | 3.37E−01 | 1.051 | 1658 | 0.176 | 11552 | 0.168 |
| rs4529201 | C | 44659472 | 1.09E−02 | 1.105 | 1659 | 0.531 | 11539 | 0.506 |
| rs4415084 | T | 44708016 | 9.02E−06 | 1.194 | 1660 | 0.415 | 11562 | 0.373 |
| rs2218080 | G | 44759831 | 3.37E−05 | 1.181 | 1660 | 0.405 | 11562 | 0.366 |
| rs11747159 | T | 44783211 | 7.62E−06 | 1.197 | 1658 | 0.397 | 11551 | 0.354 |
| rs2330572 | C | 44786490 | 2.38E−05 | 1.184 | 1660 | 0.405 | 11561 | 0.365 |
| rs994793 | G | 44788748 | 2.19E−05 | 1.185 | 1658 | 0.405 | 11560 | 0.365 |
| rs6885754 | A | 44811554 | 9.68E−01 | 1.007 | 1660 | 0.014 | 11550 | 0.013 |
| rs7712949 | T | 44815846 | 1.19E−05 | 1.193 | 1659 | 0.392 | 11547 | 0.350 |
| rs11746980 | A | 44823379 | 1.98E−05 | 1.186 | 1660 | 0.405 | 11561 | 0.365 |
| rs16901964 | T | 44828756 | 1.97E−05 | 1.188 | 1660 | 0.390 | 11560 | 0.350 |
| rs727305 | C | 44841543 | 1.51E−05 | 1.191 | 1660 | 0.390 | 11516 | 0.349 |
| rs10462081 | A | 44846166 | 2.13E−05 | 1.187 | 1657 | 0.390 | 11557 | 0.350 |
| rs13183209 | A | 44849250 | 1.92E−05 | 1.188 | 1660 | 0.390 | 11555 | 0.350 |
| rs13159598 | G | 44851427 | 3.31E−05 | 1.182 | 1644 | 0.402 | 11513 | 0.363 |
| rs3761648 | G | 44853580 | 8.57E−06 | 1.202 | 1589 | 0.387 | 10844 | 0.344 |
| rs13174122 | C | 44856241 | 3.63E−05 | 1.181 | 1658 | 0.390 | 11498 | 0.351 |
| rs11746506 | T | 44858067 | 2.12E−05 | 1.187 | 1660 | 0.389 | 11561 | 0.350 |
| rs12188871 | A | 44859505 | 1.50E−05 | 1.191 | 1657 | 0.390 | 11532 | 0.349 |
| rs9637783 | G | 44865147 | 1.74E−05 | 1.190 | 1655 | 0.389 | 11520 | 0.349 |
| rs4457089 | T | 44867237 | 2.06E−05 | 1.187 | 1660 | 0.389 | 11560 | 0.349 |
| rs6867533 | T | 44872793 | 6.23E−06 | 1.200 | 1641 | 0.398 | 11355 | 0.355 |
| rs6896350 | C | 44878072 | 2.09E−05 | 1.187 | 1660 | 0.389 | 11559 | 0.350 |
| rs1371025 | C | 44879734 | 2.06E−05 | 1.187 | 1660 | 0.389 | 11557 | 0.349 |
| rs6451775 | G | 44882289 | 2.21E−05 | 1.187 | 1660 | 0.389 | 11561 | 0.350 |
| rs729599 | C | 44887761 | 2.21E−05 | 1.187 | 1660 | 0.389 | 11561 | 0.350 |
| rs987394 | T | 44891879 | 2.16E−05 | 1.187 | 1660 | 0.389 | 11558 | 0.349 |
| rs4440370 | A | 44898853 | 2.17E−05 | 1.187 | 1659 | 0.389 | 11559 | 0.350 |
| rs4492119 | A | 44901115 | 7.18E−06 | 1.200 | 1645 | 0.387 | 11340 | 0.345 |
| rs7703497 | A | 44902529 | 2.12E−05 | 1.187 | 1659 | 0.389 | 11559 | 0.349 |
| rs4395640 | T | 44914601 | 8.63E−06 | 1.197 | 1652 | 0.395 | 11497 | 0.353 |
| rs7716600 | A | 44920506 | 3.12E−05 | 1.214 | 1660 | 0.241 | 11560 | 0.208 |
| rs4412123 | T | 44921789 | 1.10E−05 | 1.192 | 1660 | 0.409 | 11560 | 0.367 |

TABLE 1-continued

Association results for Illumina SNPs in the 5p12 region:

| SNP | Allele | Position bld34 | P-value | OR | Cases | Frq. Cases | Controls | Frq. Controls |
|---|---|---|---|---|---|---|---|---|
| rs7705343 | G | 44925078 | 1.31E−05 | 1.190 | 1658 | 0.409 | 11558 | 0.368 |
| rs4129642 | G | 44943630 | 1.11E−05 | 1.194 | 1655 | 0.396 | 11518 | 0.355 |
| rs9790879 | C | 44945386 | 1.27E−05 | 1.191 | 1659 | 0.409 | 11561 | 0.368 |
| rs10462084 | G | 44946850 | 2.31E−01 | 1.067 | 1659 | 0.155 | 11562 | 0.147 |
| rs9791056 | T | 44949392 | 7.66E−06 | 1.197 | 1660 | 0.396 | 11562 | 0.354 |
| rs6880275 | T | 44954436 | 7.76E−06 | 1.198 | 1648 | 0.395 | 11484 | 0.353 |
| rs6870136 | G | 44956163 | 7.51E−06 | 1.197 | 1660 | 0.396 | 11559 | 0.354 |
| rs6881563 | C | 44958354 | 7.28E−06 | 1.198 | 1660 | 0.396 | 11561 | 0.354 |
| rs7703618 | G | 44960080 | 6.93E−06 | 1.198 | 1659 | 0.396 | 11557 | 0.354 |
| rs10077814 | C | 44962290 | 1.24E−05 | 1.191 | 1659 | 0.407 | 11561 | 0.366 |
| rs6451783 | G | 44963794 | 9.41E−06 | 1.195 | 1660 | 0.395 | 11563 | 0.353 |
| rs4298259 | G | 44966212 | 9.35E−06 | 1.195 | 1660 | 0.395 | 11562 | 0.353 |
| rs7728431 | T | 44968180 | 9.96E−06 | 1.195 | 1660 | 0.394 | 11559 | 0.353 |
| rs12517690 | A | 44984794 | 9.56E−06 | 1.195 | 1660 | 0.395 | 11562 | 0.353 |
| rs3935213 | A | 45006945 | 3.89E−02 | 1.112 | 1659 | 0.182 | 11561 | 0.167 |
| rs6866995 | C | 45022348 | 3.77E−02 | 1.112 | 1660 | 0.182 | 11563 | 0.167 |
| rs2067980 | G | 45027818 | 9.89E−04 | 1.200 | 1660 | 0.155 | 11555 | 0.132 |
| rs3923826 | C | 45118278 | 2.49E−02 | 1.137 | 1660 | 0.870 | 11562 | 0.855 |
| rs11743309 | A | 45167889 | 2.15E−01 | 1.067 | 1660 | 0.836 | 11559 | 0.826 |
| rs12654948 | T | 45211216 | 1.28E−01 | 1.094 | 1651 | 0.878 | 11260 | 0.868 |
| rs12515820 | G | 45238970 | 4.07E−02 | 1.126 | 1660 | 0.135 | 11558 | 0.122 |
| rs12515179 | C | 45292596 | 4.86E−02 | 1.120 | 1660 | 0.138 | 11562 | 0.125 |
| rs10512876 | G | 45295105 | 7.73E−01 | 1.025 | 1660 | 0.055 | 11561 | 0.054 |
| rs10035564 | G | 45298001 | 1.79E−04 | 1.178 | 1650 | 0.291 | 11477 | 0.258 |
| rs13180087 | C | 45311269 | 5.28E−02 | 1.127 | 1659 | 0.117 | 11563 | 0.105 |
| rs4866929 | A | 45312090 | 9.34E−02 | 1.068 | 1660 | 0.484 | 11560 | 0.468 |
| rs981782 | T | 45331219 | 2.28E−04 | 1.159 | 1601 | 0.458 | 10706 | 0.421 |
| rs981782 | T | 45331219 | 1.05E−01 | 1.066 | 1660 | 0.470 | 11562 | 0.454 |
| rs9790873 | C | 45337015 | 3.61E−02 | 1.133 | 1660 | 0.128 | 11554 | 0.115 |
| rs9292918 | G | 45346536 | 4.21E−03 | 1.161 | 1656 | 0.176 | 11546 | 0.155 |
| rs6895055 | A | 45366909 | 2.34E−03 | 1.172 | 1660 | 0.177 | 11551 | 0.155 |
| rs6888352 | A | 45371416 | 2.72E−03 | 1.169 | 1659 | 0.177 | 11551 | 0.155 |
| rs994092 | G | 45381260 | 2.49E−03 | 1.171 | 1660 | 0.177 | 11557 | 0.155 |
| rs10473384 | A | 45389311 | 2.34E−03 | 1.172 | 1659 | 0.177 | 11560 | 0.155 |
| rs1501357 | G | 45410376 | 2.61E−03 | 1.170 | 1660 | 0.177 | 11563 | 0.155 |
| rs12517615 | C | 45412289 | 6.70E−02 | 1.190 | 1647 | 0.047 | 11286 | 0.040 |
| rs1501362 | T | 45423708 | 2.85E−03 | 1.167 | 1660 | 0.179 | 11558 | 0.157 |
| rs6451798 | T | 45433355 | 3.11E−03 | 1.166 | 1660 | 0.179 | 11560 | 0.157 |
| rs6414906 | C | 45451822 | 9.05E−03 | 1.112 | 1658 | 0.375 | 11560 | 0.351 |
| rs13162651 | C | 45455401 | 5.54E−02 | 1.081 | 1655 | 0.375 | 11363 | 0.357 |
| rs1483310 | G | 45459859 | 7.27E−02 | 1.178 | 1655 | 0.051 | 11413 | 0.044 |
| rs12659024 | T | 45463191 | 9.87E−01 | 1.001 | 1658 | 0.080 | 11549 | 0.080 |
| rs6892290 | G | 45472638 | 1.08E−02 | 1.109 | 1660 | 0.375 | 11560 | 0.351 |
| rs6451801 | A | 45484934 | 1.02E−02 | 1.110 | 1660 | 0.375 | 11560 | 0.351 |
| rs13354798 | C | 45502578 | 1.16E−02 | 1.108 | 1660 | 0.377 | 11563 | 0.353 |
| rs12651887 | T | 45515924 | 1.19E−01 | 1.076 | 1657 | 0.225 | 11549 | 0.212 |
| rs1471683 | A | 45524926 | 7.07E−02 | 1.088 | 1660 | 0.232 | 11562 | 0.217 |
| rs2337414 | A | 45614170 | 1.12E−01 | 1.100 | 1660 | 0.884 | 11562 | 0.874 |
| rs1852598 | G | 45648477 | 2.93E−01 | 1.049 | 1660 | 0.245 | 11562 | 0.237 |
| rs11743392 | T | 45660476 | 4.43E−04 | 1.150 | 1614 | 0.490 | 10826 | 0.455 |
| rs1534391 | T | 45714539 | 6.74E−02 | 1.117 | 1652 | 0.884 | 11396 | 0.873 |
| rs2879074 | C | 45761710 | 1.49E−02 | 1.103 | 1660 | 0.384 | 11560 | 0.361 |
| rs4380674 | C | 45814898 | 2.50E−01 | 1.053 | 1660 | 0.259 | 11563 | 0.249 |
| rs7447717 | A | 45815753 | 1.29E−02 | 1.105 | 1660 | 0.384 | 11559 | 0.361 |
| rs4388219 | A | 45826251 | 1.41E−01 | 1.063 | 1660 | 0.328 | 11555 | 0.315 |
| rs10941703 | C | 45827373 | 1.02E−01 | | | 0.364 | 11561 | 0.349 |
| rs10941704 | G | 45829007 | 2.99E−01 | 1.049 | 1657 | 0.245 | 11531 | 0.236 |
| rs4551074 | T | 45838254 | 2.15E−01 | 1.057 | 1660 | 0.260 | 11561 | 0.249 |
| rs13155321 | G | 45842047 | 9.36E−02 | 1.071 | 1660 | 0.367 | 11559 | 0.351 |
| rs7733616 | C | 45844224 | 1.59E−01 | 1.063 | 1630 | 0.290 | 11372 | 0.278 |
| rs10069793 | G | 45848652 | 6.09E−02 | 1.079 | 1650 | 0.367 | 11465 | 0.349 |
| rs13176359 | T | 45859776 | 2.72E−01 | 1.050 | 1660 | 0.267 | 11552 | 0.258 |
| rs4866973 | A | 45862187 | 2.03E−01 | 1.059 | 1657 | 0.259 | 11530 | 0.248 |
| rs4242126 | A | 45871874 | 2.80E−01 | 1.051 | 1660 | 0.245 | 11561 | 0.236 |
| rs6865429 | G | 45876009 | 9.87E−02 | 1.069 | 1659 | 0.366 | 11561 | 0.351 |
| rs10461763 | G | 45884708 | 5.07E−01 | 1.075 | 1659 | 0.034 | 11557 | 0.032 |
| rs7730617 | A | 45885804 | 1.53E−01 | 1.063 | 1659 | 0.294 | 11557 | 0.281 |
| rs13175559 | C | 45900128 | 1.10E−01 | 1.067 | 1660 | 0.368 | 11560 | 0.353 |
| rs11951003 | A | 45902630 | 1.09E−01 | 1.067 | 1659 | 0.368 | 11559 | 0.353 |
| rs4331911 | G | 45904876 | 1.55E−01 | 1.060 | 1627 | 0.360 | 11297 | 0.347 |
| rs13340341 | T | 45906437 | 1.53E−01 | 1.060 | 1660 | 0.363 | 11556 | 0.349 |
| rs12109205 | G | 45922179 | 2.53E−01 | 1.051 | 1660 | 0.288 | 11559 | 0.278 |
| rs4368738 | T | 45938289 | 1.67E−01 | 1.061 | 1659 | 0.294 | 11561 | 0.281 |
| rs9637799 | G | 45948109 | 5.03E−01 | 1.075 | 1660 | 0.034 | 11560 | 0.032 |
| rs6862657 | A | 45951498 | 1.03E−01 | 1.069 | 1656 | 0.366 | 11533 | 0.351 |

TABLE 1-continued

Association results for Illumina SNPs in the 5p12 region:

| SNP | Allele | Position bld34 | P-value | OR | Cases | Frq. Cases | Controls | Frq. Controls |
|---|---|---|---|---|---|---|---|---|
| rs7443189 | A | 45958468 | 6.09E−01 | 1.057 | 1654 | 0.034 | 11519 | 0.032 |
| rs11948152 | C | 46000128 | 1.89E−01 | 1.054 | 1644 | 0.580 | 11377 | 0.567 |
| rs7443384 | G | 46006394 | 1.01E−01 | 1.070 | 1660 | 0.345 | 11562 | 0.330 |
| rs7701444 | C | 46014363 | 1.05E−01 | 1.068 | 1660 | 0.369 | 11561 | 0.354 |
| rs13352566 | T | 46042403 | 2.03E−01 | 1.059 | 1648 | 0.260 | 11420 | 0.249 |
| rs4370277 | G | 46094169 | 2.40E−01 | 1.048 | 1636 | 0.402 | 11316 | 0.390 |
| rs12173206 | A | 46121458 | 5.02E−01 | 1.076 | 1659 | 0.034 | 11551 | 0.032 |
| rs10066479 | G | 46142988 | 1.85E−01 | 1.054 | 1660 | 0.401 | 11550 | 0.388 |
| rs12515804 | C | 46144107 | 1.69E−01 | 1.056 | 1660 | 0.401 | 11561 | 0.388 |
| rs13175755 | T | 46145281 | 2.58E−01 | 1.083 | 1660 | 0.086 | 11563 | 0.080 |
| rs7720482 | T | 46151664 | 1.66E−01 | 1.057 | 1659 | 0.402 | 11559 | 0.389 |
| rs4975890 | C | 46159139 | 2.75E−01 | 1.047 | 1656 | 0.330 | 11552 | 0.320 |
| rs12690679 | C | 46206288 | 3.19E−01 | 1.040 | 1659 | 0.423 | 11556 | 0.414 |
| rs12697527 | T | 46247605 | 2.98E−01 | 1.042 | 1658 | 0.419 | 11533 | 0.409 |
| rs13168297 | T | 46273834 | 5.02E−01 | 1.028 | 1649 | 0.348 | 11438 | 0.342 |
| rs4975957 | A | 46310803 | 2.97E−01 | 1.042 | 1660 | 0.420 | 11549 | 0.410 |
| rs12659648 | C | 46330355 | 4.96E−01 | 1.028 | 1652 | 0.349 | 11541 | 0.343 |
| rs13355128 | T | 46332613 | 3.32E−01 | 1.041 | 1614 | 0.649 | 10822 | 0.639 |
| rs10941803 | C | 46393984 | 3.56E−01 | 1.039 | 1613 | 0.343 | 11166 | 0.335 |

Shown are the SNP names, the identity of the risk allele, the location (in NCBI Build 34 coordinates, the P-value and Odds Ratio (OR) for Breast Cancer association, the numbers of individuals tested and the allele frequencies in the Breast Cancer Case and the Control groups respectively.

TABLE 2

Replication of signal from SNP rs7703618 in an independent Icelandic Breast Cancer Case/Control sample:

| rs7703618 (G) | Frequency | | | |
|---|---|---|---|---|
| Cohort (Cases/Controls) | Cases | Controls | OR | P |
| Iceland 1 (1599/11558) | 0.396 | 0.354 | 1.20 | 1.1E−05 |
| Iceland 2 (591/1314) | 0.392 | 0.353 | 1.18 | 2.9E−02 |
| Iceland combined (2190/12872) | 0.395 | 0.354 | 1.19 | 5.3E−07 |

TABLE 3

HapMap SNPs with $r^2$ values >0.2 in relation to key SNPs in equivalence classes A-F.

| SNP 1 | SNP 2 | D' | R2 | p-min |
|---|---|---|---|---|
| SNP A = rs4415084 | | | | |
| rs4415084 | rs7735881 | 1.000 | 1.000 | 3.35E−36 |
| rs4415084 | rs7723539 | 1.000 | 1.000 | 3.35E−36 |
| rs4415084 | rs4492118 | 1.000 | 1.000 | 5.45E−36 |
| rs4415084 | rs4463188 | 1.000 | 1.000 | 1.87E−35 |
| rs4415084 | rs920329 | 1.000 | 1.000 | 7.12E−36 |
| rs4415084 | rs7720551 | 1.000 | 1.000 | 3.35E−36 |
| rs4415084 | rs714130 | 1.000 | 1.000 | 3.35E−36 |
| rs4415084 | rs6874055 | 1.000 | 1.000 | 3.37E−36 |
| rs4415084 | rs6861560 | 1.000 | 1.000 | 3.35E−36 |
| rs4415084 | rs6451770 | 1.000 | 1.000 | 3.35E−36 |
| rs4415084 | rs4571480 | 1.000 | 1.000 | 1.43E−35 |
| rs4415084 | rs4419600 | 1.000 | 1.000 | 3.35E−36 |
| rs4415084 | rs4415085 | 1.000 | 1.000 | 3.35E−36 |
| rs4415084 | rs2218081 | 1.000 | 1.000 | 3.35E−36 |
| rs4415084 | rs2165010 | 1.000 | 1.000 | 3.37E−36 |
| rs4415084 | rs2165009 | 1.000 | 1.000 | 5.45E−36 |
| rs4415084 | rs2013513 | 1.000 | 1.000 | 1.43E−35 |
| rs4415084 | rs1821936 | 1.000 | 1.000 | 5.45E−36 |
| rs4415084 | rs1438825 | 1.000 | 1.000 | 3.35E−36 |
| rs4415084 | rs13156930 | 1.000 | 1.000 | 3.35E−36 |
| rs4415084 | rs12522626 | 1.000 | 1.000 | 8.86E−36 |
| rs4415084 | rs12515012 | 1.000 | 1.000 | 3.35E−36 |
| rs4415084 | rs12187196 | 1.000 | 1.000 | 3.35E−36 |
| rs4415084 | rs10941678 | 1.000 | 1.000 | 5.45E−36 |
| rs4415084 | rs4321755 | 1.000 | 1.000 | 3.35E−36 |
| rs4415084 | rs10941677 | 1.000 | 1.000 | 1.43E−35 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs4415084 | rs10805685 | 1.000 | 1.000 | 5.45E−36 |
| rs4415084 | rs16901937 | 1.000 | 0.965 | 4.27E−34 |
| rs4415084 | rs920328 | 1.000 | 0.931 | 3.70E−32 |
| rs4415084 | rs7380559 | 0.923 | 0.766 | 1.13E−23 |
| rs4415084 | rs4518409 | 0.923 | 0.766 | 1.13E−23 |
| rs4415084 | rs1438821 | 0.923 | 0.766 | 1.13E−23 |
| rs4415084 | rs1438820 | 0.923 | 0.766 | 1.13E−23 |
| rs4415084 | rs13362132 | 0.923 | 0.766 | 1.13E−23 |
| rs4415084 | rs13160259 | 0.923 | 0.766 | 1.13E−23 |
| rs4415084 | rs11958808 | 0.923 | 0.766 | 1.13E−23 |
| rs4415084 | rs1061310 | 0.923 | 0.766 | 1.13E−23 |
| rs4415084 | rs10512865 | 0.923 | 0.766 | 1.13E−23 |
| rs4415084 | rs1048758 | 0.923 | 0.766 | 1.13E−23 |
| rs4415084 | rs10044096 | 0.923 | 0.766 | 1.13E−23 |
| rs4415084 | rs9292913 | 0.922 | 0.765 | 1.72E−23 |
| rs4415084 | rs13177711 | 0.922 | 0.765 | 1.72E−23 |
| rs4415084 | rs11949847 | 0.921 | 0.764 | 2.62E−23 |
| rs4415084 | rs4329028 | 0.923 | 0.763 | 2.84E−23 |
| rs4415084 | rs7716571 | 0.923 | 0.763 | 2.33E−23 |
| rs4415084 | rs7711697 | 0.922 | 0.762 | 1.14E−22 |
| rs4415084 | rs7380878 | 0.921 | 0.762 | 4.30E−23 |
| rs4415084 | rs10043344 | 0.921 | 0.761 | 6.56E−23 |
| rs4415084 | rs10040082 | 0.957 | 0.738 | 2.38E−22 |
| rs4415084 | rs7717459 | 0.919 | 0.706 | 1.84E−21 |
| rs4415084 | rs6893319 | 0.919 | 0.706 | 1.84E−21 |
| rs4415084 | rs6872254 | 0.919 | 0.706 | 1.84E−21 |
| rs4415084 | rs6451778 | 0.919 | 0.706 | 1.84E−21 |
| rs4415084 | rs4373287 | 0.919 | 0.706 | 1.84E−21 |
| rs4415084 | rs1866406 | 0.919 | 0.706 | 1.84E−21 |
| rs4415084 | rs1438822 | 0.919 | 0.706 | 1.84E−21 |
| rs4415084 | rs1438819 | 0.919 | 0.706 | 1.84E−21 |
| rs4415084 | rs13189120 | 0.919 | 0.706 | 1.84E−21 |
| rs4415084 | rs13155698 | 0.919 | 0.706 | 1.84E−21 |
| rs4415084 | rs13154781 | 0.919 | 0.706 | 1.84E−21 |
| rs4415084 | rs10462080 | 0.919 | 0.706 | 1.84E−21 |
| rs4415084 | rs10065638 | 0.919 | 0.706 | 1.84E−21 |
| rs4415084 | rs10059086 | 0.919 | 0.706 | 1.84E−21 |
| rs4415084 | rs10057521 | 0.919 | 0.706 | 1.84E−21 |
| rs4415084 | rs10053247 | 0.919 | 0.706 | 1.84E−21 |
| rs4415084 | rs10041518 | 0.919 | 0.706 | 1.84E−21 |
| rs4415084 | rs10040488 | 0.919 | 0.706 | 1.84E−21 |
| rs4415084 | rs10039866 | 0.919 | 0.706 | 1.84E−21 |
| rs4415084 | rs12513749 | 0.919 | 0.706 | 3.69E−21 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs4415084 | rs6875933 | 0.919 | 0.706 | 3.67E−21 |
| rs4415084 | rs7736092 | 0.918 | 0.705 | 2.73E−21 |
| rs4415084 | rs10070037 | 0.918 | 0.705 | 2.73E−21 |
| rs4415084 | rs6871052 | 0.918 | 0.705 | 5.47E−21 |
| rs4415084 | rs7708506 | 0.917 | 0.704 | 4.05E−21 |
| rs4415084 | rs4642377 | 0.920 | 0.704 | 1.85E−21 |
| rs4415084 | rs4457088 | 0.919 | 0.703 | 2.72E−21 |
| rs4415084 | rs10038554 | 0.919 | 0.703 | 2.72E−21 |
| rs4415084 | rs3747479 | 0.919 | 0.701 | 3.77E−21 |
| rs4415084 | rs6894324 | 0.918 | 0.701 | 6.83E−21 |
| rs4415084 | rs9790896 | 0.880 | 0.700 | 8.38E−21 |
| rs4415084 | rs6875287 | 0.915 | 0.699 | 4.58E−20 |
| rs4415084 | rs6868232 | 0.918 | 0.697 | 1.16E−20 |
| rs4415084 | rs11741772 | 0.916 | 0.697 | 2.05E−20 |
| rs4415084 | rs9292914 | 0.904 | 0.694 | 6.03E−18 |
| rs4415084 | rs11951760 | 0.912 | 0.694 | 6.63E−20 |
| rs4415084 | rs12518851 | 0.908 | 0.685 | 2.88E−18 |
| rs4415084 | rs7715731 | 0.915 | 0.685 | 1.60E−19 |
| rs4415084 | rs1438827 | 0.881 | 0.675 | 2.82E−20 |
| rs4415084 | rs12651949 | 0.911 | 0.665 | 4.20E−16 |
| rs4415084 | rs11948186 | 0.914 | 0.649 | 1.74E−19 |
| rs4415084 | rs10051592 | 0.914 | 0.649 | 1.74E−19 |
| rs4415084 | rs16902086 | 0.802 | 0.559 | 2.08E−16 |
| rs4415084 | rs3935086 | 0.905 | 0.537 | 5.09E−16 |
| rs4415084 | rs10512875 | 0.901 | 0.517 | 6.18E−15 |
| rs4415084 | rs10941679 | 1.000 | 0.513 | 5.36E−17 |
| rs4415084 | rs4613718 | 1.000 | 0.454 | 3.93E−17 |
| rs4415084 | rs930395 | 1.000 | 0.402 | 1.56E−13 |
| rs4415084 | rs10044408 | 1.000 | 0.330 | 6.94E−11 |
| rs4415084 | rs6869488 | 0.856 | 0.287 | 6.68E−09 |
| rs4415084 | rs4460145 | 0.856 | 0.287 | 6.68E−09 |
| rs4415084 | rs7709262 | 0.847 | 0.275 | 5.02E−08 |
| rs4415084 | rs6874127 | 0.847 | 0.273 | 8.18E−08 |
| rs4415084 | rs13183434 | 1.000 | 0.266 | 2.69E−09 |
| rs4415084 | rs7716101 | 0.843 | 0.264 | 9.59E−08 |
| rs4415084 | rs7709661 | 0.843 | 0.264 | 9.59E−08 |
| rs4415084 | rs6894974 | 0.843 | 0.264 | 9.59E−08 |
| rs4415084 | rs6885307 | 0.843 | 0.264 | 9.59E−08 |
| rs4415084 | rs4533894 | 0.843 | 0.264 | 9.59E−08 |
| rs4415084 | rs12521639 | 0.843 | 0.264 | 9.59E−08 |
| rs4415084 | rs12054976 | 0.843 | 0.264 | 9.59E−08 |
| rs4415084 | rs7731099 | 0.839 | 0.264 | 1.12E−07 |
| rs4415084 | rs7701679 | 0.841 | 0.263 | 1.15E−07 |
| rs4415084 | rs6862655 | 0.739 | 0.262 | 3.65E−08 |
| rs4415084 | rs10059745 | 0.739 | 0.262 | 3.65E−08 |
| rs4415084 | rs6451796 | 0.840 | 0.255 | 1.80E−07 |
| rs4415084 | rs3923055 | 0.840 | 0.255 | 1.80E−07 |
| rs4415084 | rs1501361 | 0.840 | 0.255 | 1.80E−07 |
| rs4415084 | rs1392973 | 0.840 | 0.255 | 1.80E−07 |
| rs4415084 | rs6866354 | 0.734 | 0.254 | 5.71E−08 |
| rs4415084 | rs4639238 | 0.736 | 0.254 | 5.70E−08 |
| rs4415084 | rs12374507 | 0.736 | 0.254 | 5.70E−08 |
| rs4415084 | rs10066953 | 0.736 | 0.254 | 5.70E−08 |
| rs4415084 | rs4371761 | 0.839 | 0.252 | 2.37E−07 |
| rs4415084 | rs10054521 | 0.733 | 0.249 | 8.38E−08 |
| rs4415084 | rs4502832 | 0.838 | 0.246 | 1.74E−07 |
| rs4415084 | rs4485937 | 0.838 | 0.246 | 1.74E−07 |
| rs4415084 | rs4389695 | 0.838 | 0.246 | 1.74E−07 |
| rs4415084 | rs4296810 | 0.838 | 0.246 | 1.74E−07 |
| rs4415084 | rs10941692 | 0.838 | 0.246 | 1.74E−07 |
| rs4415084 | rs12522398 | 0.832 | 0.243 | 2.89E−07 |
| rs4415084 | rs4866900 | 0.923 | 0.232 | 4.31E−08 |
| rs4415084 | rs4493682 | 0.816 | 0.212 | 3.37E−06 |
| rs4415084 | rs4308490 | 0.811 | 0.210 | 4.58E−06 |
| rs4415084 | rs6893494 | 0.814 | 0.206 | 3.96E−06 |
| rs4415084 | rs12523157 | 0.814 | 0.206 | 3.96E−06 |
| rs4415084 | rs11954598 | 0.814 | 0.206 | 3.96E−06 |
| rs4415084 | rs7720104 | 0.809 | 0.205 | 5.34E−06 |
| rs4415084 | rs6864149 | 0.810 | 0.204 | 4.47E−06 |
| rs4415084 | rs983940 | 1.000 | 0.204 | 4.35E−09 |
| rs4415084 | rs6451767 | 1.000 | 0.204 | 4.35E−09 |
| rs4415084 | rs1482663 | 1.000 | 0.204 | 4.35E−09 |
| rs4415084 | rs1351633 | 1.000 | 0.204 | 4.35E−09 |
| rs4415084 | rs10079222 | 1.000 | 0.204 | 4.35E−09 |
| rs4415084 | rs12514414 | 0.804 | 0.202 | 7.18E−06 |
| rs4415084 | rs6876773 | 0.802 | 0.201 | 0.00001 |
| rs4415084 | rs7711446 | 0.802 | 0.201 | 0.000012 |
| SNP B = rs7703618 | | | | |
| rs7703618 | rs9292914 | 1.000 | 1.000 | 1.09E−30 |
| rs7703618 | rs7717459 | 1.000 | 1.000 | 2.19E−35 |
| rs7703618 | rs7715731 | 1.000 | 1.000 | 3.83E−33 |
| rs7703618 | rs7736092 | 1.000 | 1.000 | 3.33E−35 |
| rs7703618 | rs7708506 | 1.000 | 1.000 | 3.33E−35 |
| rs7703618 | rs6875287 | 1.000 | 1.000 | 2.28E−34 |
| rs7703618 | rs10041518 | 1.000 | 1.000 | 2.19E−35 |
| rs7703618 | rs10039866 | 1.000 | 1.000 | 2.19E−35 |
| rs7703618 | rs10038554 | 1.000 | 1.000 | 9.82E−35 |
| rs7703618 | rs6894324 | 1.000 | 1.000 | 9.82E−35 |
| rs7703618 | rs6893319 | 1.000 | 1.000 | 2.19E−35 |
| rs7703618 | rs6875933 | 1.000 | 1.000 | 2.19E−35 |
| rs7703618 | rs6872254 | 1.000 | 1.000 | 2.19E−35 |
| rs7703618 | rs6871052 | 1.000 | 1.000 | 3.33E−35 |
| rs7703618 | rs6868232 | 1.000 | 1.000 | 1.90E−34 |
| rs7703618 | rs6451778 | 1.000 | 1.000 | 2.19E−35 |
| rs7703618 | rs4642377 | 1.000 | 1.000 | 6.45E−35 |
| rs7703618 | rs4457088 | 1.000 | 1.000 | 9.82E−35 |
| rs7703618 | rs4373287 | 1.000 | 1.000 | 2.19E−35 |
| rs7703618 | rs3747479 | 1.000 | 1.000 | 1.44E−34 |
| rs7703618 | rs1866406 | 1.000 | 1.000 | 2.19E−35 |
| rs7703618 | rs1438822 | 1.000 | 1.000 | 2.19E−35 |
| rs7703618 | rs1438819 | 1.000 | 1.000 | 2.19E−35 |
| rs7703618 | rs13189120 | 1.000 | 1.000 | 2.19E−35 |
| rs7703618 | rs13155698 | 1.000 | 1.000 | 2.19E−35 |
| rs7703618 | rs13154781 | 1.000 | 1.000 | 2.19E−35 |
| rs7703618 | rs12651949 | 1.000 | 1.000 | 1.89E−31 |
| rs7703618 | rs12518851 | 1.000 | 1.000 | 5.31E−33 |
| rs7703618 | rs12513749 | 1.000 | 1.000 | 2.19E−35 |
| rs7703618 | rs11951760 | 1.000 | 1.000 | 1.18E−33 |
| rs7703618 | rs11741772 | 1.000 | 1.000 | 3.34E−34 |
| rs7703618 | rs10462080 | 1.000 | 1.000 | 2.19E−35 |
| rs7703618 | rs10070037 | 1.000 | 1.000 | 3.33E−35 |
| rs7703618 | rs10065638 | 1.000 | 1.000 | 2.19E−35 |
| rs7703618 | rs10059086 | 1.000 | 1.000 | 2.19E−35 |
| rs7703618 | rs10057521 | 1.000 | 1.000 | 2.19E−35 |
| rs7703618 | rs10053247 | 1.000 | 1.000 | 2.19E−35 |
| rs7703618 | rs10040488 | 1.000 | 1.000 | 2.19E−35 |
| rs7703618 | rs10040082 | 1.000 | 1.000 | 1.50E−34 |
| rs7703618 | rs1438827 | 1.000 | 0.964 | 2.55E−33 |
| rs7703618 | rs7711697 | 1.000 | 0.929 | 2.12E−31 |
| rs7703618 | rs11958808 | 1.000 | 0.929 | 7.53E−32 |
| rs7703618 | rs10044096 | 1.000 | 0.929 | 7.53E−32 |
| rs7703618 | rs7380559 | 1.000 | 0.929 | 7.53E−32 |
| rs7703618 | rs4518490 | 1.000 | 0.929 | 7.53E−32 |
| rs7703618 | rs4329028 | 1.000 | 0.929 | 2.12E−31 |
| rs7703618 | rs1438821 | 1.000 | 0.929 | 7.53E−32 |
| rs7703618 | rs1438820 | 1.000 | 0.929 | 7.53E−32 |
| rs7703618 | rs13362132 | 1.000 | 0.929 | 7.53E−32 |
| rs7703618 | rs13160259 | 1.000 | 0.929 | 7.53E−32 |
| rs7703618 | rs1061310 | 1.000 | 0.929 | 7.53E−32 |
| rs7703618 | rs10512865 | 1.000 | 0.929 | 7.53E−32 |
| rs7703618 | rs1048758 | 1.000 | 0.929 | 7.53E−32 |
| rs7703618 | rs7716571 | 1.000 | 0.929 | 4.57E−31 |
| rs7703618 | rs9292913 | 1.000 | 0.928 | 1.15E−31 |
| rs7703618 | rs7380878 | 1.000 | 0.928 | 3.22E−31 |
| rs7703618 | rs13177711 | 1.000 | 0.928 | 1.15E−31 |
| rs7703618 | rs10043344 | 1.000 | 0.928 | 4.91E−31 |
| rs7703618 | rs11949847 | 1.000 | 0.928 | 1.75E−31 |
| rs7703618 | rs9790896 | 0.962 | 0.858 | 7.84E−27 |
| rs7703618 | rs920328 | 0.923 | 0.764 | 1.31E−23 |
| rs7703618 | rs4571480 | 0.922 | 0.731 | 2.33E−22 |
| rs7703618 | rs11948186 | 0.883 | 0.723 | 1.25E−21 |
| rs7703618 | rs10051592 | 0.883 | 0.723 | 1.25E−21 |
| rs7703618 | rs7735881 | 0.921 | 0.708 | 7.34E−22 |
| rs7703618 | rs7723539 | 0.921 | 0.708 | 7.34E−22 |
| rs7703618 | rs714130 | 0.921 | 0.708 | 7.34E−22 |
| rs7703618 | rs6861560 | 0.921 | 0.708 | 7.34E−22 |
| rs7703618 | rs6451770 | 0.921 | 0.708 | 7.34E−22 |
| rs7703618 | rs4419600 | 0.921 | 0.708 | 7.34E−22 |
| rs7703618 | rs4415085 | 0.921 | 0.708 | 7.34E−22 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs7703618 | rs4321755 | 0.921 | 0.708 | 7.34E−22 |
| rs7703618 | rs2218081 | 0.921 | 0.708 | 7.34E−22 |
| rs7703618 | rs1438825 | 0.921 | 0.708 | 7.34E−22 |
| rs7703618 | rs13156930 | 0.921 | 0.708 | 7.34E−22 |
| rs7703618 | rs12515012 | 0.921 | 0.708 | 7.34E−22 |
| rs7703618 | rs12187196 | 0.921 | 0.708 | 7.34E−22 |
| rs7703618 | rs7720551 | 0.920 | 0.707 | 1.46E−21 |
| rs7703618 | rs6874055 | 0.919 | 0.706 | 1.84E−21 |
| rs7703618 | rs2165010 | 0.919 | 0.706 | 1.84E−21 |
| rs7703618 | rs920329 | 0.920 | 0.706 | 2.91E−21 |
| rs7703618 | rs10805685 | 0.921 | 0.706 | 1.09E−21 |
| rs7703618 | rs1821936 | 0.921 | 0.705 | 2.18E−21 |
| rs7703618 | rs10941678 | 0.921 | 0.705 | 2.18E−21 |
| rs7703618 | rs4463188 | 0.918 | 0.704 | 3.64E−21 |
| rs7703618 | rs2013513 | 0.919 | 0.704 | 2.72E−21 |
| rs7703618 | rs10941677 | 0.919 | 0.704 | 2.72E−21 |
| rs7703618 | rs4492118 | 0.921 | 0.703 | 1.62E−21 |
| rs7703618 | rs2165009 | 0.921 | 0.703 | 1.62E−21 |
| rs7703618 | rs12522626 | 0.921 | 0.703 | 1.62E−21 |
| rs7703618 | rs16901937 | 0.920 | 0.682 | 4.51E−21 |
| rs7703618 | rs16902086 | 0.812 | 0.635 | 1.69E−18 |
| rs7703618 | rs3935086 | 0.865 | 0.570 | 1.75E−16 |
| rs7703618 | rs10512875 | 0.865 | 0.570 | 1.75E−16 |
| rs7703618 | rs930395 | 1.000 | 0.482 | 9.85E−16 |
| rs7703618 | rs10941679 | 0.842 | 0.435 | 2.26E−12 |
| rs7703618 | rs4613718 | 1.000 | 0.384 | 5.94E−15 |
| rs7703618 | rs4502832 | 0.925 | 0.349 | 3.00E−10 |
| rs7703618 | rs4485937 | 0.925 | 0.349 | 3.00E−10 |
| rs7703618 | rs4389695 | 0.925 | 0.349 | 3.00E−10 |
| rs7703618 | rs10941692 | 0.925 | 0.349 | 3.00E−10 |
| rs7703618 | rs12522398 | 0.923 | 0.349 | 5.27E−10 |
| rs7703618 | rs6869488 | 0.865 | 0.342 | 3.96E−10 |
| rs7703618 | rs4460145 | 0.865 | 0.342 | 3.96E−10 |
| rs7703618 | rs10044408 | 0.917 | 0.334 | 7.15E−09 |
| rs7703618 | rs7731099 | 0.856 | 0.327 | 2.53E−09 |
| rs7703618 | rs7716101 | 0.856 | 0.317 | 3.51E−09 |
| rs7703618 | rs7709661 | 0.856 | 0.317 | 3.51E−09 |
| rs7703618 | rs6894974 | 0.856 | 0.317 | 3.51E−09 |
| rs7703618 | rs6885307 | 0.856 | 0.317 | 3.51E−09 |
| rs7703618 | rs4533894 | 0.856 | 0.317 | 3.51E−09 |
| rs7703618 | rs12521639 | 0.856 | 0.317 | 3.51E−09 |
| rs7703618 | rs12054976 | 0.856 | 0.317 | 3.51E−09 |
| rs7703618 | rs7701679 | 0.852 | 0.315 | 8.33E−09 |
| rs7703618 | rs4371761 | 0.852 | 0.305 | 9.59E−09 |
| rs7703618 | rs4296810 | 0.851 | 0.296 | 7.62E−09 |
| rs7703618 | rs1909937 | 0.911 | 0.282 | 2.53E−08 |
| rs7703618 | rs16902068 | 0.911 | 0.282 | 2.53E−08 |
| rs7703618 | rs1472584 | 0.911 | 0.282 | 2.53E−08 |
| rs7703618 | rs1392970 | 0.911 | 0.282 | 2.53E−08 |
| rs7703618 | rs12523398 | 0.911 | 0.282 | 2.53E−08 |
| rs7703618 | rs12521953 | 0.911 | 0.282 | 2.53E−08 |
| rs7703618 | rs12516488 | 0.911 | 0.282 | 2.53E−08 |
| rs7703618 | rs12514615 | 0.911 | 0.282 | 2.53E−08 |
| rs7703618 | rs12153189 | 0.911 | 0.282 | 2.53E−08 |
| rs7703618 | rs12153053 | 0.911 | 0.282 | 2.53E−08 |
| rs7703618 | rs11953498 | 0.911 | 0.282 | 2.53E−08 |
| rs7703618 | rs10941693 | 0.911 | 0.282 | 2.53E−08 |
| rs7703618 | rs4357042 | 0.910 | 0.282 | 2.95E−08 |
| rs7703618 | rs12523359 | 0.910 | 0.282 | 2.95E−08 |
| rs7703618 | rs12522305 | 0.910 | 0.282 | 2.95E−08 |
| rs7703618 | rs4533895 | 0.909 | 0.281 | 3.44E−08 |
| rs7703618 | rs6898476 | 0.907 | 0.281 | 4.74E−08 |
| rs7703618 | rs6451796 | 0.786 | 0.267 | 1.07E−07 |
| rs7703618 | rs3923055 | 0.786 | 0.267 | 1.07E−07 |
| rs7703618 | rs1501361 | 0.786 | 0.267 | 1.07E−07 |
| rs7703618 | rs1392973 | 0.786 | 0.267 | 1.07E−07 |
| rs7703618 | rs4566805 | 0.903 | 0.266 | 1.31E−07 |
| rs7703618 | rs12520430 | 0.906 | 0.266 | 5.16E−08 |
| rs7703618 | rs1405918 | 0.636 | 0.265 | 8.95E−08 |
| rs7703618 | rs13183434 | 0.907 | 0.262 | 5.17E−08 |
| rs7703618 | rs7446090 | 0.835 | 0.259 | 1.68E−07 |
| rs7703618 | rs4493682 | 0.833 | 0.259 | 1.97E−07 |
| rs7703618 | rs7720104 | 0.831 | 0.258 | 2.29E−07 |
| rs7703618 | rs4308490 | 0.831 | 0.258 | 2.75E−07 |
| rs7703618 | rs7711444 | 0.901 | 0.254 | 4.18E−07 |
| rs7703618 | rs6893494 | 0.831 | 0.250 | 2.47E−07 |
| rs7703618 | rs12523157 | 0.831 | 0.250 | 2.47E−07 |
| rs7703618 | rs11954598 | 0.831 | 0.250 | 2.47E−07 |
| rs7703618 | rs6864149 | 0.827 | 0.249 | 2.79E−07 |
| rs7703618 | rs12514414 | 0.823 | 0.247 | 4.51E−07 |
| rs7703618 | rs12520124 | 0.591 | 0.247 | 6.18E−07 |
| rs7703618 | rs6876773 | 0.822 | 0.246 | 6.39E−07 |
| rs7703618 | rs13187565 | 0.603 | 0.246 | 1.02E−06 |
| rs7703618 | rs7711446 | 0.821 | 0.246 | 7.62E−07 |
| rs7703618 | rs2337483 | 0.623 | 0.246 | 2.67E−07 |
| rs7703618 | rs7709262 | 0.727 | 0.242 | 5.48E−07 |
| rs7703618 | rs2580260 | 0.598 | 0.241 | 3.14E−06 |
| rs7703618 | rs6874127 | 0.726 | 0.240 | 8.96E−07 |
| rs7703618 | rs2589162 | 0.617 | 0.238 | 6.61E−07 |
| rs7703618 | rs6890289 | 0.823 | 0.237 | 7.69E−07 |
| rs7703618 | rs6892627 | 0.593 | 0.231 | 5.31E−07 |
| rs7703618 | rs6451814 | 0.593 | 0.231 | 5.31E−07 |
| rs7703618 | rs2337952 | 0.593 | 0.231 | 5.31E−07 |
| rs7703618 | rs2049656 | 0.593 | 0.231 | 5.31E−07 |
| rs7703618 | rs1483303 | 0.593 | 0.231 | 5.31E−07 |
| rs7703618 | rs17343002 | 1.000 | 0.229 | 2.29E−09 |
| rs7703618 | rs6893773 | 0.584 | 0.225 | 9.49E−07 |
| rs7703618 | rs2337951 | 0.584 | 0.225 | 9.49E−07 |
| rs7703618 | rs10078625 | 0.584 | 0.225 | 9.49E−07 |
| rs7703618 | rs10036065 | 0.581 | 0.224 | 7.95E−07 |
| rs7703618 | rs7705696 | 0.571 | 0.218 | 1.42E−06 |
| rs7703618 | rs2625494 | 0.586 | 0.218 | 1.15E−06 |
| rs7703618 | rs2580258 | 0.586 | 0.218 | 1.15E−06 |
| rs7703618 | rs1351720 | 0.586 | 0.218 | 1.15E−06 |
| rs7703618 | rs12110137 | 0.586 | 0.218 | 1.15E−06 |
| rs7703618 | rs10073636 | 0.586 | 0.218 | 1.15E−06 |
| rs7703618 | rs10043792 | 0.586 | 0.218 | 1.15E−06 |
| rs7703618 | rs1384732 | 0.573 | 0.215 | 2.06E−06 |
| rs7703618 | rs6451810 | 0.584 | 0.214 | 1.52E−06 |
| rs7703618 | rs6860200 | 0.550 | 0.212 | 2.47E−06 |
| rs7703618 | rs755048 | 0.567 | 0.211 | 2.41E−06 |
| rs7703618 | rs7732970 | 0.554 | 0.208 | 2.28E−06 |
| rs7703618 | rs6892594 | 0.554 | 0.208 | 2.28E−06 |
| rs7703618 | rs6451804 | 0.554 | 0.208 | 2.28E−06 |
| rs7703618 | rs7444176 | 0.572 | 0.208 | 2.55E−06 |
| rs7703618 | rs9687260 | 0.550 | 0.205 | 2.05E−06 |
| rs7703618 | rs7706116 | 0.550 | 0.205 | 2.05E−06 |
| rs7703618 | rs1501358 | 0.750 | 0.204 | 2.77E−06 |
| rs7703618 | rs12655983 | 0.750 | 0.204 | 2.77E−06 |
| SNP C = rs2067980 | | | | |
| rs2067980 | rs13183434 | 0.931 | 0.863 | 1.68E−17 |
| rs2067980 | rs10044408 | 0.767 | 0.444 | 2.19E−09 |
| rs2067980 | rs1501358 | 0.713 | 0.436 | 1.93E−09 |
| rs2067980 | rs12655983 | 0.713 | 0.436 | 1.93E−09 |
| rs2067980 | rs6451796 | 0.779 | 0.434 | 7.64E−10 |
| rs2067980 | rs3923055 | 0.779 | 0.434 | 7.64E−10 |
| rs2067980 | rs1501361 | 0.779 | 0.434 | 7.64E−10 |
| rs2067980 | rs1392973 | 0.779 | 0.434 | 7.64E−10 |
| rs2067980 | rs6874127 | 0.778 | 0.430 | 9.74E−10 |
| rs2067980 | rs7709262 | 0.776 | 0.408 | 1.92E−09 |
| rs2067980 | rs930395 | 0.774 | 0.383 | 4.51E−09 |
| rs2067980 | rs6451795 | 0.640 | 0.350 | 8.08E−08 |
| rs2067980 | rs11948186 | 1.000 | 0.329 | 8.10E−11 |
| rs2067980 | rs10051592 | 1.000 | 0.329 | 8.10E−11 |
| rs2067980 | rs6861150 | 0.577 | 0.324 | 3.93E−07 |
| rs2067980 | rs10473387 | 0.743 | 0.298 | 4.83E−07 |
| rs2067980 | rs16902086 | 1.000 | 0.294 | 4.00E−10 |
| rs2067980 | rs7711697 | 1.000 | 0.291 | 4.65E−10 |
| rs2067980 | rs7716571 | 1.000 | 0.288 | 1.57E−09 |
| rs2067980 | rs10941679 | 0.759 | 0.288 | 1.55E−07 |
| rs2067980 | rs10043344 | 1.000 | 0.286 | 6.31E−10 |
| rs2067980 | rs7380559 | 1.000 | 0.283 | 6.59E−10 |
| rs2067980 | rs4518409 | 1.000 | 0.283 | 6.59E−10 |
| rs2067980 | rs4329028 | 1.000 | 0.283 | 1.89E−09 |
| rs2067980 | rs1438821 | 1.000 | 0.283 | 6.59E−10 |
| rs2067980 | rs1438820 | 1.000 | 0.283 | 6.59E−10 |
| rs2067980 | rs13362132 | 1.000 | 0.283 | 6.59E−10 |
| rs2067980 | rs13160259 | 1.000 | 0.283 | 6.59E−10 |
| rs2067980 | rs11958808 | 1.000 | 0.283 | 6.59E−10 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs2067980 | rs1061310 | 1.000 | 0.283 | 6.59E−10 |
| rs2067980 | rs10512865 | 1.000 | 0.283 | 6.59E−10 |
| rs2067980 | rs1048758 | 1.000 | 0.283 | 6.59E−10 |
| rs2067980 | rs10044096 | 1.000 | 0.283 | 6.59E−10 |
| rs2067980 | rs9292913 | 1.000 | 0.280 | 7.66E−10 |
| rs2067980 | rs7380878 | 1.000 | 0.280 | 2.18E−09 |
| rs2067980 | rs13177711 | 1.000 | 0.280 | 7.66E−10 |
| rs2067980 | rs11949847 | 1.000 | 0.278 | 8.92E−10 |
| rs2067980 | rs7721731 | 0.736 | 0.276 | 1.54E−06 |
| rs2067980 | rs9790896 | 1.000 | 0.275 | 1.04E−09 |
| rs2067980 | rs1483309 | 0.753 | 0.270 | 2.69E−07 |
| rs2067980 | rs1483306 | 0.753 | 0.270 | 2.69E−07 |
| rs2067980 | rs13358718 | 0.753 | 0.270 | 2.69E−07 |
| rs2067980 | rs10073055 | 0.753 | 0.270 | 2.69E−07 |
| rs2067980 | rs10472404 | 0.750 | 0.268 | 5.28E−07 |
| rs2067980 | rs12697498 | 0.741 | 0.266 | 2.58E−06 |
| rs2067980 | rs4463188 | 1.000 | 0.259 | 3.60E−09 |
| rs2067980 | rs4571480 | 1.000 | 0.258 | 2.32E−09 |
| rs2067980 | rs2013513 | 1.000 | 0.258 | 2.32E−09 |
| rs2067980 | rs10941677 | 1.000 | 0.258 | 2.32E−09 |
| rs2067980 | rs4532370 | 0.750 | 0.256 | 4.73E−07 |
| rs2067980 | rs1483312 | 0.750 | 0.256 | 4.73E−07 |
| rs2067980 | rs1351719 | 0.750 | 0.256 | 4.73E−07 |
| rs2067980 | rs12656485 | 0.750 | 0.256 | 4.73E−07 |
| rs2067980 | rs6877477 | 0.802 | 0.255 | 1.27E−06 |
| rs2067980 | rs6868232 | 0.900 | 0.254 | 3.11E−07 |
| rs2067980 | rs7715731 | 0.893 | 0.254 | 8.48E−07 |
| rs2067980 | rs7735881 | 1.000 | 0.254 | 2.71E−09 |
| rs2067980 | rs7723539 | 1.000 | 0.254 | 2.71E−09 |
| rs2067980 | rs7720551 | 1.000 | 0.254 | 2.71E−09 |
| rs2067980 | rs714130 | 1.000 | 0.254 | 2.71E−09 |
| rs2067980 | rs6874055 | 1.000 | 0.254 | 7.25E−09 |
| rs2067980 | rs6861560 | 1.000 | 0.254 | 2.71E−09 |
| rs2067980 | rs6451770 | 1.000 | 0.254 | 2.71E−09 |
| rs2067980 | rs4419600 | 1.000 | 0.254 | 2.71E−09 |
| rs2067980 | rs4415085 | 1.000 | 0.254 | 2.71E−09 |
| rs2067980 | rs4321755 | 1.000 | 0.254 | 2.71E−09 |
| rs2067980 | rs2218081 | 1.000 | 0.254 | 2.71E−09 |
| rs2067980 | rs2165010 | 1.000 | 0.254 | 7.25E−09 |
| rs2067980 | rs1438825 | 1.000 | 0.254 | 2.71E−09 |
| rs2067980 | rs13156930 | 1.000 | 0.254 | 2.71E−09 |
| rs2067980 | rs12515012 | 1.000 | 0.254 | 2.71E−09 |
| rs2067980 | rs12187196 | 1.000 | 0.254 | 2.71E−09 |
| rs2067980 | rs4452566 | 0.813 | 0.254 | 5.19E−07 |
| rs2067980 | rs10040082 | 0.906 | 0.252 | 1.42E−07 |
| rs2067980 | rs3747479 | 0.900 | 0.252 | 3.55E−07 |
| rs2067980 | rs920329 | 1.000 | 0.251 | 3.15E−09 |
| rs2067980 | rs1821936 | 1.000 | 0.251 | 3.15E−09 |
| rs2067980 | rs10941678 | 1.000 | 0.251 | 3.15E−09 |
| rs2067980 | rs10805685 | 1.000 | 0.251 | 3.15E−09 |
| rs2067980 | rs7717459 | 0.905 | 0.249 | 1.51E−07 |
| rs2067980 | rs6893319 | 0.905 | 0.249 | 1.51E−07 |
| rs2067980 | rs6875933 | 0.905 | 0.249 | 1.51E−07 |
| rs2067980 | rs6872254 | 0.905 | 0.249 | 1.51E−07 |
| rs2067980 | rs6451778 | 0.905 | 0.249 | 1.51E−07 |
| rs2067980 | rs4373287 | 0.905 | 0.249 | 1.51E−07 |
| rs2067980 | rs1866406 | 0.905 | 0.249 | 1.51E−07 |
| rs2067980 | rs1438822 | 0.905 | 0.249 | 1.51E−07 |
| rs2067980 | rs1438819 | 0.905 | 0.249 | 1.51E−07 |
| rs2067980 | rs13189120 | 0.905 | 0.249 | 1.51E−07 |
| rs2067980 | rs13155698 | 0.905 | 0.249 | 1.51E−07 |
| rs2067980 | rs13154781 | 0.905 | 0.249 | 1.51E−07 |
| rs2067980 | rs10462080 | 0.905 | 0.249 | 1.51E−07 |
| rs2067980 | rs10065638 | 0.905 | 0.249 | 1.51E−07 |
| rs2067980 | rs10059086 | 0.905 | 0.249 | 1.51E−07 |
| rs2067980 | rs10057521 | 0.905 | 0.249 | 1.51E−07 |
| rs2067980 | rs10053247 | 0.905 | 0.249 | 1.51E−07 |
| rs2067980 | rs10041518 | 0.905 | 0.249 | 1.51E−07 |
| rs2067980 | rs10040488 | 0.905 | 0.249 | 1.51E−07 |
| rs2067980 | rs10039866 | 0.905 | 0.249 | 1.51E−07 |
| rs2067980 | rs6875287 | 0.904 | 0.249 | 2.50E−07 |
| rs2067980 | rs4492118 | 1.000 | 0.249 | 3.66E−09 |
| rs2067980 | rs2165009 | 1.000 | 0.249 | 3.66E−09 |
| rs2067980 | rs12522626 | 1.000 | 0.249 | 3.66E−09 |
| rs2067980 | rs12513749 | 0.903 | 0.248 | 3.02E−07 |
| rs2067980 | rs7736092 | 0.905 | 0.247 | 1.73E−07 |
| rs2067980 | rs6871052 | 0.905 | 0.247 | 1.73E−07 |
| rs2067980 | rs10070037 | 0.905 | 0.247 | 1.73E−07 |
| rs2067980 | rs11741772 | 0.899 | 0.247 | 4.65E−07 |
| rs2067980 | rs4642377 | 0.899 | 0.247 | 4.29E−07 |
| rs2067980 | rs6451806 | 0.734 | 0.245 | 1.74E−06 |
| rs2067980 | rs16901937 | 1.000 | 0.245 | 4.22E−09 |
| rs2067980 | rs7708506 | 0.904 | 0.244 | 1.99E−07 |
| rs2067980 | rs6894324 | 0.899 | 0.244 | 4.89E−07 |
| rs2067980 | rs4457088 | 0.899 | 0.244 | 4.89E−07 |
| rs2067980 | rs10038554 | 0.899 | 0.244 | 4.89E−07 |
| rs2067980 | rs2878967 | 0.747 | 0.243 | 8.09E−07 |
| rs2067980 | rs1564684 | 0.747 | 0.243 | 8.09E−07 |
| rs2067980 | rs12651949 | 0.864 | 0.242 | 0.000056 |
| rs2067980 | rs12518851 | 0.896 | 0.240 | 1.34E−06 |
| rs2067980 | rs1438827 | 0.904 | 0.240 | 2.40E−07 |
| rs2067980 | rs9292914 | 0.887 | 0.237 | 2.40E−06 |
| rs2067980 | rs11951760 | 0.892 | 0.230 | 1.31E−06 |
| rs2067980 | rs7447532 | 1.000 | 0.222 | 0.000037 |
| rs2067980 | rs5004228 | 1.000 | 0.222 | 0.000037 |
| rs2067980 | rs11750364 | 1.000 | 0.222 | 0.000038 |
| rs2067980 | rs13357090 | 1.000 | 0.222 | 0.000037 |
| rs2067980 | rs920328 | 0.901 | 0.221 | 5.82E−07 |
| rs2067980 | rs10462095 | 0.737 | 0.221 | 3.73E−06 |
| rs2067980 | rs16902199 | 0.736 | 0.219 | 2.22E−06 |
| rs2067980 | rs7724971 | 0.740 | 0.219 | 2.21E−06 |
| rs2067980 | rs7719703 | 0.740 | 0.219 | 2.21E−06 |
| rs2067980 | rs7700252 | 0.740 | 0.219 | 2.21E−06 |
| rs2067980 | rs6898646 | 0.740 | 0.219 | 2.21E−06 |
| rs2067980 | rs6894784 | 0.740 | 0.219 | 2.21E−06 |
| rs2067980 | rs6894273 | 0.740 | 0.219 | 2.21E−06 |
| rs2067980 | rs6886950 | 0.740 | 0.219 | 2.21E−06 |
| rs2067980 | rs4437383 | 0.740 | 0.219 | 2.21E−06 |
| rs2067980 | rs2337954 | 0.740 | 0.219 | 2.21E−06 |
| rs2067980 | rs16902221 | 0.740 | 0.219 | 2.21E−06 |
| rs2067980 | rs16902217 | 0.740 | 0.219 | 2.21E−06 |
| rs2067980 | rs1483308 | 0.740 | 0.219 | 2.21E−06 |
| rs2067980 | rs13359915 | 0.740 | 0.219 | 2.21E−06 |
| rs2067980 | rs13357427 | 0.740 | 0.219 | 2.21E−06 |
| rs2067980 | rs12109155 | 0.740 | 0.219 | 2.21E−06 |
| rs2067980 | rs10473389 | 0.740 | 0.219 | 2.21E−06 |
| rs2067980 | rs10074312 | 0.740 | 0.219 | 2.21E−06 |
| rs2067980 | rs10066821 | 0.740 | 0.219 | 2.21E−06 |
| rs2067980 | rs1852595 | 0.739 | 0.217 | 2.48E−06 |
| rs2067980 | rs13159362 | 0.739 | 0.217 | 2.48E−06 |
| rs2067980 | rs10214369 | 0.739 | 0.217 | 2.48E−06 |
| rs2067980 | rs13361609 | 0.739 | 0.215 | 2.79E−06 |
| rs2067980 | rs7445730 | 0.723 | 0.211 | 6.63E−06 |
| rs2067980 | rs4339358 | 0.723 | 0.211 | 6.63E−06 |
| rs2067980 | rs4242125 | 0.723 | 0.211 | 6.63E−06 |
| rs2067980 | rs4560554 | 0.728 | 0.209 | 0.000011 |
| rs2067980 | rs4626346 | 0.737 | 0.208 | 3.54E−06 |
| rs2067980 | rs10052977 | 0.737 | 0.208 | 3.54E−06 |
| rs2067980 | rs3935086 | 0.730 | 0.208 | 7.29E−06 |
| rs2067980 | rs4132311 | 0.697 | 0.204 | 0.000013 |
| rs2067980 | rs4283798 | 0.730 | 0.201 | 8.64E−06 |
| SNP D = rs10035564 | | | | |
| rs10035564 | rs11948186 | 1.000 | 1.000 | 1.31E−34 |
| rs10035564 | rs10051592 | 1.000 | 1.000 | 1.31E−34 |
| rs10035564 | rs16902086 | 1.000 | 0.894 | 6.99E−30 |
| rs10035564 | rs9292914 | 0.954 | 0.874 | 8.22E−24 |
| rs10035564 | rs7711697 | 0.959 | 0.822 | 8.14E−25 |
| rs10035564 | rs3935086 | 1.000 | 0.819 | 2.75E−26 |
| rs10035564 | rs10512875 | 1.000 | 0.819 | 2.75E−26 |
| rs10035564 | rs7380559 | 0.959 | 0.794 | 1.31E−24 |
| rs10035564 | rs4518409 | 0.959 | 0.794 | 1.31E−24 |
| rs10035564 | rs1438821 | 0.959 | 0.794 | 1.31E−24 |
| rs10035564 | rs1438820 | 0.959 | 0.794 | 1.31E−24 |
| rs10035564 | rs13362132 | 0.959 | 0.794 | 1.31E−24 |
| rs10035564 | rs13160259 | 0.959 | 0.794 | 1.31E−24 |
| rs10035564 | rs11958808 | 0.959 | 0.794 | 1.31E−24 |
| rs10035564 | rs1061310 | 0.959 | 0.794 | 1.31E−24 |
| rs10035564 | rs10512865 | 0.959 | 0.794 | 1.31E−24 |
| rs10035564 | rs1048758 | 0.959 | 0.794 | 1.31E−24 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs10035564 | rs10044096 | 0.959 | 0.794 | 1.31E-24 |
| rs10035564 | rs4329028 | 0.958 | 0.793 | 3.59E-24 |
| rs10035564 | rs7716571 | 0.958 | 0.792 | 4.90E-24 |
| rs10035564 | rs13177711 | 0.959 | 0.792 | 1.92E-24 |
| rs10035564 | rs9292913 | 0.959 | 0.792 | 3.86E-24 |
| rs10035564 | rs7380878 | 0.958 | 0.791 | 5.25E-24 |
| rs10035564 | rs11949847 | 0.959 | 0.790 | 2.82E-24 |
| rs10035564 | rs9790896 | 0.959 | 0.790 | 4.42E-24 |
| rs10035564 | rs10043344 | 0.958 | 0.789 | 7.72E-24 |
| rs10035564 | rs11741772 | 0.880 | 0.745 | 1.24E-21 |
| rs10035564 | rs6875287 | 0.882 | 0.745 | 1.24E-21 |
| rs10035564 | rs7717459 | 0.880 | 0.721 | 1.72E-21 |
| rs10035564 | rs6893319 | 0.880 | 0.721 | 1.72E-21 |
| rs10035564 | rs6872254 | 0.880 | 0.721 | 1.72E-21 |
| rs10035564 | rs6451778 | 0.880 | 0.721 | 1.72E-21 |
| rs10035564 | rs4373287 | 0.880 | 0.721 | 1.72E-21 |
| rs10035564 | rs1866406 | 0.880 | 0.721 | 1.72E-21 |
| rs10035564 | rs1438822 | 0.880 | 0.721 | 1.72E-21 |
| rs10035564 | rs1438819 | 0.880 | 0.721 | 1.72E-21 |
| rs10035564 | rs13189120 | 0.880 | 0.721 | 1.72E-21 |
| rs10035564 | rs13155698 | 0.880 | 0.721 | 1.72E-21 |
| rs10035564 | rs13154781 | 0.880 | 0.721 | 1.72E-21 |
| rs10035564 | rs10462080 | 0.880 | 0.721 | 1.72E-21 |
| rs10035564 | rs10065638 | 0.880 | 0.721 | 1.72E-21 |
| rs10035564 | rs10059086 | 0.880 | 0.721 | 1.72E-21 |
| rs10035564 | rs10057521 | 0.880 | 0.721 | 1.72E-21 |
| rs10035564 | rs10053247 | 0.880 | 0.721 | 1.72E-21 |
| rs10035564 | rs10041518 | 0.880 | 0.721 | 1.72E-21 |
| rs10035564 | rs10040488 | 0.880 | 0.721 | 1.72E-21 |
| rs10035564 | rs10039866 | 0.880 | 0.721 | 1.72E-21 |
| rs10035564 | rs12513749 | 0.880 | 0.721 | 3.45E-21 |
| rs10035564 | rs6875933 | 0.880 | 0.720 | 3.43E-21 |
| rs10035564 | rs7736092 | 0.880 | 0.719 | 2.46E-21 |
| rs10035564 | rs6871052 | 0.880 | 0.719 | 2.46E-21 |
| rs10035564 | rs10070037 | 0.880 | 0.719 | 2.46E-21 |
| rs10035564 | rs7708506 | 0.880 | 0.719 | 3.76E-21 |
| rs10035564 | rs4642377 | 0.877 | 0.718 | 4.69E-21 |
| rs10035564 | rs12651949 | 0.859 | 0.718 | 3.09E-17 |
| rs10035564 | rs3747479 | 0.877 | 0.717 | 6.57E-21 |
| rs10035564 | rs6894324 | 0.877 | 0.716 | 6.70E-21 |
| rs10035564 | rs4457088 | 0.877 | 0.716 | 6.70E-21 |
| rs10035564 | rs10038554 | 0.877 | 0.716 | 6.70E-21 |
| rs10035564 | rs6868232 | 0.874 | 0.715 | 1.28E-20 |
| rs10035564 | rs10040082 | 0.877 | 0.714 | 9.58E-21 |
| rs10035564 | rs11951760 | 0.875 | 0.706 | 1.16E-19 |
| rs10035564 | rs7715731 | 0.866 | 0.704 | 3.88E-19 |
| rs10035564 | rs12518851 | 0.871 | 0.700 | 1.86E-18 |
| rs10035564 | rs1438827 | 0.879 | 0.692 | 1.28E-20 |
| rs10035564 | rs10941677 | 0.915 | 0.669 | 3.88E-20 |
| rs10035564 | rs7735881 | 0.914 | 0.649 | 9.79E-20 |
| rs10035564 | rs7723539 | 0.914 | 0.649 | 9.79E-20 |
| rs10035564 | rs714130 | 0.914 | 0.649 | 9.79E-20 |
| rs10035564 | rs6861560 | 0.914 | 0.649 | 9.79E-20 |
| rs10035564 | rs6451770 | 0.914 | 0.649 | 9.79E-20 |
| rs10035564 | rs4419600 | 0.914 | 0.649 | 9.79E-20 |
| rs10035564 | rs4415085 | 0.914 | 0.649 | 9.79E-20 |
| rs10035564 | rs4321755 | 0.914 | 0.649 | 9.79E-20 |
| rs10035564 | rs2218081 | 0.914 | 0.649 | 9.79E-20 |
| rs10035564 | rs1438825 | 0.914 | 0.649 | 9.79E-20 |
| rs10035564 | rs13156930 | 0.914 | 0.649 | 9.79E-20 |
| rs10035564 | rs12515012 | 0.914 | 0.649 | 9.79E-20 |
| rs10035564 | rs12187196 | 0.914 | 0.649 | 9.79E-20 |
| rs10035564 | rs7720551 | 0.914 | 0.648 | 1.95E-19 |
| rs10035564 | rs6874055 | 0.912 | 0.647 | 2.45E-19 |
| rs10035564 | rs2165010 | 0.912 | 0.647 | 2.45E-19 |
| rs10035564 | rs920329 | 0.913 | 0.647 | 1.91E-19 |
| rs10035564 | rs10941678 | 0.914 | 0.646 | 1.42E-19 |
| rs10035564 | rs10805685 | 0.914 | 0.646 | 1.42E-19 |
| rs10035564 | rs1821936 | 0.914 | 0.646 | 2.84E-19 |
| rs10035564 | rs4463188 | 0.911 | 0.645 | 4.78E-19 |
| rs10035564 | rs4571480 | 0.912 | 0.644 | 3.53E-19 |
| rs10035564 | rs2013513 | 0.912 | 0.644 | 3.53E-19 |
| rs10035564 | rs4492118 | 0.914 | 0.643 | 2.06E-19 |
| rs10035564 | rs2165009 | 0.914 | 0.643 | 2.06E-19 |
| rs10035564 | rs12522626 | 0.914 | 0.643 | 2.06E-19 |
| rs10035564 | rs16901937 | 0.913 | 0.625 | 4.75E-19 |
| rs10035564 | rs920328 | 0.834 | 0.580 | 4.14E-17 |
| rs10035564 | rs6869488 | 1.000 | 0.489 | 1.22E-15 |
| rs10035564 | rs4460145 | 1.000 | 0.489 | 1.22E-15 |
| rs10035564 | rs7731099 | 1.000 | 0.478 | 4.71E-15 |
| rs10035564 | rs7716101 | 1.000 | 0.463 | 7.32E-15 |
| rs10035564 | rs7709661 | 1.000 | 0.463 | 7.32E-15 |
| rs10035564 | rs7701679 | 1.000 | 0.463 | 8.99E-15 |
| rs10035564 | rs6894974 | 1.000 | 0.463 | 7.32E-15 |
| rs10035564 | rs6885307 | 1.000 | 0.463 | 7.32E-15 |
| rs10035564 | rs4533894 | 1.000 | 0.463 | 7.32E-15 |
| rs10035564 | rs12521639 | 1.000 | 0.463 | 7.32E-15 |
| rs10035564 | rs12054976 | 1.000 | 0.463 | 7.32E-15 |
| rs10035564 | rs4371761 | 1.000 | 0.452 | 2.30E-14 |
| rs10035564 | rs4502832 | 1.000 | 0.438 | 4.20E-14 |
| rs10035564 | rs4485937 | 1.000 | 0.438 | 4.20E-14 |
| rs10035564 | rs4389695 | 1.000 | 0.438 | 4.20E-14 |
| rs10035564 | rs4296810 | 1.000 | 0.438 | 4.20E-14 |
| rs10035564 | rs12522398 | 1.000 | 0.438 | 6.21E-14 |
| rs10035564 | rs10941692 | 1.000 | 0.438 | 4.20E-14 |
| rs10035564 | rs10044408 | 1.000 | 0.425 | 2.83E-13 |
| rs10035564 | rs7720104 | 1.000 | 0.400 | 1.04E-12 |
| rs10035564 | rs4493682 | 1.000 | 0.400 | 8.66E-13 |
| rs10035564 | rs4308490 | 1.000 | 0.400 | 1.04E-12 |
| rs10035564 | rs6876773 | 1.000 | 0.390 | 1.45E-12 |
| rs10035564 | rs7711446 | 1.000 | 0.388 | 2.05E-12 |
| rs10035564 | rs6893494 | 1.000 | 0.388 | 1.21E-12 |
| rs10035564 | rs12523157 | 1.000 | 0.388 | 1.21E-12 |
| rs10035564 | rs12514414 | 1.000 | 0.388 | 2.44E-12 |
| rs10035564 | rs11954598 | 1.000 | 0.388 | 1.21E-12 |
| rs10035564 | rs6864149 | 1.000 | 0.388 | 1.44E-12 |
| rs10035564 | rs6898476 | 1.000 | 0.375 | 5.36E-12 |
| rs10035564 | rs6890289 | 1.000 | 0.375 | 4.52E-12 |
| rs10035564 | rs4533895 | 1.000 | 0.375 | 4.52E-12 |
| rs10035564 | rs7709262 | 0.869 | 0.370 | 1.13E-10 |
| rs10035564 | rs1405918 | 0.768 | 0.368 | 6.67E-11 |
| rs10035564 | rs4357042 | 1.000 | 0.364 | 7.23E-12 |
| rs10035564 | rs1909937 | 1.000 | 0.364 | 6.12E-12 |
| rs10035564 | rs1472584 | 1.000 | 0.364 | 6.12E-12 |
| rs10035564 | rs1392970 | 1.000 | 0.364 | 6.12E-12 |
| rs10035564 | rs12523398 | 1.000 | 0.364 | 6.12E-12 |
| rs10035564 | rs12523359 | 1.000 | 0.364 | 7.23E-12 |
| rs10035564 | rs12522305 | 1.000 | 0.364 | 7.23E-12 |
| rs10035564 | rs12521953 | 1.000 | 0.364 | 6.12E-12 |
| rs10035564 | rs12516488 | 1.000 | 0.364 | 6.12E-12 |
| rs10035564 | rs12153189 | 1.000 | 0.364 | 6.12E-12 |
| rs10035564 | rs12153053 | 1.000 | 0.364 | 6.12E-12 |
| rs10035564 | rs11953498 | 1.000 | 0.364 | 6.12E-12 |
| rs10035564 | rs10941693 | 1.000 | 0.364 | 6.12E-12 |
| rs10035564 | rs16902068 | 1.000 | 0.364 | 6.12E-12 |
| rs10035564 | rs12514615 | 1.000 | 0.364 | 6.12E-12 |
| rs10035564 | rs6874127 | 0.865 | 0.357 | 3.92E-10 |
| rs10035564 | rs13187565 | 0.747 | 0.357 | 1.02E-09 |
| rs10035564 | rs4613718 | 1.000 | 0.356 | 6.97E-14 |
| rs10035564 | rs2625494 | 0.766 | 0.354 | 9.14E-11 |
| rs10035564 | rs2580258 | 0.766 | 0.354 | 9.14E-11 |
| rs10035564 | rs1351720 | 0.766 | 0.354 | 9.14E-11 |
| rs10035564 | rs12110137 | 0.766 | 0.354 | 9.14E-11 |
| rs10035564 | rs10073636 | 0.766 | 0.354 | 9.14E-11 |
| rs10035564 | rs10043792 | 0.766 | 0.354 | 9.14E-11 |
| rs10035564 | rs12520124 | 0.722 | 0.351 | 7.29E-10 |
| rs10035564 | rs4566805 | 1.000 | 0.350 | 3.68E-12 |
| rs10035564 | rs12520430 | 1.000 | 0.349 | 2.49E-11 |
| rs10035564 | rs6451796 | 0.863 | 0.345 | 5.58E-10 |
| rs10035564 | rs3923055 | 0.863 | 0.345 | 5.58E-10 |
| rs10035564 | rs1501361 | 0.863 | 0.345 | 5.58E-10 |
| rs10035564 | rs1392973 | 0.863 | 0.345 | 5.58E-10 |
| rs10035564 | rs2589162 | 0.756 | 0.340 | 6.65E-10 |
| rs10035564 | rs13183434 | 1.000 | 0.340 | 2.99E-11 |
| rs10035564 | rs7446090 | 0.922 | 0.339 | 6.66E-11 |
| rs10035564 | rs2580260 | 0.727 | 0.338 | 3.86E-10 |
| rs10035564 | rs7711444 | 1.000 | 0.337 | 6.16E-11 |
| rs10035564 | rs7446182 | 0.724 | 0.326 | 7.25E-10 |
| rs10035564 | rs6892627 | 0.724 | 0.326 | 7.25E-10 |
| rs10035564 | rs6451814 | 0.724 | 0.326 | 7.25E-10 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs10035564 | rs2337952 | 0.724 | 0.326 | 7.25E−10 |
| rs10035564 | rs2049656 | 0.724 | 0.326 | 7.25E−10 |
| rs10035564 | rs1483303 | 0.724 | 0.326 | 7.25E−10 |
| rs10035564 | rs12654213 | 0.721 | 0.324 | 6.86E−10 |
| rs10035564 | rs7717787 | 0.715 | 0.323 | 1.43E−09 |
| rs10035564 | rs7705696 | 0.715 | 0.323 | 1.43E−09 |
| rs10035564 | rs6893773 | 0.717 | 0.322 | 1.41E−09 |
| rs10035564 | rs2337951 | 0.717 | 0.322 | 1.41E−09 |
| rs10035564 | rs10078625 | 0.717 | 0.322 | 1.41E−09 |
| rs10035564 | rs2337483 | 0.721 | 0.322 | 1.78E−09 |
| rs10035564 | rs10036065 | 0.713 | 0.320 | 1.23E−09 |
| rs10035564 | rs755048 | 0.712 | 0.315 | 2.62E−09 |
| rs10035564 | rs1384732 | 0.710 | 0.314 | 3.47E−09 |
| rs10035564 | rs6451810 | 0.718 | 0.308 | 2.46E−09 |
| rs10035564 | rs6860200 | 0.678 | 0.307 | 5.17E−09 |
| rs10035564 | rs7732970 | 0.682 | 0.300 | 4.88E−09 |
| rs10035564 | rs6892594 | 0.682 | 0.300 | 4.88E−09 |
| rs10035564 | rs6451804 | 0.682 | 0.300 | 4.88E−09 |
| rs10035564 | rs7711528 | 0.838 | 0.299 | 3.91E−08 |
| rs10035564 | rs9687260 | 0.679 | 0.298 | 4.57E−09 |
| rs10035564 | rs7706116 | 0.679 | 0.298 | 4.57E−09 |
| rs10035564 | rs6451802 | 0.617 | 0.293 | 5.15E−08 |
| rs10035564 | rs4455566 | 0.672 | 0.293 | 8.79E−09 |
| rs10035564 | rs6451793 | 0.784 | 0.285 | 8.16E−08 |
| rs10035564 | rs10039283 | 0.674 | 0.283 | 1.09E−08 |
| rs10035564 | rs6895191 | 0.672 | 0.279 | 1.47E−08 |
| rs10035564 | rs6878425 | 0.672 | 0.279 | 1.47E−08 |
| rs10035564 | rs10462097 | 0.672 | 0.279 | 1.47E−08 |
| rs10035564 | rs7444176 | 0.672 | 0.279 | 2.05E−08 |
| rs10035564 | rs16902084 | 0.780 | 0.273 | 1.87E−07 |
| rs10035564 | rs1501358 | 0.838 | 0.272 | 4.94E−08 |
| rs10035564 | rs12655983 | 0.838 | 0.272 | 4.94E−08 |
| rs10035564 | rs16902083 | 0.778 | 0.265 | 1.49E−07 |
| rs10035564 | rs10941679 | 0.634 | 0.263 | 1.41E−07 |
| rs10035564 | rs6882139 | 0.632 | 0.258 | 6.10E−08 |
| rs10035564 | rs6451843 | 0.624 | 0.252 | 1.14E−07 |
| rs10035564 | rs6862655 | 0.815 | 0.250 | 3.35E−08 |
| rs10035564 | rs10059745 | 0.815 | 0.250 | 3.35E−08 |
| rs10035564 | rs7718785 | 0.521 | 0.246 | 2.76E−07 |
| rs10035564 | rs7444405 | 0.626 | 0.244 | 1.36E−07 |
| rs10035564 | rs4639238 | 0.812 | 0.243 | 4.87E−08 |
| rs10035564 | rs12374507 | 0.812 | 0.243 | 4.87E−08 |
| rs10035564 | rs10066953 | 0.812 | 0.243 | 4.87E−08 |
| rs10035564 | rs930395 | 0.686 | 0.242 | 4.25E−07 |
| rs10035564 | rs6866354 | 0.807 | 0.241 | 8.01E−08 |
| rs10035564 | rs10054521 | 0.811 | 0.239 | 6.85E−08 |
| rs10035564 | rs12520938 | 0.589 | 0.235 | 3.01E−07 |
| rs10035564 | rs7709131 | 0.592 | 0.234 | 3.01E−07 |
| rs10035564 | rs7445572 | 0.592 | 0.234 | 3.01E−07 |
| rs10035564 | rs6861150 | 0.818 | 0.227 | 8.14E−07 |
| rs10035564 | rs6451795 | 0.757 | 0.222 | 1.20E−06 |
| rs10035564 | rs13156198 | 0.585 | 0.220 | 6.49E−07 |
| rs10035564 | rs4569881 | 0.553 | 0.211 | 1.33E−06 |
| rs10035564 | rs13361919 | 0.553 | 0.211 | 1.33E−06 |
| rs10035564 | rs13185201 | 0.553 | 0.211 | 1.33E−06 |
| rs10035564 | rs10941740 | 0.561 | 0.210 | 4.73E−06 |
| rs10035564 | rs12697517 | 0.603 | 0.209 | 2.07E−06 |
| rs10035564 | rs12697503 | 0.600 | 0.209 | 2.90E−06 |
| rs10035564 | rs7443976 | 0.578 | 0.208 | 1.36E−06 |
| SNP E = rs11743392 | | | | |
| rs11743392 | rs13179818 | 0.927 | 0.831 | 4.07E−26 |
| rs11743392 | rs2625494 | 1.000 | 0.527 | 1.80E−19 |
| rs11743392 | rs2580258 | 1.000 | 0.527 | 1.80E−19 |
| rs11743392 | rs1351720 | 1.000 | 0.527 | 1.80E−19 |
| rs11743392 | rs6451810 | 1.000 | 0.527 | 3.30E−19 |
| rs11743392 | rs12110137 | 1.000 | 0.527 | 1.80E−19 |
| rs11743392 | rs10073636 | 1.000 | 0.527 | 1.80E−19 |
| rs11743392 | rs10043792 | 1.000 | 0.527 | 1.80E−19 |
| rs11743392 | rs1384732 | 1.000 | 0.517 | 4.95E−19 |
| rs11743392 | rs755048 | 1.000 | 0.513 | 8.25E−19 |
| rs11743392 | rs7446182 | 1.000 | 0.509 | 6.24E−19 |
| rs11743392 | rs2337483 | 1.000 | 0.509 | 1.13E−18 |
| rs11743392 | rs2049656 | 1.000 | 0.509 | 6.24E−19 |
| rs11743392 | rs1483303 | 1.000 | 0.509 | 6.24E−19 |
| rs11743392 | rs6892627 | 1.000 | 0.509 | 6.24E−19 |
| rs11743392 | rs6451814 | 1.000 | 0.509 | 6.24E−19 |
| rs11743392 | rs2589162 | 1.000 | 0.509 | 2.03E−18 |
| rs11743392 | rs2337952 | 1.000 | 0.509 | 6.24E−19 |
| rs11743392 | rs1405918 | 1.000 | 0.509 | 6.24E−19 |
| rs11743392 | rs12654213 | 1.000 | 0.509 | 6.24E−19 |
| rs11743392 | rs7444176 | 1.000 | 0.505 | 1.08E−17 |
| rs11743392 | rs6893773 | 1.000 | 0.505 | 1.03E−18 |
| rs11743392 | rs2580260 | 1.000 | 0.505 | 1.03E−18 |
| rs11743392 | rs2337951 | 1.000 | 0.505 | 1.03E−18 |
| rs11743392 | rs10078625 | 1.000 | 0.505 | 1.03E−18 |
| rs11743392 | rs10036065 | 1.000 | 0.505 | 1.03E−18 |
| rs11743392 | rs7717787 | 1.000 | 0.500 | 1.72E−18 |
| rs11743392 | rs7705696 | 1.000 | 0.500 | 1.72E−18 |
| rs11743392 | rs7732970 | 1.000 | 0.492 | 2.09E−18 |
| rs11743392 | rs6892594 | 1.000 | 0.492 | 2.09E−18 |
| rs11743392 | rs6451804 | 1.000 | 0.492 | 2.09E−18 |
| rs11743392 | rs9687260 | 1.000 | 0.492 | 2.09E−18 |
| rs11743392 | rs7706116 | 1.000 | 0.492 | 2.09E−18 |
| rs11743392 | rs4455566 | 1.000 | 0.487 | 3.45E−18 |
| rs11743392 | rs6860200 | 1.000 | 0.483 | 5.74E−18 |
| rs11743392 | rs13187565 | 1.000 | 0.479 | 1.77E−16 |
| rs11743392 | rs12520124 | 1.000 | 0.475 | 5.19E−17 |
| rs11743392 | rs7444405 | 0.951 | 0.461 | 1.77E−15 |
| rs11743392 | rs10039283 | 0.951 | 0.461 | 1.77E−15 |
| rs11743392 | rs7443976 | 0.951 | 0.460 | 3.54E−15 |
| rs11743392 | rs6895191 | 0.950 | 0.460 | 3.12E−15 |
| rs11743392 | rs6878425 | 0.950 | 0.460 | 3.12E−15 |
| rs11743392 | rs10462097 | 0.950 | 0.460 | 3.12E−15 |
| rs11743392 | rs6882139 | 0.950 | 0.444 | 5.53E−15 |
| rs11743392 | rs13156198 | 0.949 | 0.444 | 1.11E−14 |
| rs11743392 | rs10041478 | 0.948 | 0.438 | 3.12E−14 |
| rs11743392 | rs6451843 | 0.948 | 0.438 | 3.57E−14 |
| rs11743392 | rs10042199 | 0.947 | 0.433 | 8.75E−14 |
| rs11743392 | rs12520938 | 0.948 | 0.429 | 4.12E−14 |
| rs11743392 | rs7709131 | 0.948 | 0.428 | 3.36E−14 |
| rs11743392 | rs7445572 | 0.948 | 0.428 | 3.36E−14 |
| rs11743392 | rs6884716 | 0.948 | 0.428 | 3.36E−14 |
| rs11743392 | rs4302598 | 0.948 | 0.428 | 3.36E−14 |
| rs11743392 | rs4277924 | 0.948 | 0.428 | 3.36E−14 |
| rs11743392 | rs13361118 | 0.948 | 0.428 | 3.36E−14 |
| rs11743392 | rs13155231 | 0.948 | 0.428 | 3.36E−14 |
| rs11743392 | rs12654375 | 0.948 | 0.428 | 3.36E−14 |
| rs11743392 | rs12652235 | 0.948 | 0.428 | 3.36E−14 |
| rs11743392 | rs12523291 | 0.948 | 0.428 | 3.36E−14 |
| rs11743392 | rs12188166 | 0.948 | 0.428 | 3.36E−14 |
| rs11743392 | rs10941727 | 0.948 | 0.428 | 3.36E−14 |
| rs11743392 | rs6451802 | 1.000 | 0.428 | 9.62E−16 |
| rs11743392 | rs10805706 | 0.948 | 0.428 | 3.36E−14 |
| rs11743392 | rs4569881 | 0.947 | 0.413 | 9.91E−14 |
| rs11743392 | rs13361919 | 0.947 | 0.413 | 9.91E−14 |
| rs11743392 | rs13185201 | 0.947 | 0.413 | 9.91E−14 |
| rs11743392 | rs10941740 | 0.942 | 0.410 | 1.20E−12 |
| rs11743392 | rs12697503 | 0.856 | 0.402 | 3.42E−12 |
| rs11743392 | rs13186830 | 0.944 | 0.395 | 1.42E−12 |
| rs11743392 | rs12697517 | 0.848 | 0.390 | 1.27E−11 |
| rs11743392 | rs7713759 | 0.852 | 0.383 | 7.89E−12 |
| rs11743392 | rs13164722 | 0.852 | 0.383 | 7.89E−12 |
| rs11743392 | rs12153540 | 0.852 | 0.383 | 7.89E−12 |
| rs11743392 | rs11958686 | 0.849 | 0.381 | 1.35E−11 |
| rs11743392 | rs12697523 | 0.851 | 0.378 | 1.23E−11 |
| rs11743392 | rs12690678 | 0.851 | 0.378 | 1.23E−11 |
| rs11743392 | rs12656953 | 0.851 | 0.378 | 1.23E−11 |
| rs11743392 | rs7718785 | 1.000 | 0.362 | 3.18E−14 |
| rs11743392 | rs7719500 | 1.000 | 0.276 | 1.59E−11 |
| rs11743392 | rs2589181 | 1.000 | 0.276 | 1.59E−11 |
| rs11743392 | rs4367308 | 1.000 | 0.276 | 1.59E−11 |
| rs11743392 | rs4282323 | 1.000 | 0.276 | 1.59E−11 |
| rs11743392 | rs10041772 | 1.000 | 0.276 | 1.59E−11 |
| rs11743392 | rs10041767 | 1.000 | 0.276 | 1.59E−11 |
| rs11743392 | rs4283798 | 1.000 | 0.274 | 2.54E−11 |
| rs11743392 | rs13188585 | 1.000 | 0.270 | 6.52E−11 |
| rs11743392 | rs4626346 | 1.000 | 0.265 | 3.64E−11 |
| rs11743392 | rs13361609 | 1.000 | 0.265 | 4.42E−11 |
| rs11743392 | rs4975889 | 1.000 | 0.260 | 6.07E−11 |

TABLE 3-continued

HapMap SNPs with $r^2$ values >0.2 in relation to key SNPs in equivalence classes A-F.

| SNP 1 | SNP 2 | D' | R2 | p-min |
|---|---|---|---|---|
| rs11743392 | rs1852595 | 1.000 | 0.260 | 6.07E−11 |
| rs11743392 | rs10214369 | 1.000 | 0.260 | 6.07E−11 |
| rs11743392 | rs7700252 | 1.000 | 0.255 | 8.24E−11 |
| rs11743392 | rs1483308 | 1.000 | 0.255 | 8.24E−11 |
| rs11743392 | rs9686580 | 1.000 | 0.255 | 8.24E−11 |
| rs11743392 | rs7724971 | 1.000 | 0.255 | 8.24E−11 |
| rs11743392 | rs7719703 | 1.000 | 0.255 | 8.24E−11 |
| rs11743392 | rs7714713 | 1.000 | 0.255 | 8.24E−11 |
| rs11743392 | rs7703405 | 1.000 | 0.255 | 8.24E−11 |
| rs11743392 | rs7447232 | 1.000 | 0.255 | 8.24E−11 |
| rs11743392 | rs6898646 | 1.000 | 0.255 | 8.24E−11 |
| rs11743392 | rs6894784 | 1.000 | 0.255 | 8.24E−11 |
| rs11743392 | rs6894273 | 1.000 | 0.255 | 8.24E−11 |
| rs11743392 | rs6886950 | 1.000 | 0.255 | 8.24E−11 |
| rs11743392 | rs4560554 | 1.000 | 0.255 | 1.63E−10 |
| rs11743392 | rs4452566 | 1.000 | 0.255 | 1.16E−10 |
| rs11743392 | rs4437383 | 1.000 | 0.255 | 8.24E−11 |
| rs11743392 | rs4407637 | 1.000 | 0.255 | 8.24E−11 |
| rs11743392 | rs2337954 | 1.000 | 0.255 | 8.24E−11 |
| rs11743392 | rs16902221 | 1.000 | 0.255 | 8.24E−11 |
| rs11743392 | rs16902217 | 1.000 | 0.255 | 8.24E−11 |
| rs11743392 | rs13359915 | 1.000 | 0.255 | 8.24E−11 |
| rs11743392 | rs13357427 | 1.000 | 0.255 | 8.24E−11 |
| rs11743392 | rs13159362 | 1.000 | 0.255 | 1.16E−10 |
| rs11743392 | rs12109155 | 1.000 | 0.255 | 8.24E−11 |
| rs11743392 | rs10074312 | 1.000 | 0.255 | 8.24E−11 |
| rs11743392 | rs10066821 | 1.000 | 0.255 | 8.24E−11 |
| rs11743392 | rs10473389 | 1.000 | 0.255 | 8.24E−11 |
| rs11743392 | rs6414908 | 1.000 | 0.253 | 2.47E−10 |
| rs11743392 | rs10462095 | 1.000 | 0.252 | 1.87E−10 |
| rs11743392 | rs7445730 | 1.000 | 0.249 | 1.37E−10 |
| rs11743392 | rs4339358 | 1.000 | 0.249 | 1.37E−10 |
| rs11743392 | rs4242125 | 1.000 | 0.249 | 1.37E−10 |
| rs11743392 | rs16902199 | 1.000 | 0.249 | 1.37E−10 |
| rs11743392 | rs12655230 | 1.000 | 0.249 | 1.37E−10 |
| rs11743392 | rs6877477 | 1.000 | 0.243 | 3.19E−10 |
| rs11743392 | rs7706959 | 1.000 | 0.239 | 3.06E−10 |
| rs11743392 | rs7446602 | 1.000 | 0.239 | 3.06E−10 |
| rs11743392 | rs13356124 | 1.000 | 0.239 | 3.06E−10 |
| rs11743392 | rs4132311 | 1.000 | 0.237 | 3.86E−10 |
| rs11743392 | rs2878967 | 1.000 | 0.234 | 4.04E−10 |
| rs11743392 | rs16902186 | 1.000 | 0.234 | 4.04E−10 |
| rs11743392 | rs1564684 | 1.000 | 0.234 | 4.04E−10 |
| rs11743392 | rs1405916 | 1.000 | 0.234 | 4.04E−10 |
| rs11743392 | rs12653475 | 1.000 | 0.234 | 4.04E−10 |
| rs11743392 | rs12697498 | 1.000 | 0.232 | 1.15E−09 |
| rs11743392 | rs7722380 | 1.000 | 0.228 | 6.74E−10 |
| rs11743392 | rs4532370 | 1.000 | 0.224 | 8.78E−10 |
| rs11743392 | rs1483312 | 1.000 | 0.224 | 8.78E−10 |
| rs11743392 | rs1351719 | 1.000 | 0.224 | 8.78E−10 |
| rs11743392 | rs12656485 | 1.000 | 0.224 | 8.78E−10 |
| rs11743392 | rs10052977 | 0.919 | 0.224 | 7.24E−08 |
| rs11743392 | rs6451806 | 1.000 | 0.219 | 1.98E−09 |
| rs11743392 | rs1483309 | 1.000 | 0.215 | 1.89E−09 |
| rs11743392 | rs1483306 | 1.000 | 0.215 | 1.89E−09 |
| rs11743392 | rs13358718 | 1.000 | 0.215 | 1.89E−09 |
| rs11743392 | rs10472404 | 1.000 | 0.215 | 1.89E−09 |
| rs11743392 | rs10073055 | 1.000 | 0.215 | 1.89E−09 |
| rs11743392 | rs12518113 | 0.846 | 0.209 | 6.42E−07 |
| rs11743392 | rs4288123 | 1.000 | 0.209 | 3.15E−09 |
| rs11743392 | rs17268006 | 0.767 | 0.205 | 1.34E−06 |
| rs11743392 | rs4975924 | 0.844 | 0.204 | 8.60E−07 |
| rs11743392 | rs4128583 | 0.844 | 0.204 | 8.60E−07 |
| rs11743392 | rs12697524 | 0.844 | 0.204 | 8.60E−07 |
| rs11743392 | rs12523279 | 0.844 | 0.204 | 8.60E−07 |
| rs11743392 | rs12522090 | 0.844 | 0.204 | 8.60E−07 |
| rs11743392 | rs12019302 | 0.844 | 0.204 | 8.60E−07 |
| rs11743392 | rs11949184 | 0.844 | 0.204 | 8.60E−07 |
| rs11743392 | rs10941798 | 0.844 | 0.204 | 8.60E−07 |
| rs11743392 | rs10462111 | 0.844 | 0.204 | 8.60E−07 |
| rs11743392 | rs10941748 | 0.844 | 0.204 | 1.01E−06 |
| rs11743392 | rs4975948 | 0.836 | 0.202 | 1.67E−06 |
| rs11743392 | rs7721731 | 1.000 | 0.201 | 9.28E−09 |
| SNP F = rs7716600 | | | | |
| rs7716600 | rs930395 | 1.000 | 1.000 | 3.05E−27 |
| rs7716600 | rs10941679 | 1.000 | 0.777 | 1.77E−21 |
| rs7716600 | rs12651949 | 1.000 | 0.505 | 4.24E−14 |
| rs7716600 | rs7715731 | 1.000 | 0.482 | 2.21E−14 |
| rs7716600 | rs10040082 | 1.000 | 0.480 | 2.37E−15 |
| rs7716600 | rs6868232 | 1.000 | 0.473 | 8.95E−15 |
| rs7716600 | rs7717459 | 1.000 | 0.471 | 2.94E−15 |
| rs7716600 | rs4642377 | 1.000 | 0.471 | 8.77E−15 |
| rs7716600 | rs10041518 | 1.000 | 0.471 | 2.94E−15 |
| rs7716600 | rs10040488 | 1.000 | 0.471 | 2.94E−15 |
| rs7716600 | rs10039866 | 1.000 | 0.471 | 2.94E−15 |
| rs7716600 | rs6893319 | 1.000 | 0.471 | 2.94E−15 |
| rs7716600 | rs6875933 | 1.000 | 0.471 | 2.94E−15 |
| rs7716600 | rs6872254 | 1.000 | 0.471 | 2.94E−15 |
| rs7716600 | rs6451778 | 1.000 | 0.471 | 2.94E−15 |
| rs7716600 | rs4373287 | 1.000 | 0.471 | 2.94E−15 |
| rs7716600 | rs1866406 | 1.000 | 0.471 | 2.94E−15 |
| rs7716600 | rs1438822 | 1.000 | 0.471 | 2.94E−15 |
| rs7716600 | rs1438819 | 1.000 | 0.471 | 2.94E−15 |
| rs7716600 | rs13189120 | 1.000 | 0.471 | 2.94E−15 |
| rs7716600 | rs13155698 | 1.000 | 0.471 | 2.94E−15 |
| rs7716600 | rs13154781 | 1.000 | 0.471 | 2.94E−15 |
| rs7716600 | rs12513749 | 1.000 | 0.471 | 2.94E−15 |
| rs7716600 | rs10462080 | 1.000 | 0.471 | 2.94E−15 |
| rs7716600 | rs10065638 | 1.000 | 0.471 | 2.94E−15 |
| rs7716600 | rs10059086 | 1.000 | 0.471 | 2.94E−15 |
| rs7716600 | rs10057521 | 1.000 | 0.471 | 2.94E−15 |
| rs7716600 | rs10053247 | 1.000 | 0.471 | 2.94E−15 |
| rs7716600 | rs7736092 | 1.000 | 0.468 | 3.68E−15 |
| rs7716600 | rs4457088 | 1.000 | 0.468 | 1.09E−14 |
| rs7716600 | rs10038554 | 1.000 | 0.468 | 1.09E−14 |
| rs7716600 | rs6894324 | 1.000 | 0.468 | 1.09E−14 |
| rs7716600 | rs6871052 | 1.000 | 0.468 | 3.68E−15 |
| rs7716600 | rs3747479 | 1.000 | 0.468 | 1.09E−14 |
| rs7716600 | rs10070037 | 1.000 | 0.468 | 3.68E−15 |
| rs7716600 | rs7708506 | 1.000 | 0.465 | 4.60E−15 |
| rs7716600 | rs6875287 | 1.000 | 0.461 | 1.69E−14 |
| rs7716600 | rs11741772 | 1.000 | 0.461 | 4.98E−14 |
| rs7716600 | rs12518851 | 1.000 | 0.459 | 2.75E−14 |
| rs7716600 | rs1438827 | 1.000 | 0.454 | 6.91E−15 |
| rs7716600 | rs11951760 | 1.000 | 0.451 | 3.30E−14 |
| rs7716600 | rs10043344 | 1.000 | 0.444 | 1.35E−14 |
| rs7716600 | rs11958808 | 1.000 | 0.437 | 1.57E−14 |
| rs7716600 | rs10044096 | 1.000 | 0.437 | 1.57E−14 |
| rs7716600 | rs7711697 | 1.000 | 0.437 | 4.46E−14 |
| rs7716600 | rs7380559 | 1.000 | 0.437 | 1.57E−14 |
| rs7716600 | rs4518409 | 1.000 | 0.437 | 1.57E−14 |
| rs7716600 | rs4329028 | 1.000 | 0.437 | 4.46E−14 |
| rs7716600 | rs1438821 | 1.000 | 0.437 | 1.57E−14 |
| rs7716600 | rs1438820 | 1.000 | 0.437 | 1.57E−14 |
| rs7716600 | rs13362132 | 1.000 | 0.437 | 1.57E−14 |
| rs7716600 | rs13160259 | 1.000 | 0.437 | 1.57E−14 |
| rs7716600 | rs1061310 | 1.000 | 0.437 | 1.57E−14 |
| rs7716600 | rs10512865 | 1.000 | 0.437 | 1.57E−14 |
| rs7716600 | rs1048758 | 1.000 | 0.437 | 1.57E−14 |
| rs7716600 | rs9292913 | 1.000 | 0.434 | 1.96E−14 |
| rs7716600 | rs7380878 | 1.000 | 0.434 | 5.55E−14 |
| rs7716600 | rs7716571 | 1.000 | 0.434 | 5.55E−14 |
| rs7716600 | rs13177711 | 1.000 | 0.434 | 1.96E−14 |
| rs7716600 | rs11949847 | 1.000 | 0.431 | 2.45E−14 |
| rs7716600 | rs920328 | 1.000 | 0.421 | 3.47E−14 |
| rs7716600 | rs9292914 | 1.000 | 0.404 | 7.68E−11 |
| rs7716600 | rs4571480 | 1.000 | 0.400 | 1.17E−13 |
| rs7716600 | rs2013513 | 1.000 | 0.400 | 1.17E−13 |
| rs7716600 | rs7735881 | 1.000 | 0.392 | 1.56E−13 |
| rs7716600 | rs7723539 | 1.000 | 0.392 | 1.56E−13 |
| rs7716600 | rs7720551 | 1.000 | 0.392 | 1.56E−13 |
| rs7716600 | rs714130 | 1.000 | 0.392 | 1.56E−13 |
| rs7716600 | rs6874055 | 1.000 | 0.392 | 4.15E−13 |
| rs7716600 | rs6861560 | 1.000 | 0.392 | 1.56E−13 |
| rs7716600 | rs6451770 | 1.000 | 0.392 | 1.56E−13 |

TABLE 3-continued

HapMap SNPs with r² values >0.2 in relation to key SNPs in equivalence classes A-F.

| SNP 1 | SNP 2 | D' | R2 | p-min |
|---|---|---|---|---|
| rs7716600 | rs4419600 | 1.000 | 0.392 | 1.56E-13 |
| rs7716600 | rs4415085 | 1.000 | 0.392 | 1.56E-13 |
| rs7716600 | rs4321755 | 1.000 | 0.392 | 1.56E-13 |
| rs7716600 | rs2218081 | 1.000 | 0.392 | 1.56E-13 |
| rs7716600 | rs2165010 | 1.000 | 0.392 | 4.15E-13 |
| rs7716600 | rs1438825 | 1.000 | 0.392 | 1.56E-13 |
| rs7716600 | rs13156930 | 1.000 | 0.392 | 1.56E-13 |
| rs7716600 | rs12515012 | 1.000 | 0.392 | 1.56E-13 |
| rs7716600 | rs12187196 | 1.000 | 0.392 | 1.56E-13 |
| rs7716600 | rs4463188 | 1.000 | 0.390 | 7.67E-13 |
| rs7716600 | rs920329 | 1.000 | 0.389 | 1.95E-13 |
| rs7716600 | rs1821936 | 1.000 | 0.389 | 1.95E-13 |
| rs7716600 | rs10941678 | 1.000 | 0.389 | 1.95E-13 |
| rs7716600 | rs10941677 | 1.000 | 0.389 | 5.16E-13 |
| rs7716600 | rs10805685 | 1.000 | 0.389 | 1.95E-13 |
| rs7716600 | rs4492118 | 1.000 | 0.385 | 2.44E-13 |
| rs7716600 | rs2165009 | 1.000 | 0.385 | 2.44E-13 |
| rs7716600 | rs12522626 | 1.000 | 0.385 | 2.44E-13 |
| rs7716600 | rs16901937 | 1.000 | 0.378 | 3.20E-13 |
| rs7716600 | rs9790896 | 0.931 | 0.370 | 6.39E-11 |
| rs7716600 | rs1482698 | 0.926 | 0.328 | 2.69E-10 |
| rs7716600 | rs13183434 | 0.685 | 0.314 | 1.52E-07 |
| rs7716600 | rs1482685 | 0.848 | 0.256 | 3.88E-08 |
| rs7716600 | rs1384451 | 0.848 | 0.256 | 3.88E-08 |
| rs7716600 | rs2200123 | 0.757 | 0.252 | 8.51E-07 |
| rs7716600 | rs11749656 | 1.000 | 0.248 | 4.20E-06 |
| rs7716600 | rs1482667 | 0.779 | 0.234 | 2.90E-07 |
| rs7716600 | rs11948186 | 0.679 | 0.233 | 9.05E-07 |
| rs7716600 | rs10051592 | 0.679 | 0.233 | 9.05E-07 |
| rs7716600 | rs10473355 | 0.770 | 0.231 | 5.67E-07 |
| rs7716600 | rs10472394 | 0.778 | 0.231 | 3.47E-07 |
| rs7716600 | rs2877162 | 0.777 | 0.229 | 3.52E-07 |
| rs7716600 | rs2330551 | 0.777 | 0.229 | 3.52E-07 |
| rs7716600 | rs10055789 | 0.777 | 0.229 | 3.52E-07 |
| rs7716600 | rs10055953 | 0.776 | 0.226 | 4.20E-07 |
| rs7716600 | rs987852 | 0.775 | 0.221 | 5.02E-07 |
| rs7716600 | rs4242112 | 0.775 | 0.221 | 5.02E-07 |
| rs7716600 | rs2330553 | 0.775 | 0.221 | 5.02E-07 |
| rs7716600 | rs12054807 | 0.775 | 0.221 | 5.02E-07 |
| rs7716600 | rs2877163 | 0.774 | 0.219 | 5.99E-07 |
| rs7716600 | rs10941665 | 0.774 | 0.219 | 5.99E-07 |
| rs7716600 | rs7356597 | 0.763 | 0.214 | 1.35E-06 |
| rs7716600 | rs10473354 | 0.760 | 0.207 | 1.87E-06 |

SNP 1 is the Illumina SNP with the lowest P-value in each of equivalence classes A-F.
SNP 2 is the HapMap SNP that is correlated to SNP 1.
D' is the mean D' value across all combinations of the alleles of SNP 1 and SNP 2.
R2 is the square of the correlation coefficient between the two SNPs.
p-min is the P-value corresponding to the strongest linkage disequilibrium observed between alleles of SNP 1 and SNP 2.

TABLE 4

Sequence Contexts of Key SNPs.

Key SNP A: rs4415084 deCODE Name: SG05S3092
(SEQ ID NO: 235)
caggttatgctactcctggaggacctctcaaaaggaagctgtttgt
tctatttctttctcatctgtcccaggactaggtattgcattaggagat
cccttgcttcccactgctgcttttaaatcatttcatttccttcttccc
ttcattcttcccaaatgcaaggtctttcaactttcatttcgtgctaca
ctctgcccttattgctgctctctggaatttgtggtcactgtccctca
tacactgaaaactcacatacctctactctagccctgttgtattcctg
atgacttgagca[C/T]ccaagggagtgatacatacagcactggtcaa
tcatttctttacctgccacacatacagcaatcttaatttcaatagcc
ttagccactcattcccaaataatgcttggatcatgcacattatcatga
gtaaatacacccatgtctgaaatcctgatttcaagtacttcccaattt
ttctgtctttctttactttcagctcacagaaacaattcttccaccat
attaaaaactctaatccaattcacttgttccaccacttttttttattca
ttattctctcctgtctttactttcttcct

TABLE 4-continued

Sequence Contexts of Key SNPs.

Key SNP B: rs7703618 deCODE Name: SG05S3065
(SEQ ID NO: 140)
gtgaggacacagagccaaaccatttcaccagagggctgagtaactcta
atctggcaggatgattatcctacacaggttgcaatggccctgaaatt
tggacgcactttgtgagagaccagtgtctagataactaggaactaggt
aaatgttggagagctgcttcccttcatttctgtcattgtctgtttcat
ttcctttgcattgtttgttgatctgtattaaacaaaaatgaaagcaaa
ccttgtatctgagtctccattttaccaatcctcacatttatggttca
gtgtcttagtct[A/G]gtttcgaataacaagaaccttttgtacttgg
aagtataaaacttgatagcagcaacattattgatatttagagctcagt
acctgtctaattacaggcaggcagaaagaagtgtcaaggtattcttgc
ttatcaggtcacaggtaatttcttcctctaagaattcataaactgata
gactaatattggagaaagaaatgcaatttaattgctgaaagtctgttt
cagtttactggtcttgtaatagaggtaaaattctaaacaacttgggga
gctttggtgagaattaaaataggtgggtg Key SNP C: rs2067980 deCODE Name: SG05S3114
(SEQ ID NO: 160)
gaatatgacgtcatataggcattaatttccatgttatgaattcaccag
taaaattgtttaaacagagaagtaaacaagacgtaatgttattcagg
taaaagtagagagggaaaagaaatattggaaccagttcagcaaccaaa
atggtgccagagcccaagcatgagttattaaaggctggtggttcctct
ctcctgacccattaccattcttatctctgatgctccaggctgtcagtt
tcttctttttgaccatatacaggtaaggaaagcccatttatgagct
attttatttcca[A/G]gttttaaaaatgtcaattgatataggctatg
atctacagtaatgcttaatctattgaagttttttgcatcaaattccatc
ttaagatgcaagcctgaagcccatttaatgccaaatgtaaatacaagt
gctagtttcaaagggcaagattcaaagaaagacaaacagaagaaaagt
attttaattgctatctaaaagaaggctgtgttcttgggtgaatacttt
gttgatgtattttggggtagaaacagagggagaaataattatgtaatgt
taagctgttttctaaaattccagggctcc Key SNP D: rs10035564 deCODE Name: SG05S3104
acaataagttttagtgatattagatttttttcatttttggaagaaga
acagaaaaagtgtaaaaagatggaataatatagaaaatggtagctgga
ggattcaaagaagaactcacttttatcatgtcaaagctaaaatataaa
ttgtagattttgcatatgtacaatgagcagaaacacatagctgaagaa
agaagtgtgctaaataaataaatgaagtattaatgattgagcagagtc
ttagaaagttggacatgttaagagcattgaatctatttagccttttcat
gccatgcccaaa[A/G]tcagaatttttaacctatactaggactttaag
acaaaaaataggcaaacaaaatcacaaagtgttacaattgacatatgc
agtgaattgtttcccttaaaaacaacatttttttttttagttatatcac
tactataaaatttattcttcaacaggcaactaaacgtaatctggttta
atcttttttataaaggaacattttaaagtaattcttttctcctaaca
gaccatctatttcctctaaatctctttagctttaatatctattttag
cgataaacagtgcatgaaataaacagctc Key SNP E: rs11743392 deCODE Name: SG05S3093
aatctttcaaatatattcatctctcacttatttagggactgattatcc
aatttgtgaactatccctgtggcttctcctcttttctctaatgatttc
tcctctgcctatttccttaaatcgttttaatactaaatgagctgcatg
aaaacagaaaagaagctaaagcagcaaaatttgatacatataaacagt
actgcaaaagaatttcatttgtgctcatatgttttttgaattttcaatt
ttctgttaccccacttccatatttcacactccagattatgtcacccca
cccaactcccaa[C/T]aatttgaaattcaaatttggaaattcatcta
ttggttcatttagttggaaactgcatattcacaggtggagagtggaat
atatttcaaaaccacagagaaaaaaaaaaaaacgtaattcaacttcgt
taatttgttttaattttccaaagctggaaattgtctctatatctcaa
ttgatgagtttctgagctaaaacaaaacaaaacaaaacaaacatca
ttttcctgtaaccagatttcactgctttcattctaagcaagatgatata
aataacaatgagtagtcaagtatttattc Key SNP F: rs7716600
(SEQ ID NO: 125)
SG05S3097
aggcctaatggttgtatatatatattttttatttggtagcagaaaag
actttaaaatatgttgatgtttgcgaggtaaagcatctatgtagggca
ttactatcaaggctttttttttctgcttgagtctatattacaaacatt
ttattatgtctctgctgagattaattaaatgtgcaaattttcaattc
ctaatataaagataaaatgtaaagttgatccaaaaatacaaaaaagt
gataaaacttagtttgtaatatagactcatatatcatattttagttc
tatttcaatgct[A/G]tctagaattttttatcattgctttttacctga
agattcaaattgttttggcatcagtcgggaaatcagtttgtttagcta TABLE 4-continued Sequence Contexts of Key SNPs.

```
gcaaaaatagacattaataaataaacccagaatacttagaagagatag
atagggacccagatctctcaagaaatacggctacagctaattgctatt
tctacacaaattaacaagcaagctataaactggcatgtgggattttt
ttttttttttttctctgagacaaggtttcactctctctcccagacggg
agtgcagtggtaccatcttggttcagggc
```

TABLE 5

SNP and Centaurus Assay Description:

SNP name: SG05S3065 or rs7703618

Mapping information (Build 34)

chr5: 44.960080+

Assay SG05S3065.c1 of type CENTAURUS, status Verified

Forward Primer: GCAAACCTTGTATCTGAGTCTCCAT

Reverse Primer: GTGACCTGATAAGCAAGAATACCT

Vic probe: CTTA*GTCTGGT

Fam probe: TCT*T*A*GTCTAGT

Enhancer: TCGAATAACAAGAACC

*indicates a modified base as described in [Kutyavin, et al., (2006), Nucleic Acids Res, 34, e128].

EXAMPLE 2

Refinement of Association Signal on Chromosome 5p12, Correlation with Clinical Variables and Investigation of FGFR2 Locus on Chromosome 10q26

The signals we have identified on chromosome 5p12 localize to a large stretch of chromosome 5p12-11 exhibiting a low recombination. From this region we selected 10 SNPs from the Illumina Hap300 chip set, generated Centaurus SNP assays [Kutyavin, et al., (2006), Nucleic Acids Res, 34, e128] and typed them in additional samples from Iceland, and in replication samples from Sweden, Holland, Spain and the United States. In total, 5028 cases and 32090 controls of European ancestry were studied. The most strongly associated Illumina SNP in the region was rs4415084, the T allele giving a combined odds ratio (OR) of 1.16 and a P value of $6.4 \times 10^{-10}$, which meets the Bonferroni criteria for genome-wide significance (Table 6). In the replication samples alone, rs4415084 gave an OR of 1.14 ($P=7.5 \times 10^{-5}$). To refine the signal, we typed a further 11 SNPs that were not on the Illumina chip, but were in LD with Hap300 SNPs giving a substantial signal. Data from these SNPs is presented in Tables 6 and 7. The strongest overall signal (OR 1.19, $P=2.9 \times 10^{-11}$) originated from the G allele of rs10941679, a non-Illumina SNP that is correlated to rs4415084 (D'=0.99, $r^2=0.51$ in the Icelandic population, Table 8).

Allele G-rs10941679 is less common than T-rs4415084 and is almost completely contained on the T-rs4415084 background. However, in a multivariate analysis, T-rs4415084 retained nominal significance after correction for G-rs10941679 (P=0.042), and vice versa (P=0.0017, Table 9). Therefore, despite being highly correlated, neither SNP accounts completely for the observed signal at 5p12. We concluded that both T-rs4415084 and G-rs10941679 confer risk of breast cancer. Multivariate analysis revealed that the signal from SNP rs7703618 could be accounted for entirely by either T-rs4415084 or G-rs10941679 (Table 9).

We reviewed the medical records of the patients, if they were available, and analyzed the combined data from the Icelandic and replication sample sets for the two risk variants at 5p12 and marker rs1219648 at the FGFR2 locus on chromosome 10. All three variants conferred significantly greater risk of estrogen receptor (ER) positive breast cancer than of ER negative tumours (Tables 6 and 10). A similar preferential risk was seen for progesterone receptor positive tumours for the 5p12 variants (Table 10). We previously reported that susceptibility variants on 2q35 and 16q12 are particularly associated with ER positive tumours [Stacey, et al., (2007), Nat Genet]. The present findings add further support to the notion that ER positive and ER negative tumours have different genetic components to their risks.

The 5p12 SNPs also showed associations with lower histological grade, which was explained by the association with ER status in multivariate analysis. The FGFR2 SNP was more frequent in node positive than node negative tumours. There were no significant associations with tumour stage or histopathology (Table 10). No variant showed a significant association with age at diagnosis. The FGFR2SNP was associated with a family history of breast cancer, in line with previous reports [Huijts, et al., (2007), Breast Cancer Res, 9, R78; Easton, et al., (2007), Nature 447:1087-93]. Similar tendencies, though not statistically significant, were observed for the 5p12 SNPs (Table 11).

Methods

Patient and Control Selection:

Collection of blood samples and medical information from study subjects was conducted with informed consent and ethical review board approval in accordance with the Declaration of Helsinki.

Iceland:

Records of breast cancer diagnoses were obtained from the Icelandic Cancer Registry (ICR). The ICR contains all cases of invasive breast tumours and ductal or lobular carcinoma in-situ diagnosed in Iceland from Jan. 1, 1955. All prevalent cases living in Iceland who had a diagnosis entered into the ICR up to the end of December 2006 were eligible to participate in the study. The ICR contained records of 4785 individuals diagnosed during this period. Consent, samples and successful genotypes were obtained from approximately 2277 patients. Of these, genotypes were derived from Illumina Hap300 chips for 1791 patients and from Centaurus assays for 486 patients. The 26,199 Icelandic controls consisted of individuals selected from ongoing Illumina-based genome-wide association studies at deCODE. Individuals with a diagnosis of breast cancer in the ICR were excluded. Both male and female genders were included. In the Icelandic controls (and the foreign replication control groups described below) there were no significant differences between genders in the frequencies of SNPs listed in Table 6. Therefore we considered that these control groups provided reasonable representations of the population frequencies of the SNPs under investigation.

Spain:

The Spanish study patients were recruited from the Oncology Department of Zaragoza Hospital between March 2006 and August 2007. Genotyping was carried out satisfactorily on approximately 642 patients. The 1540 successfully genotyped controls had attended the University Hospital in Zaragoza for diseases other than cancer. Controls were questioned to rule out prior cancers before drawing the blood sample. All patients and controls were of European ethnicity.

Sweden:

The Swedish sample sets consisted of Familial and Consecutive patient series. The Familial breast cancer recruitment group consisted of 347 breast cancer patients who had been referred to the oncogenetic counselling clinic of the Karolinska University Hospital, Stockholm for investigation of a family history of breast cancer. Each patient came from a distinct family. All cases who met the current criteria for BRCA mutation screening had tested negative. The Consecutive breast cancer recruitment group was comprised of 482 consecutively recruited patients who were treated surgically for primary invasive breast cancer at the Departments of Oncology at Huddinge and Söder Hospitals (covering the population of southern Stockholm) from October 1998 to May 2000. Family history was not taken into account in the selection of patients for recruitment. Controls were 1302 blood donors and 448 cancer-free individuals of both genders. All controls were collected at the Karolinska University Hospital, Stockholm. There was no evidence of significant heterogeneity between the Familial and Consecutive series for any of the SNPs tested.

Holland:

Female patients diagnosed with breast cancer in the period 2005-2006 were selected from the regional cancer registry held by the Comprehensive Cancer Centre East in Nijmegen, the Netherlands. This cancer center keeps a population-based cancer registry and covers the eastern part of the Netherlands, a region with 1.3 million inhabitants. All patients diagnosed with breast cancer before the age of 70 were invited to participate in the study. The Comprehensive Cancer Centre East collected the clinical and pathology data for all patients in the cancer registry. These standard cancer registry data were supplemented with more detailed. data by extraction from the medical files in the hospitals where the patients were treated. Controls were collected in a survey in 2002-2003 by the Radboud University Nijmegen Medical Center. This survey, The Nijmegen Biomedical Study, was based on an age-stratified random sample of the population of Nijmegen. From this group 2034 control individuals, age-matched by frequency to the patient population, were selected and genotyped.

U.S. Multiethnic Cohort:

The Multiethnic Cohort study (MEC) consists of over 215,000 men and women in Hawaii and Los Angeles (with additional African-Americans from elsewhere in California). The cohort is comprised predominantly of African Americans, Native Hawaiians, Japanese Americans, Latinos and European Americans who entered the study between 1993 and 1996 by completing a 26-page self-administered questionnaire that asked detailed information about dietary habits, demographic factors, personal behaviors, history of prior medical conditions, family history of common cancers, and for women, reproductive history and exogenous hormone use. The participants were between the ages 45 and 75 at enrolment. Incident cancers in the MEC are identified by cohort linkage to population-based cancer Surveillance, Epidemiology and End Results (SEER) registries covering Hawaii and Los Angeles County, and to the California State cancer registry covering all of California. Beginning in 1994, blood samples were collected from incident breast cancer cases and a random sample of MEC participants to serve as a control pool for genetic analyses in the cohort. Eligible cases in the nested breast cancer case-control study consisted of women with incident invasive cancer diagnosed after enrolment in the MEC through Dec. 31, 2002. Controls were participants without breast cancer prior to entry into the cohort and without a diagnosis up to Dec. 31, 2002. Controls were frequency matched to cases based on race/ethnicity and age (in 5-year intervals).

Nigeria:

We obtained genotypes from 689 incident breast cancer cases and 469 controls from Ibadan, Nigeria. Cases were consecutively recruited at presentation and later histologically confirmed in the Departments of Surgery and Radiotherapy, University College Hospital, Ibadan, Nigeria. This hospital serves a catchment area of 3 million people and is an oncology referral centre for other hospitals in the region. Population-based controls were recruited randomly from the community adjoining the hospital. After a community consultation process, control subjects were invited to attend a clinic set up for the purposes of the study. Controls were cancer-free at recruitment and over 18 years of age.

Genotyping

Approximately 1791 Icelandic patients and 26199 controls were genotyped on Illumina Hap300 SNP arrays, as described previously [Stacey, et al., (2007), Nat Genet. 39:865-9]. All other genotyping was carried out using Nanongen Centaurus assays [Kutyavin, et al., (2006), Nucleic Acids Res, 34, e128] that were generated for SNPs shown in Table 7. Primer sequences are available on request. Centaurus SNP assays were validated by genotyping the HapMap CEU samples and comparing the genotypes with published data. Assays were rejected if they showed ≥1.5% mismatches with the HapMap data. Approximately 10% of the Icelandic case samples were genotyped on both Illumina and Nanogen platforms and the observed mismatch rate was lower than 0.5%. All genotyping was carried out at the deCODE Genetics facility. All physical coordinates are given according to NCBI Build 35.

Clinical Parameters

Estrogen and progesterone receptor status was derived from immunohistochemical or immunometric assay results reported in medical records. A receptor level of ≥10 fmol/mg or an immunohistochemical observation of ≥10% positive nuclei was considered to be positive. Stage was determined according to the American Joint Committee on Cancer, $6^{th}$ Edition. Histological subtype was determined from SNOMED-M (or equivalent ICDO) codes as follows: "Invasive Ductal Carcinoma": 8500/3, 8521/3; "DCIS" (Ductal Carcinoma In-Situ and related in-situ carcinomas): 8500/2, 8050/2, 8201/2, 8501/2, 8503/2, 8507/2, 8522/2; "Invasive Lobular Carcinoma": 8520/3; "LCIS" (Lobular Carcinoma In-Situ): 8520/2; "Tubular or Mucinous": 8211/3, 8480/3, 8481/3; "Medullary Carcinoma": 8510/3, 8512/3; "Mixed Invasive": 8522/3, 8523/3, 8524/3, 8541/3, 8543/3; "Other Invasive": 8050/3, 8141/3, 8200/3, 8260/3, 8323/3, 8401/3, 8490/3, 8501/3, 8503/3, 8504/3, 8530/3, 8540/3. Tumours with the following non-specific codes were excluded from analysis of histopathological types: 8000/3, 8010/2, 8010/3, 8010/6, 8020/3, 8140/2, 8140/3, 8230/3. Histological Grade was specified according to the Nottingham (Elston-Ellis) modification of the Scarff-Bloom-Richardson) system. Node status was analyzed for stages I to IIIB and was based on pathological staging obtained by axillary lymph node dissection and/or sentinel node biopsy. The Sweden Familal sample set was not used in analysis of clinical parameters.

Statistical Analyses

We calculated the OR for each SNP allele assuming the multiplicative model; i.e. assuming that the relative risk of the two alleles that a person carries multiplies. Allelic frequencies and OR are presented for the markers. The associated P values were calculated with the standard likelihood ratio $\chi^2$ statistic as implemented in the NEMO software package (Gretarsdottir S., et al., *Nat. Genet.* 35:131-38 (2003)). Confidence intervals were calculated assuming that the estimate of OR has a log-normal distribution. For SNPs that were in strong LD, whenever the genotype of one SNP was missing for an individual, the genotype of the correlated SNPs were used to impute genotypes through a likelihood approach as previously described (Gretarsdottir S., et al., *Nat. Genet.* 35:131-38 (2003)). This ensured that results presented for different SNPs were based on the same number of individuals, allowing meaningful comparisons of OR and P-values. Joint analyses of multiple case-control replication groups were carried out using a Mantel-Haenszel model in which the groups were allowed to have different population frequencies for alleles or genotypes but were assumed to have common relative risks. The tests of heterogeneity were performed by assuming that the allele frequencies were the same in all groups under the null hypothesis, but each group had a different allele frequency under the alternative hypothesis. Joint analyses of multiple groups of cases were performed using an extended Mantel-Haenszel model that corresponds to a polytomous logistic regression using the group indicator as a covariate. There was no evidence of heterogeneity between the replication sample sets for any of the SNPs tested. Association of risk variants with age at diagnosis and with histological grade were tested by linear regression between the parameter value and the number of copies of the risk allele carried by each individual.

For analysis of family history we calculated for each genotype a familial relative risk for first degree relatives by adapting our previously described method (Amundadottir L. T., et al., *PLoS Med.* 1:e65 (2004)) to accommodate genotype-specific familial relative risks ($gfRR_{gt}$). For each SNP genotype we determined a $gfRR_{gt}$ as:

$$gfRR_{gt} = \frac{a/r}{x/n}$$

where r is the number of first-degree relatives of breast cancer patients with genotype gt (counting multiple times those individuals who are related to more than one patient with genotype gt and a is the number of first-degree relatives of breast cancer patients with genotype gt who are themselves affected with breast cancer. In the denominator, n is the size of the population and x is the number of people in the population affected with the disease (from ICR records). In order to compare the observed $gfRR_{gt}$ of one genotype with another, we calculated the ratio $gfRR_{gt1}/gfRR_{gt2}$. The significance of these latter ratios was determined by simulation: Controls groups for each $gfRR_{gt}$ were drawn randomly from the set of breast cancer patients genotyped for the SNP in question. The control groups were the same size as each corresponding observed $gfRR_{gt}$ group and were matched on the numbers of parents listed in the Icelandic Genealogical Database (0, 1, or 2). Ten thousand iterations of control group $gfRR_{gt1}/gfRR_{gt2}$ ratios were calculated and the P value determined by counting how often the ratio for the control groups matched or exceed the observed $gfRR_{gt1}/gfRR_{gt2}$.

We calculated genotype specific ORs, by estimating the genotype frequencies in the population assuming Hardy-Weinberg equilibrium. No significant deviations from multiplicity were observed. Potential interactions between loci were examined using correlation tests of allele counts and by case-control association of carriers and non-carriers. No significant interactions were observed.

Some of the Icelandic patients and controls are related to each other, both within and between groups, causing the $\chi^2$ statistic to have a mean>1. We estimated the inflation factor by simulating genotypes through the Icelandic genealogy, as described previously (Grant S. F., et al., *Nat Genet.* 38:320-3 (2006)), and corrected the $\chi^2$ statistics for Icelandic OR's accordingly. The estimated inflation factor was 1.08 for the complete set of Icelanders (cases and controls) and smaller, but ≥1, for all the other subsets used in the analysis of the clinical phenotypes.

TABLE 6

Association of SNPs in 5p12 and 10q26 loci with risk for breast cancer

| Location | SNP | Allele | Sample Set | Number Cases | Number Controls | Frequency Cases | Frequency Controls | OR[a] | 95% CI | P[b] |
|---|---|---|---|---|---|---|---|---|---|---|
| 5p12 | rs4415084 | T | Iceland[c] | 2277 | 26199 | 0.409 | 0.372 | 1.17 | (1.10, 1.25) | $1.9 \times 10^{-6}$ |
| | | | Sweden | 833 | 1750 | 0.443 | 0.417 | 1.11 | (0.99, 1.25) | $8.0 \times 10^{-2}$ |
| | | | Holland | 744 | 2034 | 0.433 | 0.402 | 1.13 | (1.01, 1.28) | $3.9 \times 10^{-2}$ |
| | | | Spain | 642 | 1540 | 0.396 | 0.362 | 1.16 | (1.01, 1.33) | $3.3 \times 10^{-2}$ |
| | | | MEC European Americans | 532 | 567 | 0.471 | 0.424 | 1.21 | (1.01, 1.43) | $3.5 \times 10^{-6}$ |
| | | | Non-Icelanders[d] | 2751 | 5891 | 0.436 | 0.401 | 1.14 | (1.07, 1.22) | $7.5 \times 10^{-5}$ |
| | | | All samples[d] | 5028 | 32090 | 0.431 | 0.396 | 1.16 | (1.10, 1.21) | $6.4 \times 10^{-10}$ |
| | | | CGEMS[a] | 1141 | 1140 | 0.437 | 0.395 | 1.19 | | $2.2 \times 10^{-3}$ |
| | | | All ER Positive[d] | 2729 | 32090 | 0.444 | 0.396 | 1.23 | (1.16, 1.30) | $1.8 \times 10^{-11}$ |
| | | | All ER Negative[d] | 744 | 32090 | 0.391 | 0.396 | 0.98 | (0.88, 1.10) | $7.7 \times 10^{-1}$ |
| | | | All ER Positive vs Negative[d] | 2729 | 744 | 0.444 | 0.391 | 1.25 | (1.11, 1.41) | $2.0 \times 10^{-4}$ |
| 5p12 | rs10941679 | G | Iceland[c] | 2277 | 26199 | 0.269 | 0.235 | 1.20 | (1.11, 1.29) | $2.2 \times 10^{-6}$ |
| | | | Sweden | 833 | 1750 | 0.312 | 0.273 | 1.21 | (1.06, 1.37) | $3.8 \times 10^{-3}$ |
| | | | Holland | 744 | 2034 | 0.298 | 0.258 | 1.22 | (1.07, 1.39) | $3.2 \times 10^{-3}$ |
| | | | Spain | 642 | 1540 | 0.214 | 0.198 | 1.10 | (0.94, 1.30) | $2.3 \times 10^{-1}$ |
| | | | MEC European Americans | 532 | 567 | 0.293 | 0.253 | 1.23 | (1.02, 1.48) | $3.4 \times 10^{-2}$ |
| | | | Non-Icelanders[d] | 2751 | 5891 | 0.279 | 0.245 | 1.19 | (1.11, 1.28) | $2.9 \times 10^{-6}$ |
| | | | All samples[d] | 5028 | 32090 | 0.277 | 0.243 | 1.19 | (1.13, 1.26) | $2.9 \times 10^{-11}$ |
| | | | All ER Positive[d] | 2736 | 32090 | 0.288 | 0.243 | 1.27 | (1.19, 1.35) | $2.5 \times 10^{-12}$ |
| | | | All ER Negative[d] | 744 | 32090 | 0.254 | 0.243 | 1.05 | (0.92, 1.18) | $4.8 \times 10^{-1}$ |
| | | | All ER Positive vs Negative[d] | 2736 | 744 | 0.288 | 0.254 | 1.21 | (1.06, 1.38) | $4.2 \times 10^{-3}$ |

TABLE 6-continued

Association of SNPs in 5p12 and 10q26 loci with risk for breast cancer

| Location | SNP | Allele | Sample Set | Number Cases | Number Controls | Frequency Cases | Frequency Controls | OR[a] | 95% CI | P[b] |
|---|---|---|---|---|---|---|---|---|---|---|
| 5p12 | rs7703618 | G | All samples[d] | 5028 | 32090 | 0.389 | 0.366 | 1.13 | (1.08, 1.18) | $3.3 \times 10^{-7}$ |
| 5p12 | rs10035564 | G | All samples[d] | 5028 | 32090 | 0.312 | 0.301 | 1.10 | (1.04, 1.15) | $5.3 \times 10^{-4}$ |
| 5p12 | rs4866929 | A | All samples[d] | 5028 | 32090 | 0.527 | 0.519 | 1.04 | (1.00, 1.09) | $6.7 \times 10^{-2}$ |
| 5p12 | rs981782 | T | All samples[d] | 5028 | 32090 | 0.507 | 0.500 | 1.04 | (0.99, 1.09) | $1.0 \times 10^{-1}$ |
| 10q26 | rs1219648 | G | Iceland[c] | 2270 | 26190 | 0.492 | 0.453 | 1.17 | (1.10, 1.25) | $1.2 \times 10^{-6}$ |
| | | | Sweden | 822 | 1725 | 0.456 | 0.381 | 1.37 | (1.21, 1.54) | $3.0 \times 10^{-7}$ |
| | | | Holland | 741 | 2001 | 0.455 | 0.389 | 1.31 | (1.17, 1.48) | $8.7 \times 10^{-6}$ |
| | | | Spain | 635 | 1493 | 0.477 | 0.424 | 1.24 | (1.09, 1.41) | $1.5 \times 10^{-3}$ |
| | | | Non-Icelanders[d] | 2198 | 5219 | 0.463 | 0.398 | 1.31 | (1.22, 1.41) | $1.2 \times 10^{-13}$ |
| | | | All samples[d] | 4468 | 31409 | 0.470 | 0.412 | 1.23 | (1.17, 1.29) | $1.3 \times 10^{-17}$ |
| | | | All ER Positive[d] | 2354 | 31409 | 0.481 | 0.412 | 1.29 | (1.22, 1.38) | $3.4 \times 10^{-16}$ |
| | | | All ER Negative[d] | 657 | 31409 | 0.413 | 0.412 | 0.99 | (0.88, 1.10) | $8.3 \times 10^{-1}$ |
| | | | All ER Positive vs Negative[d] | 2354 | 657 | 0.481 | 0.413 | 1.30 | (1.15, 1.47) | $2.9 \times 10^{-5}$ |

[a]Allelic Odds Ratios calculated under the multiplicative model
[b]All P values are two sided and have been adjusted for relatedness and other potential stratification of the Icelandic cases and controls.
[c]Icelandic data are combined Illumina and Centaurus assay-derived replication data sets.
[d]For analyses of combined data for the "Non-Icelanders", "All Samples" and ER groups, the OR and P values were calculated using the Mantel-Haenszel method, and the frequencies as simple (arithmetic) means of the frequencies of individual groups.
[e]CGEMS data are displayed for comparative purposes only and were not included in any of the calculations.

TABLE 7

Association with breast cancer for all variants tested in 5p12

| Sample Set | Number Cases | Number Controls | Frequency Cases | Frequency Controls | OR | 95% CI | P | Allele | SNP |
|---|---|---|---|---|---|---|---|---|---|
| Iceland | 2277 | 26199 | 0.409 | 0.372 | 1.17 | (1.10, 1.25) | 1.9E−06 | T | rs4415084 |
| Sweden | 833 | 1750 | 0.443 | 0.417 | 1.11 | (0.99, 1.25) | 8.0E−02 | | |
| Holland | 744 | 2034 | 0.433 | 0.402 | 1.13 | (1.01, 1.28) | 3.9E−02 | | |
| Spain | 642 | 1540 | 0.396 | 0.362 | 1.16 | (1.01, 1.33) | 3.3E−02 | | |
| MEC European American | 532 | 567 | 0.471 | 0.424 | 1.21 | (1.01, 1.43) | 3.5E−02 | | |
| Non-Icelanders | 2751 | 5891 | 0.436 | 0.401 | 1.14 | (1.07, 1.22) | 7.5E−05 | | |
| All European Ancestry | 5028 | 32090 | 0.431 | 0.396 | 1.16 | (1.10, 1.21) | 6.4E−10 | | |
| MEC African American | 428 | 457 | 0.630 | 0.641 | 0.95 | (0.78, 1.16) | 6.5E−01 | | |
| Nigeria | 689 | 469 | 0.689 | 0.648 | 1.20 | (1.00, 1.44) | 4.6E−02 | | |
| Iceland | 2277 | 26199 | 0.269 | 0.235 | 1.20 | (1.11, 1.29) | 2.2E−06 | G | rs10941679 |
| Sweden | 833 | 1750 | 0.312 | 0.273 | 1.21 | (1.06, 1.37) | 3.8E−03 | | |
| Holland | 744 | 2034 | 0.298 | 0.258 | 1.22 | (1.07, 1.39) | 3.2E−03 | | |
| Spain | 642 | 1540 | 0.214 | 0.198 | 1.10 | (0.94, 1.30) | 2.3E−01 | | |
| MEC European American | 532 | 567 | 0.293 | 0.253 | 1.23 | (1.02, 1.48) | 3.4E−02 | | |
| Non-Icelanders | 2751 | 5891 | 0.279 | 0.245 | 1.19 | (1.11, 1.28) | 2.9E−06 | | |
| All European Ancestry | 5028 | 32090 | 0.277 | 0.243 | 1.19 | (1.13, 1.26) | 2.9E−11 | | |
| MEC African American | 428 | 457 | 0.218 | 0.213 | 1.03 | (0.82, 1.29) | 8.0E−01 | | |
| Nigeria | 689 | 469 | 0.175 | 0.191 | 0.90 | (0.72, 1.12) | 3.3E−01 | | |
| Iceland | 2277 | 26199 | 0.393 | 0.356 | 1.18 | (1.10, 1.25) | 9.8E−07 | G | rs7703618 |
| Sweden | 833 | 1750 | 0.405 | 0.386 | 1.08 | (0.96, 1.22) | 1.9E−01 | | |
| Holland | 744 | 2034 | 0.398 | 0.383 | 1.06 | (0.94, 1.20) | 3.3E−01 | | |
| Spain | 642 | 1540 | 0.324 | 0.313 | 1.05 | (0.91, 1.21) | 4.8E−01 | | |
| MEC European American | 532 | 567 | 0.427 | 0.391 | 1.16 | (0.98, 1.38) | 9.2E−02 | | |
| Non-Icelanders | 2751 | 5891 | 0.388 | 0.368 | 1.08 | (1.01, 1.16) | 2.3E−02 | | |
| All European Ancestry | 5028 | 32090 | 0.389 | 0.366 | 1.13 | (1.08, 1.18) | 3.3E−07 | | |
| MEC African American | 428 | 457 | 0.349 | 0.348 | 1.01 | (0.83, 1.22) | 9.4E−01 | | |
| Nigeria | 689 | 469 | 0.327 | 0.335 | 0.96 | (0.81, 1.15) | 6.9E−01 | | |
| Iceland | 2277 | 26199 | 0.288 | 0.261 | 1.14 | (1.07, 1.23) | 1.8E−04 | G | rs10035564 |
| Sweden | 833 | 1750 | 0.322 | 0.313 | 1.04 | (0.92, 1.18) | 5.1E−01 | | |
| Holland | 744 | 2034 | 0.331 | 0.319 | 1.06 | (0.93, 1.20) | 3.9E−01 | | |
| Spain | 642 | 1540 | 0.309 | 0.310 | 0.99 | (0.86, 1.14) | 9.1E−01 | | |
| Non-Icelanders | 2751 | 5891 | 0.321 | 0.314 | 1.03 | (0.96, 1.09) | 4.0E−01 | | |
| All European Ancestry | 5028 | 32090 | 0.312 | 0.301 | 1.10 | (1.04, 1.15) | 5.3E−04 | | |

TABLE 7-continued

Association with breast cancer for all variants tested in 5p12

| Sample Set | Number | | Frequency | | OR | 95% CI | P | Allele | SNP |
|---|---|---|---|---|---|---|---|---|---|
| | Cases | Controls | Cases | Controls | | | | | |
| Nigeria | 689 | 469 | 0.767 | 0.739 | 1.17 | (0.95, 1.43) | 1.3E−01 | | |
| Iceland | 2277 | 26199 | 0.484 | 0.468 | 1.07 | (1.00, 1.14) | 4.6E−02 | A | rs4866929 |
| Sweden | 833 | 1750 | 0.515 | 0.514 | 1.01 | (0.90, 1.13) | 9.3E−01 | | |
| Holland | 744 | 2034 | 0.549 | 0.551 | 0.99 | (0.88, 1.12) | 8.8E−01 | | |
| Spain | 642 | 1540 | 0.502 | 0.489 | 1.05 | (0.93, 1.20) | 4.2E−01 | | |
| MEC European American | 532 | 567 | 0.585 | 0.572 | 1.05 | (0.89, 1.25) | 5.4E−01 | | |
| Non-Icelanders | 2751 | 5891 | 0.538 | 0.531 | 1.02 | (0.96, 1.09) | 5.6E−01 | | |
| All European Ancestry | 5028 | 32090 | 0.527 | 0.519 | 1.04 | (1.00, 1.09) | 6.7E−02 | | |
| MEC African American | 428 | 457 | 0.884 | 0.893 | 0.92 | (0.68, 1.24) | 5.7E−01 | | |
| Nigeria | 689 | 469 | 0.999 | 0.999 | NA | NA | NA | T | rs981782 |
| Iceland | 2277 | 26199 | 0.472 | 0.458 | 1.06 | (0.99, 1.13) | 8.4E−02 | | |
| Sweden | 833 | 1750 | 0.512 | 0.509 | 1.01 | (0.90, 1.14) | 8.4E−01 | | |
| Holland | 744 | 2034 | 0.544 | 0.543 | 1.00 | (0.89, 1.13) | 9.5E−01 | | |
| Spain | 642 | 1540 | 0.501 | 0.489 | 1.05 | (0.92, 1.19) | 5.0E−01 | | |
| Non-Icelanders | 2751 | 5891 | 0.519 | 0.514 | 1.02 | (0.95, 1.10) | 6.2E−01 | | |
| All European Ancestry | 5028 | 32090 | 0.507 | 0.500 | 1.04 | (0.99, 1.09) | 1.0E−01 | | |
| Nigeria | 689 | 469 | 0.999 | 0.999 | NA | NA | NA | T | rs4613718 |
| Iceland | 2277 | 26199 | 0.618 | 0.591 | 1.12 | (1.04, 1.21) | 3.5E−03 | | |
| Sweden | 833 | 1750 | 0.616 | 0.594 | 1.10 | (0.97, 1.24) | 1.3E−01 | | |
| Holland | 744 | 2034 | 0.637 | 0.593 | 1.20 | (1.06, 1.36) | 3.0E−03 | | |
| Spain | 642 | 1540 | 0.635 | 0.609 | 1.12 | (0.98, 1.28) | 9.8E−02 | | |
| Non-Icelanders | 2751 | 5891 | 0.629 | 0.599 | 1.16 | (1.08, 1.24) | 6.4E−05 | | |
| All European Ancestry | 5028 | 32090 | 0.627 | 0.597 | 1.14 | (1.08, 1.20) | 1.3E−06 | | |
| Nigeria | 689 | 469 | 0.763 | 0.755 | 1.05 | (0.86, 1.28) | 6.4E−01 | | |
| Iceland | 2277 | 26199 | 0.402 | 0.367 | 1.16 | (1.09, 1.24) | 5.2E−06 | G | rs994793 |
| Sweden | 833 | 1750 | 0.434 | 0.414 | 1.09 | (0.97, 1.22) | 1.7E−01 | | |
| Holland | 744 | 2034 | 0.438 | 0.411 | 1.12 | (0.99, 1.26) | 7.2E−02 | | |
| Spain | 642 | 1540 | 0.374 | 0.352 | 1.10 | (0.96, 1.26) | 1.6E−01 | | |
| Non-Icelanders | 2751 | 5891 | 0.415 | 0.392 | 1.11 | (1.03, 1.19) | 4.9E−03 | | |
| All European Ancestry | 5028 | 32090 | 0.412 | 0.386 | 1.14 | (1.09, 1.20) | 6.0E−08 | | |
| Nigeria | 689 | 469 | 0.623 | 0.611 | 1.05 | (0.88, 1.25) | 5.9E−01 | | |
| Iceland | 2277 | 26199 | 0.398 | 0.363 | 1.16 | (1.09, 1.24) | 4.7E−06 | T | rs6867533 |
| Sweden | 833 | 1750 | 0.431 | 0.412 | 1.08 | (0.96, 1.22) | 1.9E−01 | | |
| Holland | 744 | 2034 | 0.430 | 0.408 | 1.09 | (0.97, 1.23) | 1.4E−01 | | |
| Spain | 642 | 1540 | 0.370 | 0.349 | 1.10 | (0.96, 1.26) | 1.8E−01 | | |
| Non-Icelanders | 2751 | 5891 | 0.410 | 0.390 | 1.10 | (1.02, 1.18) | 9.8E−03 | | |
| All European Ancestry | 5028 | 32090 | 0.407 | 0.383 | 1.14 | (1.08, 1.19) | 1.1E−07 | | |
| Nigeria | 689 | 469 | 0.545 | 0.528 | 1.07 | (0.90, 1.27) | 4.3E−01 | | |
| Iceland | 2277 | 26199 | 0.236 | 0.209 | 1.17 | (1.08, 1.26) | 5.7E−05 | A | rs7716600 |
| Sweden | 833 | 1750 | 0.265 | 0.239 | 1.15 | (1.01, 1.32) | 3.8E−02 | | |
| Holland | 744 | 2034 | 0.254 | 0.235 | 1.11 | (0.97, 1.27) | 1.4E−01 | | |
| Spain | 642 | 1540 | 0.177 | 0.177 | 1.00 | (0.84, 1.19) | 9.8E−01 | | |
| Non-Icelanders | 2751 | 5891 | 0.232 | 0.217 | 1.11 | (1.02, 1.20) | 1.8E−02 | | |
| All European Ancestry | 5028 | 32090 | 0.233 | 0.215 | 1.15 | (1.08, 1.21) | 1.8E−06 | | |
| Nigeria | 689 | 469 | 0.169 | 0.194 | 0.85 | (0.68, 1.06) | 1.4E−01 | | |
| Iceland | 2277 | 26199 | 0.312 | 0.283 | 1.15 | (1.07, 1.24) | 8.0E−05 | A | rs3935086 |
| Sweden | 833 | 1750 | 0.316 | 0.311 | 1.02 | (0.90, 1.16) | 7.5E−01 | | |
| Holland | 744 | 2034 | 0.321 | 0.321 | 1.00 | (0.88, 1.14) | 9.8E−01 | | |
| Spain | 642 | 1540 | 0.308 | 0.310 | 0.99 | (0.86, 1.14) | 9.0E−01 | | |
| MEC European American | 532 | 567 | 0.380 | 0.349 | 1.15 | (0.94, 1.40) | 1.9E−01 | | |
| Non-Icelanders | 2751 | 5891 | 0.331 | 0.323 | 1.02 | (0.95, 1.10) | 5.6E−01 | | |
| All European Ancestry | 5028 | 32090 | 0.327 | 0.315 | 1.09 | (1.03, 1.14) | 1.3E−03 | | |
| CGEMS | NA | NA | NA | NA | NA | | NA | | |
| MEC African American | 428 | 457 | 0.706 | 0.702 | 1.02 | (0.84, 1.24) | 8.3E−01 | | |
| Nigeria | 689 | 469 | 0.831 | 0.799 | 1.24 | (1.00, 1.54) | 5.5E−02 | | |
| Iceland | 2277 | 26199 | 0.151 | 0.131 | 1.17 | (1.07, 1.28) | 4.7E−04 | G | rs2067980 |
| Sweden | 833 | 1750 | 0.165 | 0.148 | 1.14 | (0.97, 1.34) | 1.2E−01 | | |
| Holland | 744 | 2034 | 0.159 | 0.165 | 0.96 | (0.82, 1.13) | 6.0E−01 | | |
| Spain | 642 | 1540 | 0.126 | 0.139 | 0.89 | (0.73, 1.08) | 2.3E−01 | | |
| MEC European American | NA | NA | NA | NA | NA | | NA | | |

TABLE 7-continued

Association with breast cancer for all variants tested in 5p12

| Sample Set | Number | | Frequency | | OR | 95% CI | P | Allele | SNP |
|---|---|---|---|---|---|---|---|---|---|
| | Cases | Controls | Cases | Controls | | | | | |
| Non-Icelanders | 2751 | 5891 | 0.150 | 0.151 | 1.00 | (0.93, 1.09) | 9.5E−01 | | |
| All European Ancestry | 5028 | 32090 | 0.150 | 0.146 | 1.10 | (1.03, 1.17) | 6.3E−03 | | |
| Nigeria | 689 | 469 | 0.085 | 0.089 | 0.96 | (0.71, 1.30) | 7.7E−01 | | |
| Iceland | 2277 | 26199 | 0.199 | 0.182 | 1.12 | (1.03, 1.22) | 8.2E−03 | A | rs7731099 |
| Sweden | 833 | 1750 | 0.188 | 0.196 | 0.95 | (0.82, 1.10) | 5.0E−01 | | |
| Holland | 744 | 2034 | 0.200 | 0.198 | 1.02 | (0.88, 1.18) | 8.4E−01 | | |
| Spain | 642 | 1540 | 0.189 | 0.186 | 1.02 | (0.86, 1.20) | 8.2E−01 | | |
| MEC European American | NA | NA | NA | NA | NA | | NA | | |
| Non-Icelanders | 2751 | 5891 | 0.192 | 0.193 | 0.99 | (0.90, 1.10) | 8.9E−01 | | |
| All European Ancestry | 5028 | 32090 | 0.194 | 0.190 | 1.06 | (1.00, 1.13) | 5.9E−02 | | |
| Nigeria | 689 | 469 | 0.494 | 0.476 | 1.07 | (0.90, 1.28) | 4.1E−01 | | |
| Iceland | 2277 | 26199 | 0.123 | 0.105 | 1.20 | (1.08, 1.33) | 6.3E−04 | A | rs13183434 |
| Sweden | 833 | 1750 | 0.130 | 0.116 | 1.14 | (0.96, 1.37) | 1.4E−01 | | |
| Holland | 744 | 2034 | 0.130 | 0.136 | 0.95 | (0.80, 1.13) | 5.8E−01 | | |
| Spain | 642 | 1540 | 0.108 | 0.117 | 0.91 | (0.74, 1.12) | 3.8E−01 | | |
| Non-Icelanders | 2751 | 5891 | 0.123 | 0.123 | 1.00 | (0.85, 1.19) | 9.6E−01 | | |
| All European Ancestry | 5028 | 32090 | 0.123 | 0.118 | 1.12 | (1.04, 1.20) | 2.7E−03 | | |
| Nigeria | 689 | 469 | 0.072 | 0.072 | 1.00 | (0.73, 1.38) | 9.9E−01 | | |
| Iceland | 2277 | 26199 | 0.254 | 0.233 | 1.12 | (1.04, 1.21) | 2.1E−03 | G | rs10512875 |
| Sweden | 833 | 1750 | 0.282 | 0.279 | 1.01 | (0.89, 1.15) | 8.4E−01 | | |
| Holland | 744 | 2034 | 0.297 | 0.283 | 1.07 | (0.94, 1.22) | 3.0E−01 | | |
| Spain | 642 | 1540 | 0.277 | 0.280 | 0.99 | (0.85, 1.14) | 8.7E−01 | | |
| Non-Icelanders | 2751 | 5891 | 0.286 | 0.281 | 1.02 | (0.96, 1.09) | 5.3E−01 | | |
| All European Ancestry | 5028 | 32090 | 0.278 | 0.269 | 1.08 | (1.02, 1.14) | 5.2E−03 | | |
| Nigeria | 689 | 469 | 0.569 | 0.536 | 1.15 | (0.96, 1.36) | 1.3E−01 | | |
| Iceland | 2277 | 26199 | 0.285 | 0.262 | 1.12 | (1.05, 1.21) | 1.3E−03 | G | rs16902086 |
| Sweden | 833 | 1750 | 0.340 | 0.325 | 1.07 | (0.95, 1.21) | 2.8E−01 | | |
| Holland | 744 | 2034 | 0.335 | 0.329 | 1.03 | (0.91, 1.17) | 6.6E−01 | | |
| Spain | 642 | 1540 | 0.312 | 0.311 | 1.01 | (0.88, 1.16) | 9.1E−01 | | |
| MEC European American | 532 | 567 | 0.381 | 0.378 | 1.02 | (0.85, 1.21) | 8.7E−01 | | |
| Non-Icelanders | 2751 | 5891 | 0.342 | 0.335 | 1.03 | (0.96, 1.11) | 3.5E−01 | | |
| All European Ancestry | 5028 | 32090 | 0.331 | 0.321 | 1.08 | (1.02, 1.13) | 3.5E−03 | | |
| MEC African American | 428 | 457 | 0.689 | 0.687 | 1.01 | (0.83, 1.23) | 9.3E−01 | | |
| Nigeria | 689 | 469 | 0.791 | 0.747 | 1.28 | (1.05, 1.57) | 1.4E−02 | | |
| Iceland | 2277 | 26199 | 0.122 | 0.107 | 1.16 | (1.04, 1.30) | 9.9E−03 | A | rs6861150 |
| Sweden | 833 | 1750 | 0.123 | 0.123 | 1.00 | (0.83, 1.19) | 9.7E−01 | | |
| Holland | 744 | 2034 | 0.122 | 0.121 | 1.01 | (0.84, 1.21) | 9.1E−01 | | |
| Spain | 642 | 1540 | 0.110 | 0.119 | 0.91 | (0.74, 1.12) | 3.7E−01 | | |
| Non-Icelanders | 2751 | 5891 | 0.118 | 0.121 | 0.98 | (0.91, 1.07) | 7.0E−01 | | |
| All European Ancestry | 5028 | 32090 | 0.119 | 0.118 | 1.07 | (0.98, 1.15) | 1.2E−01 | | |
| Nigeria | 689 | 469 | 0.070 | 0.068 | 1.02 | (0.74, 1.40) | 9.2E−01 | | |
| Iceland | 2277 | 26199 | 0.127 | 0.111 | 1.17 | (1.04, 1.30) | 6.7E−03 | C | rs6451795 |
| Sweden | 833 | 1750 | 0.133 | 0.132 | 1.01 | (0.85, 1.20) | 9.1E−01 | | |
| Holland | 744 | 2034 | 0.130 | 0.130 | 1.00 | (0.84, 1.20) | 9.8E−01 | | |
| Spain | 642 | 1540 | 0.116 | 0.129 | 0.89 | (0.73, 1.09) | 2.6E−01 | | |
| Non-Icelanders | 2751 | 5891 | 0.127 | 0.130 | 0.97 | (0.87, 1.08) | 5.8E−01 | | |
| All European Ancestry | 5028 | 32090 | 0.127 | 0.125 | 1.06 | (0.99, 1.15) | 1.1E−01 | | |
| Nigeria | 689 | 469 | 0.474 | 0.463 | 1.05 | (0.88, 1.25) | 6.0E−01 | | |
| Iceland | 2277 | 26199 | 0.497 | 0.475 | 1.09 | (1.02, 1.16) | 6.7E−03 | T | rs11743392 |
| Sweden | 833 | 1750 | 0.499 | 0.513 | 0.95 | (0.84, 1.06) | 3.6E−01 | | |
| Holland | 744 | 2034 | 0.542 | 0.554 | 0.95 | (0.85, 1.07) | 4.2E−01 | | |
| Spain | 642 | 1540 | 0.498 | 0.485 | 1.05 | (0.93, 1.20) | 4.2E−01 | | |
| Non-Icelanders | 2751 | 5891 | 0.513 | 0.517 | 0.98 | (0.91, 1.05) | 5.6E−01 | | |
| All European Ancestry | 5028 | 32090 | 0.509 | 0.507 | 1.04 | (0.99, 1.09) | 9.5E−02 | | |
| Nigeria | 689 | 469 | 0.999 | 0.999 | NA | NA | NA | | |
| Iceland | 2277 | 26199 | 0.408 | 0.372 | 1.17 | (1.09, 1.25) | 1.8E−05 | T | rs7718785 |
| Sweden | 833 | 1750 | 0.382 | 0.406 | 0.90 | (0.80, 1.02) | 9.9E−02 | | |
| Holland | 744 | 2034 | 0.424 | 0.438 | 0.94 | (0.84, 1.06) | 3.5E−01 | | |
| Spain | 642 | 1540 | 0.408 | 0.400 | 1.03 | (0.90, 1.18) | 6.5E−01 | | |
| MEC European American | 532 | 567 | 0.472 | 0.463 | 1.04 | (0.86, 1.26) | 7.0E−01 | | |

TABLE 7-continued

Association with breast cancer for all variants tested in 5p12

| Sample Set | Number Cases | Number Controls | Frequency Cases | Frequency Controls | OR | 95% CI | P | Allele | SNP |
|---|---|---|---|---|---|---|---|---|---|
| Non-Icelanders | 2751 | 5891 | 0.422 | 0.427 | 0.96 | (0.90, 1.03) | 2.8E−01 | | |
| All European Ancestry | 5028 | 32090 | 0.419 | 0.416 | 1.05 | (1.00, 1.11) | 3.1E−02 | | |
| MEC African American | 428 | 457 | 0.659 | 0.675 | 0.93 | (0.70, 1.23) | 6.1E−01 | | |
| Nigeria | 689 | 469 | 0.710 | 0.663 | 1.24 | (1.03, 1.49) | 2.0E−02 | | |
| Iceland | 2277 | 26199 | 0.505 | 0.530 | 0.90 | (0.85, 0.97) | 2.9E−03 | G | rs13179818 |
| Sweden | 833 | 1750 | 0.507 | 0.492 | 1.06 | (0.95, 1.20) | 3.0E−01 | | |
| Holland | 744 | 2034 | 0.435 | 0.436 | 1.00 | (0.88, 1.12) | 9.4E−01 | | |
| Spain | 642 | 1540 | 0.495 | 0.537 | 0.84 | (0.74, 0.96) | 1.1E−02 | | |
| Non-Icelanders | 2751 | 5891 | 0.479 | 0.488 | 0.97 | (0.90, 1.04) | 4.3E−01 | | |
| All European Ancestry | 5028 | 32090 | 0.485 | 0.499 | 0.93 | (0.89, 0.98) | 6.0E−03 | | |
| Nigeria | 689 | 469 | 0.001 | 0.014 | 0.07 | (0.02, 0.28) | 2.1E−04 | | |

Allelic Odds Ratios calculated under the multiplicative model. All P values are two sided and have been adjusted for relatedness and other potential stratification of the Icelandic cases and controls. Icelandic data are combined Illumina and Centaurus assay-derived replication data sets. For analyses of combined data for the "Non-Icelanders" and "All European Ancestry" the OR and P values were calculated using the Mantel-Haenszel method, and the frequencies as simple (arithmetic) means of the frequencies of individual groups. CGEMS data are displayed for comparative purposes only and were not included in any of the calculations.

TABLE 8

LD relations between 5p12 SNPs in Iceland

| | rs981782 | rs4866929 | rs7703618 | rs10035564 | rs4415084 | rs10941679 | |
|---|---|---|---|---|---|---|---|
| rs981782 | NA | 0.94 | 0.10 | 0.38 | 0.06 | 0.01 | r2 |
| rs4866929 | 0.99 | NA | 0.11 | 0.37 | 0.07 | 0.02 | |
| rs7703618 | 0.39 | 0.43 | NA | 0.46 | 0.81 | 0.45 | |
| rs10035564 | 0.95 | 0.96 | 0.85 | NA | 0.37 | 0.13 | |
| rs4415084 | 0.29 | 0.32 | 0.94 | 0.79 | NA | 0.51 | |
| rs10941679 | 0.18 | 0.24 | 0.90 | 0.39 | 0.99 | NA | |
| | | | D' | | | | |

TABLE 9

Multivariate analysis of SNPs in 5p12

| | Adjusted for | | | | | | | | | | | |
|---|---|---|---|---|---|---|---|---|---|---|---|---|
| | rs4415084 | | rs10941679 | | rs7703618 | | rs10035564 | | rs4866929 | | rs981782 | |
| Tested Variant | P | OR | P | OR | P | OR | P | OR | P | OR | P | OR |
| rs4415084 | NA | NA | 4.2E−02 | 1.07 | 3.8E−04 | 1.19 | 2.8E−07 | 1.16 | 3.6E−09 | 1.16 | 2.6E−09 | 1.16 |
| rs10941679 | 1.7E−03 | 1.13 | NA | NA | 1.8E−05 | 1.17 | 1.3E−08 | 1.18 | 1.4E−10 | 1.19 | 1.0E−10 | 1.19 |
| rs7703618 | 4.9E−01 | 0.97 | 5.2E−01 | 1.02 | NA | NA | 1.8E−04 | 1.13 | 1.9E−06 | 1.13 | 1.4E−06 | 1.13 |
| rs10035564 | 6.9E−01 | 0.99 | 4.6E−01 | 1.02 | 8.9E−01 | 0.99 | NA | NA | 3.6E−03 | 1.10 | 1.9E−03 | 1.11 |
| rs4866929 | 9.8E−01 | 1.00 | 6.2E−01 | 1.01 | 9.2E−01 | 1.00 | 9.5E−01 | 0.99 | NA | NA | 4.0E−01 | 1.06 |
| rs981782 | 9.7E−01 | 1.00 | 6.3E−01 | 1.01 | 8.8E−01 | 1.00 | 5.6E−01 | 0.98 | 7.6E−01 | 0.98 | NA | NA |

TABLE 10

Clinical Correlations

| Sample/Comparison | Number Cases | Number Controls | Frequency Cases | Frequency Controls | OR | 95% CI | P | Allele | SNP |
|---|---|---|---|---|---|---|---|---|---|
| Estrogen Receptor test: ER positive vs control | | | | | | | | | |
| Iceland | 1129 | 26199 | 0.428 | 0.372 | 1.26 | (1.16, 1.38) | 8.9E−08 | 4 | rs4415084 |
| Sweden | 377 | 1750 | 0.443 | 0.417 | 1.11 | (0.95, 1.30) | 1.9E−01 | 4 | rs4415084 |
| Holland | 541 | 2034 | 0.441 | 0.403 | 1.17 | (1.02, 1.34) | 2.4E−02 | 4 | rs4415084 |

TABLE 10-continued

Clinical Correlations

| Sample/Comparison | Number | | Frequency | | OR | 95% CI | P | Allele | SNP |
|---|---|---|---|---|---|---|---|---|---|
| | Cases | Controls | Cases | Controls | | | | | |
| Spain | 320 | 1540 | 0.420 | 0.362 | 1.28 | (1.07, 1.52) | 6.4E−03 | 4 | rs4415084 |
| MEC European American | 362 | 567 | 0.486 | 0.424 | 1.28 | (1.06, 1.56) | 1.1E−02 | 4 | rs4415084 |
| All European Ancestry | 2729 | 32090 | 0.444 | 0.396 | 1.23 | (1.16, 1.30) | 1.8E−11 | 4 | rs4415084 |
| test: ER negative vs control | | | | | | | | | |
| Iceland | 361 | 26199 | 0.373 | 0.372 | 1.00 | (0.00, inf) | 1.0E+00 | 4 | rs4415084 |
| Sweden | 77 | 1750 | 0.384 | 0.417 | 0.87 | (0.62, 1.21) | 4.0E−01 | 4 | rs4415084 |
| Holland | 125 | 2034 | 0.388 | 0.402 | 0.94 | (0.72, 1.22) | 6.4E−01 | 4 | rs4415084 |
| Spain | 98 | 1540 | 0.343 | 0.361 | 0.92 | (0.68, 1.25) | 5.9E−01 | 4 | rs4415084 |
| MEC European American | 83 | 567 | 0.470 | 0.424 | 1.20 | (0.86, 1.68) | 2.9E−01 | 4 | rs4415084 |
| All European Ancestry | 744 | 32090 | 0.391 | 0.396 | 0.98 | (0.88, 1.10) | 7.7E−01 | 4 | rs4415084 |
| test: ER positive vs negative | | | | | | | | | |
| Iceland | 1129 | 361 | 0.428 | 0.373 | 1.26 | (1.06, 1.50) | 8.2E−03 | 4 | rs4415084 |
| Sweden | 377 | 77 | 0.443 | 0.384 | 1.28 | (0.90, 1.82) | 1.7E−01 | 4 | rs4415084 |
| Holland | 541 | 125 | 0.441 | 0.388 | 1.25 | (0.94, 1.65) | 1.3E−01 | 4 | rs4415084 |
| Spain | 320 | 98 | 0.420 | 0.343 | 1.39 | (1.00, 1.94) | 5.2E−02 | 4 | rs4415084 |
| MEC European American | 362 | 83 | 0.486 | 0.470 | 1.07 | (0.75, 1.51) | 7.2E−01 | 4 | rs4415084 |
| All European Ancestry | 2729 | 744 | 0.444 | 0.391 | 1.25 | (1.11, 1.41) | 2.0E−04 | 4 | rs4415084 |
| test: ER positive vs control | | | | | | | | | |
| Iceland | 1134 | 26199 | 0.284 | 0.236 | 1.29 | (1.17, 1.42) | 3.1E−07 | 3 | rs10941679 |
| Sweden | 377 | 1750 | 0.307 | 0.273 | 1.18 | (0.99, 1.40) | 6.4E−02 | 3 | rs10941679 |
| Holland | 541 | 2034 | 0.304 | 0.258 | 1.26 | (1.09, 1.46) | 2.4E−03 | 3 | rs10941679 |
| Spain | 320 | 1540 | 0.244 | 0.197 | 1.31 | (1.07, 1.61) | 9.5E−03 | 3 | rs10941679 |
| MEC European American | 364 | 567 | 0.302 | 0.253 | 1.28 | (1.04, 1.58) | 2.0E−02 | 3 | rs10941679 |
| All European Ancestry | 2736 | 32090 | 0.288 | 0.243 | 1.27 | (1.19, 1.35) | 2.5E−12 | 3 | rs10941679 |
| test: ER negative vs control | | | | | | | | | |
| Iceland | 361 | 26199 | 0.242 | 0.236 | 1.03 | (0.86, 1.24) | 7.2E−01 | 3 | rs10941679 |
| Sweden | 77 | 1750 | 0.266 | 0.273 | 0.97 | (0.67, 1.39) | 8.5E−01 | 3 | rs10941679 |
| Holland | 125 | 2034 | 0.267 | 0.258 | 1.05 | (0.78, 1.40) | 7.5E−01 | 3 | rs10941679 |
| Spain | 98 | 1540 | 0.184 | 0.197 | 0.91 | (0.63, 1.32) | 6.3E−01 | 3 | rs10941679 |
| MEC European American | 83 | 567 | 0.313 | 0.253 | 1.35 | (0.94, 1.93) | 1.0E−01 | 3 | rs10941679 |
| All European Ancestry | 744 | 32090 | 0.254 | 0.243 | 1.05 | (0.92, 1.18) | 4.8E−01 | 3 | rs10941679 |
| test: ER positive vs negative | | | | | | | | | |
| Iceland | 1134 | 361 | 0.284 | 0.242 | 1.25 | (1.03, 1.51) | 2.5E−02 | 3 | rs10941679 |
| Sweden | 377 | 77 | 0.307 | 0.266 | 1.22 | (0.83, 1.79) | 3.1E−01 | 3 | rs10941679 |
| Holland | 541 | 125 | 0.304 | 0.267 | 1.20 | (0.89, 1.64) | 2.4E−01 | 3 | rs10941679 |
| Spain | 320 | 98 | 0.244 | 0.184 | 1.43 | (0.96, 2.13) | 7.5E−02 | 3 | rs10941679 |
| MEC European American | 364 | 83 | 0.302 | 0.313 | 0.95 | (0.66, 1.37) | 7.7E−01 | 3 | rs10941679 |
| All European Ancestry | 2736 | 744 | 0.288 | 0.254 | 1.21 | (1.06, 1.38) | 4.2E−03 | 3 | rs10941679 |
| test: ER positive vs control | | | | | | | | | |
| Iceland | 1126 | 26190 | 0.504 | 0.453 | 1.23 | (1.13, 1.34) | 1.6E−06 | 3 | rs1219648 |
| Sweden | 372 | 1725 | 0.466 | 0.381 | 1.42 | (1.21, 1.67) | 1.6E−05 | 3 | rs1219648 |
| Holland | 539 | 2001 | 0.468 | 0.389 | 1.39 | (1.21, 1.59) | 2.5E−06 | 3 | rs1219648 |
| Spain | 317 | 1493 | 0.484 | 0.424 | 1.27 | (1.07, 1.51) | 5.8E−03 | 3 | rs1219648 |
| MEC European American | NA | NA | NA | NA | NA | (0.00, 0.00) | NA | 3 | rs1219648 |
| All European Ancestry | 2354 | 31409 | 0.481 | 0.412 | 1.29 | (1.22, 1.38) | 3.4E−16 | 3 | rs1219648 |
| test: ER negative vs control | | | | | | | | | |
| Iceland | 360 | 26190 | 0.440 | 0.453 | 0.95 | (0.82, 1.10) | 5.0E−01 | 3 | rs1219648 |
| Sweden | 76 | 1725 | 0.349 | 0.381 | 0.87 | (0.62, 1.22) | 4.3E−01 | 3 | rs1219648 |
| Holland | 124 | 2001 | 0.399 | 0.389 | 1.04 | (0.80, 1.36) | 7.5E−01 | 3 | rs1219648 |
| Spain | 97 | 1493 | 0.464 | 0.424 | 1.17 | (0.88, 1.57) | 2.8E−01 | 3 | rs1219648 |
| MEC European American | NA | NA | NA | NA | NA | (0.00, 0.00) | NA | 3 | rs1219648 |
| All European Ancestry | 657 | 31409 | 0.413 | 0.412 | 0.99 | (0.88, 1.10) | 8.3E−01 | 3 | rs1219648 |
| test: ER positive vs negative | | | | | | | | | |
| Iceland | 1126 | 360 | 0.504 | 0.440 | 1.29 | (1.09, 1.53) | 2.7E−03 | 3 | rs1219648 |
| Sweden | 372 | 76 | 0.466 | 0.349 | 1.63 | (1.14, 2.34) | 7.3E−03 | 3 | rs1219648 |
| Holland | 539 | 124 | 0.468 | 0.399 | 1.33 | (1.00, 1.75) | 4.7E−02 | 3 | rs1219648 |
| Spain | 317 | 97 | 0.484 | 0.464 | 1.08 | (0.79, 1.50) | 6.2E−01 | 3 | rs1219648 |
| MEC European American | NA | NA | NA | NA | NA | (0.00, 0.00) | NA | 3 | rs1219648 |
| All European Ancestry | 2354 | 657 | 0.481 | 0.413 | 1.30 | (1.15, 1.47) | 2.9E−05 | 3 | rs1219648 |
| Progesterone Receptor | | | | | | | | | |
| test: PR positive vs control | | | | | | | | | |
| Iceland | 1049 | 26199 | 0.422 | 0.372 | 1.23 | (1.13, 1.35) | 3.8E−06 | 4 | rs4415084 |
| Sweden | 300 | 1750 | 0.445 | 0.417 | 1.12 | (0.94, 1.34) | 2.0E−01 | 4 | rs4415084 |
| Holland | 404 | 2034 | 0.442 | 0.403 | 1.17 | (1.01, 1.37) | 4.0E−02 | 4 | rs4415084 |
| Spain | 269 | 1540 | 0.424 | 0.361 | 1.30 | (1.08, 1.57) | 6.0E−03 | 4 | rs4415084 |

TABLE 10-continued

Clinical Correlations

| | Number | | Frequency | | | | | | |
|---|---|---|---|---|---|---|---|---|---|
| Sample/Comparison | Cases | Controls | Cases | Controls | OR | 95% CI | P | Allele | SNP |
| MEC European American | 294 | 567 | 0.490 | 0.424 | 1.30 | (1.06, 1.60) | 1.2E−02 | 4 | rs4415084 |
| All European Ancestry | 2316 | 32090 | 0.445 | 0.396 | 1.22 | (1.15, 1.30) | 7.3E−10 | 4 | rs4415084 |
| test: PR negative vs control | | | | | | | | | |
| Iceland | 424 | 26199 | 0.393 | 0.372 | 1.09 | (0.95, 1.25) | 2.2E−01 | 4 | rs4415084 |
| Sweden | 98 | 1750 | 0.393 | 0.417 | 0.90 | (0.67, 1.21) | 5.0E−01 | 4 | rs4415084 |
| Holland | 260 | 2034 | 0.415 | 0.402 | 1.05 | (0.88, 1.27) | 5.8E−01 | 4 | rs4415084 |
| Spain | 144 | 1540 | 0.352 | 0.362 | 0.96 | (0.74, 1.23) | 7.4E−01 | 4 | rs4415084 |
| MEC European American | 126 | 567 | 0.468 | 0.424 | 1.19 | (0.89, 1.59) | 2.3E−01 | 4 | rs4415084 |
| All European Ancestry | 1052 | 32090 | 0.404 | 0.396 | 1.05 | (0.96, 1.15) | 2.7E−01 | 4 | rs4415084 |
| test: PR positive vs negative | | | | | | | | | |
| Iceland | 1049 | 424 | 0.422 | 0.393 | 1.13 | (0.96, 1.33) | 1.4E−01 | 4 | rs4415084 |
| Sweden | 300 | 98 | 0.445 | 0.393 | 1.24 | (0.89, 1.72) | 2.0E−01 | 4 | rs4415084 |
| Holland | 404 | 260 | 0.442 | 0.415 | 1.11 | (0.89, 1.39) | 3.4E−01 | 4 | rs4415084 |
| Spain | 269 | 144 | 0.424 | 0.351 | 1.36 | (1.01, 1.84) | 4.2E−02 | 4 | rs4415084 |
| MEC European American | 294 | 126 | 0.489 | 0.467 | 1.09 | (0.80, 1.49) | 5.8E−01 | 4 | rs4415084 |
| All European Ancestry | 2316 | 1052 | 0.445 | 0.404 | 1.16 | (1.04, 1.29) | 6.2E−03 | 4 | rs4415084 |
| test: PR positive vs control | | | | | | | | | |
| Iceland | 1054 | 26199 | 0.284 | 0.235 | 1.29 | (1.17, 1.43) | 5.8E−07 | 3 | rs10941679 |
| Sweden | 300 | 1750 | 0.307 | 0.273 | 1.18 | (0.98, 1.43) | 8.9E−02 | 3 | rs10941679 |
| Holland | 404 | 2034 | 0.299 | 0.258 | 1.23 | (1.04, 1.46) | 1.5E−02 | 3 | rs10941679 |
| Spain | 269 | 1540 | 0.240 | 0.197 | 1.28 | (1.03, 1.60) | 2.7E−02 | 3 | rs10941679 |
| MEC European American | 296 | 567 | 0.307 | 0.253 | 1.31 | (1.05, 1.64) | 1.7E−02 | 3 | rs10941679 |
| All European Ancestry | 2323 | 32090 | 0.288 | 0.243 | 1.27 | (1.18, 1.36) | 7.2E−11 | 3 | rs10941679 |
| test: PR negative vs control | | | | | | | | | |
| Iceland | 424 | 26199 | 0.243 | 0.236 | 1.04 | (0.88, 1.22) | 6.3E−01 | 3 | rs10941679 |
| Sweden | 98 | 1750 | 0.265 | 0.273 | 0.96 | (0.69, 1.33) | 8.1E−01 | 3 | rs10941679 |
| Holland | 260 | 2034 | 0.294 | 0.258 | 1.20 | (0.98, 1.47) | 8.2E−02 | 3 | rs10941679 |
| Spain | 144 | 1540 | 0.208 | 0.197 | 1.07 | (0.79, 1.44) | 6.6E−01 | 3 | rs10941679 |
| MEC European American | 126 | 567 | 0.313 | 0.253 | 1.35 | (1.00, 1.83) | 5.0E−02 | 3 | rs10941679 |
| All European Ancestry | 1052 | 32090 | 0.265 | 0.243 | 1.11 | (1.00, 1.23) | 5.4E−02 | 3 | rs10941679 |
| test: PR positive vs negative | | | | | | | | | |
| Iceland | 1054 | 424 | 0.284 | 0.243 | 1.24 | (1.03, 1.48) | 2.3E−02 | 3 | rs10941679 |
| Sweden | 300 | 98 | 0.307 | 0.265 | 1.23 | (0.86, 1.76) | 2.6E−01 | 3 | rs10941679 |
| Holland | 404 | 260 | 0.300 | 0.294 | 1.03 | (0.81, 1.31) | 8.1E−01 | 3 | rs10941679 |
| Spain | 269 | 144 | 0.240 | 0.208 | 1.20 | (0.85, 1.69) | 3.0E−01 | 3 | rs10941679 |
| MEC European American | 296 | 126 | 0.307 | 0.313 | 0.97 | (0.71, 1.33) | 8.5E−01 | 3 | rs10941679 |
| All European Ancestry | 2323 | 1052 | 0.288 | 0.265 | 1.14 | (1.02, 1.28) | 2.7E−02 | 3 | rs10941679 |
| test: PR positive vs control | | | | | | | | | |
| Iceland | 1047 | 26190 | 0.492 | 0.453 | 1.17 | (1.07, 1.28) | 4.6E−04 | 3 | rs1219648 |
| Sweden | 295 | 1725 | 0.456 | 0.381 | 1.36 | (1.14, 1.63) | 5.8E−04 | 3 | rs1219648 |
| Holland | 403 | 2001 | 0.457 | 0.389 | 1.32 | (1.13, 1.54) | 3.7E−04 | 3 | rs1219648 |
| Spain | 266 | 1493 | 0.477 | 0.424 | 1.24 | (1.03, 1.49) | 2.3E−02 | 3 | rs1219648 |
| MEC European American | NA | NA | NA | NA | NA | (0.00, 0.00) | NA | 3 | rs1219648 |
| All European Ancestry | 2011 | 31409 | 0.470 | 0.412 | 1.23 | (1.15, 1.32) | 7.1E−10 | 3 | rs1219648 |
| test: PR negative vs control | | | | | | | | | |
| Iceland | 423 | 26190 | 0.470 | 0.453 | 1.07 | (0.94, 1.23) | 3.1E−01 | 3 | rs1219648 |
| Sweden | 97 | 1725 | 0.407 | 0.381 | 1.12 | (0.83, 1.50) | 4.6E−01 | 3 | rs1219648 |
| Holland | 258 | 2001 | 0.448 | 0.389 | 1.27 | (1.06, 1.53) | 1.0E−02 | 3 | rs1219648 |
| Spain | 143 | 1493 | 0.490 | 0.424 | 1.30 | (1.02, 1.66) | 3.4E−02 | 3 | rs1219648 |
| MEC European American | NA | NA | NA | NA | NA | (0.00, 0.00) | NA | 3 | rs1219648 |
| All European Ancestry | 921 | 31409 | 0.454 | 0.412 | 1.16 | (1.06, 1.28) | 2.1E−03 | 3 | rs1219648 |
| test: PR positive vs negative | | | | | | | | | |
| Iceland | 1047 | 423 | 0.492 | 0.470 | 1.09 | (0.93, 1.28) | 2.9E−01 | 3 | rs1219648 |
| Sweden | 295 | 97 | 0.456 | 0.407 | 1.22 | (0.88, 1.69) | 2.4E−01 | 3 | rs1219648 |
| Holland | 403 | 258 | 0.457 | 0.448 | 1.04 | (0.83, 1.29) | 7.5E−01 | 3 | rs1219648 |
| Spain | 266 | 143 | 0.477 | 0.490 | 0.95 | (0.71, 1.27) | 7.4E−01 | 3 | rs1219648 |
| MEC European American | NA | NA | NA | NA | NA | (0.00, 0.00) | NA | 3 | rs1219648 |
| All European Ancestry | 2011 | 921 | 0.470 | 0.454 | 1.07 | (0.96, 1.19) | 2.5E−01 | 3 | rs1219648 |
| Histopathology: | | | | | | | | | |
| test: Invasive Ductal vs Control | | | | | | | | | |
| All European Ancestry | 2897 | 32090 | 0.431 | 0.396 | 1.17 | (1.10, 1.24) | 1.6E−07 | 4 | rs4415084 |
| All European Ancestry | 2899 | 32090 | 0.276 | 0.243 | 1.18 | (1.11, 1.26) | 4.7E−07 | 3 | rs10941679 |
| All European Ancestry | 2512 | 31409 | 0.465 | 0.412 | 1.21 | (1.14, 1.29) | 2.8E−10 | 3 | rs1219648 |

TABLE 10-continued

Clinical Correlations

| Sample/Comparison | Number | | Frequency | | OR | 95% CI | P | Allele | SNP |
|---|---|---|---|---|---|---|---|---|---|
| | Cases | Controls | Cases | Controls | | | | | |
| test: Invasive Lobular vs Control | | | | | | | | | |
| All European Ancestry | 419 | 32090 | 0.422 | 0.396 | 1.07 | (0.93, 1.23) | 3.4E−01 | 4 | rs4415084 |
| All European Ancestry | 419 | 32090 | 0.264 | 0.243 | 1.13 | (0.97, 1.33) | 1.2E−01 | 3 | rs10941679 |
| All European Ancestry | 363 | 31409 | 0.519 | 0.412 | 1.38 | (1.19, 1.60) | 2.2E−05 | 3 | rs1219648 |
| test: Tubular vs Control | | | | | | | | | |
| All European Ancestry | 187 | 32090 | 0.444 | 0.396 | 1.20 | (0.98, 1.48) | 7.8E−02 | 4 | rs4415084 |
| All European Ancestry | 187 | 32090 | 0.321 | 0.243 | 1.22 | (0.97, 1.53) | 9.6E−02 | 3 | rs10941679 |
| All European Ancestry | 149 | 31409 | 0.445 | 0.412 | 1.18 | (0.94, 1.49) | 1.5E−01 | 3 | rs1219648 |
| test: Other Invasive vs Control | | | | | | | | | |
| All European Ancestry | 75 | 30340 | 0.367 | 0.390 | 0.89 | (0.64, 1.24) | 4.9E−01 | 4 | rs4415084 |
| All European Ancestry | 75 | 30340 | 0.241 | 0.236 | 1.01 | (0.00, inf) | 1.0E+00 | 3 | rs10941679 |
| All European Ancestry | 58 | 29684 | 0.458 | 0.422 | 1.24 | (0.86, 1.79) | 2.5E−01 | 3 | rs1219648 |
| test: Mixed Invasive vs Control | | | | | | | | | |
| All European Ancestry | 192 | 30550 | 0.461 | 0.404 | 1.31 | (1.07, 1.61) | 8.5E−03 | 4 | rs4415084 |
| All European Ancestry | 192 | 30550 | 0.323 | 0.255 | 1.46 | (1.17, 1.83) | 8.0E−04 | 3 | rs10941679 |
| All European Ancestry | 147 | 29916 | 0.486 | 0.407 | 1.35 | (1.07, 1.71) | 1.1E−02 | 3 | rs1219648 |
| test: Medullary vs Control | | | | | | | | | |
| All European Ancestry | 43 | 30340 | 0.425 | 0.390 | 1.15 | (0.74, 1.77) | 5.4E−01 | 4 | rs4415084 |
| All European Ancestry | 43 | 30340 | 0.313 | 0.236 | 1.13 | (0.68, 1.87) | 6.3E−01 | 3 | rs10941679 |
| All European Ancestry | 42 | 29684 | 0.424 | 0.422 | 0.99 | (0.64, 1.53) | 9.7E−01 | 3 | rs1219648 |
| test: DCIS vs Control | | | | | | | | | |
| All European Ancestry | 275 | 30340 | 0.468 | 0.390 | 1.25 | (1.05, 1.49) | 1.1E−02 | 4 | rs4415084 |
| All European Ancestry | 275 | 30340 | 0.268 | 0.236 | 1.31 | (1.09, 1.59) | 5.1E−03 | 3 | rs10941679 |
| All European Ancestry | 272 | 29684 | 0.360 | 0.422 | 1.05 | (0.88, 1.25) | 5.9E−01 | 3 | rs1219648 |
| test: LCIS vs Control | | | | | | | | | |
| All European Ancestry | 28 | 29773 | 0.239 | 0.379 | 0.72 | (0.41, 1.27) | 2.6E−01 | 4 | rs4415084 |
| All European Ancestry | 28 | 29773 | 0.169 | 0.230 | 0.90 | (0.46, 1.78) | 7.7E−01 | 3 | rs10941679 |
| All European Ancestry | 28 | 29684 | 0.492 | 0.422 | 1.18 | (0.69, 2.00) | 5.4E−01 | 3 | rs1219648 |
| test: Other Non-invasive vs Control | | | | | | | | | |
| All European Ancestry | 12 | 28233 | 0.429 | 0.387 | 1.15 | (0.50, 2.65) | 7.5E−01 | 4 | rs4415084 |
| All European Ancestry | 12 | 28233 | 0.343 | 0.247 | 1.55 | (0.64, 3.77) | 3.4E−01 | 3 | rs10941679 |
| All European Ancestry | 12 | 28191 | 0.493 | 0.421 | 1.17 | (0.51, 2.64) | 7.1E−01 | 3 | rs1219648 |
| test: Heterogeneity, All Types | | | | | | | | | |
| All European Ancestry | NA | NA | NA | NA | NA | (0.00, 0.00) | 1.9E−01 | 4 | rs4415084 |
| All European Ancestry | NA | NA | NA | NA | NA | (0.00, 0.00) | 5.8E−01 | 3 | rs10941679 |
| All European Ancestry | NA | NA | NA | NA | NA | (0.00, 0.00) | 5.8E−01 | 3 | rs1219648 |
| test: Heterogeneity, Invasive Types | | | | | | | | | |
| All European Ancestry | NA | NA | NA | NA | NA | (0.00, 0.00) | 4.4E−01 | 4 | rs4415084 |
| All European Ancestry | NA | NA | NA | NA | NA | (0.00, 0.00) | 5.1E−01 | 3 | rs10941679 |
| All European Ancestry | NA | NA | NA | NA | NA | (0.00, 0.00) | 6.1E−01 | 3 | rs1219648 |
| Stage test: Stage 0 (in-situ) vs Control | | | | | | | | | |
| All European Ancestry | 267 | 29773 | 0.391 | 0.379 | 1.21 | (1.02, 1.45) | 2.9E−02 | 4 | rs4415084 |
| All European Ancestry | 267 | 29773 | 0.294 | 0.230 | 1.27 | (1.05, 1.55) | 1.5E−02 | 3 | rs10941679 |
| All European Ancestry | 265 | 29684 | 0.399 | 0.422 | 1.02 | (0.85, 1.21) | 8.5E−01 | 3 | rs1219648 |
| test: Stage 1 vs Control | | | | | | | | | |
| All European Ancestry | 1394 | 31523 | 0.412 | 0.388 | 1.19 | (1.10, 1.29) | 2.1E−05 | 4 | rs4415084 |
| All European Ancestry | 1394 | 31523 | 0.273 | 0.241 | 1.19 | (1.09, 1.30) | 1.5E−04 | 3 | rs10941679 |
| All European Ancestry | 1385 | 31409 | 0.473 | 0.412 | 1.23 | (1.13, 1.33) | 4.1E−07 | 3 | rs1219648 |
| test: Stage 2 vs Control | | | | | | | | | |
| All European Ancestry | 1161 | 31523 | 0.408 | 0.388 | 1.10 | (1.01, 1.21) | 2.5E−02 | 4 | rs4415084 |
| All European Ancestry | 1161 | 31523 | 0.272 | 0.241 | 1.22 | (1.11, 1.35) | 4.9E−05 | 3 | rs10941679 |
| All European Ancestry | 1156 | 31409 | 0.468 | 0.412 | 1.22 | (1.12, 1.33) | 5.3E−06 | 3 | rs1219648 |
| test: Stage 3 & 4 vs Control | | | | | | | | | |
| All European Ancestry | 438 | 31523 | 0.424 | 0.388 | 1.12 | (0.97, 1.29) | 1.1E−01 | 4 | rs4415084 |
| All European Ancestry | 438 | 31523 | 0.273 | 0.241 | 1.14 | (0.97, 1.33) | 1.1E−01 | 3 | rs10941679 |
| All European Ancestry | 435 | 31409 | 0.486 | 0.412 | 1.31 | (1.14, 1.50) | 1.1E−04 | 3 | rs1219648 |

TABLE 10-continued

Clinical Correlations

| Sample/Comparison | Number Cases | Number Controls | Frequency Cases | Frequency Controls | OR | 95% CI | P | Allele | SNP |
|---|---|---|---|---|---|---|---|---|---|
| test: Heterogeneity, Stages 1-4 | | | | | | | | | |
| All European Ancestry | NA | NA | NA | NA | NA | (0.00, 0.00) | 3.9E−01 | 4 | rs4415084 |
| All European Ancestry | NA | NA | NA | NA | NA | (0.00, 0.00) | 6.8E−01 | 3 | rs10941679 |
| All European Ancestry | NA | NA | NA | NA | NA | (0.00, 0.00) | 6.3E−01 | 3 | rs1219648 |
| test: All Invasvie Stages (1-4) vs Control | | | | | | | | | |
| All European Ancestry | 3233 | 31523 | 0.416 | 0.388 | 1.15 | (1.09, 1.22) | 4.6E−07 | 4 | rs4415084 |
| All European Ancestry | 3233 | 31523 | 0.271 | 0.241 | 1.19 | (1.12, 1.27) | 1.6E−08 | 3 | rs10941679 |
| All European Ancestry | 3216 | 31409 | 0.472 | 0.412 | 1.24 | (1.17, 1.31) | 7.6E−15 | 3 | rs1219648 |
| test: In-situ (Stage 0) vs Invasive (Stage 1-4) | | | | | | | | | |
| All European Ancestry | 267 | 2749 | 0.391 | 0.410 | 1.04 | (0.86, 1.24) | 7.0E−01 | 4 | rs4415084 |
| All European Ancestry | 267 | 2749 | 0.294 | 0.260 | 1.05 | (0.86, 1.29) | 6.0E−01 | 3 | rs10941679 |
| All European Ancestry | 265 | 2739 | 0.399 | 0.480 | 0.84 | (0.70, 1.00) | 5.2E−02 | 3 | rs1219648 |
| Grade test: Grade 1 vs Control | | | | | | | | | |
| All European Ancestry | 471 | 31523 | 0.443 | 0.388 | 1.26 | (1.10, 1.44) | 6.6E−04 | 4 | rs4415084 |
| All European Ancestry | 471 | 31523 | 0.295 | 0.241 | 1.25 | (1.08, 1.45) | 2.5E−03 | 3 | rs10941679 |
| All European Ancestry | 467 | 31409 | 0.479 | 0.412 | 1.21 | (1.06, 1.39) | 4.4E−03 | 3 | rs1219648 |
| test: Grade 2 vs Control | | | | | | | | | |
| All European Ancestry | 985 | 31523 | 0.428 | 0.388 | 1.20 | (1.09, 1.31) | 1.8E−04 | 4 | rs4415084 |
| All European Ancestry | 985 | 31523 | 0.287 | 0.241 | 1.27 | (1.15, 1.41) | 5.5E−06 | 3 | rs10941679 |
| All European Ancestry | 981 | 31409 | 0.476 | 0.412 | 1.31 | (1.19, 1.43) | 1.8E−08 | 3 | rs1219648 |
| test: Grade 3 vs Control | | | | | | | | | |
| All European Ancestry | 690 | 31523 | 0.402 | 0.388 | 1.05 | (0.94, 1.17) | 4.2E−01 | 4 | rs4415084 |
| All European Ancestry | 690 | 31523 | 0.251 | 0.241 | 1.05 | (0.92, 1.19) | 4.7E−01 | 3 | rs10941679 |
| All European Ancestry | 683 | 31409 | 0.447 | 0.412 | 1.13 | (1.01, 1.26) | 2.8E−02 | 3 | rs1219648 |
| test: Trend Test Grade | | | | | | | | | |
| All European Ancestry | NA | NA | NA | NA | NA | (0.00, 0.00) | 1.8E−02 | 4 | rs4415084 |
| All European Ancestry | NA | NA | NA | NA | NA | (0.00, 0.00) | 2.0E−02 | 3 | rs10941679 |
| All European Ancestry | NA | NA | NA | NA | NA | (0.00, 0.00) | 2.9E−01 | 3 | rs1219648 |
| Node Status test: Node positive vs control | | | | | | | | | |
| All European Ancestry | 1120 | 31523 | 0.407 | 0.388 | 1.10 | (1.01, 1.21) | 2.6E−02 | 4 | rs4415084 |
| All European Ancestry | 1122 | 31523 | 0.264 | 0.241 | 1.16 | (1.05, 1.28) | 3.2E−03 | 3 | rs10941679 |
| All European Ancestry | 1113 | 31409 | 0.484 | 0.412 | 1.32 | (1.21, 1.44) | 2.0E−10 | 3 | rs1219648 |
| test: Node negative vs control | | | | | | | | | |
| All European Ancestry | 1883 | 31523 | 0.421 | 0.388 | 1.18 | (1.10, 1.26) | 4.3E−06 | 4 | rs4415084 |
| All European Ancestry | 1886 | 31523 | 0.276 | 0.241 | 1.22 | (1.12, 1.31) | 7.4E−07 | 3 | rs10941679 |
| All European Ancestry | 1873 | 31409 | 0.470 | 0.412 | 1.20 | (1.12, 1.28) | 3.0E−07 | 3 | rs1219648 |
| test: Node positive vs negative | | | | | | | | | |
| All European Ancestry | 1120 | 1883 | 0.406 | 0.421 | 0.94 | (0.84, 1.05) | 2.6E−01 | 4 | rs4415084 |
| All European Ancestry | 1122 | 1886 | 0.264 | 0.277 | 0.97 | (0.86, 1.09) | 5.6E−01 | 3 | rs10941679 |
| All European Ancestry | 1113 | 1873 | 0.484 | 0.470 | 1.11 | (1.00, 1.24) | 4.7E−02 | 3 | rs1219648 |

TABLE 11

1° Familial Relative Risks by SNP Genotype

| SNP | Location | Genotype 1 | # Affected with Genotype 1 | gfRRgt1 | # of Affected 1° Relatives for Genotype 1 | Genotype 2 | # Affected with Genotype 2 | gfRRgt 2 | # of Affected 1° Relatives for Genotype 2 | gfRRgt1/ gfRRgt2 | P-value |
|---|---|---|---|---|---|---|---|---|---|---|---|
| rs4415084 | 5p12 | C/T | 1089 | 1.758 | 317 | C/C | 781 | 1.632 | 202 | 1.077 | 0.0822 |
| | | T/T | 373 | 1.932 | 111 | C/C | 781 | 1.632 | 202 | 1.184 | 0.0511 |
| | | T/T | 373 | 1.932 | 111 | C/T | 1089 | 1.758 | 317 | 1.099 | 0.2410 |

TABLE 11-continued

1° Familial Relative Risks by SNP Genotype

| SNP | Location | Genotype 1 | # Affected with Genotype 1 | gfRRgt1 | # of Affected 1° Relatives for Genotype 1 | Genotype 2 | # Affected with Genotype 2 | gfRRgt 2 | # of Affected 1° Relatives for Genotype 2 | gfRRgt1/ gfRRgt2 | P-value |
|---|---|---|---|---|---|---|---|---|---|---|---|
| rs10941679 | 5p12 | A/G | 884 | 1.832 | 262 | A/A | 1152 | 1.694 | 311 | 1.081 | 0.1314 |
|  |  | G/G | 148 | 2.192 | 50 | A/A | 1152 | 1.694 | 311 | 1.294 | 0.0599 |
|  |  | G/G | 148 | 2.192 | 50 | A/G | 884 | 1.832 | 262 | 1.197 | 0.1581 |
| rs1219648 | 10q26 | A/G | 1107 | 1.709 | 301 | A/A | 600 | 1.532 | 152 | 1.115 | 0.1152 |
|  |  | G/G | 563 | 2.063 | 186 | A/A | 600 | 1.532 | 152 | 1.346 | 0.0019 |
|  |  | G/G | 563 | 2.063 | 186 | A/G | 1107 | 1.709 | 301 | 1.207 | 0.0076 |

TABLE 12

Surrogate markers for marker rs4415084. Markers with values of $r^2$ greater than 0.2 to rs4415084 in the HapMap CEU dataset (http://www.hapmap.org) in a 1 Mb interval flanking the marker were selected. Shown is the name of the correlated SNP, values for $r^2$ and D' to rs4415084, and the corresponding P-value, as well as the position of the surrogate marker in NCBI Build 36 and a reference to the sequence id containing flanking sequnces for the marker.

| Anchor SNP | Corr SNP | $r^2$ | D' | P-value | Pos in Bld 36 | SEQ ID NO: |
|---|---|---|---|---|---|---|
| rs4415084 | rs4866900 | 0.236675 | 0.92417 | 3.02E−08 | 44480857 | 1 |
| rs4415084 | rs7712213 | 0.20783 | 1 | 4.15E−09 | 44487026 | 2 |
| rs4415084 | rs1482690 | 0.201693 | 1 | 5.32E−09 | 44524597 | 3 |
| rs4415084 | rs1482663 | 0.207207 | 1 | 3.23E−09 | 44578859 | 4 |
| rs4415084 | rs1351633 | 0.207207 | 1 | 3.23E−09 | 44579608 | 5 |
| rs4415084 | rs983940 | 0.207207 | 1 | 3.23E−09 | 44579893 | 6 |
| rs4415084 | rs4866905 | 0.207207 | 1 | 3.23E−09 | 44591624 | 7 |
| rs4415084 | rs10079222 | 0.207207 | 1 | 3.23E−09 | 44597230 | 8 |
| rs4415084 | rs4463187 | 0.259028 | 0.738181 | 3.59E−08 | 44604412 | 9 |
| rs4415084 | rs10054521 | 0.254284 | 0.736037 | 5.31E−08 | 44611928 | 10 |
| rs4415084 | rs10059745 | 0.267307 | 0.741785 | 2.28E−08 | 44622995 | 11 |
| rs4415084 | rs6862655 | 0.267307 | 0.741785 | 2.28E−08 | 44626667 | 12 |
| rs4415084 | rs4639238 | 0.267307 | 0.741785 | 2.28E−08 | 44627752 | 13 |
| rs4415084 | rs10066953 | 0.259028 | 0.738181 | 3.59E−08 | 44636753 | 14 |
| rs4415084 | rs12374507 | 0.259028 | 0.738181 | 3.59E−08 | 44640070 | 15 |
| rs4415084 | rs4573006 | 0.259028 | 0.738181 | 3.59E−08 | 44647407 | 16 |
| rs4415084 | rs4529201 | 0.259028 | 0.738181 | 3.59E−08 | 44649728 | 17 |
| rs4415084 | rs6866354 | 0.259028 | 0.738181 | 3.59E−08 | 44662567 | 18 |
| rs4415084 | rs4463188 | 1 | 1 | 7.12E−36 | 44678427 | 19 |
| rs4415084 | rs4321755 | 1 | 1 | 1.28E−36 | 44681952 | 20 |
| rs4415084 | rs4492118 | 1 | 1 | 2.08E−36 | 44682382 | 21 |
| rs4415084 | rs4613718 | 0.459459 | 1 | 2.24E−17 | 44685701 | 22 |
| rs4415084 | rs7735881 | 1 | 1 | 1.28E−36 | 44685933 | 23 |
| rs4415084 | rs7723539 | 1 | 1 | 1.28E−36 | 44695967 | 24 |
| rs4415084 | rs10805685 | 1 | 1 | 2.08E−36 | 44697715 | 25 |
| rs4415084 | rs10941677 | 1 | 1 | 5.45E−36 | 44698156 | 26 |
| rs4415084 | rs4415084 | 1 | 1 | — | 44698272 | 235 |
| rs4415084 | rs4415085 | 1 | 1 | 1.28E−36 | 44698716 | 27 |
| rs4415084 | rs7720551 | 1 | 1 | 1.28E−36 | 44700234 | 28 |
| rs4415084 | rs6874055 | 1 | 1 | 3.35E−36 | 44702722 | 29 |
| rs4415084 | rs4419600 | 1 | 1 | 1.28E−36 | 44714291 | 30 |
| rs4415084 | rs12187196 | 1 | 1 | 1.28E−36 | 44719576 | 31 |
| rs4415084 | rs12522626 | 1 | 1 | 3.38E−36 | 44721455 | 32 |
| rs4415084 | rs4571480 | 1 | 1 | 5.45E−36 | 44722945 | 33 |
| rs4415084 | rs6451770 | 1 | 1 | 1.28E−36 | 44727152 | 34 |
| rs4415084 | rs12515012 | 1 | 1 | 1.28E−36 | 44730292 | 35 |
| rs4415084 | rs2165009 | 1 | 1 | 2.08E−36 | 44733673 | 36 |
| rs4415084 | rs13156930 | 1 | 1 | 1.28E−36 | 44733792 | 37 |
| rs4415084 | rs920328 | 0.93135 | 1 | 1.41E−32 | 44734808 | 38 |
| rs4415084 | rs1821936 | 1 | 1 | 2.08E−36 | 44735239 | 39 |
| rs4415084 | rs714130 | 1 | 1 | 1.28E−36 | 44737175 | 40 |
| rs4415084 | rs2013513 | 1 | 1 | 5.45E−36 | 44738063 | 41 |
| rs4415084 | rs920329 | 1 | 1 | 2.71E−36 | 44738264 | 42 |
| rs4415084 | rs2218081 | 1 | 1 | 1.28E−36 | 44740897 | 43 |
| rs4415084 | rs10941679 | 0.512661 | 1 | 2.03E−17 | 44742255 | 44 |
| rs4415084 | rs2165010 | 1 | 1 | 3.35E−36 | 44742537 | 45 |
| rs4415084 | rs1438825 | 1 | 1 | 1.28E−36 | 44742688 | 46 |
| rs4415084 | rs6861560 | 1 | 1 | 1.28E−36 | 44744135 | 47 |
| rs4415084 | rs16901937 | 0.965497 | 1 | 1.66E−34 | 44744898 | 48 |

TABLE 12-continued

Surrogate markers for marker rs4415084. Markers with values of $r^2$ greater than 0.2 to rs4415084 in the HapMap CEU dataset (http://www.hapmap.org) in a 1 Mb interval flanking the marker were selected. Shown is the name of the correlated SNP, values for $r^2$ and D' to rs4415084, and the corresponding P-value, as well as the position of the surrogate marker in NCBI Build 36 and a reference to the sequence id containing flanking sequnces for the marker.

| Anchor SNP | Corr SNP | $r^2$ | D' | P-value | Pos in Bld 36 | SEQ ID NO: |
|---|---|---|---|---|---|---|
| rs4415084 | rs2218080 | 0.930737 | 0.964747 | 2.74E-31 | 44750087 | 49 |
| rs4415084 | rs11747159 | 0.708022 | 0.920891 | 7.34E-22 | 44773467 | 50 |
| rs4415084 | rs2330572 | 0.736776 | 0.889429 | 7.58E-23 | 44776746 | 51 |
| rs4415084 | rs994793 | 0.736776 | 0.889429 | 7.58E-23 | 44779004 | 52 |
| rs4415084 | rs1438827 | 0.677153 | 0.884157 | 1.15E-20 | 44787713 | 53 |
| rs4415084 | rs11949847 | 0.766182 | 0.922578 | 1.05E-23 | 44787926 | 54 |
| rs4415084 | rs7712949 | 0.708022 | 0.920891 | 7.34E-22 | 44806102 | 55 |
| rs4415084 | rs13154781 | 0.708022 | 0.920891 | 7.34E-22 | 44810784 | 56 |
| rs4415084 | rs11746980 | 0.767952 | 0.924573 | 4.51E-24 | 44813635 | 57 |
| rs4415084 | rs7711697 | 0.764101 | 0.924114 | 4.56E-23 | 44816160 | 58 |
| rs4415084 | rs16901964 | 0.708022 | 0.920891 | 7.34E-22 | 44819012 | 59 |
| rs4415084 | rs6875933 | 0.707417 | 0.920497 | 1.46E-21 | 44822453 | 60 |
| rs4415084 | rs727305 | 0.708022 | 0.920891 | 7.34E-22 | 44831799 | 61 |
| rs4415084 | rs13177711 | 0.767079 | 0.923589 | 6.86E-24 | 44832719 | 62 |
| rs4415084 | rs1438820 | 0.767952 | 0.924573 | 4.51E-24 | 44833527 | 63 |
| rs4415084 | rs1438819 | 0.708022 | 0.920891 | 7.34E-22 | 44833603 | 64 |
| rs4415084 | rs12651949 | 0.664841 | 0.910999 | 4.20E-16 | 44833869 | 65 |
| rs4415084 | rs10462080 | 0.708022 | 0.920891 | 7.34E-22 | 44834809 | 66 |
| rs4415084 | rs10462081 | 0.708022 | 0.920891 | 7.34E-22 | 44836422 | 67 |
| rs4415084 | rs13183209 | 0.708022 | 0.920891 | 7.34E-22 | 44839506 | 68 |
| rs4415084 | rs6872254 | 0.708022 | 0.920891 | 7.34E-22 | 44839541 | 69 |
| rs4415084 | rs7717459 | 0.708022 | 0.920891 | 7.34E-22 | 44840282 | 70 |
| rs4415084 | rs13159598 | 0.767952 | 0.924573 | 4.51E-24 | 44841683 | 71 |
| rs4415084 | rs3761648 | 0.701985 | 0.919139 | 5.44E-21 | 44843836 | 72 |
| rs4415084 | rs3747479 | 0.701985 | 0.919139 | 5.44E-21 | 44844919 | 73 |
| rs4415084 | rs1866406 | 0.708022 | 0.920891 | 7.34E-22 | 44845702 | 74 |
| rs4415084 | rs13174122 | 0.708022 | 0.920891 | 7.34E-22 | 44846497 | 75 |
| rs4415084 | rs11746506 | 0.708022 | 0.920891 | 7.34E-22 | 44848323 | 76 |
| rs4415084 | rs12188871 | 0.679189 | 0.918911 | 7.59E-21 | 44849761 | 77 |
| rs4415084 | rs11741772 | 0.698764 | 0.917793 | 8.18E-21 | 44850354 | 78 |
| rs4415084 | rs7716571 | 0.762262 | 0.923792 | 2.31E-23 | 44852741 | 79 |
| rs4415084 | rs7720787 | 0.767952 | 0.924573 | 4.51E-24 | 44853066 | 80 |
| rs4415084 | rs9637783 | 0.708022 | 0.920891 | 7.34E-22 | 44855403 | 81 |
| rs4415084 | rs1061310 | 0.767952 | 0.924573 | 4.51E-24 | 44856607 | 82 |
| rs4415084 | rs4457089 | 0.708022 | 0.920891 | 7.34E-22 | 44857493 | 83 |
| rs4415084 | rs13189120 | 0.708022 | 0.920891 | 7.34E-22 | 44858040 | 84 |
| rs4415084 | rs930395 | 0.402174 | 1 | 5.87E-14 | 44858215 | 85 |
| rs4415084 | rs10512865 | 0.767952 | 0.924573 | 4.51E-24 | 44859124 | 86 |
| rs4415084 | rs6867533 | 0.767952 | 0.924573 | 4.51E-24 | 44863049 | 87 |
| rs4415084 | rs6868232 | 0.698768 | 0.920271 | 4.63E-21 | 44863437 | 88 |
| rs4415084 | rs12513749 | 0.707719 | 0.920694 | 1.47E-21 | 44863960 | 89 |
| rs4415084 | rs12518851 | 0.687491 | 0.910529 | 1.15E-18 | 44863988 | 90 |
| rs4415084 | rs1048758 | 0.767952 | 0.924573 | 4.51E-24 | 44864351 | 91 |
| rs4415084 | rs13155698 | 0.708022 | 0.920891 | 7.34E-22 | 44864438 | 92 |
| rs4415084 | rs13160259 | 0.767952 | 0.924573 | 4.51E-24 | 44864721 | 93 |
| rs4415084 | rs6896350 | 0.708022 | 0.920891 | 7.34E-22 | 44868328 | 94 |
| rs4415084 | rs1371025 | 0.707156 | 0.91986 | 1.09E-21 | 44869990 | 95 |
| rs4415084 | rs4596389 | 0.708022 | 0.920891 | 7.34E-22 | 44872313 | 96 |
| rs4415084 | rs6451775 | 0.708022 | 0.920891 | 7.34E-22 | 44872545 | 97 |
| rs4415084 | rs7380559 | 0.767952 | 0.924573 | 4.51E-24 | 44872767 | 98 |
| rs4415084 | rs729599 | 0.708022 | 0.920891 | 7.34E-22 | 44878017 | 99 |
| rs4415084 | rs987394 | 0.708022 | 0.920891 | 7.34E-22 | 44882135 | 100 |
| rs4415084 | rs7715731 | 0.686969 | 0.917461 | 6.41E-20 | 44882601 | 101 |
| rs4415084 | rs4440370 | 0.708022 | 0.920891 | 7.34E-22 | 44889109 | 102 |
| rs4415084 | rs4492119 | 0.707417 | 0.920497 | 1.46E-21 | 44891371 | 103 |
| rs4415084 | rs7703497 | 0.708022 | 0.920891 | 7.34E-22 | 44892785 | 104 |
| rs4415084 | rs6451778 | 0.708022 | 0.920891 | 7.34E-22 | 44893745 | 105 |
| rs4415084 | rs13362132 | 0.767952 | 0.924573 | 4.51E-24 | 44894017 | 106 |
| rs4415084 | rs1438821 | 0.762608 | 0.922391 | 2.84E-23 | 44894208 | 107 |
| rs4415084 | rs1438822 | 0.708022 | 0.920891 | 7.34E-22 | 44894929 | 108 |
| rs4415084 | rs4373287 | 0.708022 | 0.920891 | 7.34E-22 | 44898641 | 109 |
| rs4415084 | rs6871052 | 0.706847 | 0.919658 | 2.18E-21 | 44899074 | 110 |
| rs4415084 | rs6893319 | 0.708022 | 0.920891 | 7.34E-22 | 44899486 | 111 |
| rs4415084 | rs10053247 | 0.708022 | 0.920891 | 7.34E-22 | 44899716 | 112 |
| rs4415084 | rs10040082 | 0.739047 | 0.957789 | 9.28E-23 | 44901611 | 113 |
| rs4415084 | rs10057521 | 0.708022 | 0.920891 | 7.34E-22 | 44901743 | 114 |
| rs4415084 | rs10065638 | 0.708022 | 0.920891 | 7.34E-22 | 44901919 | 115 |
| rs4415084 | rs6894324 | 0.702623 | 0.919555 | 2.73E-21 | 44903093 | 116 |
| rs4415084 | rs4395640 | 0.708022 | 0.920891 | 7.34E-22 | 44904857 | 117 |
| rs4415084 | rs10070037 | 0.708022 | 0.920891 | 7.34E-22 | 44905994 | 118 |
| rs4415084 | rs4518409 | 0.767952 | 0.924573 | 4.51E-24 | 44906609 | 119 |

TABLE 12-continued

Surrogate markers for marker rs4415084. Markers with values of $r^2$ greater than 0.2 to rs4415084 in the HapMap CEU dataset (http://www.hapmap.org) in a 1 Mb interval flanking the marker were selected. Shown is the name of the correlated SNP, values for $r^2$ and D' to rs4415084, and the corresponding P-value, as well as the position of the surrogate marker in NCBI Build 36 and a reference to the sequence id containing flanking sequnces for the marker.

| Anchor SNP | Corr SNP | $r^2$ | D' | P-value | Pos in Bld 36 | SEQ ID NO: |
|---|---|---|---|---|---|---|
| rs4415084 | rs9292913 | 0.767079 | 0.923589 | 6.86E−24 | 44906636 | 120 |
| rs4415084 | rs9292914 | 0.69671 | 0.906242 | 2.34E−18 | 44907138 | 121 |
| rs4415084 | rs10059086 | 0.708022 | 0.920891 | 7.34E−22 | 44907764 | 122 |
| rs4415084 | rs11951760 | 0.695917 | 0.914383 | 2.65E−20 | 44907929 | 123 |
| rs4415084 | rs4329028 | 0.767952 | 0.924573 | 4.51E−24 | 44908110 | 124 |
| rs4415084 | rs7716600 | 0.391985 | 1 | 1.56E−13 | 44910762 | 125 |
| rs4415084 | rs4412123 | 0.767952 | 0.924573 | 4.51E−24 | 44912045 | 126 |
| rs4415084 | rs7705343 | 0.767952 | 0.924573 | 4.51E−24 | 44915334 | 127 |
| rs4415084 | rs10040488 | 0.708022 | 0.920891 | 7.34E−22 | 44916045 | 128 |
| rs4415084 | rs4642377 | 0.703488 | 0.920589 | 1.84E−21 | 44920997 | 129 |
| rs4415084 | rs4391175 | 0.708022 | 0.920891 | 7.34E−22 | 44925813 | 130 |
| rs4415084 | rs4129642 | 0.708022 | 0.920891 | 7.34E−22 | 44933886 | 131 |
| rs4415084 | rs9790879 | 0.767952 | 0.924573 | 4.51E−24 | 44935642 | 132 |
| rs4415084 | rs9790896 | 0.702742 | 0.88242 | 3.43E−21 | 44935848 | 133 |
| rs4415084 | rs4457088 | 0.702623 | 0.919555 | 2.73E−21 | 44936711 | 134 |
| rs4415084 | rs4866784 | 0.708022 | 0.920891 | 7.34E−22 | 44936888 | 135 |
| rs4415084 | rs9791056 | 0.708022 | 0.920891 | 7.34E−22 | 44939648 | 136 |
| rs4415084 | rs6880275 | 0.708022 | 0.920891 | 7.34E−22 | 44944692 | 137 |
| rs4415084 | rs6870136 | 0.708022 | 0.920891 | 7.34E−22 | 44946419 | 138 |
| rs4415084 | rs6881563 | 0.708022 | 0.920891 | 7.34E−22 | 44948610 | 139 |
| rs4415084 | rs7703618 | 0.708022 | 0.920891 | 7.34E−22 | 44950336 | 140 |
| rs4415084 | rs10077814 | 0.767952 | 0.924573 | 4.51E−24 | 44952546 | 141 |
| rs4415084 | rs6451783 | 0.708022 | 0.920891 | 7.34E−22 | 44954050 | 142 |
| rs4415084 | rs4298259 | 0.708022 | 0.920891 | 7.34E−22 | 44956468 | 143 |
| rs4415084 | rs7736092 | 0.707156 | 0.91986 | 1.09E−21 | 44956752 | 144 |
| rs4415084 | rs7728431 | 0.705178 | 0.920232 | 1.49E−21 | 44958436 | 145 |
| rs4415084 | rs7708506 | 0.706267 | 0.918803 | 1.62E−21 | 44958461 | 146 |
| rs4415084 | rs10039866 | 0.708022 | 0.920891 | 7.34E−22 | 44960818 | 147 |
| rs4415084 | rs10043344 | 0.762771 | 0.922377 | 2.62E−23 | 44962275 | 148 |
| rs4415084 | rs10038554 | 0.702623 | 0.919555 | 2.73E−21 | 44962864 | 149 |
| rs4415084 | rs10044096 | 0.767952 | 0.924573 | 4.51E−24 | 44963122 | 150 |
| rs4415084 | rs10041518 | 0.708022 | 0.920891 | 7.34E−22 | 44963163 | 151 |
| rs4415084 | rs12517690 | 0.708022 | 0.920891 | 7.34E−22 | 44975050 | 152 |
| rs4415084 | rs6875287 | 0.700475 | 0.917171 | 1.83E−20 | 44977387 | 153 |
| rs4415084 | rs11958808 | 0.767952 | 0.924573 | 4.51E−24 | 44980847 | 154 |
| rs4415084 | rs3935086 | 0.519752 | 0.904005 | 1.24E−15 | 44996680 | 155 |
| rs4415084 | rs3935213 | 0.267659 | 0.850441 | 2.47E−08 | 44997201 | 156 |
| rs4415084 | rs4460145 | 0.278388 | 0.8543 | 1.01E−08 | 45004083 | 157 |
| rs4415084 | rs6869488 | 0.278388 | 0.8543 | 1.01E−08 | 45006273 | 158 |
| rs4415084 | rs6866995 | 0.259219 | 0.847224 | 3.63E−08 | 45012604 | 159 |
| rs4415084 | rs2067980 | 0.265513 | 1 | 1.01E−09 | 45018074 | 160 |
| rs4415084 | rs4296810 | 0.238566 | 0.836134 | 2.48E−07 | 45019919 | 161 |
| rs4415084 | rs7709661 | 0.243662 | 0.834245 | 4.06E−07 | 45039846 | 162 |
| rs4415084 | rs6894974 | 0.254787 | 0.839261 | 1.68E−07 | 45056288 | 163 |
| rs4415084 | rs4533894 | 0.255659 | 0.841387 | 1.41E−07 | 45060826 | 164 |
| rs4415084 | rs4371761 | 0.244535 | 0.83644 | 3.42E−07 | 45061977 | 165 |
| rs4415084 | rs7716101 | 0.255659 | 0.841387 | 1.41E−07 | 45065624 | 166 |
| rs4415084 | rs7731099 | 0.262636 | 0.841176 | 1.12E−07 | 45073783 | 167 |
| rs4415084 | rs7701679 | 0.232155 | 0.828648 | 9.87E−07 | 45078551 | 168 |
| rs4415084 | rs12522398 | 0.225046 | 0.82443 | 8.11E−07 | 45085230 | 169 |
| rs4415084 | rs4502832 | 0.238566 | 0.836134 | 2.48E−07 | 45087138 | 170 |
| rs4415084 | rs11948186 | 0.65068 | 0.916552 | 6.95E−20 | 45087191 | 171 |
| rs4415084 | rs12054976 | 0.255659 | 0.841387 | 1.41E−07 | 45093077 | 172 |
| rs4415084 | rs4485937 | 0.238566 | 0.836134 | 2.48E−07 | 45101400 | 173 |
| rs4415084 | rs4389695 | 0.238566 | 0.836134 | 2.48E−07 | 45107668 | 174 |
| rs4415084 | rs13183434 | 0.265513 | 1 | 1.01E−09 | 45110390 | 175 |
| rs4415084 | rs12521639 | 0.255659 | 0.841387 | 1.41E−07 | 45114238 | 176 |
| rs4415084 | rs10051592 | 0.65068 | 0.916552 | 6.95E−20 | 45126063 | 177 |
| rs4415084 | rs6885307 | 0.255659 | 0.841387 | 1.41E−07 | 45130260 | 178 |
| rs4415084 | rs10805692 | 0.238566 | 0.836134 | 2.48E−07 | 45135215 | 179 |
| rs4415084 | rs10941692 | 0.238566 | 0.836134 | 2.48E−07 | 45135535 | 180 |

TABLE 13

Surrogate SNP markers for marker rs10941679. Markers with values of $r^2$ greater than 0.2 to rs10941679 in the HapMap CEU dataset (http://www.hapmap.org) in a 1 Mb interval flanking the marker were selected. Shown is the name of the correlated SNP, values for $r^2$ and D' to rs10941679, and the corresponding P-value, as well as the position of the surrogate marker in NCBI Build 36 and a reference to the sequence id containing flanking sequnces for the marker.

| Discovery SNP | Corr SNP | $R^2$ | D' | P-value | Pos in Bld 36 | SEQ ID NO: |
|---|---|---|---|---|---|---|
| rs10941679 | rs10473354 | 0.234357 | 0.697983 | 3.79E−07 | 44432110 | 181 |
| rs10941679 | rs12054807 | 0.251051 | 0.712181 | 9.37E−08 | 44433098 | 182 |
| rs10941679 | rs10941665 | 0.248052 | 0.711093 | 1.16E−07 | 44434453 | 183 |
| rs10941679 | rs7356597 | 0.242799 | 0.701296 | 2.48E−07 | 44435967 | 184 |
| rs10941679 | rs2200123 | 0.292463 | 0.700877 | 6.90E−08 | 44444748 | 185 |
| rs10941679 | rs10472394 | 0.263453 | 0.71647 | 5.64E−08 | 44445489 | 186 |
| rs10941679 | rs10055789 | 0.260073 | 0.715333 | 5.92E−08 | 44446940 | 187 |
| rs10941679 | rs10055953 | 0.257042 | 0.714293 | 7.33E−08 | 44447011 | 188 |
| rs10941679 | rs2330551 | 0.260073 | 0.715333 | 5.92E−08 | 44448702 | 189 |
| rs10941679 | rs987852 | 0.251051 | 0.712181 | 9.37E−08 | 44450245 | 190 |
| rs10941679 | rs1482668 | 0.251051 | 0.712181 | 9.37E−08 | 44450407 | 191 |
| rs10941679 | rs2877162 | 0.260073 | 0.715333 | 5.92E−08 | 44451149 | 192 |
| rs10941679 | rs2877163 | 0.248052 | 0.711093 | 1.16E−07 | 44451226 | 193 |
| rs10941679 | rs2330553 | 0.251051 | 0.712181 | 9.37E−08 | 44451426 | 194 |
| rs10941679 | rs1482667 | 0.251717 | 0.704607 | 1.60E−07 | 44452403 | 195 |
| rs10941679 | rs4242112 | 0.251051 | 0.712181 | 9.37E−08 | 44452490 | 196 |
| rs10941679 | rs1384451 | 0.281037 | 0.766758 | 1.07E−08 | 44455011 | 197 |
| rs10941679 | rs1482685 | 0.281037 | 0.766758 | 1.07E−08 | 44456232 | 198 |
| rs10941679 | rs13357659 | 0.281037 | 0.766758 | 1.07E−08 | 44468642 | 199 |
| rs10941679 | rs6893590 | 0.220962 | 0.919347 | 1.03E−07 | 44487227 | 200 |
| rs10941679 | rs8180484 | 0.20433 | 0.915674 | 2.43E−07 | 44507720 | 201 |
| rs10941679 | rs1384450 | 0.20433 | 0.915674 | 2.43E−07 | 44515901 | 202 |
| rs10941679 | rs10941667 | 0.20528 | 0.915899 | 2.44E−07 | 44530438 | 203 |
| rs10941679 | rs16901890 | 0.218876 | 0.628697 | 3.40E−06 | 44548272 | 204 |
| rs10941679 | rs2128434 | 0.20415 | 0.913386 | 4.85E−07 | 44549566 | 205 |
| rs10941679 | rs2128435 | 0.212203 | 0.917481 | 1.43E−07 | 44552968 | 206 |
| rs10941679 | rs4866777 | 0.220312 | 0.919213 | 8.32E−08 | 44574747 | 207 |
| rs10941679 | rs1482698 | 0.353461 | 0.830339 | 9.52E−11 | 44575210 | 208 |
| rs10941679 | rs4866902 | 0.219257 | 0.917008 | 1.66E−07 | 44580477 | 209 |
| rs10941679 | rs10805684 | 0.220312 | 0.919213 | 8.32E−08 | 44587002 | 210 |
| rs10941679 | rs7708449 | 0.242956 | 0.664362 | 3.43E−07 | 44604983 | 211 |
| rs10941679 | rs7713139 | 0.237133 | 0.661966 | 5.11E−07 | 44605617 | 212 |
| rs10941679 | rs10462078 | 0.242956 | 0.664362 | 3.43E−07 | 44621291 | 213 |
| rs10941679 | rs7448715 | 0.242956 | 0.664362 | 3.43E−07 | 44621309 | 214 |
| rs10941679 | rs4866911 | 0.242956 | 0.664362 | 3.43E−07 | 44622497 | 215 |
| rs10941679 | rs4392631 | 0.242956 | 0.664362 | 3.43E−07 | 44628924 | 216 |
| rs10941679 | rs4866779 | 0.252735 | 0.668197 | 2.11E−07 | 44659107 | 217 |
| rs10941679 | rs11952948 | 0.246642 | 0.662849 | 4.89E−07 | 44663041 | 218 |
| rs10941679 | rs4463188 | 0.510791 | 1 | 1.02E−16 | 44678427 | 19 |
| rs10941679 | rs4321755 | 0.512661 | 1 | 2.03E−17 | 44681952 | 20 |
| rs10941679 | rs4492118 | 0.509261 | 1 | 2.69E−17 | 44682382 | 21 |
| rs10941679 | rs4613718 | 0.235547 | 1 | 4.63E−10 | 44685701 | 22 |
| rs10941679 | rs7735881 | 0.512661 | 1 | 2.03E−17 | 44685933 | 23 |
| rs10941679 | rs7723539 | 0.512661 | 1 | 2.03E−17 | 44695967 | 24 |
| rs10941679 | rs10805685 | 0.509261 | 1 | 2.69E−17 | 44697715 | 25 |
| rs10941679 | rs10941677 | 0.509261 | 1 | 7.08E−17 | 44698156 | 26 |
| rs10941679 | rs4415084 | 0.512661 | 1 | 2.03E−17 | 44698272 | 219 |
| rs10941679 | rs4415085 | 0.512661 | 1 | 2.03E−17 | 44698716 | 27 |
| rs10941679 | rs7720551 | 0.512661 | 1 | 2.03E−17 | 44700234 | 28 |
| rs10941679 | rs6874055 | 0.512661 | 1 | 5.36E−17 | 44702722 | 29 |
| rs10941679 | rs4419600 | 0.512661 | 1 | 2.03E−17 | 44714291 | 30 |
| rs10941679 | rs12187196 | 0.512661 | 1 | 2.03E−17 | 44719576 | 31 |
| rs10941679 | rs12522626 | 0.505814 | 1 | 3.57E−17 | 44721455 | 32 |
| rs10941679 | rs4571480 | 0.509261 | 1 | 7.08E−17 | 44722945 | 33 |
| rs10941679 | rs6451770 | 0.512661 | 1 | 2.03E−17 | 44727152 | 34 |
| rs10941679 | rs12515012 | 0.512661 | 1 | 2.03E−17 | 44730292 | 35 |
| rs10941679 | rs2165009 | 0.509261 | 1 | 2.69E−17 | 44733673 | 36 |
| rs10941679 | rs13156930 | 0.512661 | 1 | 2.03E−17 | 44733792 | 37 |
| rs10941679 | rs920328 | 0.55045 | 1 | 2.49E−18 | 44734808 | 38 |
| rs10941679 | rs1821936 | 0.509261 | 1 | 2.69E−17 | 44735239 | 39 |
| rs10941679 | rs714130 | 0.512661 | 1 | 2.03E−17 | 44737175 | 40 |
| rs10941679 | rs2013513 | 0.509261 | 1 | 7.08E−17 | 44738063 | 41 |
| rs10941679 | rs920329 | 0.509261 | 1 | 2.69E−17 | 44738264 | 42 |
| rs10941679 | rs2218081 | 0.512661 | 1 | 2.03E−17 | 44740897 | 43 |
| rs10941679 | rs10941679 | 1 | 1 | — | 44742255 | 236 |
| rs10941679 | rs2165010 | 0.512661 | 1 | 5.36E−17 | 44742537 | 45 |
| rs10941679 | rs1438825 | 0.512661 | 1 | 2.03E−17 | 44742688 | 46 |
| rs10941679 | rs6861560 | 0.512661 | 1 | 2.03E−17 | 44744135 | 47 |
| rs10941679 | rs16901937 | 0.494973 | 1 | 5.47E−17 | 44744898 | 48 |

TABLE 13-continued

Surrogate SNP markers for marker rs10941679. Markers with values of $r^2$ greater than 0.2 to rs10941679 in the HapMap CEU dataset (http://www.hapmap.org) in a 1 Mb interval flanking the marker were selected. Shown is the name of the correlated SNP, values for $r^2$ and D' to rs10941679, and the corresponding P-value, as well as the position of the surrogate marker in NCBI Build 36 and a reference to the sequence id containing flanking sequnces for the marker.

| Discovery SNP | Corr SNP | $R^2$ | D' | P-value | Pos in Bld 36 | SEQ ID NO: |
|---|---|---|---|---|---|---|
| rs10941679 | rs2218080 | 0.456436 | 0.943571 | 5.90E−14 | 44750087 | 49 |
| rs10941679 | rs11747159 | 0.434894 | 0.841573 | 2.26E−12 | 44773467 | 50 |
| rs10941679 | rs2330572 | 0.383744 | 0.834953 | 3.61E−11 | 44776746 | 51 |
| rs10941679 | rs994793 | 0.383744 | 0.834953 | 3.61E−11 | 44779004 | 52 |
| rs10941679 | rs1438827 | 0.417031 | 0.839428 | 5.91E−12 | 44787713 | 53 |
| rs10941679 | rs11949847 | 0.39369 | 0.836361 | 2.42E−11 | 44787926 | 54 |
| rs10941679 | rs7712949 | 0.434894 | 0.841573 | 2.26E−12 | 44806102 | 55 |
| rs10941679 | rs13154781 | 0.434894 | 0.841573 | 2.26E−12 | 44810784 | 56 |
| rs10941679 | rs11746980 | 0.4 | 0.837222 | 1.49E−11 | 44813635 | 57 |
| rs10941679 | rs7711697 | 0.396173 | 0.831574 | 3.79E−11 | 44816160 | 58 |
| rs10941679 | rs16901964 | 0.434894 | 0.841573 | 2.26E−12 | 44819012 | 59 |
| rs10941679 | rs6875933 | 0.434894 | 0.841573 | 2.26E−12 | 44822453 | 60 |
| rs10941679 | rs727305 | 0.434894 | 0.841573 | 2.26E−12 | 44831799 | 61 |
| rs10941679 | rs13177711 | 0.396866 | 0.836797 | 1.90E−11 | 44832719 | 62 |
| rs10941679 | rs1438820 | 0.4 | 0.837222 | 1.49E−11 | 44833527 | 63 |
| rs10941679 | rs1438819 | 0.434894 | 0.841573 | 2.26E−12 | 44833603 | 64 |
| rs10941679 | rs12651949 | 0.412815 | 0.797511 | 1.53E−08 | 44833869 | 65 |
| rs10941679 | rs10462080 | 0.434894 | 0.841573 | 2.26E−12 | 44834809 | 66 |
| rs10941679 | rs10462081 | 0.434894 | 0.841573 | 2.26E−12 | 44836422 | 67 |
| rs10941679 | rs13183209 | 0.434894 | 0.841573 | 2.26E−12 | 44839506 | 68 |
| rs10941679 | rs6872254 | 0.434894 | 0.841573 | 2.26E−12 | 44839541 | 69 |
| rs10941679 | rs7717459 | 0.434894 | 0.841573 | 2.26E−12 | 44840282 | 70 |
| rs10941679 | rs13159598 | 0.4 | 0.837222 | 1.49E−11 | 44841683 | 71 |
| rs10941679 | rs3761648 | 0.44764 | 0.843009 | 1.34E−12 | 44843836 | 72 |
| rs10941679 | rs3747479 | 0.44764 | 0.843009 | 1.34E−12 | 44844919 | 73 |
| rs10941679 | rs1866406 | 0.434894 | 0.841573 | 2.26E−12 | 44845702 | 74 |
| rs10941679 | rs13174122 | 0.434894 | 0.841573 | 2.26E−12 | 44846497 | 75 |
| rs10941679 | rs11746506 | 0.434894 | 0.841573 | 2.26E−12 | 44848323 | 76 |
| rs10941679 | rs12188871 | 0.453652 | 0.843661 | 8.25E−13 | 44849761 | 77 |
| rs10941679 | rs11741772 | 0.420989 | 0.832079 | 1.87E−11 | 44850354 | 78 |
| rs10941679 | rs7716571 | 0.392326 | 0.8282 | 7.08E−11 | 44852741 | 79 |
| rs10941679 | rs7720787 | 0.4 | 0.837222 | 1.49E−11 | 44853066 | 80 |
| rs10941679 | rs9637783 | 0.434894 | 0.841573 | 2.26E−12 | 44855403 | 81 |
| rs10941679 | rs1061310 | 0.4 | 0.837222 | 1.49E−11 | 44856607 | 82 |
| rs10941679 | rs4457089 | 0.434894 | 0.841573 | 2.26E−12 | 44857493 | 83 |
| rs10941679 | rs13189120 | 0.434894 | 0.841573 | 2.26E−12 | 44858040 | 84 |
| rs10941679 | rs930395 | 0.784483 | 1 | 4.20E−22 | 44858215 | 85 |
| rs10941679 | rs10512865 | 0.4 | 0.837222 | 1.49E−11 | 44859124 | 86 |
| rs10941679 | rs6867533 | 0.4 | 0.837222 | 1.49E−11 | 44863049 | 87 |
| rs10941679 | rs6868232 | 0.426748 | 0.830195 | 1.62E−11 | 44863437 | 88 |
| rs10941679 | rs12513749 | 0.43365 | 0.840368 | 4.47E−12 | 44863960 | 89 |
| rs10941679 | rs12518851 | 0.419161 | 0.830617 | 5.99E−11 | 44863988 | 90 |
| rs10941679 | rs1048758 | 0.4 | 0.837222 | 1.49E−11 | 44864351 | 91 |
| rs10941679 | rs13155698 | 0.434894 | 0.841573 | 2.26E−12 | 44864438 | 92 |
| rs10941679 | rs13160259 | 0.4 | 0.837222 | 1.49E−11 | 44864721 | 93 |
| rs10941679 | rs6896350 | 0.434894 | 0.841573 | 2.26E−12 | 44868328 | 94 |
| rs10941679 | rs1371025 | 0.431852 | 0.841219 | 2.88E−12 | 44869990 | 95 |
| rs10941679 | rs4596389 | 0.434894 | 0.841573 | 2.26E−12 | 44872313 | 96 |
| rs10941679 | rs6451775 | 0.434894 | 0.841573 | 2.26E−12 | 44872545 | 97 |
| rs10941679 | rs7380559 | 0.4 | 0.837222 | 1.49E−11 | 44872767 | 98 |
| rs10941679 | rs729599 | 0.434894 | 0.841573 | 2.26E−12 | 44878017 | 99 |
| rs10941679 | rs987394 | 0.434894 | 0.841573 | 2.26E−12 | 44882135 | 100 |
| rs10941679 | rs7715731 | 0.41132 | 0.816216 | 1.82E−10 | 44882601 | 101 |
| rs10941679 | rs4440370 | 0.434894 | 0.841573 | 2.26E−12 | 44889109 | 102 |
| rs10941679 | rs4492119 | 0.434894 | 0.841573 | 2.26E−12 | 44891371 | 103 |
| rs10941679 | rs7703497 | 0.434894 | 0.841573 | 2.26E−12 | 44892785 | 104 |
| rs10941679 | rs6451778 | 0.434894 | 0.841573 | 2.26E−12 | 44893745 | 105 |
| rs10941679 | rs13362132 | 0.4 | 0.837222 | 1.49E−11 | 44894017 | 106 |
| rs10941679 | rs1438821 | 0.387517 | 0.828917 | 5.73E−11 | 44894208 | 107 |
| rs10941679 | rs1438822 | 0.434894 | 0.841573 | 2.26E−12 | 44894929 | 108 |
| rs10941679 | rs4373287 | 0.434894 | 0.841573 | 2.26E−12 | 44898641 | 109 |
| rs10941679 | rs6871052 | 0.430591 | 0.839995 | 5.70E−12 | 44899074 | 110 |
| rs10941679 | rs6893319 | 0.434894 | 0.841573 | 2.26E−12 | 44899486 | 111 |
| rs10941679 | rs10053247 | 0.434894 | 0.841573 | 2.26E−12 | 44899716 | 112 |
| rs10941679 | rs10040082 | 0.444569 | 0.84267 | 1.72E−12 | 44901611 | 113 |
| rs10941679 | rs10057521 | 0.434894 | 0.841573 | 2.26E−12 | 44901743 | 114 |
| rs10941679 | rs10065638 | 0.434894 | 0.841573 | 2.26E−12 | 44901919 | 115 |
| rs10941679 | rs6894324 | 0.427926 | 0.835715 | 7.66E−12 | 44903093 | 116 |
| rs10941679 | rs4395640 | 0.434894 | 0.841573 | 2.26E−12 | 44904857 | 117 |

TABLE 13-continued

Surrogate SNP markers for marker rs10941679. Markers with values of $r^2$ greater than 0.2 to rs10941679 in the HapMap CEU dataset (http://www.hapmap.org) in a 1 Mb interval flanking the marker were selected. Shown is the name of the correlated SNP, values for $r^2$ and D' to rs10941679, and the corresponding P-value, as well as the position of the surrogate marker in NCBI Build 36 and a reference to the sequence id containing flanking sequnces for the marker.

| Discovery SNP | Corr SNP | $R^2$ | D' | P-value | Pos in Bld 36 | SEQ ID NO: |
|---|---|---|---|---|---|---|
| rs10941679 | rs10070037 | 0.434894 | 0.841573 | 2.26E−12 | 44905994 | 118 |
| rs10941679 | rs4518409 | 0.4 | 0.837222 | 1.49E−11 | 44906609 | 119 |
| rs10941679 | rs9292913 | 0.396866 | 0.836797 | 1.90E−11 | 44906636 | 120 |
| rs10941679 | rs9292914 | 0.446215 | 0.924223 | 9.11E−11 | 44907138 | 121 |
| rs10941679 | rs10059086 | 0.434894 | 0.841573 | 2.26E−12 | 44907764 | 122 |
| rs10941679 | rs11951760 | 0.466609 | 0.885323 | 1.29E−12 | 44907929 | 123 |
| rs10941679 | rs4329028 | 0.4 | 0.837222 | 1.49E−11 | 44908110 | 124 |
| rs10941679 | rs7716600 | 0.7772 | 1 | 1.77E−21 | 44910762 | 125 |
| rs10941679 | rs4412123 | 0.4 | 0.837222 | 1.49E−11 | 44912045 | 126 |
| rs10941679 | rs7705343 | 0.4 | 0.837222 | 1.49E−11 | 44915334 | 127 |
| rs10941679 | rs10040488 | 0.434894 | 0.841573 | 2.26E−12 | 44916045 | 128 |
| rs10941679 | rs4642377 | 0.43096 | 0.836082 | 6.03E−12 | 44920997 | 129 |
| rs10941679 | rs4391175 | 0.434894 | 0.841573 | 2.26E−12 | 44925813 | 130 |
| rs10941679 | rs4129642 | 0.434894 | 0.841573 | 2.26E−12 | 44933886 | 131 |
| rs10941679 | rs9790879 | 0.4 | 0.837222 | 1.49E−11 | 44935642 | 132 |
| rs10941679 | rs9790896 | 0.340217 | 0.780757 | 9.70E−10 | 44935848 | 133 |
| rs10941679 | rs4457088 | 0.427926 | 0.835715 | 7.66E−12 | 44936711 | 134 |
| rs10941679 | rs4866784 | 0.434894 | 0.841573 | 2.26E−12 | 44936888 | 135 |
| rs10941679 | rs9791056 | 0.434894 | 0.841573 | 2.26E−12 | 44939648 | 136 |
| rs10941679 | rs6880275 | 0.434894 | 0.841573 | 2.26E−12 | 44944692 | 137 |
| rs10941679 | rs6870136 | 0.434894 | 0.841573 | 2.26E−12 | 44946419 | 138 |
| rs10941679 | rs6881563 | 0.434894 | 0.841573 | 2.26E−12 | 44948610 | 139 |
| rs10941679 | rs7703618 | 0.434894 | 0.841573 | 2.26E−12 | 44950336 | 140 |
| rs10941679 | rs10077814 | 0.4 | 0.837222 | 1.49E−11 | 44952546 | 141 |
| rs10941679 | rs6451783 | 0.434894 | 0.841573 | 2.26E−12 | 44954050 | 142 |
| rs10941679 | rs4298259 | 0.434894 | 0.841573 | 2.26E−12 | 44956468 | 143 |
| rs10941679 | rs7736092 | 0.431852 | 0.841219 | 2.88E−12 | 44956752 | 144 |
| rs10941679 | rs7728431 | 0.431223 | 0.838562 | 4.37E−12 | 44958436 | 145 |
| rs10941679 | rs7708506 | 0.428766 | 0.840855 | 3.67E−12 | 44958461 | 146 |
| rs10941679 | rs10039866 | 0.434894 | 0.841573 | 2.26E−12 | 44960818 | 147 |
| rs10941679 | rs10043344 | 0.407626 | 0.83823 | 1.23E−11 | 44962275 | 148 |
| rs10941679 | rs10038554 | 0.427926 | 0.835715 | 7.66E−12 | 44962864 | 149 |
| rs10941679 | rs10044096 | 0.4 | 0.837222 | 1.49E−11 | 44963122 | 150 |
| rs10941679 | rs10041518 | 0.434894 | 0.841573 | 2.26E−12 | 44963163 | 151 |
| rs10941679 | rs12517690 | 0.434894 | 0.841573 | 2.26E−12 | 44975050 | 152 |
| rs10941679 | rs6875287 | 0.419968 | 0.833288 | 3.75E−11 | 44977387 | 153 |
| rs10941679 | rs11958808 | 0.4 | 0.837222 | 1.49E−11 | 44980847 | 154 |
| rs10941679 | rs2067980 | 0.304748 | 0.767084 | 4.34E−08 | 45018074 | 160 |
| rs10941679 | rs11948186 | 0.266543 | 0.634593 | 1.36E−07 | 45087191 | 171 |
| rs10941679 | rs13183434 | 0.243358 | 0.685481 | 9.99E−07 | 45110390 | 175 |
| rs10941679 | rs10051592 | 0.266543 | 0.634593 | 1.36E−07 | 45126063 | 177 |

TABLE 14

Surrogate SNP markers for marker rs1219648. Markers with values of $r^2$ greater than 0.2 to rs1219648 in the HapMap CEU dataset (http://www.hapmap.org) in a 1 Mb interval flanking the marker were selected. Shown is the name of the correlated SNP, values for $r^2$ and D' to rs1219648, and the corresponding P-value, as well as the position of the surrogate marker in NCBI Build 36 and a reference to the sequence id containing flanking sequnces for the marker.

| Discovery SNP | Corr SNP | $R^2$ | D' | P-value | Pos in Bld 36 | SEQ ID NO: |
|---|---|---|---|---|---|---|
| rs1219648 | rs3750817 | 0.487805 | 1 | 5.60E−18 | 123322567 | 220 |
| rs1219648 | rs11200014 | 0.964392 | 1 | 9.67E−33 | 123324920 | 221 |
| rs1219648 | rs2912780 | 0.965418 | 1 | 2.47E−34 | 123327107 | 222 |
| rs1219648 | rs2981579 | 0.965418 | 1 | 2.47E−34 | 123327325 | 223 |
| rs1219648 | rs1078806 | 0.966387 | 1 | 3.53E−35 | 123328965 | 224 |
| rs1219648 | rs2981578 | 0.844156 | 1 | 5.28E−30 | 123330301 | 225 |
| rs1219648 | rs1219648 | 1 | 1 | — | 123336180 | 237 |
| rs1219648 | rs1219643 | 0.272727 | 1 | 6.24E−10 | 123338345 | 226 |
| rs1219648 | rs2912774 | 1 | 1 | 2.49E−37 | 123338652 | 227 |
| rs1219648 | rs2936870 | 1 | 1 | 2.49E−37 | 123338892 | 228 |
| rs1219648 | rs17102287 | 0.446154 | 1 | 8.77E−16 | 123340181 | 229 |

TABLE 14-continued

Surrogate SNP markers for marker rs1219648. Markers with values of $r^2$ greater than 0.2 to rs1219648 in the HapMap CEU dataset (http://www.hapmap.org) in a 1 Mb interval flanking the marker were selected. Shown is the name of the correlated SNP, values for $r^2$ and D' to rs1219648, and the corresponding P-value, as well as the position of the surrogate marker in NCBI Build 36 and a reference to the sequence id containing flanking sequnces for the marker.

| Discovery SNP | Corr SNP | R² | D' | P-value | Pos in Bld 36 | SEQ ID NO: |
|---|---|---|---|---|---|---|
| rs1219648 | rs2860197 | 1 | 1 | 7.38E−37 | 123341292 | 230 |
| rs1219648 | rs2420946 | 1 | 1 | 1.03E−36 | 123341314 | 231 |
| rs1219648 | rs2981582 | 1 | 1 | 2.49E−37 | 123342307 | 232 |
| rs1219648 | rs3135715 | 0.426087 | 1 | 3.82E−15 | 123344716 | 233 |
| rs1219648 | rs1047111 | 0.215627 | 0.90484 | 5.80E−07 | 123347551 | 234 |

The invention claimed is:

1. A method for determining an increased susceptibility to breast cancer in a human individual who has not been diagnosed with breast cancer, comprising:
analyzing a nucleic acid sample obtained from the individual to detect the presence of allele T of polymorphic marker rs4415084 in the nucleic acid sample,
determining an increased genetic susceptibility to breast cancer in the individual from the presence of the allele in the nucleic acid sample, and
performing at least one of clinical breast examination (CBE), X-ray mammography, and contrast-enhanced magnetic resonance imaging (CE-MRI) in the individual determined to have the increased genetic susceptibility to breast cancer.

2. The method according to claim 1, wherein the determining an increased genetic susceptibility includes calculating a risk score for the human individual that includes a relative risk (RR) or odds ratio (OR) of at least 1.10 attributable to allele T of polymorphic marker rs4415084 being present in the nucleic acid sample.

3. The method of claim 1, further comprising analyzing non-genetic information to make risk assessment, diagnosis, or prognosis of the individual.

4. The method of claim 3, wherein the non-genetic information is selected from age, gender, ethnicity, socioeconomic status, previous disease diagnosis, medical history of subject, family history of breast cancer, biochemical measurements, and clinical measurements.

5. A method of determining risk of developing at least a second primary breast tumor in a human individual previously diagnosed with breast cancer, the method comprising:
analyzing a nucleic acid sample obtained from the individual to detect the presence of allele T of polymorphic marker rs4415084 in a nucleic acid sample obtained from the individual,
determining an increased genetic risk of developing at least a second primary breast tumor in the individual previously diagnosed with breast cancer from the presence of the allele in the nucleic acid sample, and
performing at least one of clinical breast examination (CBE), X-ray mammography, and contrast-enhanced magnetic resonance imaging (CE-MRI) in the individual determined to have the increased genetic susceptibility to breast cancer.

6. The method according to claim 1, wherein the analyzing of the nucleic acid sample comprises amplifying a segment of a nucleic acid that comprises the polymorphic marker by Polymerase Chain Reaction (PCR), using a nucleotide primer pair flanking the polymorphic marker.

7. The method according to claim 1, wherein the analyzing of the nucleic acid sample is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology.

8. The method according to claim 7, wherein the process comprises allele-specific probe hybridization.

9. The method according to claim 7, wherein the process is microarray technology.

10. The method according to claim 1, comprising:
1) contacting copies of the nucleic acid with a detection oligonucleotide probe and an enhancer oligonucleotide probe under conditions for specific hybridization of the oligonucleotide probe with the nucleic acid; wherein
a) the detection oligonucleotide probe is from 5-100 nucleotides in length and specifically hybridizes to a first segment of a nucleic acid whose nucleotide sequence is given by SEQ ID NO: 235;
b) the detection oligonucleotide probe comprises a detectable label at its 3' terminus and a quenching moiety at its 5' terminus;
c) the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and
d) a single base gap exists between the first segment and the second segment, such that when the oligonucleotide probe and the enhancer oligonucleotide probe are both hybridized to the nucleic acid, a single base gap exists between the oligonucleotides;

2) treating the nucleic acid with an endonuclease that will cleave the detectable label from the 3' terminus of the detection probe to release free detectable label when the detection probe is hybridized to the nucleic acid; and 3) measuring free detectable label, wherein the presence of the free detectable label indicates that the detection probe specifically hybridizes to the first segment of the nucleic acid, and indicates the sequence of the polymorphic site as the complement of the detection probe.

11. The method according to claim 1, wherein the step of determining an increased genetic susceptibility is performed with a computer using a computer-readable medium on which is stored: an identifier for polymorphic marker rs4415084; an indicator of the frequency of at least one allele of polymorphic marker rs4415084 in a plurality of individuals diagnosed with breast cancer; and an indicator of the frequency of the least one allele of said at least one polymorphic markers in a plurality of reference individuals.

12. The method according to claim 1, wherein the step of determining an increased genetic susceptibility is performed using an apparatus comprising:
a computer readable memory;
a processor; and
a routine stored on the computer readable memory and adapted to be executed on the processor to analyze marker information for at least one human individual with respect to at least one polymorphic marker that is rs4415084 and generate an output based on the marker information, wherein the output comprises an individual risk measure of the at least one marker as a genetic indicator of breast cancer susceptibility for the human individual.

13. The method according to claim 12, wherein the routine further comprises a risk measure for breast cancer associated with the at least one marker, wherein the risk measure is based on a comparison of the frequency of at least one allele of the at least one polymorphic marker in a plurality of individuals diagnosed with breast cancer and an indicator of the frequency of the at least one allele of at least one polymorphic marker in a plurality of reference individuals, and wherein the individual risk measure for the human individual is based on a comparison of the carrier status of the individual for the at least one marker and the risk measure for the at least one marker allele.

14. The method according to claim 1, comprising determining that the individual is homozygous for allele T of polymorphic marker rs4415084, and determining increased susceptibility to breast cancer from the presence of the homozygous T allele.

15. The method according to claim 7, wherein the process is allele-specific probe hybridization or nucleic acid sequencing.

16. The method according to claim 1 that comprises analyzing the nucleic acid sample by contacting nucleic acid from the sample with at least one oligonucleotide probe that is 15 to 500 nucleotides in length and that hybridizes to a segment of a nucleic acid whose sequence is shown in SEQ ID NO: 235, or the complement thereof, wherein the hybridization is sequence-specific and identifies the presence or absence of allele T of rs4415084.

17. The method according to claim 1, comprising calculating a risk score that includes a genetic susceptibility calculation based on the determination of the presence of allele T of rs4415084.

18. The method according to claim 1, further comprising decreasing the interval between repeated screening in an individual determined to have the increased genetic susceptibility to breast cancer, wherein the screening comprises the at least one of CBE, X-ray mammography, and CE-MRI.

19. A method of using a nucleic acid sample isolated from a human individual who has not been diagnosed with breast cancer, for determining an increased susceptibility to breast cancer in the individual, the method comprising:
analyzing the nucleic acid sample to detect the presence of allele T of polymorphic marker rs4415084,
determining an increased genetic susceptibility to breast cancer for the human individual from evidence that allele T of polymorphic marker rs4415084 is present in the nucleic acid sample, and
performing at least one of clinical breast examination (CBE), X-ray mammography, and contrast-enhanced magnetic resonance imaging (CE-MRI) in the individual determined to have the increased genetic susceptibility to breast cancer.

20. The method of claim 19, wherein determining an increased susceptibility includes calculating a risk score for the human individual that includes a genetic risk component attributed to allele T of polymorphic marker rs4415084 being present in the nucleic acid sample from the individual.

21. The method according to claim 19, wherein the analyzing of the nucleic acid sample is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, single-stranded conformation analysis and microarray technology.

22. The method according to claim 1, further comprising detecting at least one allele of at least one polymorphic marker selected from the group consisting of rs920328, rs1821936, rs13156930, rs4571480, rs920329, rs2013513, rs714130, rs12187196, rs12522626, rs6861560, rs2165009, rs2165010, rs2218081, rs1438825, rs12515012, rs4492118, rs4419600, rs6874055, rs7720551, rs10805685, rs4415085, rs7723539, rs4415084, rs4321755, rs10941677, rs4463188, rs7735881, rs16901937, rs10941679, rs7712949, rs13154781, rs1438827, rs10040082, rs10040488, rs10057521, rs11951760, rs10065638, rs6894324, rs6451770, rs10059086, rs4129642, rs4395640, rs4391175, rs10070037, rs9292914, rs4642377, rs11747159, rs2218080, rs727305, rs13183209, rs6872254, rs7717459, rs1438819, rs10462080, rs10462081, rs16901964, rs6875933, rs12651949, rs4457088, rs987394, rs7715731, rs4440370, rs4492119, rs729599, rs1866406, rs13174122, rs12188871, rs9637783, rs6868232, rs12513749, rs4596389, rs3761648, rs11746506, rs11741772, rs4457089, rs13189120, rs12518851, rs13155698, rs6896350, rs1371025, rs4866784, rs3747479, rs7708506, rs6451775, rs10038554, rs10041518, rs9791056, rs10039866, rs6880275, rs6881563, rs7736092, rs4298259, rs7728431, rs7703618, rs12517690, rs7716600, rs6451783, rs6870136, rs6875287, rs7703497, rs930395, rs6451778, rs6893319, rs1438822, rs4373287, rs6871052, rs10053247, rs11746980, rs11949847, rs2330572, rs994793, rs7705343, rs4329028, rs9790879, rs9292913, rs4412123, rs4518409, rs9790896, rs11948186, rs10043344, rs13159598, rs1438820, rs13177711, rs10044096, rs1061310, rs10512865, rs6867533, rs7716571, rs7720787, rs7711697, rs1048758, rs13160259, rs7380559, rs10077814, rs10051592, rs1438821, rs13362132, rs11958808 and rs3935086.

* * * * *